US012606844B2

(12) United States Patent
Feng et al.

(10) Patent No.: US 12,606,844 B2
(45) Date of Patent: Apr. 21, 2026

(54) METHODS AND SYSTEMS FOR TARGETED GENE MANIPULATION

(71) Applicant: The Chinese University of Hong Kong, Shatin (CN)

(72) Inventors: Bo Feng, Shatin (CN); Xiangjun He, Shatin (CN); Zhenjie Zhang, Shatin (CN); Kwan Yuen Katherine Xue, Shatin (CN)

(73) Assignee: The Chinese University of Hong Kong, Hong Kong (CN)

( * ) Notice: Subject to any disclaimer, the term of this patent is extended or adjusted under 35 U.S.C. 154(b) by 55 days.

(21) Appl. No.: 18/412,406

(22) Filed: Jan. 12, 2024

(65) Prior Publication Data

US 2024/0368623 A1    Nov. 7, 2024

Related U.S. Application Data

(63) Continuation of application No. 15/354,329, filed on Nov. 17, 2016, now Pat. No. 11,905,521.

(60) Provisional application No. 62/288,974, filed on Jan. 29, 2016, provisional application No. 62/256,514, filed on Nov. 17, 2015.

(51) Int. Cl.
| | |
|---|---|
| *C12Q 1/68* | (2018.01) |
| *C12N 9/22* | (2006.01) |
| *C12N 15/10* | (2006.01) |
| *C12N 15/85* | (2006.01) |
| *C12Q 1/6897* | (2018.01) |

(52) U.S. Cl.
CPC .............. *C12N 15/85* (2013.01); *C12N 9/22* (2013.01); *C12N 15/102* (2013.01); *C12N 15/1086* (2013.01); *C12Q 1/6897* (2013.01)

(58) Field of Classification Search
CPC ........ C12N 15/85; C12N 9/22; C12N 15/102; C12N 2310/20; C12Q 1/6897
See application file for complete search history.

(56) References Cited

U.S. PATENT DOCUMENTS

| | | | |
|---|---|---|---|
| 8,871,445 B2 | 10/2014 | Cong et al. | |
| 8,889,356 B2 | 11/2014 | Zhang | |
| 9,260,723 B2 | 2/2016 | Mali et al. | |
| 9,970,030 B2 | 5/2018 | Cameron et al. | |
| 2010/0210712 A1* | 8/2010 | Hansen | C12N 15/111 |
| | | | 435/325 |
| 2013/0326645 A1 | 12/2013 | Cost et al. | |
| 2014/0273226 A1 | 9/2014 | Wu | |
| 2015/0020223 A1 | 1/2015 | Zhang et al. | |
| 2016/0208243 A1 | 7/2016 | Zhang et al. | |
| 2016/0298134 A1 | 10/2016 | Chen et al. | |
| 2017/0022507 A1 | 1/2017 | Reyon et al. | |
| 2019/0024074 A1 | 1/2019 | Maresca et al. | |

FOREIGN PATENT DOCUMENTS

| | | |
|---|---|---|
| WO | 2013/169802 A2 | 11/2013 |
| WO | 2015/054253 A1 | 4/2015 |

OTHER PUBLICATIONS

He et al (NAR published online Feb. 4, 2016, vol. 44, No. 9 pp. 1-14) (Year: 2016).*
Liu et al "Genomic discovery of potent chromatin insulators for human gene therapy" Nat Biotech, 2015 vol. 33, No. 2: Epub Jan. 12, 2015; pp. 198-203) (Year: 2015).*
Suzuki_et_al_Nov._16_2016 (Year: 2016).*
Capecchi, "Gene targeting in mice: functional analysis of the mammalian genome for the twenty-first century," Nat Rev Genet 6, 507-12 (2005).
Casola, "Mouse models for miRNA expression: the ROSA26 locus," Methods Mol Biol 667, 145-63 (2010).
Feng, et al., "Reprogramming of fibroblasts into induced pluripotent stem cells with orphan nuclear receptor Esrrb," Nat Cell Biol 11, 197-203 (2009).
Heyer, et al., "Regulation of homologous recombination in eukaryotes," Annu Rev Genet 44, 113-39 (2010).
Hisano, et al., "Precise in-frame integration of exogenous DNA mediated by CRISPR/Cas9 system in zebrafish," Sci Rep 5, 8841 (2015).
Hsu, et al., "Development and applications of CRISPR-Cas9 for genome engineering," Cell 157, 1262-78 (2014).
Hu, et al., "Direct activation of human and mouse Oct4 genes using engineered TALE and Cas9 transcription factors," Nucleic Acids Research 42, 4375-4390 (2014).
Hwang, et al., "Efficient genome editing in zebrafish using a CRISPR-Cas system," Nat Biotechnol 31, 227-9 (2013).
Jiang, et al., "RNA-guided editing of bacterial genomes using CRISPR-Cas systems," Nat Biotech 31, 233-239 (2013).
Kearns, et al., "NA, Genga RM, Enuameh MS, Garber M, Wolfe SA & Maehr R. Cas9 effector-mediated regulation of transcription and differentiation in human pluripotent stem cells," Development 141, 219-23 (2014).
Koller, et al., "Germ-line transmission of a planned alteration made in a hypoxanthine phosphoribosyltransferase gene by homologous recombination in embryonic stem cells," Proc Natl Acad Sci U S A 86, 8927-31 (1989).
Li, et al., "Intron targeting-mediated and endogenous gene integrity-maintaining knockin in zebrafish using the CRISPR/Cas9 system," Cell Res 25, 634-7 (2015).
Lieber, "The mechanism of double-strand DNA break repair by the nonhomologous DNA end-joining pathway," Annu Rev Biochem 79, 181-211 (2010).
Liu, et al., "Genomic discovery of potent chromatin insulators for human gene therapy," Nat Biotech, 2015. 33(2): p. 198-203.
Maruyama, et al., "Increasing the efficiency of precise genome editing with CRISPR-Cas9 by inhibition of nonhomologous end joining," Nat Biotechnol 33, 538-42 (2015).

(Continued)

*Primary Examiner* — Catherine S Hibbert

(74) *Attorney, Agent, or Firm* — Kilpatrick Townsend & Stockton LLP

(57) ABSTRACT

The present invention provides novel methods and systems, including cell lines, recombinant polynucleotide constructs, compositions, and kits, for targeted yet universal genomic manipulation.

17 Claims, 53 Drawing Sheets

Specification includes a Sequence Listing.

(56)                    References Cited

OTHER PUBLICATIONS

Merkle, et al., "Efficient CRISPR-Cas9-Mediated Generation of Knockin Human Pluripotent Stem Cells Lacking Undesired Mutations at the Targeted Locus," Cell Rep 11, 875-83 (2015).

Musunuru, "Genome editing of human pluripotent stem cells to generate human cellular disease models," Dis Model Mech 6, 896-904 (2013).

Nakayama, "Homologous recombination in human iPS and ES cells for use in gene correction therapy," Drug Discov Today 15, 198-202 (2010).

Sterneckert , et al., "Investigating human disease using stem cell models," Nat Rev Genet 15, 625-39 (2014).

Szymczak, et al., "Correction of multi-gene deficiency in vivo using a single 'self-cleaving' 2A peptide-based retroviral vector," Nat Biotechnol 22, 589-94 (2004).

Takahashi, et al., "Induction of pluripotent stem cells from adult human fibroblasts by defined factors," Cell 131, 861-72 (2007).

Thomson, et al., "Embryonic stem cell lines derived from human blastocysts," Science 282, 1145-7 (1998).

Van Rensburg, et al., "Chromatin structure of two genomic sites for targeted transgene integration in induced pluripotent stem cells and hematopoietic stem cells," Gene Ther 20, 201-14 (2013).

Wang, et al., "One-step generation of mice carrying mutations in multiple genes by CRISPR/Cas-mediated genome engineering," Cell 153, 910-8 (2013).

Woltjen, et al., "piggyBac transposition reprograms fibroblasts to induced pluripotent stem cells," Nature 458, 766-70 (2009).

Yu, et al., "Small molecules enhance CRISPR genome editing in pluripotent stem cells," Cell Stem Cell 16, 142-7 (2015).

Zetsche,et al., Cpf1 Is a Single RNA-Guided Endonuclease of a Class 2 CRISPR-Cas System, Cell. 163(3): p. 759-771.

Zhu, et al., "A CRISPR/Cas-Mediated Selection-free Knockin Strategy in Human Embryonic Stem Cells," Stem Cell Reports 4, 1103-11 (2015).

Vasquez et al., "Manipulating the mammalian genome by homologous recombination," PNAS, Jul. 17, 2001, vol. 98, No. 15, pp. 8403-8410.

Suzuki et al (Nature, vol. 540, Dec. 1, 2016; published online Nov. 16, 2016). (Year: 2016).

Finotti et al "Recent trends in the gene therapy of B-thalassemia" (Journal of Blood Medicine: 2015 vol. 6, pp. 69-85). (Year:2015).

Humbert et al (Crit Rev Biochem Mol Biol. May 2012; 47(3): 264-281 published May 1, 2013). (Year: 2013).

Burgess ("Insulating form genotoxicity" Nature Reviews Genetics published online Jan. 28, 2015). (Year: 2015).

Li et al (Stem Cells and Development vol. 24, No. 24, 2015 pp. 2925-2942). (Year: 2015).

Auer et al entitled "Highly efficient CRISPR/Cas9-mediated knock-in in zebrafish by homology-independent DNA repair" (Genome Research 2014 vol. 24, pp. 142-153). (Year: 2014).

Wang et al (Scientific Reports 2015 vol. 5: 17517, pp. 1-11 ). (Year: 2015).

Orfi Dissertation (McGill University May 2016). (Year: 2016).

Hasegawa et al "Generation of CRISPR/Cas9-mediated bicistronic knock-in ins1-cre driver mice" (Exp. Anim. vol 65, No. 3, pp. 319-327, published online Apr. 2016). (Year: 2016).

Geisinger Dissertation (Jun. 2015). (Year: 2015).

Dickinson et al (Nature Methods vol. 10, No. 10, published Sep. 1, 2013, pp. 1028-1036). (Year: 2013).

Kawakami et al (Developmental Cell, vol. 7, pp. 133-144, 2004).

Taniwaki et al (Develop. Growth Differ. 2005, vol. 47, pp. 163-172).

Kimura et al (Nature 2014, vol. 4, No. 6545, pp. 1-7).

* cited by examiner

HEK293T-AAVS1(B)GFP

HEK293T-AAVS1(B)GFP (B)cGFPdonor-HDR.B + sg-A

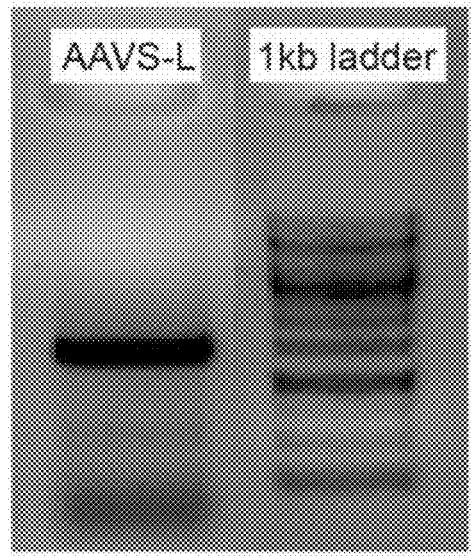 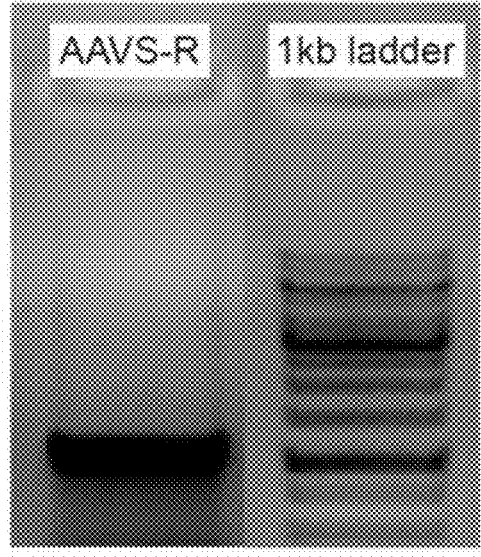
H1-(B)GFP
*FIG. 4A*
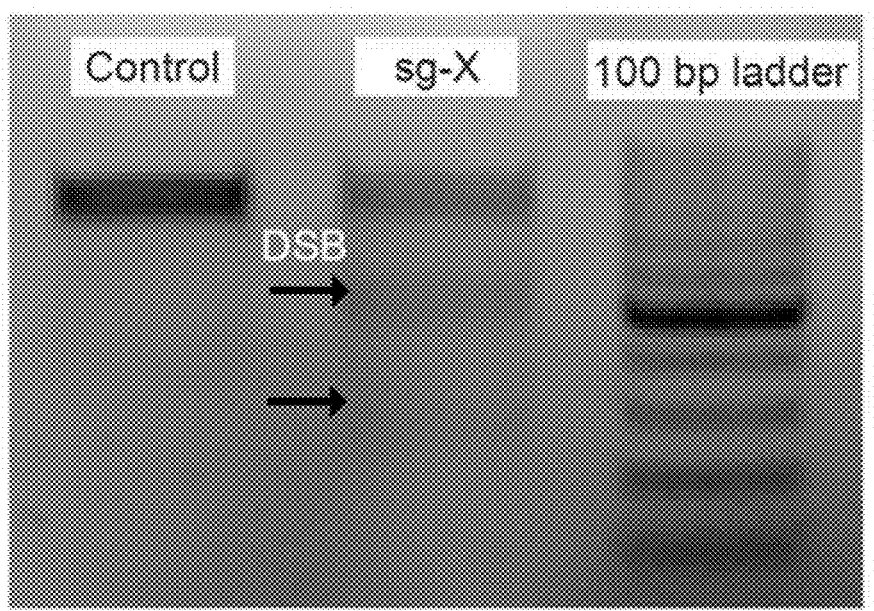
H1-(B)GFP
*FIG. 4B*

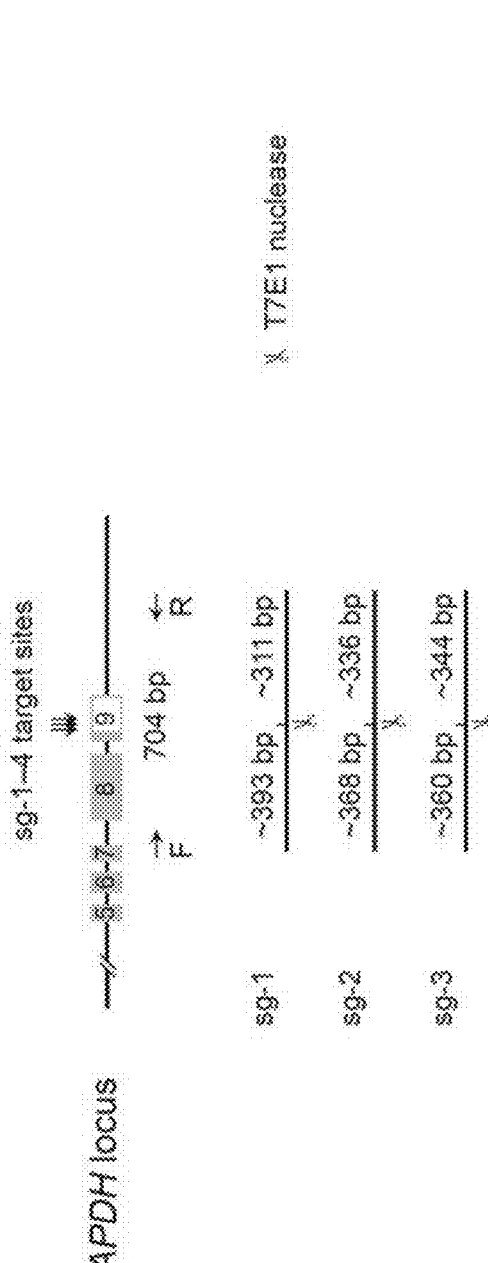
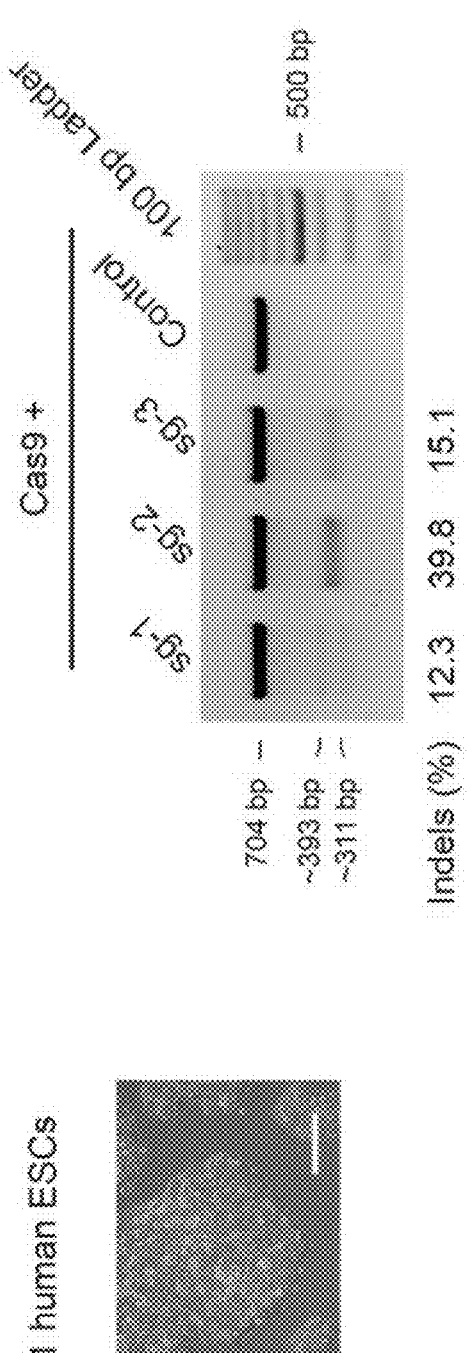
FIG. 5A

FIG. 6C

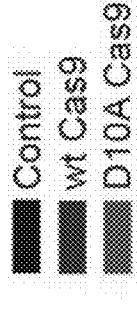
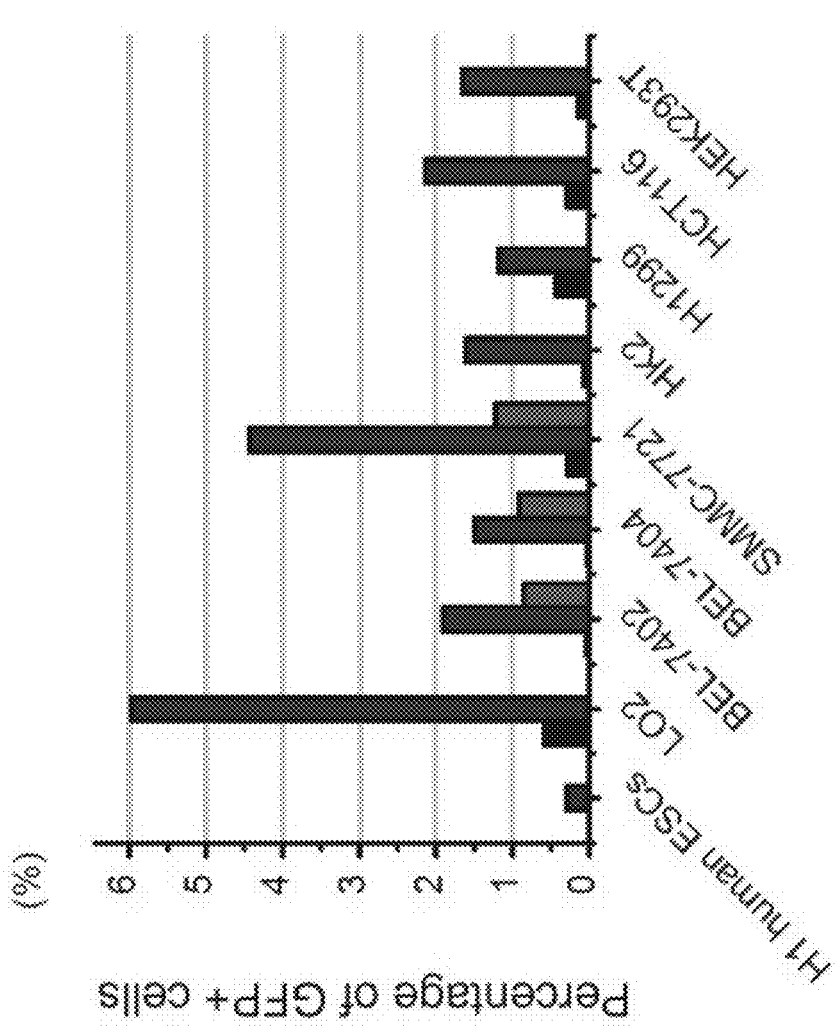
*FIG. 6D*

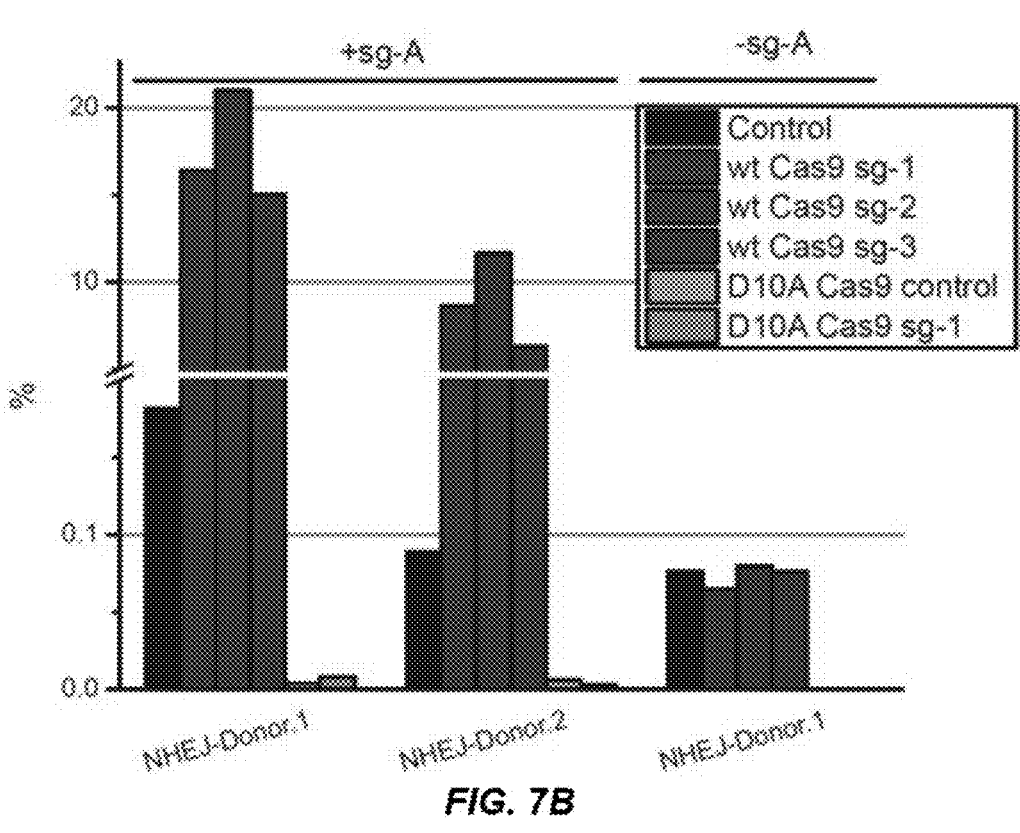
*FIG. 7B*
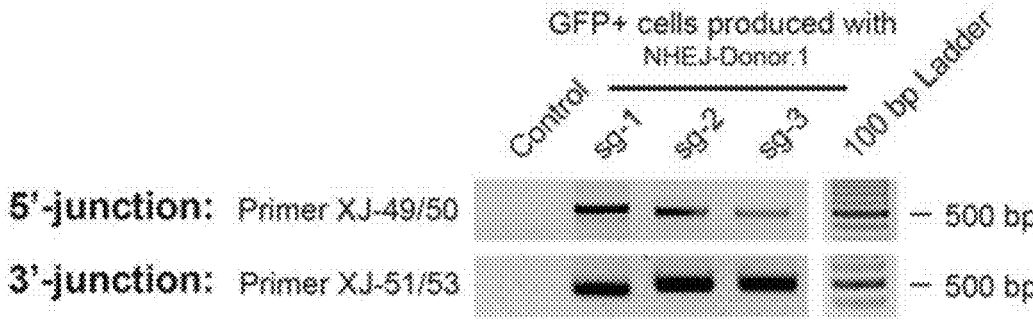
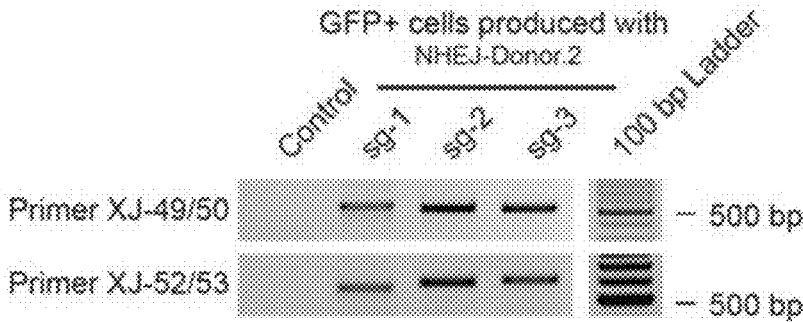
*FIG. 7C*

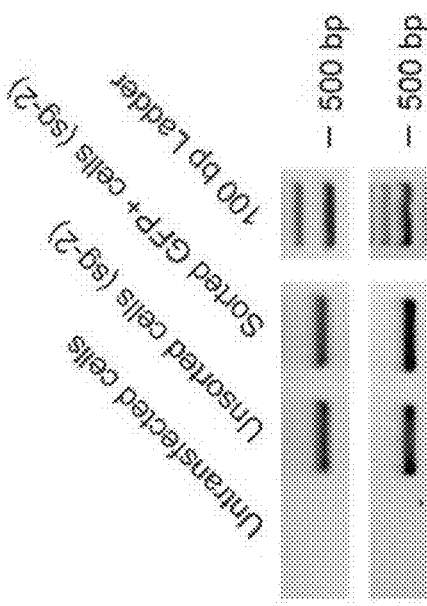
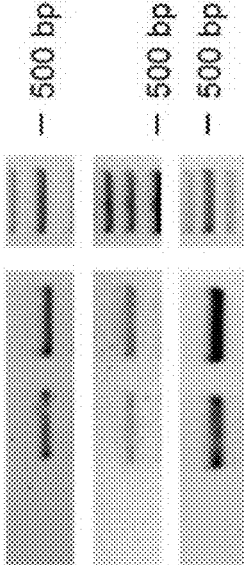
Targeting with NHEJ-Donor.2
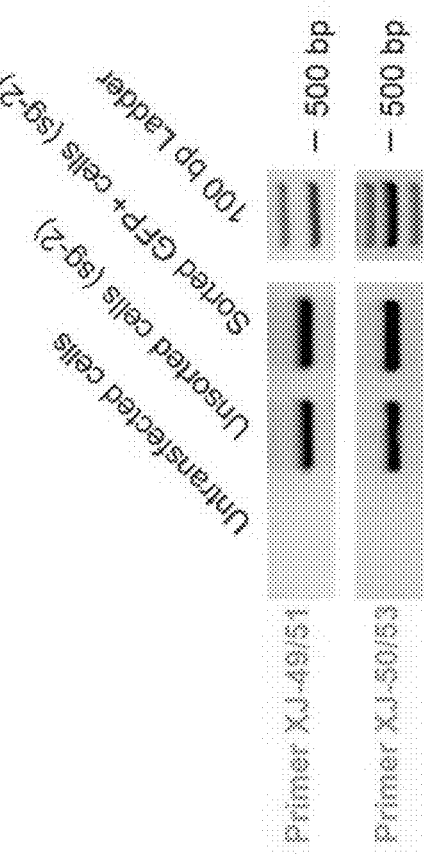
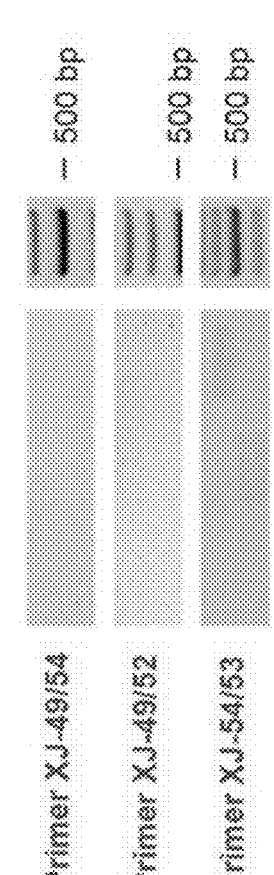
Targeting with NHEJ-Donor.1
FIG. 8B

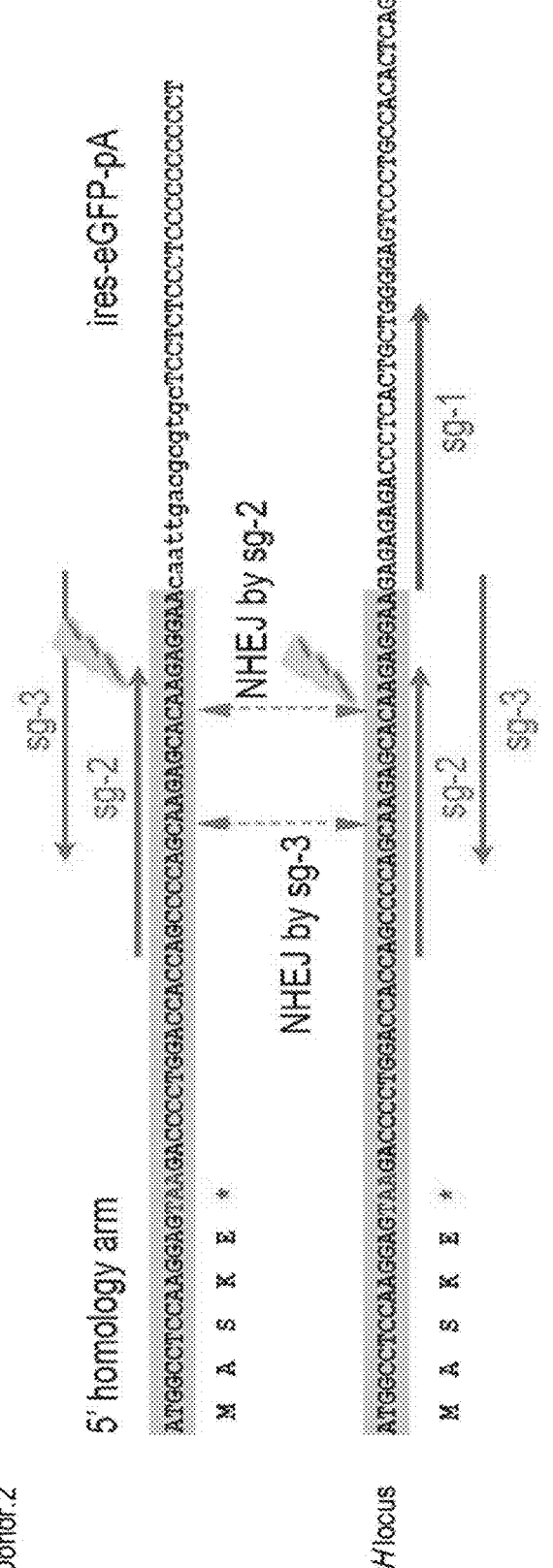
FIG. 9E

5'-junctions of NHEJ-targeting induced with sg-2 or sg-3

FIG. 9E (Continued)

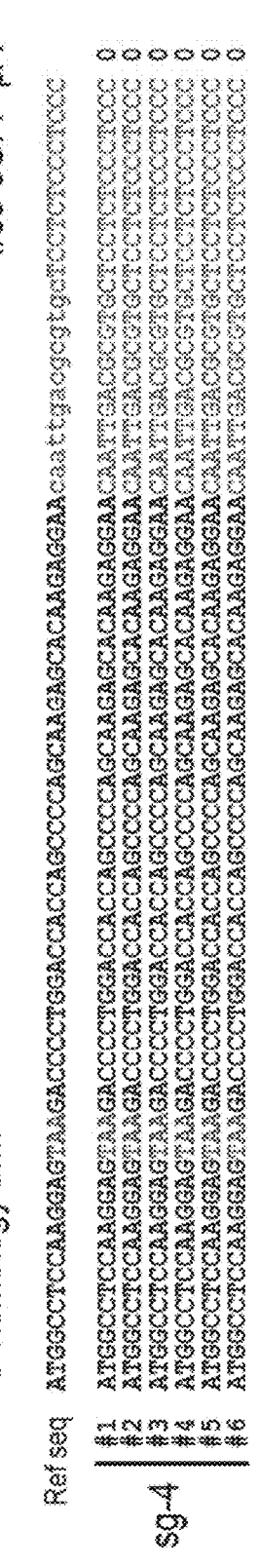
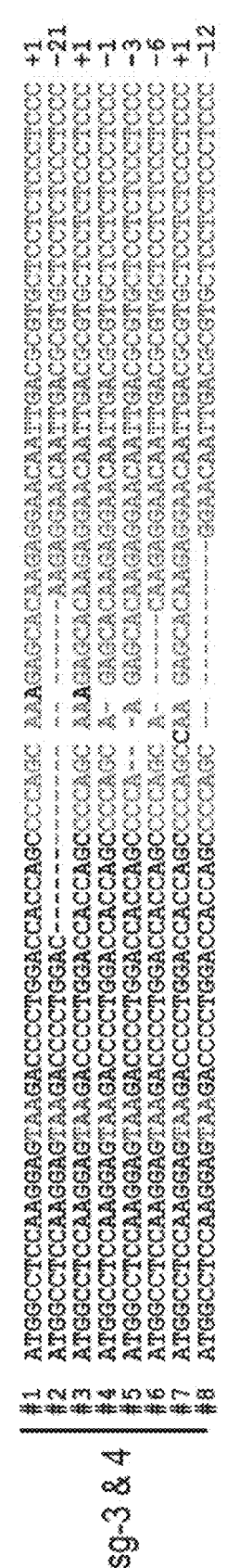
*FIG. 9E (Continued)*

5'-Junction: Primer XJ-55/50

3'-Junction: Primer XJ-51/56

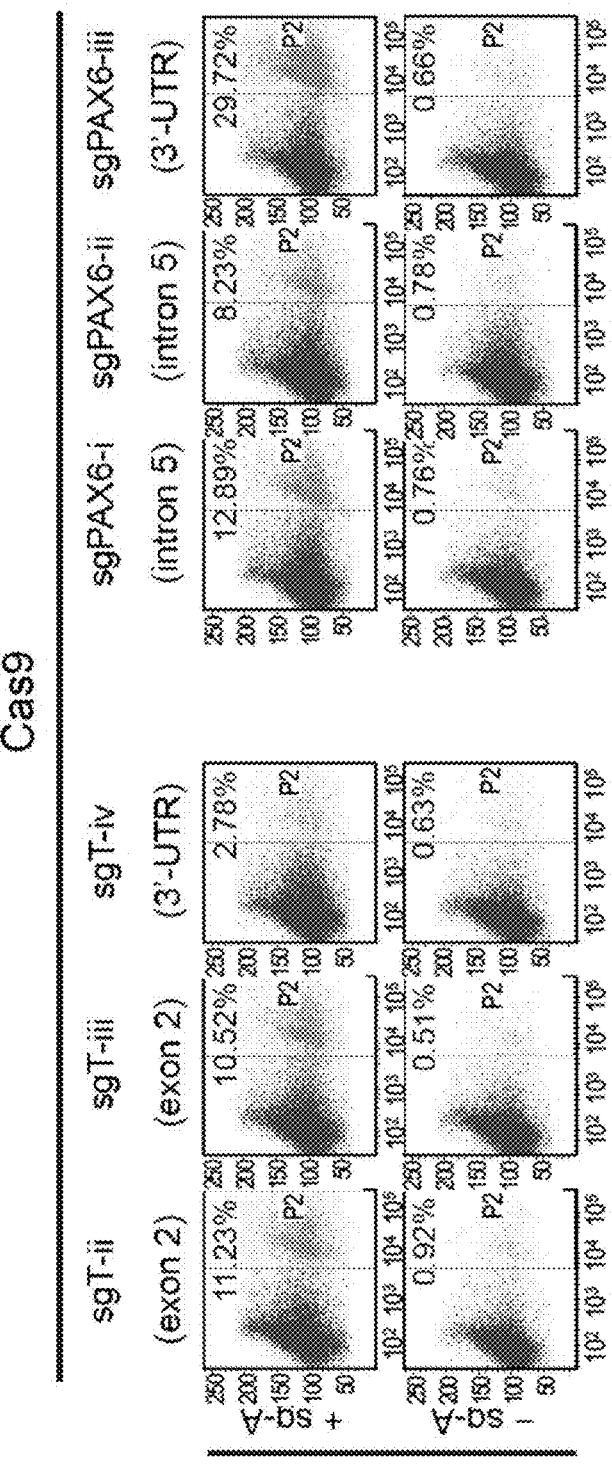
*FIG. 14A (continued)*

Fig. 15 A
Gene specific sg-RNA
targeting on 3'-UTR
Genome locus
NH-S donor 4 for silent
gene targeting
sg-A
NHEJ
CRE
Fig. 15 B
IRES-TD-PGK-GFP donor
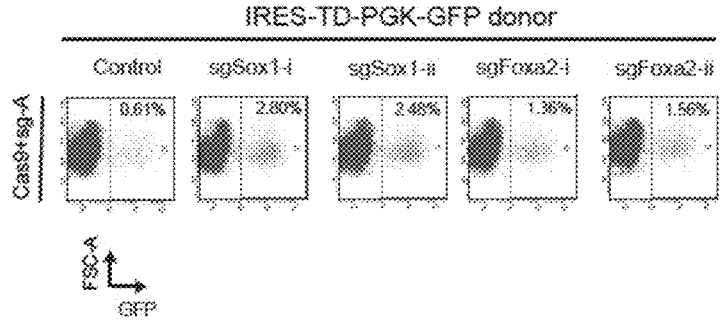
Fig. 15 C
IRES-TD-PGK-GFP donor

A

B

A

B

Fig. 18
A    Endogenous genome locus
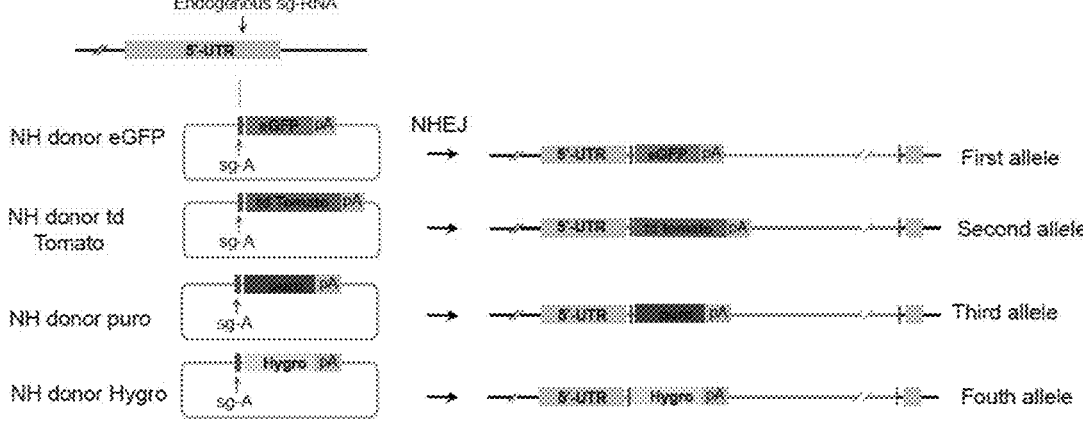
Fig. 18 B
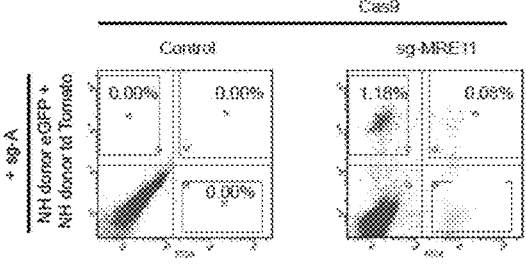

SEQUENCE LISTING

```
Sequence total quantity: 325
SEQ ID NO: 1              moltype = DNA  length = 20
FEATURE                   Location/Qualifiers
misc_feature              1..20
                          note = Description of sequence: Synthetic oligonucleotide
                           sequence.
source                    1..20
                          mol_type = other DNA
                          organism = synthetic construct
SEQUENCE: 1
gagagagacc ctcactgctg                                             20

SEQ ID NO: 2              moltype = DNA  length = 20
FEATURE                   Location/Qualifiers
misc_feature              1..20
                          note = Description of sequence: Synthetic oligonucleotide
                           sequence.
source                    1..20
                          mol_type = other DNA
                          organism = synthetic construct
SEQUENCE: 2
agccccagca agagcacaag                                             20

SEQ ID NO: 3              moltype = DNA  length = 20
FEATURE                   Location/Qualifiers
source                    1..20
                          mol_type = other DNA
                          organism = synthetic construct
misc_feature              1..20
                          note = Description of sequence: Synthetic oligonucleotide
                           sequence.
SEQUENCE: 3
cttcctcttg tgctcttgct                                             20

SEQ ID NO: 4              moltype = DNA  length = 20
FEATURE                   Location/Qualifiers
source                    1..20
                          mol_type = other DNA
                          organism = synthetic construct
```

-continued

```
misc_feature           1..20
                       note = Description of sequence: Synthetic oligonucleotide
                        sequence.
SEQUENCE: 4
gccatgtaga ccccttgaag                                          20

SEQ ID NO: 5           moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 5
gagatcgagt gccgcatcac                                          20

SEQ ID NO: 6           moltype = DNA  length = 20
FEATURE                Location/Qualifiers
misc_feature           1..20
                       note = Description of sequence: Synthetic oligonucleotide
                        sequence.
source                 1..20
                       mol_type = other DNA
                       organism = synthetic construct
SEQUENCE: 6
aagattcatc accgctttga                                          20

SEQ ID NO: 7           moltype = DNA  length = 20
FEATURE                Location/Qualifiers
misc_feature           1..20
                       note = Description of sequence: Synthetic oligonucleotide
                        sequence.
source                 1..20
                       mol_type = other DNA
                       organism = synthetic construct
SEQUENCE: 7
ttaaactaca gaacacccac                                          20

SEQ ID NO: 8           moltype = DNA  length = 20
FEATURE                Location/Qualifiers
misc_feature           1..20
                       note = Description of sequence: Synthetic oligonucleotide
                        sequence.
source                 1..20
                       mol_type = other DNA
                       organism = synthetic construct
SEQUENCE: 8
tctggcagac tcattgcagc                                          20

SEQ ID NO: 9           moltype = DNA  length = 20
FEATURE                Location/Qualifiers
misc_feature           1..20
                       note = Description of sequence: Synthetic oligonucleotide
                        sequence.
source                 1..20
                       mol_type = other DNA
                       organism = synthetic construct
SEQUENCE: 9
tagggtagaa ttgttacagc                                          20

SEQ ID NO: 10          moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 10
aatatgagat gcgttgttac                                          20

SEQ ID NO: 11          moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
```

-continued

```
                             sequence.
SEQUENCE: 11
gtaacaacgc atctcatatt                                          20

SEQ ID NO: 12        moltype = DNA   length = 20
FEATURE              Location/Qualifiers
source               1..20
                     mol_type = other DNA
                     organism = synthetic construct
misc_feature         1..20
                     note = Description of sequence: Synthetic oligonucleotide
                       sequence.
SEQUENCE: 12
ctgcaggctg gggcggatca                                          20

SEQ ID NO: 13        moltype = DNA   length = 20
FEATURE              Location/Qualifiers
source               1..20
                     mol_type = other DNA
                     organism = synthetic construct
misc_feature         1..20
                     note = Description of sequence: Synthetic oligonucleotide
                       sequence.
SEQUENCE: 13
gaagtgtgta acactgcttc                                          20

SEQ ID NO: 14        moltype = DNA   length = 20
FEATURE              Location/Qualifiers
source               1..20
                     mol_type = other DNA
                     organism = synthetic construct
misc_feature         1..20
                     note = Description of sequence: Synthetic oligonucleotide
                       sequence.
SEQUENCE: 14
cactgcatct ttcgggacct                                          20

SEQ ID NO: 15        moltype = DNA   length = 17
FEATURE              Location/Qualifiers
source               1..17
                     mol_type = other DNA
                     organism = synthetic construct
misc_feature         1..17
                     note = Description of sequence: Synthetic oligonucleotide
                       sequence.
SEQUENCE: 15
ggagaatgag ctgcagg                                             17

SEQ ID NO: 16        moltype = DNA   length = 17
FEATURE              Location/Qualifiers
source               1..17
                     mol_type = other DNA
                     organism = synthetic construct
misc_feature         1..17
                     note = Description of sequence: Synthetic oligonucleotide
                       sequence.
SEQUENCE: 16
gctctttccc gcgctct                                             17

SEQ ID NO: 17        moltype = DNA   length = 20
FEATURE              Location/Qualifiers
source               1..20
                     mol_type = other DNA
                     organism = synthetic construct
misc_feature         1..20
                     note = Description of sequence: Synthetic oligonucleotide
                       sequence.
SEQUENCE: 17
caaaaagtca ctgcatcttt                                          20

SEQ ID NO: 18        moltype = DNA   length = 20
FEATURE              Location/Qualifiers
misc_feature         1..20
                     note = Description of sequence: Synthetic oligonucleotide
                       sequence.
source               1..20
                     mol_type = other DNA
                     organism = synthetic construct
SEQUENCE: 18
```

-continued

```
gccttctcgc cccctccagg                                            20

SEQ ID NO: 19          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 19
ggtggtggag gtgatgggcc                                            20

SEQ ID NO: 20          moltype = DNA   length = 20
FEATURE                Location/Qualifiers
misc_feature           1..20
                       note = Description of sequence: Synthetic oligonucleotide
                         sequence.
source                 1..20
                       mol_type = other DNA
                       organism = synthetic construct
SEQUENCE: 20
ggtgaatgac atttgtgggt                                            20

SEQ ID NO: 21          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 21
gtgcctgccc ttctaggaat                                            20

SEQ ID NO: 22          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 22
ggcccacaaa tcacaggcat                                            20

SEQ ID NO: 23          moltype = DNA   length = 17
FEATURE                Location/Qualifiers
source                 1..17
                       mol_type = other DNA
                       organism = synthetic construct
misc_feature           1..17
                       note = Description of sequence: Synthetic oligonucleotide
                         sequence.
SEQUENCE: 23
gccgaccgac tgaggcc                                               17

SEQ ID NO: 24          moltype = DNA   length = 17
FEATURE                Location/Qualifiers
source                 1..17
                       mol_type = other DNA
                       organism = synthetic construct
misc_feature           1..17
                       note = Description of sequence: Synthetic oligonucleotide
                         sequence.
SEQUENCE: 24
gctgccgggc gcggagc                                               17

SEQ ID NO: 25          moltype = DNA   length = 20
FEATURE                Location/Qualifiers
misc_feature           1..20
                       note = Description of sequence: Synthetic oligonucleotide
                         sequence.
source                 1..20
                       mol_type = other DNA
                       organism = synthetic construct
SEQUENCE: 25
gttaattcag tcagtgacta                                            20
```

-continued

```
SEQ ID NO: 26           moltype = DNA   length = 20
FEATURE                 Location/Qualifiers
misc_feature            1..20
                        note = Description of sequence: Synthetic oligonucleotide
                        sequence.
source                  1..20
                        mol_type = other DNA
                        organism = synthetic construct
SEQUENCE: 26
gagagagacc ctcactgctg                                           20

SEQ ID NO: 27           moltype = DNA   length = 20
FEATURE                 Location/Qualifiers
misc_feature            1..20
                        note = Description of sequence: Synthetic oligonucleotide
                        sequence.
source                  1..20
                        mol_type = other DNA
                        organism = synthetic construct
SEQUENCE: 27
gagagagacc ctcactgctg                                           20

SEQ ID NO: 28           moltype = DNA   length = 20
FEATURE                 Location/Qualifiers
misc_feature            1..20
                        note = Description of sequence: Synthetic oligonucleotide
                        sequence.
source                  1..20
                        mol_type = other DNA
                        organism = synthetic construct
SEQUENCE: 28
gagagagacc ctcactgctg                                           20

SEQ ID NO: 29           moltype = DNA   length = 20
FEATURE                 Location/Qualifiers
misc_feature            1..20
                        note = Description of sequence: Synthetic oligonucleotide
                        sequence.
source                  1..20
                        mol_type = other DNA
                        organism = synthetic construct
SEQUENCE: 29
gagagagacc ctcactgctg                                           20

SEQ ID NO: 30           moltype = DNA   length = 20
FEATURE                 Location/Qualifiers
misc_feature            1..20
                        note = Description of sequence: Synthetic oligonucleotide
                        sequence.
source                  1..20
                        mol_type = other DNA
                        organism = synthetic construct
SEQUENCE: 30
gagagaggcc ctcactgctg                                           20

SEQ ID NO: 31           moltype = DNA   length = 20
FEATURE                 Location/Qualifiers
source                  1..20
                        mol_type = other DNA
                        organism = synthetic construct
misc_feature            1..20
                        note = Description of sequence: Synthetic oligonucleotide
                        sequence.
SEQUENCE: 31
gagagaggcc ctcactgctg                                           20

SEQ ID NO: 32           moltype = DNA   length = 20
FEATURE                 Location/Qualifiers
source                  1..20
                        mol_type = other DNA
                        organism = synthetic construct
misc_feature            1..20
                        note = Description of sequence: Synthetic oligonucleotide
                        sequence.
SEQUENCE: 32
gagagagacc ctcaatgctg                                           20

SEQ ID NO: 33           moltype = DNA   length = 20
FEATURE                 Location/Qualifiers
```

-continued

```
source                   1..20
                         mol_type = other DNA
                         organism = synthetic construct
misc_feature             1..20
                         note = Description of sequence: Synthetic oligonucleotide
                          sequence.
SEQUENCE: 33
gagagaggcc ctcactgctg                                                   20

SEQ ID NO: 34           moltype = DNA   length = 20
FEATURE                 Location/Qualifiers
misc_feature             1..20
                         note = Description of sequence: Synthetic oligonucleotide
                          sequence.
source                   1..20
                         mol_type = other DNA
                         organism = synthetic construct
SEQUENCE: 34
aagagaggcc ctcactgctg                                                   20

SEQ ID NO: 35           moltype = DNA   length = 20
FEATURE                 Location/Qualifiers
source                   1..20
                         mol_type = other DNA
                         organism = synthetic construct
misc_feature             1..20
                         note = Description of sequence: Synthetic oligonucleotide
                          sequence.
SEQUENCE: 35
gagagaggct ctcactgctg                                                   20

SEQ ID NO: 36           moltype = DNA   length = 20
FEATURE                 Location/Qualifiers
source                   1..20
                         mol_type = other DNA
                         organism = synthetic construct
misc_feature             1..20
                         note = Description of sequence: Synthetic oligonucleotide
                          sequence.
SEQUENCE: 36
tagagagagc ctcactgctg                                                   20

SEQ ID NO: 37           moltype = DNA   length = 20
FEATURE                 Location/Qualifiers
misc_feature             1..20
                         note = Description of sequence: Synthetic oligonucleotide
                          sequence.
source                   1..20
                         mol_type = other DNA
                         organism = synthetic construct
SEQUENCE: 37
gagagcggcc ctcactgctg                                                   20

SEQ ID NO: 38           moltype = DNA   length = 20
FEATURE                 Location/Qualifiers
source                   1..20
                         mol_type = other DNA
                         organism = synthetic construct
misc_feature             1..20
                         note = Description of sequence: Synthetic oligonucleotide
                          sequence.
SEQUENCE: 38
cagagagacc ctcagtgctg                                                   20

SEQ ID NO: 39           moltype = DNA   length = 20
FEATURE                 Location/Qualifiers
source                   1..20
                         mol_type = other DNA
                         organism = synthetic construct
misc_feature             1..20
                         note = Description of sequence: Synthetic oligonucleotide
                          sequence.
SEQUENCE: 39
gagagaggcc ttcactgctg                                                   20

SEQ ID NO: 40           moltype = DNA   length = 20
FEATURE                 Location/Qualifiers
source                   1..20
                         mol_type = other DNA
```

```
                         organism = synthetic construct
misc_feature            1..20
                        note = Description of sequence: Synthetic oligonucleotide
                         sequence.
SEQUENCE: 40
gagagaggcc ttcactgctg                                                        20

SEQ ID NO: 41           moltype = DNA   length = 20
FEATURE                 Location/Qualifiers
misc_feature            1..20
                        note = Description of sequence: Synthetic oligonucleotide
                         sequence.
source                  1..20
                        mol_type = other DNA
                        organism = synthetic construct
SEQUENCE: 41
gagagaggcc ctcactcctg                                                        20

SEQ ID NO: 42           moltype = DNA   length = 20
FEATURE                 Location/Qualifiers
source                  1..20
                        mol_type = other DNA
                        organism = synthetic construct
misc_feature            1..20
                        note = Description of sequence: Synthetic oligonucleotide
                         sequence.
SEQUENCE: 42
agccccagca agagcacaag                                                        20

SEQ ID NO: 43           moltype = DNA   length = 20
FEATURE                 Location/Qualifiers
source                  1..20
                        mol_type = other DNA
                        organism = synthetic construct
misc_feature            1..20
                        note = Description of sequence: Synthetic oligonucleotide
                         sequence.
SEQUENCE: 43
agccccagca agagcacaag                                                        20

SEQ ID NO: 44           moltype = DNA   length = 20
FEATURE                 Location/Qualifiers
misc_feature            1..20
                        note = Description of sequence: Synthetic oligonucleotide
                         sequence.
source                  1..20
                        mol_type = other DNA
                        organism = synthetic construct
SEQUENCE: 44
agccccagcg agagcacaag                                                        20

SEQ ID NO: 45           moltype = DNA   length = 20
FEATURE                 Location/Qualifiers
source                  1..20
                        mol_type = other DNA
                        organism = synthetic construct
misc_feature            1..20
                        note = Description of sequence: Synthetic oligonucleotide
                         sequence.
SEQUENCE: 45
agccccagta agagcacaag                                                        20

SEQ ID NO: 46           moltype = DNA   length = 20
FEATURE                 Location/Qualifiers
misc_feature            1..20
                        note = Description of sequence: Synthetic oligonucleotide
                         sequence.
source                  1..20
                        mol_type = other DNA
                        organism = synthetic construct
SEQUENCE: 46
agccccagca agagcacaac                                                        20

SEQ ID NO: 47           moltype = DNA   length = 20
FEATURE                 Location/Qualifiers
misc_feature            1..20
                        note = Description of sequence: Synthetic oligonucleotide
                         sequence.
source                  1..20
```

-continued

```
                        mol_type = other DNA
                        organism = synthetic construct
SEQUENCE: 47
agccccagca agagcacgag                                        20

SEQ ID NO: 48          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 48
agccccagca agagcacgag                                        20

SEQ ID NO: 49          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 49
agccccagca agagcacgag                                        20

SEQ ID NO: 50          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 50
agccccagtg agagcacaag                                        20

SEQ ID NO: 51          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 51
agccccagtg agagcacaag                                        20

SEQ ID NO: 52          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                        sequence.
SEQUENCE: 52
agccccagtc agagcacaag                                        20

SEQ ID NO: 53          moltype = DNA   length = 20
FEATURE                Location/Qualifiers
misc_feature           1..20
                       note = Description of sequence: Synthetic oligonucleotide
                        sequence.
source                 1..20
                       mol_type = other DNA
                       organism = synthetic construct
SEQUENCE: 53
agcccaagca acagcacaag                                        20

SEQ ID NO: 54          moltype = DNA   length = 20
FEATURE                Location/Qualifiers
misc_feature           1..20
                       note = Description of sequence: Synthetic oligonucleotide
                        sequence.
source                 1..20
                       mol_type = other DNA
                       organism = synthetic construct
```

-continued

```
SEQUENCE: 54
agccccagga agagcacagg                                                  20

SEQ ID NO: 55          moltype = DNA   length = 20
FEATURE                Location/Qualifiers
misc_feature           1..20
                       note = Description of sequence: Synthetic oligonucleotide
                         sequence.
source                 1..20
                       mol_type = other DNA
                       organism = synthetic construct
SEQUENCE: 55
agccccagcg agagcacgag                                                  20

SEQ ID NO: 56          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 56
agccccagcg agagcaccag                                                  20

SEQ ID NO: 57          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 57
gttcctcttg tgctcttgct                                                  20

SEQ ID NO: 58          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 58
cttcctcttg tgctctcgct                                                  20

SEQ ID NO: 59          moltype = DNA   length = 20
FEATURE                Location/Qualifiers
misc_feature           1..20
                       note = Description of sequence: Synthetic oligonucleotide
                         sequence.
source                 1..20
                       mol_type = other DNA
                       organism = synthetic construct
SEQUENCE: 59
cttcctctcg tgctcttgct                                                  20

SEQ ID NO: 60          moltype = DNA   length = 20
FEATURE                Location/Qualifiers
misc_feature           1..20
                       note = Description of sequence: Synthetic oligonucleotide
                         sequence.
source                 1..20
                       mol_type = other DNA
                       organism = synthetic construct
SEQUENCE: 60
cttcctctcg tgctcttgct                                                  20

SEQ ID NO: 61          moltype = DNA   length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 61
tttcctctcg tgctcttgct                                                  20
```

```
SEQ ID NO: 62          moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 62
cttcctcttg tgctcttact                                                 20

SEQ ID NO: 63          moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 63
cttcctcttg tgctgttgct                                                 20

SEQ ID NO: 64          moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 64
gccatgtaga ccccttgaag                                                 20

SEQ ID NO: 65          moltype = DNA  length = 20
FEATURE                Location/Qualifiers
source                 1..20
                       mol_type = other DNA
                       organism = synthetic construct
misc_feature           1..20
                       note = Description of sequence: Synthetic oligonucleotide
                         sequence.
SEQUENCE: 65
tccatgtaga ccccttgaag                                                 20

SEQ ID NO: 66          moltype = DNA  length = 31
FEATURE                Location/Qualifiers
source                 1..31
                       mol_type = other DNA
                       organism = synthetic construct
misc_feature           1..31
                       note = Description of sequence: Synthetic oligonucleotide
                         sequence.
SEQUENCE: 66
agagacaatt gcgcacacat tccacatcca c                                    31

SEQ ID NO: 67          moltype = DNA  length = 26
FEATURE                Location/Qualifiers
misc_feature           1..26
                       note = Description of sequence: Synthetic oligonucleotide
                         sequence.
source                 1..26
                       mol_type = other DNA
                       organism = synthetic construct
SEQUENCE: 67
agagaacgcg tggcaccggg cttgcg                                          26

SEQ ID NO: 68          moltype = DNA  length = 87
FEATURE                Location/Qualifiers
source                 1..87
                       mol_type = other DNA
                       organism = synthetic construct
misc_feature           1..87
                       note = Description of sequence: Synthetic oligonucleotide
                         sequence.
SEQUENCE: 68
agagaacgcg tgccactaac ttctccctgt tgaaacaagc aggggatgtc gaagagaatc  60
ccgggccaat ggagagcgac gagagcg                                        87
```

-continued

```
SEQ ID NO: 69            moltype = DNA   length = 42
FEATURE                  Location/Qualifiers
source                   1..42
                         mol_type = other DNA
                         organism = synthetic construct
misc_feature             1..42
                         note = Description of sequence: Synthetic oligonucleotide
                           sequence.
SEQUENCE: 69
agagaggatc ctcaatcaat cacgatgcgg gtgttggtgt ag                         42

SEQ ID NO: 70            moltype = DNA   length = 92
FEATURE                  Location/Qualifiers
source                   1..92
                         mol_type = other DNA
                         organism = synthetic construct
misc_feature             1..92
                         note = Description of sequence: Synthetic oligonucleotide
                           sequence.
SEQUENCE: 70
agagaggatc ctgaggctac gtccaggagc gcaccatctt cttcaaggac gacggcaact   60
tgattgattg atgcacgtga gcttcagcta cc                                   92

SEQ ID NO: 71            moltype = DNA   length = 30
FEATURE                  Location/Qualifiers
source                   1..30
                         mol_type = other DNA
                         organism = synthetic construct
misc_feature             1..30
                         note = Description of sequence: Synthetic oligonucleotide
                           sequence.
SEQUENCE: 71
agagaagatc tccatagagc ccaccgcatc                                       30

SEQ ID NO: 72            moltype = DNA   length = 31
FEATURE                  Location/Qualifiers
source                   1..31
                         mol_type = other DNA
                         organism = synthetic construct
misc_feature             1..31
                         note = Description of sequence: Synthetic oligonucleotide
                           sequence.
SEQUENCE: 72
agagagtcga ccggaactct gccctctaac g                                     31

SEQ ID NO: 73            moltype = DNA   length = 31
FEATURE                  Location/Qualifiers
misc_feature             1..31
                         note = Description of sequence: Synthetic oligonucleotide
                           sequence.
source                   1..31
                         mol_type = other DNA
                         organism = synthetic construct
SEQUENCE: 73
agagacaatt gcccagaacc agagccacat t                                     31

SEQ ID NO: 74            moltype = DNA   length = 33
FEATURE                  Location/Qualifiers
misc_feature             1..33
                         note = Description of sequence: Synthetic oligonucleotide
                           sequence.
source                   1..33
                         mol_type = other DNA
                         organism = synthetic construct
SEQUENCE: 74
agagagttaa cccccacct cctgttaggc aga                                    33

SEQ ID NO: 75            moltype = DNA   length = 30
FEATURE                  Location/Qualifiers
source                   1..30
                         mol_type = other DNA
                         organism = synthetic construct
misc_feature             1..30
                         note = Description of sequence: Synthetic oligonucleotide
                           sequence.
SEQUENCE: 75
agagagaatt cagagcagag ccaggaaccc                                       30

SEQ ID NO: 76            moltype = DNA   length = 31
```

```
FEATURE                 Location/Qualifiers
misc_feature            1..31
                        note = Description of sequence: Synthetic oligonucleotide
                         sequence.
source                  1..31
                        mol_type = other DNA
                        organism = synthetic construct
SEQUENCE: 76
agagagtcga cgtggagccg ttctgtgaga c                          31

SEQ ID NO: 77           moltype = DNA  length = 34
FEATURE                 Location/Qualifiers
misc_feature            1..34
                        note = Description of sequence: Synthetic oligonucleotide
                         sequence.
source                  1..34
                        mol_type = other DNA
                        organism = synthetic construct
SEQUENCE: 77
agagacaatt gaactcccag aaaggtattg caac                       34

SEQ ID NO: 78           moltype = DNA  length = 31
FEATURE                 Location/Qualifiers
source                  1..31
                        mol_type = other DNA
                        organism = synthetic construct
misc_feature            1..31
                        note = Description of sequence: Synthetic oligonucleotide
                         sequence.
SEQUENCE: 78
agagacttaa gttctgggca ggcttaaagg c                          31

SEQ ID NO: 79           moltype = DNA  length = 36
FEATURE                 Location/Qualifiers
misc_feature            1..36
                        note = Description of sequence: Synthetic oligonucleotide
                         sequence.
source                  1..36
                        mol_type = other DNA
                        organism = synthetic construct
SEQUENCE: 79
agagagaatt cagcttggca aaatcacatt tagacc                     36

SEQ ID NO: 80           moltype = DNA  length = 22
FEATURE                 Location/Qualifiers
misc_feature            1..22
                        note = Description of sequence: Synthetic oligonucleotide
                         sequence.
source                  1..22
                        mol_type = other DNA
                        organism = synthetic construct
SEQUENCE: 80
accgagctgc aagaactctt cc                                    22

SEQ ID NO: 81           moltype = DNA  length = 25
FEATURE                 Location/Qualifiers
misc_feature            1..25
                        note = Description of sequence: Synthetic oligonucleotide
                         sequence.
source                  1..25
                        mol_type = other DNA
                        organism = synthetic construct
SEQUENCE: 81
cctaagcttg gctggacgta aactc                                 25

SEQ ID NO: 82           moltype = DNA  length = 22
FEATURE                 Location/Qualifiers
misc_feature            1..22
                        note = Description of sequence: Synthetic oligonucleotide
                         sequence.
source                  1..22
                        mol_type = other DNA
                        organism = synthetic construct
SEQUENCE: 82
ccgcaacctc cccttctacg ag                                    22

SEQ ID NO: 83           moltype = DNA  length = 23
FEATURE                 Location/Qualifiers
source                  1..23
```

-continued

```
                             mol_type = other DNA
                             organism = synthetic construct
misc_feature                 1..23
                             note = Description of sequence: Synthetic oligonucleotide
                               sequence.
SEQUENCE: 83
ctggcaacta gaaggcacag tcg                                          23

SEQ ID NO: 84               moltype = DNA   length = 86
FEATURE                     Location/Qualifiers
misc_feature                 1..86
                             note = Description of sequence: Synthetic oligonucleotide
                               sequence.
source                       1..86
                             mol_type = other DNA
                             organism = synthetic construct
SEQUENCE: 84
agagaacgcg tgccactaac ttctccctgt tgaaacaagc aggggatgtc gaagagaatc   60
ccgggccaat ggtgagcaag ggcgag                                        86

SEQ ID NO: 85               moltype = DNA   length = 34
FEATURE                     Location/Qualifiers
source                       1..34
                             mol_type = other DNA
                             organism = synthetic construct
misc_feature                 1..34
                             note = Description of sequence: Synthetic oligonucleotide
                               sequence.
SEQUENCE: 85
agagaggatc cttacttgta cagctcgtcc atgc                               34

SEQ ID NO: 86               moltype = DNA   length = 29
FEATURE                     Location/Qualifiers
source                       1..29
                             mol_type = other DNA
                             organism = synthetic construct
misc_feature                 1..29
                             note = Description of sequence: Synthetic oligonucleotide
                               sequence.
SEQUENCE: 86
agagaggatc ccaccctgaa cggcgtgga                                     29

SEQ ID NO: 87               moltype = DNA   length = 23
FEATURE                     Location/Qualifiers
misc_feature                 1..23
                             note = Description of sequence: Synthetic oligonucleotide
                               sequence.
source                       1..23
                             mol_type = other DNA
                             organism = synthetic construct
SEQUENCE: 87
cccgcaacct ccccttctac gag                                           23

SEQ ID NO: 88               moltype = DNA   length = 21
FEATURE                     Location/Qualifiers
misc_feature                 1..21
                             note = Description of sequence: Synthetic oligonucleotide
                               sequence.
source                       1..21
                             mol_type = other DNA
                             organism = synthetic construct
SEQUENCE: 88
ctgcaagaac tcttcctcac g                                             21

SEQ ID NO: 89               moltype = DNA   length = 31
FEATURE                     Location/Qualifiers
misc_feature                 1..31
                             note = Description of sequence: Synthetic oligonucleotide
                               sequence.
source                       1..31
                             mol_type = other DNA
                             organism = synthetic construct
SEQUENCE: 89
agagaagatc tttagcgaga tccggtggag c                                  31

SEQ ID NO: 90               moltype = DNA   length = 31
FEATURE                     Location/Qualifiers
source                       1..31
                             mol_type = other DNA
```

-continued

```
                         organism = synthetic construct
misc_feature            1..31
                         note = Description of sequence: Synthetic oligonucleotide
                          sequence.
SEQUENCE: 90
agagacaatt ggacacgctc ccctgacttg c                                31

SEQ ID NO: 91           moltype = DNA   length = 30
FEATURE                 Location/Qualifiers
misc_feature            1..30
                         note = Description of sequence: Synthetic oligonucleotide
                          sequence.
source                  1..30
                         mol_type = other DNA
                         organism = synthetic construct
SEQUENCE: 91
agagaacgcg tctccttgga ggccatgtgg                                  30

SEQ ID NO: 92           moltype = DNA   length = 31
FEATURE                 Location/Qualifiers
source                  1..31
                         mol_type = other DNA
                         organism = synthetic construct
misc_feature            1..31
                         note = Description of sequence: Synthetic oligonucleotide
                          sequence.
SEQUENCE: 92
agagagttaa cccctgccac actcagtccc c                                31

SEQ ID NO: 93           moltype = DNA   length = 30
FEATURE                 Location/Qualifiers
misc_feature            1..30
                         note = Description of sequence: Synthetic oligonucleotide
                          sequence.
source                  1..30
                         mol_type = other DNA
                         organism = synthetic construct
SEQUENCE: 93
agagactcga gctggggtta caggcgtgcg                                  30

SEQ ID NO: 94           moltype = DNA   length = 41
FEATURE                 Location/Qualifiers
misc_feature            1..41
                         note = Description of sequence: Synthetic oligonucleotide
                          sequence.
source                  1..41
                         mol_type = other DNA
                         organism = synthetic construct
SEQUENCE: 94
agagagaatt ccaattgacg cgtgctcctc tccctccccc c                     41

SEQ ID NO: 95           moltype = DNA   length = 45
FEATURE                 Location/Qualifiers
misc_feature            1..45
                         note = Description of sequence: Synthetic oligonucleotide
                          sequence.
source                  1..45
                         mol_type = other DNA
                         organism = synthetic construct
SEQUENCE: 95
agagaagatc tacttacctg ttacttgtac agctcgtcca tgccg                 45

SEQ ID NO: 96           moltype = DNA   length = 31
FEATURE                 Location/Qualifiers
misc_feature            1..31
                         note = Description of sequence: Synthetic oligonucleotide
                          sequence.
source                  1..31
                         mol_type = other DNA
                         organism = synthetic construct
SEQUENCE: 96
agagaggatc cgacacgctc ccctgacttg c                                31

SEQ ID NO: 97           moltype = DNA   length = 32
FEATURE                 Location/Qualifiers
misc_feature            1..32
                         note = Description of sequence: Synthetic oligonucleotide
                          sequence.
source                  1..32
```

-continued

```
                              mol_type = other DNA
                              organism = synthetic construct
SEQUENCE: 97
agagacaatt gttcctcttg tgctcttgct gg                              32

SEQ ID NO: 98            moltype = DNA   length = 29
FEATURE                  Location/Qualifiers
source                   1..29
                         mol_type = other DNA
                         organism = synthetic construct
misc_feature             1..29
                         note = Description of sequence: Synthetic oligonucleotide
                           sequence.
SEQUENCE: 98
gatccgagat cgagtgccgc atcaccggc                                  29

SEQ ID NO: 99            moltype = DNA   length = 29
FEATURE                  Location/Qualifiers
misc_feature             1..29
                         note = Description of sequence: Synthetic oligonucleotide
                           sequence.
source                   1..29
                         mol_type = other DNA
                         organism = synthetic construct
SEQUENCE: 99
aattgccggt gatgcggcac tcgatctcg                                  29

SEQ ID NO: 100           moltype = DNA   length = 23
FEATURE                  Location/Qualifiers
source                   1..23
                         mol_type = other DNA
                         organism = synthetic construct
misc_feature             1..23
                         note = Description of sequence: Synthetic oligonucleotide
                           sequence.
SEQUENCE: 100
cgtgggcttg tactcggtca tgg                                        23

SEQ ID NO: 101           moltype = DNA   length = 25
FEATURE                  Location/Qualifiers
misc_feature             1..25
                         note = Description of sequence: Synthetic oligonucleotide
                           sequence.
source                   1..25
                         mol_type = other DNA
                         organism = synthetic construct
SEQUENCE: 101
gacctgcatc catctagatc tctcg                                      25

SEQ ID NO: 102           moltype = DNA   length = 24
FEATURE                  Location/Qualifiers
misc_feature             1..24
                         note = Description of sequence: Synthetic oligonucleotide
                           sequence.
source                   1..24
                         mol_type = other DNA
                         organism = synthetic construct
SEQUENCE: 102
gataccccga agagtgagtt tgcc                                       24

SEQ ID NO: 103           moltype = DNA   length = 26
FEATURE                  Location/Qualifiers
misc_feature             1..26
                         note = Description of sequence: Synthetic oligonucleotide
                           sequence.
source                   1..26
                         mol_type = other DNA
                         organism = synthetic construct
SEQUENCE: 103
gttctaattc catcagaagc tggtcg                                     26

SEQ ID NO: 104           moltype = DNA   length = 27
FEATURE                  Location/Qualifiers
misc_feature             1..27
                         note = Description of sequence: Synthetic oligonucleotide
                           sequence.
source                   1..27
                         mol_type = other DNA
                         organism = synthetic construct
```

-continued

```
SEQUENCE: 104
attgttttgc caagttctaa ttccatc                                          27

SEQ ID NO: 105          moltype = DNA   length = 26
FEATURE                 Location/Qualifiers
misc_feature            1..26
                        note = Description of sequence: Synthetic oligonucleotide
                          sequence.
source                  1..26
                        mol_type = other DNA
                        organism = synthetic construct
SEQUENCE: 105
caagtcaagc aaaattatag gtcctg                                           26

SEQ ID NO: 106          moltype = DNA   length = 19
FEATURE                 Location/Qualifiers
source                  1..19
                        mol_type = other DNA
                        organism = synthetic construct
misc_feature            1..19
                        note = Description of sequence: Synthetic oligonucleotide
                          sequence.
SEQUENCE: 106
gaaggtggtg aagcaggcg                                                   19

SEQ ID NO: 107          moltype = DNA   length = 19
FEATURE                 Location/Qualifiers
misc_feature            1..19
                        note = Description of sequence: Synthetic oligonucleotide
                          sequence.
source                  1..19
                        mol_type = other DNA
                        organism = synthetic construct
SEQUENCE: 107
gagcgggaag caaatggtt                                                   19

SEQ ID NO: 108          moltype = DNA   length = 20
FEATURE                 Location/Qualifiers
source                  1..20
                        mol_type = other DNA
                        organism = synthetic construct
misc_feature            1..20
                        note = Description of sequence: Synthetic oligonucleotide
                          sequence.
SEQUENCE: 108
ggagtccact ggcgtcttca                                                  20

SEQ ID NO: 109          moltype = DNA   length = 19
FEATURE                 Location/Qualifiers
misc_feature            1..19
                        note = Description of sequence: Synthetic oligonucleotide
                          sequence.
source                  1..19
                        mol_type = other DNA
                        organism = synthetic construct
SEQUENCE: 109
gcccaccagc tcgaactcc                                                   19

SEQ ID NO: 110          moltype = DNA   length = 23
FEATURE                 Location/Qualifiers
misc_feature            1..23
                        note = Description of sequence: Synthetic oligonucleotide
                          sequence.
source                  1..23
                        mol_type = other DNA
                        organism = synthetic construct
SEQUENCE: 110
gcggctacta cagcttcgtg gtg                                              23

SEQ ID NO: 111          moltype = DNA   length = 25
FEATURE                 Location/Qualifiers
source                  1..25
                        mol_type = other DNA
                        organism = synthetic construct
misc_feature            1..25
                        note = Description of sequence: Synthetic oligonucleotide
                          sequence.
SEQUENCE: 111
gatggagtct catactctgt tgcct                                            25
```

-continued

```
SEQ ID NO: 112           moltype = DNA   length = 19
FEATURE                  Location/Qualifiers
misc_feature             1..19
                         note = Description of sequence: Synthetic oligonucleotide
                          sequence.
source                   1..19
                         mol_type = other DNA
                         organism = synthetic construct
SEQUENCE: 112
gaaggtggtg aagcaggcg                                           19

SEQ ID NO: 113           moltype = DNA   length = 20
FEATURE                  Location/Qualifiers
misc_feature             1..20
                         note = Description of sequence: Synthetic oligonucleotide
                          sequence.
source                   1..20
                         mol_type = other DNA
                         organism = synthetic construct
SEQUENCE: 113
cctcacattg ccaaaagacg                                          20

SEQ ID NO: 114           moltype = DNA   length = 24
FEATURE                  Location/Qualifiers
source                   1..24
                         mol_type = other DNA
                         organism = synthetic construct
misc_feature             1..24
                         note = Description of sequence: Synthetic oligonucleotide
                          sequence.
SEQUENCE: 114
cgccagggtt ttcccagtca cgac                                     24

SEQ ID NO: 115           moltype = DNA   length = 22
FEATURE                  Location/Qualifiers
source                   1..22
                         mol_type = other DNA
                         organism = synthetic construct
misc_feature             1..22
                         note = Description of sequence: Synthetic oligonucleotide
                          sequence.
SEQUENCE: 115
actcccactg tcctttccta at                                       22

SEQ ID NO: 116           moltype = DNA   length = 19
FEATURE                  Location/Qualifiers
misc_feature             1..19
                         note = Description of sequence: Synthetic oligonucleotide
                          sequence.
source                   1..19
                         mol_type = other DNA
                         organism = synthetic construct
SEQUENCE: 116
gagcgggaag caaatggtt                                           19

SEQ ID NO: 117           moltype = DNA   length = 17
FEATURE                  Location/Qualifiers
misc_feature             1..17
                         note = Description of sequence: Synthetic oligonucleotide
                          sequence.
source                   1..17
                         mol_type = other DNA
                         organism = synthetic construct
SEQUENCE: 117
caggaaacag ctatgac                                             17

SEQ ID NO: 118           moltype = DNA   length = 18
FEATURE                  Location/Qualifiers
source                   1..18
                         mol_type = other DNA
                         organism = synthetic construct
misc_feature             1..18
                         note = Description of sequence: Synthetic oligonucleotide
                          sequence.
SEQUENCE: 118
ttgaggctgc tgggtctc                                            18

SEQ ID NO: 119           moltype = DNA   length = 23
```

-continued

```
FEATURE                 Location/Qualifiers
source                  1..23
                        mol_type = other DNA
                        organism = synthetic construct
misc_feature            1..23
                        note = Description of sequence: Synthetic oligonucleotide
                        sequence.
SEQUENCE: 119
gctctgaaca ggtaacagct aca                                                   23

SEQ ID NO: 120          moltype = DNA   length = 33
FEATURE                 Location/Qualifiers
source                  1..33
                        mol_type = other DNA
                        organism = synthetic construct
misc_feature            1..33
                        note = Description of sequence: Synthetic oligonucleotide
                        sequence.
SEQUENCE: 120
agagacaatt gttactcctt ggaggccatg tgg                                        33

SEQ ID NO: 121          moltype = DNA   length = 37
FEATURE                 Location/Qualifiers
misc_feature            1..37
                        note = Description of sequence: Synthetic oligonucleotide
                        sequence.
source                  1..37
                        mol_type = other DNA
                        organism = synthetic construct
SEQUENCE: 121
agagaggatc cacattaagg agaagctgtg ctacgtc                                    37

SEQ ID NO: 122          moltype = DNA   length = 37
FEATURE                 Location/Qualifiers
misc_feature            1..37
                        note = Description of sequence: Synthetic oligonucleotide
                        sequence.
source                  1..37
                        mol_type = other DNA
                        organism = synthetic construct
SEQUENCE: 122
agagacaatt gacaacaatg tgcaatcaaa gtcctcg                                    37

SEQ ID NO: 123          moltype = DNA   length = 35
FEATURE                 Location/Qualifiers
misc_feature            1..35
                        note = Description of sequence: Synthetic oligonucleotide
                        sequence.
source                  1..35
                        mol_type = other DNA
                        organism = synthetic construct
SEQUENCE: 123
agagagtcga ctctaaggag aatggcccag tcctc                                      35

SEQ ID NO: 124          moltype = DNA   length = 36
FEATURE                 Location/Qualifiers
source                  1..36
                        mol_type = other DNA
                        organism = synthetic construct
misc_feature            1..36
                        note = Description of sequence: Synthetic oligonucleotide
                        sequence.
SEQUENCE: 124
agagagttaa ccagacctca gcccatagct aaccag                                     36

SEQ ID NO: 125          moltype = DNA   length = 31
FEATURE                 Location/Qualifiers
misc_feature            1..31
                        note = Description of sequence: Synthetic oligonucleotide
                        sequence.
source                  1..31
                        mol_type = other DNA
                        organism = synthetic construct
SEQUENCE: 125
agagacaatt gcctttagag gacgggtgtt c                                          31

SEQ ID NO: 126          moltype = DNA   length = 34
FEATURE                 Location/Qualifiers
source                  1..34
```

```
                        mol_type = other DNA
                        organism = synthetic construct
misc_feature            1..34
                        note = Description of sequence: Synthetic oligonucleotide
                        sequence.
SEQUENCE: 126
agagaacgcg tcacgtcagg atagttgcag taat                                            34

SEQ ID NO: 127          moltype = DNA   length = 33
FEATURE                 Location/Qualifiers
misc_feature            1..33
                        note = Description of sequence: Synthetic oligonucleotide
                        sequence.
source                  1..33
                        mol_type = other DNA
                        organism = synthetic construct
SEQUENCE: 127
agagagaatt cgtttttgtt gttgctgttg ttg                                             33

SEQ ID NO: 128          moltype = DNA   length = 33
FEATURE                 Location/Qualifiers
source                  1..33
                        mol_type = other DNA
                        organism = synthetic construct
misc_feature            1..33
                        note = Description of sequence: Synthetic oligonucleotide
                        sequence.
SEQUENCE: 128
agagactcga gccatctttt actcacaacc ctg                                             33

SEQ ID NO: 129          moltype = DNA   length = 31
FEATURE                 Location/Qualifiers
misc_feature            1..31
                        note = Description of sequence: Synthetic oligonucleotide
                        sequence.
source                  1..31
                        mol_type = other DNA
                        organism = synthetic construct
SEQUENCE: 129
agagacaatt gggtgctttt cttgctgctg g                                               31

SEQ ID NO: 130          moltype = DNA   length = 31
FEATURE                 Location/Qualifiers
source                  1..31
                        mol_type = other DNA
                        organism = synthetic construct
misc_feature            1..31
                        note = Description of sequence: Synthetic oligonucleotide
                        sequence.
SEQUENCE: 130
agagaacgcg tcatggaagg tggcgacaca g                                               31

SEQ ID NO: 131          moltype = DNA   length = 34
FEATURE                 Location/Qualifiers
source                  1..34
                        mol_type = other DNA
                        organism = synthetic construct
misc_feature            1..34
                        note = Description of sequence: Synthetic oligonucleotide
                        sequence.
SEQUENCE: 131
agagagttaa ctggcagtct caggttaaga agga                                            34

SEQ ID NO: 132          moltype = DNA   length = 32
FEATURE                 Location/Qualifiers
source                  1..32
                        mol_type = other DNA
                        organism = synthetic construct
misc_feature            1..32
                        note = Description of sequence: Synthetic oligonucleotide
                        sequence.
SEQUENCE: 132
agagagaatt cataatgccg cttttgacact cc                                             32

SEQ ID NO: 133          moltype = DNA   length = 33
FEATURE                 Location/Qualifiers
source                  1..33
                        mol_type = other DNA
                        organism = synthetic construct
```

-continued

```
misc_feature           1..33
                       note = Description of sequence: Synthetic oligonucleotide
                        sequence.
SEQUENCE: 133
agagaggatc catggctgcc tcacaaactt cac                                 33

SEQ ID NO: 134         moltype = DNA   length = 34
FEATURE                Location/Qualifiers
source                 1..34
                       mol_type = other DNA
                       organism = synthetic construct
misc_feature           1..34
                       note = Description of sequence: Synthetic oligonucleotide
                        sequence.
SEQUENCE: 134
agagactcga ggcaatgagt ctgccagatc agag                               34

SEQ ID NO: 135         moltype = DNA   length = 27
FEATURE                Location/Qualifiers
misc_feature           1..27
                       note = Description of sequence: Synthetic oligonucleotide
                        sequence.
source                 1..27
                       mol_type = other DNA
                       organism = synthetic construct
SEQUENCE: 135
cttcaaatta gggttggagc aaaacag                                       27

SEQ ID NO: 136         moltype = DNA   length = 28
FEATURE                Location/Qualifiers
misc_feature           1..28
                       note = Description of sequence: Synthetic oligonucleotide
                        sequence.
source                 1..28
                       mol_type = other DNA
                       organism = synthetic construct
SEQUENCE: 136
atcgacaggg ttttattgtt acatttgg                                      28

SEQ ID NO: 137         moltype = DNA   length = 30
FEATURE                Location/Qualifiers
source                 1..30
                       mol_type = other DNA
                       organism = synthetic construct
misc_feature           1..30
                       note = Description of sequence: Synthetic oligonucleotide
                        sequence.
SEQUENCE: 137
tcctttctgt aaacatcttg gcttcaacac                                    30

SEQ ID NO: 138         moltype = DNA   length = 25
FEATURE                Location/Qualifiers
misc_feature           1..25
                       note = Description of sequence: Synthetic oligonucleotide
                        sequence.
source                 1..25
                       mol_type = other DNA
                       organism = synthetic construct
SEQUENCE: 138
ctcccctcag gacattttac gtttg                                         25

SEQ ID NO: 139         moltype = DNA   length = 29
FEATURE                Location/Qualifiers
source                 1..29
                       mol_type = other DNA
                       organism = synthetic construct
misc_feature           1..29
                       note = Description of sequence: Synthetic oligonucleotide
                        sequence.
SEQUENCE: 139
acacatagta tcgcatggat caaattccg                                     29

SEQ ID NO: 140         moltype = DNA   length = 24
FEATURE                Location/Qualifiers
source                 1..24
                       mol_type = other DNA
                       organism = synthetic construct
misc_feature           1..24
                       note = Description of sequence: Synthetic oligonucleotide
```

```
                               sequence.
SEQUENCE: 140
tcattttgga cctgacttgc catc                                        24

SEQ ID NO: 141           moltype = DNA  length = 24
FEATURE                  Location/Qualifiers
misc_feature             1..24
                         note = Description of sequence: Synthetic oligonucleotide
                          sequence.
source                   1..24
                         mol_type = other DNA
                         organism = synthetic construct
SEQUENCE: 141
catccctgca tctactggtg ctac                                        24

SEQ ID NO: 142           moltype = DNA  length = 28
FEATURE                  Location/Qualifiers
source                   1..28
                         mol_type = other DNA
                         organism = synthetic construct
misc_feature             1..28
                         note = Description of sequence: Synthetic oligonucleotide
                          sequence.
SEQUENCE: 142
ggaaaaacct gccaaatatg atgacacc                                    28

SEQ ID NO: 143           moltype = DNA  length = 24
FEATURE                  Location/Qualifiers
misc_feature             1..24
                         note = Description of sequence: Synthetic oligonucleotide
                          sequence.
source                   1..24
                         mol_type = other DNA
                         organism = synthetic construct
SEQUENCE: 143
tcagcccctt gttgaatacg cttg                                        24

SEQ ID NO: 144           moltype = DNA  length = 98
FEATURE                  Location/Qualifiers
source                   1..98
                         mol_type = other DNA
                         organism = synthetic construct
misc_feature             1..98
                         note = Description of sequence: SG-X Target Sequence;
                          Source: Fig. 1
SEQUENCE: 144
acccgcatcg tgattgattg aggatcctga ggctacgtcc aggagcgcac catcttcttc  60
aaggacgacg gcaacttgat tgattgatgc acgtgagc                         98

SEQ ID NO: 145           moltype = DNA  length = 116
FEATURE                  Location/Qualifiers
misc_feature             1..116
                         note = Description of sequence: Target peptide; Source:
                          FIG. 5B
source                   1..116
                         mol_type = other DNA
                         organism = synthetic construct
SEQUENCE: 145
cacatggcct ccaaggagta agacccctgg accaccagcc ccagcaagag cacaagagga  60
agagagagac cctcactgct ggggagtccc tgccacactc agtcccccac cacact      116

SEQ ID NO: 146           moltype = AA  length = 6
FEATURE                  Location/Qualifiers
REGION                   1..6
                         note = Description of sequence: Target polynucleotide;
                          Source: FIG. 5B
source                   1..6
                         mol_type = protein
                         organism = synthetic construct
SEQUENCE: 146
HMASKE                                                            6

SEQ ID NO: 147           moltype = DNA  length = 105
FEATURE                  Location/Qualifiers
source                   1..105
                         mol_type = other DNA
                         organism = synthetic construct
misc_feature             1..105
                         note = Description of sequence: Fragment Name: Ref Seq ;
```

```
                            Location: 5'-Junction; Source: FIG: 6C
SEQUENCE: 147
cacatggcct ccaaggagac gcgtgccact aacttctccc tgttgaaaca agcaggggat    60
gtcgaagaga atcccgggcc aatggagagc gacgagagcg gcctg                  105

SEQ ID NO: 148         moltype = AA   length = 35
FEATURE                Location/Qualifiers
source                 1..35
                       mol_type = protein
                       organism = synthetic construct
REGION                 1..35
                       note = Description of sequence: Fragment Name: Peptide;
                        Location: 5'-Junction; Source: FIG: 6C
SEQUENCE: 148
HMASKETRAT NFSLLKQAGD VEENPGPMES DESGL                               35

SEQ ID NO: 149         moltype = DNA   length = 105
FEATURE                Location/Qualifiers
source                 1..105
                       mol_type = other DNA
                       organism = synthetic construct
misc_feature           1..105
                       note = Description of sequence: Fragment Name: LO2 #1;
                        Location: 5'-Junction; Source: FIG: 6C
SEQUENCE: 149
cacatggcct ccaaggagac gcgtgccact aacttctccc tgttgaaaca agcaggggat    60
gtcgaagaga atcccgggcc aatggagagc gacgagagcg gcctg                  105

SEQ ID NO: 150         moltype = DNA   length = 105
FEATURE                Location/Qualifiers
source                 1..105
                       mol_type = other DNA
                       organism = synthetic construct
misc_feature           1..105
                       note = Description of sequence: Fragment Name: LO2 #2;
                        Location: 5'-Junction; Source: FIG: 6C
SEQUENCE: 150
cacatggcct ccaaggagac gcgtgccact aacttctccc tgttgaaaca agcaggggat    60
gtcgaagaga atcccgggcc aatggagagc gacgagagcg gcctg                  105

SEQ ID NO: 151         moltype = DNA   length = 105
FEATURE                Location/Qualifiers
misc_feature           1..105
                       note = Description of sequence: Fragment Name: BEL-7402 #1;
                        Location: 5'-Junction; Source: FIG: 6C
source                 1..105
                       mol_type = other DNA
                       organism = synthetic construct
SEQUENCE: 151
cacatggcct ccaaggagac gcgtgccact aacttctccc tgttgaaaca agcaggggat    60
gtcgaagaga atcccgggcc aatggagagc gacgagagcg gcctg                  105

SEQ ID NO: 152         moltype = DNA   length = 105
FEATURE                Location/Qualifiers
source                 1..105
                       mol_type = other DNA
                       organism = synthetic construct
misc_feature           1..105
                       note = Description of sequence: Fragment Name: SMMC-7721
                        #1; Location: 5'-Junction; Source: FIG: 6C
SEQUENCE: 152
cacatggcct ccaaggagac gcgtgccact aacttctccc tgttgaaaca agcaggggat    60
gtcgaagaga atcccgggcc aatggagagc gacgagagcg gcctg                  105

SEQ ID NO: 153         moltype = DNA   length = 105
FEATURE                Location/Qualifiers
misc_feature           1..105
                       note = Description of sequence: Fragment Name: SMMC-7721
                        #2; Location: 5'-Junction; Source: FIG: 6C
source                 1..105
                       mol_type = other DNA
                       organism = synthetic construct
SEQUENCE: 153
cacatggcct ccaaggagac gcgtgccact aacttctccc tgttgaaaca agcaggggat    60
gtcgaagaga atcccgggcc aatggagagc gacgagagcg gcctg                  105

SEQ ID NO: 154         moltype = DNA   length = 105
FEATURE                Location/Qualifiers
source                 1..105
```

```
                              mol_type = other DNA
                              organism = synthetic construct
misc_feature                  1..105
                              note = Description of sequence: Fragment Name: H1 hESC #1;
                               Location: 5'-Junction; Source: FIG: 6C
SEQUENCE: 154
cacatggcct ccaaggagac gcgtgccact aacttctccc tgttgaaaca agcaggggat   60
gtcgaagaga atcccgggcc aatggagagc gacgagagcg gcctg               105

SEQ ID NO: 155            moltype = DNA   length = 105
FEATURE                   Location/Qualifiers
misc_feature              1..105
                          note = Description of sequence: Fragment Name: H1 hESC #2;
                           Location: 5'-Junction; Source: FIG: 6C
source                    1..105
                          mol_type = other DNA
                          organism = synthetic construct
SEQUENCE: 155
cacatggcct ccaaggagac gcgtgccact aacttctccc tgttgaaaca agcaggggat   60
gtcgaagaga atcccgggcc aatggagagc gacgagagcg gcctg               105

SEQ ID NO: 156            moltype = DNA   length = 105
FEATURE                   Location/Qualifiers
misc_feature              1..105
                          note = Description of sequence: Fragment Name: H1 hESC #3;
                           Location: 5'-Junction; Source: FIG: 6C
source                    1..105
                          mol_type = other DNA
                          organism = synthetic construct
SEQUENCE: 156
cacatggcct ccaaggagac gcgtgccact aacttctccc tgttgaaaca agcaggggat   60
gtcgaagaga atcccgggcc aatggagagc gacgagagcg gcctg               105

SEQ ID NO: 157            moltype = DNA   length = 70
FEATURE                   Location/Qualifiers
misc_feature              1..70
                          note = Description of sequence: Fragment Name: Ref Seq ;
                           Location: 3'-Junction; Source: FIG: 6C
source                    1..70
                          mol_type = other DNA
                          organism = synthetic construct
SEQUENCE: 157
accgccggac ccggctccac cggatctcgc taaagatcaa cccctgccac actcagtccc   60
ccaccacact                                                       70

SEQ ID NO: 158            moltype = AA   length = 10
FEATURE                   Location/Qualifiers
source                    1..10
                          mol_type = protein
                          organism = synthetic construct
REGION                    1..10
                          note = Description of sequence: Fragment Name: peptide;
                           Location: 3'-Junction; Source: FIG: 6C
SEQUENCE: 158
TAGPGSTGSR                                                        10

SEQ ID NO: 159            moltype = DNA   length = 70
FEATURE                   Location/Qualifiers
misc_feature              1..70
                          note = Description of sequence: Fragment Name: LO2 #1;
                           Location: 3'-Junction; Source: FIG: 6C
source                    1..70
                          mol_type = other DNA
                          organism = synthetic construct
SEQUENCE: 159
accgccggac ccggctccac cggatctcgc taaagatcaa cccctgccac actcagtccc   60
ccaccacact                                                       70

SEQ ID NO: 160            moltype = DNA   length = 70
FEATURE                   Location/Qualifiers
source                    1..70
                          mol_type = other DNA
                          organism = synthetic construct
misc_feature              1..70
                          note = Description of sequence: Fragment Name: LO2 #2;
                           Location: 3'-Junction; Source: FIG: 6C
SEQUENCE: 160
accgccggac ccggctccac cggatctcgc taaagatcaa cccctgccac actcagtccc   60
ccaccacact                                                       70
```

-continued

```
SEQ ID NO: 161            moltype = DNA   length = 70
FEATURE                   Location/Qualifiers
misc_feature              1..70
                          note = Description of sequence: Fragment Name: BEL-7402 #1;
                           Location: 3'-Junction; Source: FIG: 6C
source                    1..70
                          mol_type = other DNA
                          organism = synthetic construct
SEQUENCE: 161
accgccggac ccggctccac cggatctcgc taaagatcaa cccctgccac actcagtccc   60
ccaccacact                                                          70

SEQ ID NO: 162            moltype = DNA   length = 70
FEATURE                   Location/Qualifiers
source                    1..70
                          mol_type = other DNA
                          organism = synthetic construct
misc_feature              1..70
                          note = Description of sequence: Fragment Name: SMMC-7721
                           #1; Location: 3'-Junction; Source: FIG: 6C
SEQUENCE: 162
accgccggac ccggctccac cggatctcgc taaagatcaa cccctgccac actcagtccc   60
ccaccacact                                                          70

SEQ ID NO: 163            moltype = DNA   length = 70
FEATURE                   Location/Qualifiers
misc_feature              1..70
                          note = Description of sequence: Fragment Name: SMMC-7721
                           #2; Location: 3'-Junction; Source: FIG: 6C
source                    1..70
                          mol_type = other DNA
                          organism = synthetic construct
SEQUENCE: 163
accgccggac ccggctccac cggatctcgc taaagatcaa cccctgccac actcagtccc   60
ccaccacact                                                          70

SEQ ID NO: 164            moltype = DNA   length = 70
FEATURE                   Location/Qualifiers
source                    1..70
                          mol_type = other DNA
                          organism = synthetic construct
misc_feature              1..70
                          note = Description of sequence: Fragment Name: H1 hESC #1;
                           Location: 3'-Junction; Source: FIG: 6C
SEQUENCE: 164
accgccggac ccggctccac cggatctcgc taaagatcaa cccctgccac actcagtccc   60
ccaccacact                                                          70

SEQ ID NO: 165            moltype = DNA   length = 70
FEATURE                   Location/Qualifiers
misc_feature              1..70
                          note = Description of sequence: Fragment Name: H1 hESC #2;
                           Location: 3'-Junction; Source: FIG: 6C
source                    1..70
                          mol_type = other DNA
                          organism = synthetic construct
SEQUENCE: 165
accgccggac ccggctccac cggatctcgc taaagatcaa cccctgccac actcagtccc   60
ccaccacact                                                          70

SEQ ID NO: 166            moltype = DNA   length = 70
FEATURE                   Location/Qualifiers
source                    1..70
                          mol_type = other DNA
                          organism = synthetic construct
misc_feature              1..70
                          note = Description of sequence: Fragment Name: H1 hESC #;
                           Location: 3'-Junction; Source: FIG: 6C
SEQUENCE: 166
accgccggac ccggctccac cggatctcgc taaagatcaa cccctgccac actcagtccc   60
ccaccacact                                                          70

SEQ ID NO: 167            moltype = DNA   length = 80
FEATURE                   Location/Qualifiers
source                    1..80
                          mol_type = other DNA
                          organism = synthetic construct
misc_feature              1..80
```

-continued

```
                            note = Description of sequence: Sequence Name:
                             NHEJ-Donor.1; Source: FIG: 7D
SEQUENCE: 167
tagaactagt ggatccgaga tcgagtgccg catcaccggc aattgacgcg tgctcctctc   60
cctcccccc ccctaacgtt                                                80

SEQ ID NO: 168             moltype = DNA   length = 100
FEATURE                    Location/Qualifiers
misc_feature               1..100
                           note = Description of sequence: Sequence Name: GAPDH locus;
                            Source: FIG: 7D
source                     1..100
                           mol_type = other DNA
                           organism = synthetic construct
SEQUENCE: 168
atggcctcca aggagtaaga cccctggacc accagcccca gcaagagcac aagaggaaga   60
gagagaccct cactgctggg gagtccctgc cacactcagt                        100

SEQ ID NO: 169             moltype = AA   length = 5
FEATURE                    Location/Qualifiers
REGION                     1..5
                           note = Description of sequence: Sequence Name: GAPDH locus
                            peptide; Source: FIG: 7D
source                     1..5
                           mol_type = protein
                           organism = synthetic construct
SEQUENCE: 169
MASKE                                                               5

SEQ ID NO: 170             moltype = DNA   length = 99
FEATURE                    Location/Qualifiers
misc_feature               1..99
                           note = Description of sequence: Fragment Name: SG-1 #1;
                            Location: 5'-Junction; Source: FIG: 7D
source                     1..99
                           mol_type = other DNA
                           organism = synthetic construct
SEQUENCE: 170
aaggagtaag acccctggac caccagcccc agcaagagca caagaggaag agagagaccc   60
tcactgcacc ggcaattgac gcgtgctcct ctccctccc                         99

SEQ ID NO: 171             moltype = DNA   length = 99
FEATURE                    Location/Qualifiers
source                     1..99
                           mol_type = other DNA
                           organism = synthetic construct
misc_feature               1..99
                           note = Description of sequence: Fragment Name: SG-1 #2;
                            Location: 5'-Junction; Source: FIG: 7D
SEQUENCE: 171
aaggagtaag acccctggac caccagcccc agcaagagca caagaggaag agagagaccc   60
tcactgcacc ggcaattgac gcgtgctcct ctccctccc                         99

SEQ ID NO: 172             moltype = DNA   length = 90
FEATURE                    Location/Qualifiers
source                     1..90
                           mol_type = other DNA
                           organism = synthetic construct
misc_feature               1..90
                           note = Description of sequence: Fragment Name: SG-1 #3;
                            Location: 5'-Junction; Source: FIG: 7D
SEQUENCE: 172
aaggagtaag acccctggac caccagcccc agcaagagca caagaggaag agagagaccc   60
tcactggcgc tgcgtgctcc tctccctccc                                   90

SEQ ID NO: 173             moltype = DNA   length = 76
FEATURE                    Location/Qualifiers
source                     1..76
                           mol_type = other DNA
                           organism = synthetic construct
misc_feature               1..76
                           note = Description of sequence: Fragment Name: SG-1 #4;
                            Location: 5'-Junction; Source: FIG: 7D
SEQUENCE: 173
aaggagtaag acccctggac caccagcccc agcaagagca caagaggaac aattgacgcg   60
tgctcctctc cctccc                                                  76

SEQ ID NO: 174             moltype = DNA   length = 99
FEATURE                    Location/Qualifiers
```

-continued

```
misc_feature            1..99
                        note = Description of sequence: Fragment Name: SG-1 #5;
                         Location: 5'-Junction; Source: FIG: 7D
source                  1..99
                        mol_type = other DNA
                        organism = synthetic construct
SEQUENCE: 174
aaggagtaag acccctggac caccagcccc agcaagagca caagaggaag agagagaccc   60
tcactgcacc ggcaattgac gcgtgctcct ctccctccc                          99

SEQ ID NO: 175         moltype = DNA   length = 74
FEATURE                Location/Qualifiers
source                 1..74
                       mol_type = other DNA
                       organism = synthetic construct
misc_feature           1..74
                       note = Description of sequence: Fragment Name: SG-2 #1;
                        Location: 5'-Junction; Source: FIG: 7D
SEQUENCE: 175
aaggagtaag acccctggac caccagcccc agcaagagca ccaccggcaa ttgacgcgtg   60
ctcctctccc tccc                                                    74

SEQ ID NO: 176         moltype = DNA   length = 74
FEATURE                Location/Qualifiers
source                 1..74
                       mol_type = other DNA
                       organism = synthetic construct
misc_feature           1..74
                       note = Description of sequence: Fragment Name: SG-2 #2;
                        Location: 5'-Junction; Source: FIG: 7D
SEQUENCE: 176
aaggagtaag acccctggac caccagcccc agcaagagca ccaccggcaa ttgacgcgtg   60
ctcctctccc tccc                                                    74

SEQ ID NO: 177         moltype = DNA   length = 76
FEATURE                Location/Qualifiers
source                 1..76
                       mol_type = other DNA
                       organism = synthetic construct
misc_feature           1..76
                       note = Description of sequence: Fragment Name: SG-2 #3;
                        Location: 5'-Junction; Source: FIG: 7D
SEQUENCE: 177
aaggagtaag acccctggac caccagcccc agcaagagca caagaggaac aattgacgcg   60
tgctcctctc cctccc                                                  76

SEQ ID NO: 178         moltype = DNA   length = 74
FEATURE                Location/Qualifiers
misc_feature           1..74
                       note = Description of sequence: Fragment Name: SG-2 #4;
                        Location: 5'-Junction; Source: FIG: 7D
source                 1..74
                       mol_type = other DNA
                       organism = synthetic construct
SEQUENCE: 178
aaggagtaag acccctggac caccagcccc agcaagagca ccaccggcaa ttgacgcgtg   60
ctcctctccc tccc                                                    74

SEQ ID NO: 179         moltype = DNA   length = 86
FEATURE                Location/Qualifiers
misc_feature           1..86
                       note = Description of sequence: Fragment Name: SG-2 #5;
                        Location: 5'-Junction; Source: FIG: 7D
source                 1..86
                       mol_type = other DNA
                       organism = synthetic construct
SEQUENCE: 179
aaggagtaaa gccctggac caccagcccc agcaagagca ccaccgggtt aaccaccggc    60
aattgacgcg tgctcctctc cctccc                                       86

SEQ ID NO: 180         moltype = DNA   length = 66
FEATURE                Location/Qualifiers
misc_feature           1..66
                       note = Description of sequence: Fragment Name: SG-3 #1;
                        Location: 5'-Junction; Source: FIG: 7D
source                 1..66
                       mol_type = other DNA
                       organism = synthetic construct
SEQUENCE: 180
```

```
aaggagtaag acccctggac caccagcccc agccaccggc aattgacgcg tgctcctctc  60
cctccc                                                             66

SEQ ID NO: 181        moltype = DNA  length = 69
FEATURE               Location/Qualifiers
misc_feature          1..69
                      note = Description of sequence: Fragment Name: SG-3 #2;
                       Location: 5'-Junction; Source: FIG: 7D
source                1..69
                      mol_type = other DNA
                      organism = synthetic construct
SEQUENCE: 181
aaggagtaag acccctggac caccagcccc agcaagcacc ggcaattgac gcgtgctcct  60
ctccctccc                                                          69

SEQ ID NO: 182        moltype = DNA  length = 66
FEATURE               Location/Qualifiers
misc_feature          1..66
                      note = Description of sequence: Fragment Name: SG-3 #3;
                       Location: 5'-Junction; Source: FIG: 7D
source                1..66
                      mol_type = other DNA
                      organism = synthetic construct
SEQUENCE: 182
aaggagtaag acccctggac caccagcccc agccaccggc aattgacgcg tgctcctctc  60
cctccc                                                             66

SEQ ID NO: 183        moltype = DNA  length = 67
FEATURE               Location/Qualifiers
misc_feature          1..67
                      note = Description of sequence: Fragment Name: SG-3 #4;
                       Location: 5'-Junction; Source: FIG: 7D
source                1..67
                      mol_type = other DNA
                      organism = synthetic construct
SEQUENCE: 183
aaggagtaag acccctggac caccagcccc agctcaccgg caattgacgc gtgctcctct  60
ccctccc                                                            67

SEQ ID NO: 184        moltype = DNA  length = 66
FEATURE               Location/Qualifiers
misc_feature          1..66
                      note = Description of sequence: Fragment Name: SG-3 #5;
                       Location: 5'-Junction; Source: FIG: 7D
source                1..66
                      mol_type = other DNA
                      organism = synthetic construct
SEQUENCE: 184
aaggagtaag acccctggac caccagcccc agccaccggc aattgacgcg tgctcctctc  60
cctccc                                                             66

SEQ ID NO: 185        moltype = DNA  length = 58
FEATURE               Location/Qualifiers
misc_feature          1..58
                      note = Description of sequence: Fragment Name: SG-1 #1;
                       Location: 3'-Junction; Source: FIG: 7D
source                1..58
                      mol_type = other DNA
                      organism = synthetic construct
SEQUENCE: 185
tagaactagt ggatccgaga tcgagtgccg catctgggga gtccctgcca cactcagt    58

SEQ ID NO: 186        moltype = DNA  length = 42
FEATURE               Location/Qualifiers
misc_feature          1..42
                      note = Description of sequence: Fragment Name: SG-1 #2;
                       Location: 3'-Junction; Source: FIG: 7D
source                1..42
                      mol_type = other DNA
                      organism = synthetic construct
SEQUENCE: 186
tagaactagt ggatccgaga tcgagtgcct gccacactaa gt                     42

SEQ ID NO: 187        moltype = DNA  length = 58
FEATURE               Location/Qualifiers
misc_feature          1..58
                      note = Description of sequence: Fragment Name: SG-1 #3;
                       Location: 3'-Junction; Source: FIG: 7D
source                1..58
```

-continued

```
                             mol_type = other DNA
                             organism = synthetic construct
SEQUENCE: 187
tagaactagt ggatccgaga tcgagtgccg catctgggga gtccctgcca cactaagt       58

SEQ ID NO: 188           moltype = DNA   length = 43
FEATURE                  Location/Qualifiers
misc_feature             1..43
                         note = Description of sequence: Fragment Name: SG-1 #4;
                          Location: 3'-Junction; Source: FIG: 7D
source                   1..43
                         mol_type = other DNA
                         organism = synthetic construct
SEQUENCE: 188
tagaactagt ggatccgaga tcggagtccc tgccacacta agt                        43

SEQ ID NO: 189           moltype = DNA   length = 51
FEATURE                  Location/Qualifiers
source                   1..51
                         mol_type = other DNA
                         organism = synthetic construct
misc_feature             1..51
                         note = Description of sequence: Fragment Name: SG-1 #5;
                          Location: 3'-Junction; Source: FIG: 7D
SEQUENCE: 189
tagaactagt ggatccgaga tcgagtgccg ggagtccctg ccacactcag t               51

SEQ ID NO: 190           moltype = DNA   length = 70
FEATURE                  Location/Qualifiers
source                   1..70
                         mol_type = other DNA
                         organism = synthetic construct
misc_feature             1..70
                         note = Description of sequence: Fragment Name: SG-2 #1;
                          Location: 3'-Junction; Source: FIG: 7D
SEQUENCE: 190
tagaactagt ggatccgaga tcgagtgccg catcaagagg aagagagaga ccctcactgc      60
tgggagtcc                                                              70

SEQ ID NO: 191           moltype = DNA   length = 70
FEATURE                  Location/Qualifiers
source                   1..70
                         mol_type = other DNA
                         organism = synthetic construct
misc_feature             1..70
                         note = Description of sequence: Fragment Name: SG-2 #2;
                          Location: 3'-Junction; Source: FIG: 7D
SEQUENCE: 191
tagaactagt ggatccgaga tcgagtgccg catcaagagg aagagagaga ccctcactgc      60
tgggagtcc                                                              70

SEQ ID NO: 192           moltype = DNA   length = 63
FEATURE                  Location/Qualifiers
source                   1..63
                         mol_type = other DNA
                         organism = synthetic construct
misc_feature             1..63
                         note = Description of sequence: Fragment Name: SG-2 #3;
                          Location: 3'-Junction; Source: FIG: 7D
SEQUENCE: 192
tagaactagt ggatccgaga tcgagtgccg cagaagagag agaccctcac tgctgggag       60
tcc                                                                    63

SEQ ID NO: 193           moltype = DNA   length = 69
FEATURE                  Location/Qualifiers
misc_feature             1..69
                         note = Description of sequence: Fragment Name: SG-2 #4;
                          Location: 3'-Junction; Source: FIG: 7D
source                   1..69
                         mol_type = other DNA
                         organism = synthetic construct
SEQUENCE: 193
tagaactagt ggatccgaga tcgagtgccg cataagagga agagagagac cctcactgct      60
ggggagtcc                                                              69

SEQ ID NO: 194           moltype = DNA   length = 71
FEATURE                  Location/Qualifiers
misc_feature             1..71
                         note = Description of sequence: Fragment Name: SG-2 #5;
```

-continued

```
                         Location: 3'-Junction; Source: FIG: 7D
source                   1..71
                         mol_type = other DNA
                         organism = synthetic construct
SEQUENCE: 194
tagaactagt ggatccgaga tcgagtgccg catataagag gaagagagag accctcactg    60
gtggggagtc c                                                          71

SEQ ID NO: 195           moltype = DNA  length = 76
FEATURE                  Location/Qualifiers
misc_feature             1..76
                         note = Description of sequence: Fragment Name: SG-3 #1;
                         Location: 3'-Junction; Source: FIG: 7D
source                   1..76
                         mol_type = other DNA
                         organism = synthetic construct
SEQUENCE: 195
tagaactagt ggatccgaga tcgagtgccg cataagagca caagaggaag agagagaccc    60
tcactgctgg ggagtc                                                     76

SEQ ID NO: 196           moltype = DNA  length = 75
FEATURE                  Location/Qualifiers
misc_feature             1..75
                         note = Description of sequence: Fragment Name: SG-3 #2;
                         Location: 3'-Junction; Source: FIG: 7D
source                   1..75
                         mol_type = other DNA
                         organism = synthetic construct
SEQUENCE: 196
tagaactagt ggatccgaga tcgagtgccg catagagcac aagaggaaga gagagaccct    60
cactgctggg gagtc                                                      75

SEQ ID NO: 197           moltype = DNA  length = 76
FEATURE                  Location/Qualifiers
source                   1..76
                         mol_type = other DNA
                         organism = synthetic construct
misc_feature             1..76
                         note = Description of sequence: Fragment Name: SG-3 #3;
                         Location: 3'-Junction; Source: FIG: 7D
SEQUENCE: 197
tagaactagt ggatccgaga tcgagtgccg cataagagca caagaggaag agagagaccc    60
tcactgctgg ggagtc                                                     76

SEQ ID NO: 198           moltype = DNA  length = 74
FEATURE                  Location/Qualifiers
misc_feature             1..74
                         note = Description of sequence: Fragment Name: SG-3 #4;
                         Location: 3'-Junction; Source: FIG: 7D
source                   1..74
                         mol_type = other DNA
                         organism = synthetic construct
SEQUENCE: 198
tagaactagt ggatccgaga tcgagtgccg caagagcaca agaggaagag agagaccctc    60
actgctgggg agtc                                                       74

SEQ ID NO: 199           moltype = DNA  length = 76
FEATURE                  Location/Qualifiers
misc_feature             1..76
                         note = Description of sequence: Fragment Name: SG-3 #5;
                         Location: 3'-Junction; Source: FIG: 7D
source                   1..76
                         mol_type = other DNA
                         organism = synthetic construct
SEQUENCE: 199
tagaactagt ggatccgaga tcgagtgccg cataagagca caagaggaag agagagaccc    60
tcactgctgg ggagtc                                                     76

SEQ ID NO: 200           moltype = DNA  length = 66
FEATURE                  Location/Qualifiers
source                   1..66
                         mol_type = other DNA
                         organism = synthetic construct
misc_feature             1..66
                         note = Description of sequence: Sequence Name:
                         NHEJ-Donor.2; Source: FIG: 7E
SEQUENCE: 200
tagaactagt ggatccgaga tcgagtgccg catcaccggc aattgacgcg tgctcctctc    60
cctccc                                                                66
```

```
SEQ ID NO: 201          moltype = DNA  length = 50
FEATURE                 Location/Qualifiers
source                  1..50
                        mol_type = other DNA
                        organism = synthetic construct
misc_feature            1..50
                        note = Description of sequence: Sequence Name:
                        NHEJ-Donor.2; Source: FIG: 7E
SEQUENCE: 201
atcggaaccc ttaatgtcga cgagatcgag tgccgcatca ccgggttaac              50

SEQ ID NO: 202          moltype = DNA  length = 100
FEATURE                 Location/Qualifiers
source                  1..100
                        mol_type = other DNA
                        organism = synthetic construct
misc_feature            1..100
                        note = Description of sequence: Sequence Name: GAPDH locus
                        ; Source: FIG: 7E
SEQUENCE: 202
atggcctcca aggagtaaga cccctggacc accagcccca gcaagagcac aagaggaaga   60
gagagaccct cactgctggg gagtccctgc cacactcagt                        100

SEQ ID NO: 203          moltype = AA  length = 5
FEATURE                 Location/Qualifiers
source                  1..5
                        mol_type = protein
                        organism = synthetic construct
REGION                  1..5
                        note = Description of sequence: Sequence Name: GAPDH locus
                         peptide; Source: FIG: 7E
SEQUENCE: 203
MASKE                                                                5

SEQ ID NO: 204          moltype = DNA  length = 99
FEATURE                 Location/Qualifiers
source                  1..99
                        mol_type = other DNA
                        organism = synthetic construct
misc_feature            1..99
                        note = Description of sequence: Sequence Name: SG-1 #1;
                         Source: FIG: 7E
SEQUENCE: 204
aaggagtaag acccctggac caccagcccc agcaagagca caagaggaag agagagaccc   60
tcactgcacc ggcaattgac gcgtgctcct ctccctccc                         99

SEQ ID NO: 205          moltype = DNA  length = 99
FEATURE                 Location/Qualifiers
misc_feature            1..99
                        note = Description of sequence: Sequence Name: SG-1 #2;
                         Source: FIG: 7E
source                  1..99
                        mol_type = other DNA
                        organism = synthetic construct
SEQUENCE: 205
aaggagtaag acccctggac caccagcccc agcaagagca caagaggaag agagagaccc   60
tcactgcacc ggcaattgac gcgtgctcct ctccctccc                         99

SEQ ID NO: 206          moltype = DNA  length = 76
FEATURE                 Location/Qualifiers
source                  1..76
                        mol_type = other DNA
                        organism = synthetic construct
misc_feature            1..76
                        note = Description of sequence: Sequence Name: SG-1 #3;
                         Source: FIG: 7E
SEQUENCE: 206
aaggagtaag acccctggac caccagcccc agcaagagca caagaggaac aattgacgcg   60
tgctcctctc cctccc                                                  76

SEQ ID NO: 207          moltype = DNA  length = 99
FEATURE                 Location/Qualifiers
source                  1..99
                        mol_type = other DNA
                        organism = synthetic construct
misc_feature            1..99
                        note = Description of sequence: Sequence Name: SG-1 #4;
                         Source: FIG: 7E
```

-continued

```
SEQUENCE: 207
aaggagtaag acccctggac caccagcccc agcaagagca caagaggaag agagagaccc  60
tcactgcacc ggcaattgac gcgtgctcct ctccctccc                         99

SEQ ID NO: 208          moltype = DNA   length = 99
FEATURE                 Location/Qualifiers
source                  1..99
                        mol_type = other DNA
                        organism = synthetic construct
misc_feature            1..99
                        note = Description of sequence: Sequence Name: SG-1 #5;
                         Source: FIG: 7E
SEQUENCE: 208
aaggagtaag acccctggac caccagcccc agcaagagca caagaggaag agagagaccc  60
tcactgcacc ggcaattgac gcgtgctcct ctccctccc                         99

SEQ ID NO: 209          moltype = DNA   length = 91
FEATURE                 Location/Qualifiers
source                  1..91
                        mol_type = other DNA
                        organism = synthetic construct
misc_feature            1..91
                        note = Description of sequence: Sequence Name: SG-1 #6;
                         Source: FIG: 7E
SEQUENCE: 209
aaggagtaag acccctggac ccccagcccc agcaagagcc caagaggaag agagagaccc  60
tcaatgggaa gcggtcagcc cattcgccgc c                                 91

SEQ ID NO: 210          moltype = DNA   length = 79
FEATURE                 Location/Qualifiers
misc_feature            1..79
                        note = Description of sequence: Sequence Name: SG-1 blank;
                         Source: FIG: 7E
source                  1..79
                        mol_type = other DNA
                        organism = synthetic construct
SEQUENCE: 210
aagctttca gcaatatcac gggtagccaa cgctatgtcc tgatagcacc ggcaattgac  60
gcgtgctcct ctccctccc                                               79

SEQ ID NO: 211          moltype = DNA   length = 99
FEATURE                 Location/Qualifiers
misc_feature            1..99
                        note = Description of sequence: Sequence Name: SG-1 #7;
                         Source: FIG: 7E
source                  1..99
                        mol_type = other DNA
                        organism = synthetic construct
SEQUENCE: 211
aaggagtaag acccctggac caccagcccc agcaagagca caagaggaag agagagaccc  60
tcactgcacc ggcaattgac gcgtgctcct ctccctccc                         99

SEQ ID NO: 212          moltype = DNA   length = 99
FEATURE                 Location/Qualifiers
source                  1..99
                        mol_type = other DNA
                        organism = synthetic construct
misc_feature            1..99
                        note = Description of sequence: Sequence Name: SG-1 #8;
                         Source: FIG: 7E
SEQUENCE: 212
aaggagtaag acccctggac caccagcccc agcaagagca caagaggaag agagagaccc  60
tcactgcacc ggcaattgac gcgtgctcct ctccctccc                         99

SEQ ID NO: 213          moltype = DNA   length = 76
FEATURE                 Location/Qualifiers
misc_feature            1..76
                        note = Description of sequence: Sequence Name: SG-1 #9;
                         Source: FIG: 7E
source                  1..76
                        mol_type = other DNA
                        organism = synthetic construct
SEQUENCE: 213
aaggagtaag acccctggac caccagcccc agcaagagca caagaggaac aattgacgcg  60
tgctcctctc cctccc                                                  76

SEQ ID NO: 214          moltype = DNA   length = 99
FEATURE                 Location/Qualifiers
misc_feature            1..99
```

```
                            note = Description of sequence: Sequence Name: SG-1 #10;
                             Source: FIG: 7E
source                      1..99
                            mol_type = other DNA
                            organism = synthetic construct
SEQUENCE: 214
aaggagtaag acccctggac caccagcccc agcaagagca caagaggaag agagagaccc   60
tcactgcacc ggcaattgac gcgtgctcct ctccctccc                          99

SEQ ID NO: 215              moltype = DNA   length = 74
FEATURE                     Location/Qualifiers
misc_feature               1..74
                            note = Description of sequence: Sequence Name: SG-2 #1;
                             Source: FIG: 7E
source                      1..74
                            mol_type = other DNA
                            organism = synthetic construct
SEQUENCE: 215
aaggagtaag acccctggac caccagcccc agcaagagca ccaccggcaa ttgacgcgtg   60
ctcctctccc tccc                                                     74

SEQ ID NO: 216              moltype = DNA   length = 86
FEATURE                     Location/Qualifiers
misc_feature               1..86
                            note = Description of sequence: Sequence Name: SG-2 #2;
                             Source: FIG: 7E
source                      1..86
                            mol_type = other DNA
                            organism = synthetic construct
SEQUENCE: 216
aaagagtaag acccctggac caccagcccc agcaagagca ccaccgggtt aaccaccggc   60
aattgacgcg tgctcctctc cctccc                                        86

SEQ ID NO: 217              moltype = DNA   length = 74
FEATURE                     Location/Qualifiers
source                      1..74
                            mol_type = other DNA
                            organism = synthetic construct
misc_feature               1..74
                            note = Description of sequence: Sequence Name: SG-2 #3;
                             Source: FIG: 7E
SEQUENCE: 217
aaggagtaag acccctggac caccagcccc agcaagagca ccaccggcaa ttgacgcgtg   60
ctcctctccc tccc                                                     74

SEQ ID NO: 218              moltype = DNA   length = 74
FEATURE                     Location/Qualifiers
misc_feature               1..74
                            note = Description of sequence: Sequence Name: SG-2 #4;
                             Source: FIG: 7E
source                      1..74
                            mol_type = other DNA
                            organism = synthetic construct
SEQUENCE: 218
aaggagtaag acccctggac caccagcccc agcaagagca ccaccggcaa ttgacgcgtg   60
ctcctctccc tccc                                                     74

SEQ ID NO: 219              moltype = DNA   length = 74
FEATURE                     Location/Qualifiers
misc_feature               1..74
                            note = Description of sequence: Sequence Name: SG-2 #5;
                             Source: FIG: 7E
source                      1..74
                            mol_type = other DNA
                            organism = synthetic construct
SEQUENCE: 219
aaggagtaag acccctggac caccagcccc agcaagagca ccaccggcaa ttgacgcgtg   60
ctcctctccc tccc                                                     74

SEQ ID NO: 220              moltype = DNA   length = 74
FEATURE                     Location/Qualifiers
source                      1..74
                            mol_type = other DNA
                            organism = synthetic construct
misc_feature               1..74
                            note = Description of sequence: Sequence Name: SG-2 #6;
                             Source: FIG: 7E
SEQUENCE: 220
aaggagtaag acccctggac caccagcccc agcaagagca ccaccggcaa ttgacgcgtg   60
```

```
ctcctctccc tccc                                                       74

SEQ ID NO: 221         moltype = DNA   length = 76
FEATURE                Location/Qualifiers
source                 1..76
                       mol_type = other DNA
                       organism = synthetic construct
misc_feature           1..76
                       note = Description of sequence: Sequence Name: SG-2 #7;
                         Source: FIG: 7E
SEQUENCE: 221
aaggagtaag acccctggac caccagcccc agcaagagca caagaggaac aattgacgcg   60
tgctcctctc cctccc                                                     76

SEQ ID NO: 222         moltype = DNA   length = 65
FEATURE                Location/Qualifiers
source                 1..65
                       mol_type = other DNA
                       organism = synthetic construct
misc_feature           1..65
                       note = Description of sequence: Sequence Name: SG-2 #8;
                         Source: FIG: 7E
SEQUENCE: 222
aaggagtaag acccctggac caccagcccc agcaagagca attgacgcgt gctcctctcc   60
ctccc                                                                 65

SEQ ID NO: 223         moltype = DNA   length = 98
FEATURE                Location/Qualifiers
source                 1..98
                       mol_type = other DNA
                       organism = synthetic construct
misc_feature           1..98
                       note = Description of sequence: Sequence Name: SG-2 #9;
                         Source: FIG: 7E
SEQUENCE: 223
aaggagtaag acccctggac caccagcccc agcaagagct cttccgcatt tgacggaaga   60
gagagacccg gcaattgacg cgtgctcctc tccctccc                            98

SEQ ID NO: 224         moltype = DNA   length = 74
FEATURE                Location/Qualifiers
source                 1..74
                       mol_type = other DNA
                       organism = synthetic construct
misc_feature           1..74
                       note = Description of sequence: Sequence Name: SG-2 #10;
                         Source: FIG: 7E
SEQUENCE: 224
aaggagtaag acccctggac caccagcccc agcaagagca ccaccggcaa ttgacgcgtg   60
ctcctctccc tccc                                                       74

SEQ ID NO: 225         moltype = DNA   length = 79
FEATURE                Location/Qualifiers
source                 1..79
                       mol_type = other DNA
                       organism = synthetic construct
misc_feature           1..79
                       note = Description of sequence: Sequence Name: SG-2 #11;
                         Source: FIG: 7E
SEQUENCE: 225
aaggagtaag acccctggac caccagcccc agcaagagca ctcgagcacc ggcaattgac   60
gcgtgctcct ctccctccc                                                  79

SEQ ID NO: 226         moltype = DNA   length = 66
FEATURE                Location/Qualifiers
misc_feature           1..66
                       note = Description of sequence: Sequence Name: SG-3 #1;
                         Source: FIG: 7E
source                 1..66
                       mol_type = other DNA
                       organism = synthetic construct
SEQUENCE: 226
aaggagtaag acccctggac caccagcccc agccaccggc aattgacgcg tgctcctctc   60
cctccc                                                                66

SEQ ID NO: 227         moltype = DNA   length = 66
FEATURE                Location/Qualifiers
source                 1..66
                       mol_type = other DNA
                       organism = synthetic construct
```

-continued

```
misc_feature              1..66
                          note = Description of sequence: Sequence Name: SG-3 #2;
                           Source: FIG: 7E
SEQUENCE: 227
aaggagtaag acccctggac caccagcccc agccaccggc aattgacgcg tgctcctctc  60
cctccc                                                             66

SEQ ID NO: 228            moltype = DNA   length = 66
FEATURE                   Location/Qualifiers
source                    1..66
                          mol_type = other DNA
                          organism = synthetic construct
misc_feature              1..66
                          note = Description of sequence: Sequence Name: SG-3 #3;
                           Source: FIG: 7E
SEQUENCE: 228
aaggagtaag acccctggac caccagcccc agccaccggc aattgacgcg tgctcctctc  60
cctccc                                                             66

SEQ ID NO: 229            moltype = DNA   length = 59
FEATURE                   Location/Qualifiers
misc_feature              1..59
                          note = Description of sequence: Sequence Name: SG-3 #4;
                           Source: FIG: 7E
source                    1..59
                          mol_type = other DNA
                          organism = synthetic construct
SEQUENCE: 229
aaggagtaag acccctggac caccagcccc agcccttgac gcgtgctcct ctccctccc   59

SEQ ID NO: 230            moltype = DNA   length = 66
FEATURE                   Location/Qualifiers
source                    1..66
                          mol_type = other DNA
                          organism = synthetic construct
misc_feature              1..66
                          note = Description of sequence: Sequence Name: SG-3 #5;
                           Source: FIG: 7E
SEQUENCE: 230
aaggagtaag acccctggac caccagcccc agccaccggc aattgacgcg tgctcctctc  60
cctccc                                                             66

SEQ ID NO: 231            moltype = DNA   length = 66
FEATURE                   Location/Qualifiers
source                    1..66
                          mol_type = other DNA
                          organism = synthetic construct
misc_feature              1..66
                          note = Description of sequence: Sequence Name: SG-3 #6;
                           Source: FIG: 7E
SEQUENCE: 231
aaggagtaag acccctggac caccagcccc agccaccggc aattgacgcg tgctcctctc  60
cctccc                                                             66

SEQ ID NO: 232            moltype = DNA   length = 53
FEATURE                   Location/Qualifiers
misc_feature              1..53
                          note = Description of sequence: Sequence Name: SG-3 #7;
                           Source: FIG: 7E
source                    1..53
                          mol_type = other DNA
                          organism = synthetic construct
SEQUENCE: 232
aaggagtaag acccctggac caccggcaat tgacgcgtgc tcctctccct ccc         53

SEQ ID NO: 233            moltype = DNA   length = 66
FEATURE                   Location/Qualifiers
misc_feature              1..66
                          note = Description of sequence: Sequence Name: SG-3 #8;
                           Source: FIG: 7E
source                    1..66
                          mol_type = other DNA
                          organism = synthetic construct
SEQUENCE: 233
aaggagtaag acccctggac caccagcccc agccaccggc aattgacgcg tgctcctctc  60
cctccc                                                             66

SEQ ID NO: 234            moltype = DNA   length = 66
FEATURE                   Location/Qualifiers
```

-continued

```
misc_feature            1..66
                        note = Description of sequence: Sequence Name: SG-3 #9;
                         Source: FIG: 7E
source                  1..66
                        mol_type = other DNA
                        organism = synthetic construct
SEQUENCE: 234
aaggagtaag acccctggac caccagcccc agccaccggc aattgacgcg tgctcctctc  60
cctccc                                                            66

SEQ ID NO: 235          moltype = DNA   length = 66
FEATURE                 Location/Qualifiers
misc_feature            1..66
                        note = Description of sequence: Sequence Name: SG-3 #10;
                         Source: FIG: 7E
source                  1..66
                        mol_type = other DNA
                        organism = synthetic construct
SEQUENCE: 235
aaggagtaag acccctggac caccagcccc agccaccggc aattgacgcg tgctcctctc  60
cctccc                                                            66

SEQ ID NO: 236          moltype = DNA   length = 53
FEATURE                 Location/Qualifiers
misc_feature            1..53
                        note = Description of sequence: Sequence Name: SG-3 #11;
                         Source: FIG: 7E
source                  1..53
                        mol_type = other DNA
                        organism = synthetic construct
SEQUENCE: 236
aaggagtaag acccctggac caccggcaat tgacgcgtgc tcctctcct ccc         53

SEQ ID NO: 237          moltype = DNA   length = 63
FEATURE                 Location/Qualifiers
source                  1..63
                        mol_type = other DNA
                        organism = synthetic construct
misc_feature            1..63
                        note = Description of sequence: Sequence Name: SG-1 #1;
                         Source: FIG: 7E
SEQUENCE: 237
atcggaaccc ttaatgtcga cgagatcgag tgccgcatct ggggagtccc tgccacacta  60
agt                                                               63

SEQ ID NO: 238          moltype = DNA   length = 63
FEATURE                 Location/Qualifiers
source                  1..63
                        mol_type = other DNA
                        organism = synthetic construct
misc_feature            1..63
                        note = Description of sequence: Sequence Name: SG-1 #2;
                         Source: FIG: 7E
SEQUENCE: 238
atcggaaccc ttaatgtcga cgagatcgag tgccgcatct ggggagtccc tgccacacta  60
agt                                                               63

SEQ ID NO: 239          moltype = DNA   length = 63
FEATURE                 Location/Qualifiers
misc_feature            1..63
                        note = Description of sequence: Sequence Name: SG-1 #3;
                         Source: FIG: 7E
source                  1..63
                        mol_type = other DNA
                        organism = synthetic construct
SEQUENCE: 239
atcggaaccc ttaatgtcga cgagatcgag tgccgcatct ggggagtccc tgccacacta  60
agt                                                               63

SEQ ID NO: 240          moltype = DNA   length = 63
FEATURE                 Location/Qualifiers
source                  1..63
                        mol_type = other DNA
                        organism = synthetic construct
misc_feature            1..63
                        note = Description of sequence: Sequence Name: SG-1 #4;
                         Source: FIG: 7E
SEQUENCE: 240
atcggaaccc ttaatgtcga cgagatcgag tgccgcatct ggggagtccc tgccacactc  60
```

```
agt                                                                       63

SEQ ID NO: 241           moltype = DNA   length = 37
FEATURE                  Location/Qualifiers
misc_feature             1..37
                         note = Description of sequence: Sequence Name: SG-1 #5;
                          Source: FIG: 7E
source                   1..37
                         mol_type = other DNA
                         organism = synthetic construct
SEQUENCE: 241
atcggaaccc ttaatgtcga cccctgccac actcagt                                  37

SEQ ID NO: 242           moltype = DNA   length = 63
FEATURE                  Location/Qualifiers
source                   1..63
                         mol_type = other DNA
                         organism = synthetic construct
misc_feature             1..63
                         note = Description of sequence: Sequence Name: SG-1 #6;
                          Source: FIG: 7E
SEQUENCE: 242
atcggaaccc ttaatgtcga cgagatcgag tgccgcatct ggggagtccc tgccacacta  60
agt                                                                       63

SEQ ID NO: 243           moltype = DNA   length = 37
FEATURE                  Location/Qualifiers
source                   1..37
                         mol_type = other DNA
                         organism = synthetic construct
misc_feature             1..37
                         note = Description of sequence: Sequence Name: SG-1 #7;
                          Source: FIG: 7E
SEQUENCE: 243
atcggaaccc ttaatgtcga cccctgccac actcagt                                  37

SEQ ID NO: 244           moltype = DNA   length = 63
FEATURE                  Location/Qualifiers
source                   1..63
                         mol_type = other DNA
                         organism = synthetic construct
misc_feature             1..63
                         note = Description of sequence: Sequence Name: SG-1 #8;
                          Source: FIG: 7E
SEQUENCE: 244
atcggaaccc ttaatgtcga cgagatcgag tgccgcatct ggggagtccc tgccacacta  60
agt                                                                       63

SEQ ID NO: 245           moltype = DNA   length = 37
FEATURE                  Location/Qualifiers
misc_feature             1..37
                         note = Description of sequence: Sequence Name: SG-1 #9;
                          Source: FIG: 7E
source                   1..37
                         mol_type = other DNA
                         organism = synthetic construct
SEQUENCE: 245
atcggaaccc ttaatgtcga cccctgccac actcagt                                  37

SEQ ID NO: 246           moltype = DNA   length = 63
FEATURE                  Location/Qualifiers
source                   1..63
                         mol_type = other DNA
                         organism = synthetic construct
misc_feature             1..63
                         note = Description of sequence: Sequence Name: SG-1 #10;
                          Source: FIG: 7E
SEQUENCE: 246
atcggaaccc ttaatgtcga cgagatcgag tgccgcatct ggggagtccc tgccacactc  60
agt                                                                       63

SEQ ID NO: 247           moltype = DNA   length = 37
FEATURE                  Location/Qualifiers
source                   1..37
                         mol_type = other DNA
                         organism = synthetic construct
misc_feature             1..37
                         note = Description of sequence: Sequence Name: SG-1 #11;
                          Source: FIG: 7E
```

-continued

```
SEQUENCE: 247
atcggaaccc ttaatgtcga cccctgccac actcagt                              37

SEQ ID NO: 248         moltype = DNA   length = 43
FEATURE                Location/Qualifiers
misc_feature           1..43
                       note = Description of sequence: Sequence Name: SG-1 #12;
                        Source: FIG: 7E
source                 1..43
                       mol_type = other DNA
                       organism = synthetic construct
SEQUENCE: 248
atcggaaccc ttaatgtcga cgagatcgag tgccgcatta agt                       43

SEQ ID NO: 249         moltype = DNA   length = 37
FEATURE                Location/Qualifiers
misc_feature           1..37
                       note = Description of sequence: Sequence Name: SG-1 #13;
                        Source: FIG: 7E
source                 1..37
                       mol_type = other DNA
                       organism = synthetic construct
SEQUENCE: 249
atcggaaccc ttaatgtcga cccctgccac actcagt                              37

SEQ ID NO: 250         moltype = DNA   length = 37
FEATURE                Location/Qualifiers
misc_feature           1..37
                       note = Description of sequence: Sequence Name: SG-1 #14;
                        Source: FIG: 7E
source                 1..37
                       mol_type = other DNA
                       organism = synthetic construct
SEQUENCE: 250
atcggaaccc ttaatgtcga cccctgccac actcagt                              37

SEQ ID NO: 251         moltype = DNA   length = 63
FEATURE                Location/Qualifiers
misc_feature           1..63
                       note = Description of sequence: Sequence Name: SG-1 #15;
                        Source: FIG: 7E
source                 1..63
                       mol_type = other DNA
                       organism = synthetic construct
SEQUENCE: 251
atcggaaccc ttaatgtcga cgagatcgag tgccgcatct ggggagtccc tgccacactc  60
agt                                                                   63

SEQ ID NO: 252         moltype = DNA   length = 37
FEATURE                Location/Qualifiers
source                 1..37
                       mol_type = other DNA
                       organism = synthetic construct
misc_feature           1..37
                       note = Description of sequence: Sequence Name: SG-1 #16;
                        Source: FIG: 7E
SEQUENCE: 252
atcggaaccc ttaatgtcga cccctgccac actcagt                              37

SEQ ID NO: 253         moltype = DNA   length = 63
FEATURE                Location/Qualifiers
source                 1..63
                       mol_type = other DNA
                       organism = synthetic construct
misc_feature           1..63
                       note = Description of sequence: Sequence Name: SG-1 #17;
                        Source: FIG: 7E
SEQUENCE: 253
atcggaaccc ttaatgtcga cgagatcgag tgccgcatct ggggagtccc tgccacactc  60
agt                                                                   63

SEQ ID NO: 254         moltype = DNA   length = 37
FEATURE                Location/Qualifiers
misc_feature           1..37
                       note = Description of sequence: Sequence Name: SG-1 #18;
                        Source: FIG: 7E
source                 1..37
                       mol_type = other DNA
                       organism = synthetic construct
```

```
SEQUENCE: 254
atcggaaccc ttaatgtcga cccctgccac actcagt                             37

SEQ ID NO: 255          moltype = DNA   length = 68
FEATURE                 Location/Qualifiers
misc_feature            1..68
                        note = Description of sequence: Sequence Name: SG-2 #1;
                         Source: FIG: 7E
source                  1..68
                        mol_type = other DNA
                        organism = synthetic construct
SEQUENCE: 255
atcggaaccc ttaatgtcga cgagatcgag tgccgcatca agaggaagag agagaccctc  60
actgctgg                                                             68

SEQ ID NO: 256          moltype = DNA   length = 68
FEATURE                 Location/Qualifiers
source                  1..68
                        mol_type = other DNA
                        organism = synthetic construct
misc_feature            1..68
                        note = Description of sequence: Sequence Name: SG-2 #2;
                         Source: FIG: 7E
SEQUENCE: 256
atcggaaccc ttaatgtcga cgagatcgag tgccgcatca agaggaagag agagaccctc  60
actgctgg                                                             68

SEQ ID NO: 257          moltype = DNA   length = 59
FEATURE                 Location/Qualifiers
source                  1..59
                        mol_type = other DNA
                        organism = synthetic construct
misc_feature            1..59
                        note = Description of sequence: Sequence Name: SG-2 #3;
                         Source: FIG: 7E
SEQUENCE: 257
atcggaaccc ttaatgtcga cgagatcgag tgccgcatga gagagaccct cactgctgg   59

SEQ ID NO: 258          moltype = DNA   length = 59
FEATURE                 Location/Qualifiers
misc_feature            1..59
                        note = Description of sequence: Sequence Name: SG-2 #4;
                         Source: FIG: 7E
source                  1..59
                        mol_type = other DNA
                        organism = synthetic construct
SEQUENCE: 258
atcggaaccc ttaatgtcga cgagatcgag tgccgcatga gagagaccct cactgctgg   59

SEQ ID NO: 259          moltype = DNA   length = 67
FEATURE                 Location/Qualifiers
source                  1..67
                        mol_type = other DNA
                        organism = synthetic construct
misc_feature            1..67
                        note = Description of sequence: Sequence Name: SG-2 #5;
                         Source: FIG: 7E
SEQUENCE: 259
atcggaaccc ttaatgtcga cgagatcgag tgccgcataa gaggaagaga gagaccctca  60
ctgctgg                                                              67

SEQ ID NO: 260          moltype = DNA   length = 65
FEATURE                 Location/Qualifiers
misc_feature            1..65
                        note = Description of sequence: Sequence Name: SG-2 #6;
                         Source: FIG: 7E
source                  1..65
                        mol_type = other DNA
                        organism = synthetic construct
SEQUENCE: 260
atcggaaccc ttaatgtcga cgagatcgag tgccgcaaga ggaagagaga gaccctcact  60
gctgg                                                                65

SEQ ID NO: 261          moltype = DNA   length = 67
FEATURE                 Location/Qualifiers
misc_feature            1..67
                        note = Description of sequence: Sequence Name: SG-2 #7;
                         Source: FIG: 7E
source                  1..67
```

```
                        mol_type = other DNA
                        organism = synthetic construct
SEQUENCE: 261
atcggaaccc ttaatgtcga cgagatcgag tgccgcataa gaggaagaga gagaccctca   60
ctgctgg                                                             67

SEQ ID NO: 262          moltype = DNA   length = 69
FEATURE                 Location/Qualifiers
source                  1..69
                        mol_type = other DNA
                        organism = synthetic construct
misc_feature            1..69
                        note = Description of sequence: Sequence Name: SG-2 #8;
                         Source: FIG: 7E
SEQUENCE: 262
atcggaaccc ttaatgtcga cgagatcgag tgccgcattc aagaggaaga gagagaccct   60
cactgctgg                                                           69

SEQ ID NO: 263          moltype = DNA   length = 68
FEATURE                 Location/Qualifiers
misc_feature            1..68
                        note = Description of sequence: Sequence Name: SG-2 #9;
                         Source: FIG: 7E
source                  1..68
                        mol_type = other DNA
                        organism = synthetic construct
SEQUENCE: 263
atcggaaccc ttaatgtcga cgagatcgag tgccgcatca agaggaagag agagaccctc   60
actgctgg                                                            68

SEQ ID NO: 264          moltype = DNA   length = 61
FEATURE                 Location/Qualifiers
source                  1..61
                        mol_type = other DNA
                        organism = synthetic construct
misc_feature            1..61
                        note = Description of sequence: Sequence Name: SG-2 #10;
                         Source: FIG: 7E
SEQUENCE: 264
atcggaaccc ttaatgtcga cgagatcgag tcaagaggaa gagagagacc ctcactgctg   60
g                                                                   61

SEQ ID NO: 265          moltype = DNA   length = 94
FEATURE                 Location/Qualifiers
source                  1..94
                        mol_type = other DNA
                        organism = synthetic construct
misc_feature            1..94
                        note = Description of sequence: Sequence Name: SG-3 #1;
                         Source: FIG: 7E
SEQUENCE: 265
atcggaaccc ttaatgtcga cgagatcgag tgccgcacaa gaggaagagc acaagaggaa   60
gagagagacc ctcactgctg gggagtccct gcca                               94

SEQ ID NO: 266          moltype = DNA   length = 88
FEATURE                 Location/Qualifiers
misc_feature            1..88
                        note = Description of sequence: Sequence Name: SG-3 #2;
                         Source: FIG: 7E
source                  1..88
                        mol_type = other DNA
                        organism = synthetic construct
SEQUENCE: 266
atcggaaccc ttaatgtcga cgagatcgag tgccgcataa gagcacaaga ggaagagaga   60
gaccctcact gctggggagt ccctgcca                                      88

SEQ ID NO: 267          moltype = DNA   length = 85
FEATURE                 Location/Qualifiers
source                  1..85
                        mol_type = other DNA
                        organism = synthetic construct
misc_feature            1..85
                        note = Description of sequence: Sequence Name: SG-3 #3;
                         Source: FIG: 7E
SEQUENCE: 267
atcggaaccc ttaatgtcga cgagatcgag tgccgcagag cacaagagga agagagagac   60
cctcactgct ggggagtccc tgcca                                         85

SEQ ID NO: 268          moltype = DNA   length = 88
```

-continued

```
FEATURE          Location/Qualifiers
misc_feature     1..88
                 note = Description of sequence: Sequence Name: SG-3 #4;
                  Source: FIG: 7E
source           1..88
                 mol_type = other DNA
                 organism = synthetic construct
SEQUENCE: 268
atcggaaccc ttaatgtcga cgagatcgag tgccgcataa gagcacaaga ggaagagaga   60
gaccctcact gctggggagt ccctgcca                                       88

SEQ ID NO: 269   moltype = DNA  length = 57
FEATURE          Location/Qualifiers
source           1..57
                 mol_type = other DNA
                 organism = synthetic construct
misc_feature     1..57
                 note = Description of sequence: Sequence Name: SG-3 #5;
                  Source: FIG: 7E
SEQUENCE: 269
atcggaaccc ttaatgttgt gattaatgag accctcactg ctggggagtc cctgcca       57

SEQ ID NO: 270   moltype = DNA  length = 88
FEATURE          Location/Qualifiers
source           1..88
                 mol_type = other DNA
                 organism = synthetic construct
misc_feature     1..88
                 note = Description of sequence: Sequence Name: SG-3 #6;
                  Source: FIG: 7E
SEQUENCE: 270
atcggaaccc ttaatgtcga cgagatcgag tgccgcataa gagcacaaga ggaagagaga   60
gaccctcact gctggggagt ccctgcca                                       88

SEQ ID NO: 271   moltype = DNA  length = 88
FEATURE          Location/Qualifiers
misc_feature     1..88
                 note = Description of sequence: Sequence Name: SG-3 #7;
                  Source: FIG: 7E
source           1..88
                 mol_type = other DNA
                 organism = synthetic construct
SEQUENCE: 271
atcggaaccc ttaatgtcga cgagatcgag tgccgcataa gagcacaaga ggaagagaga   60
gaccctcact gctggggagt ccctgcca                                       88

SEQ ID NO: 272   moltype = DNA  length = 88
FEATURE          Location/Qualifiers
source           1..88
                 mol_type = other DNA
                 organism = synthetic construct
misc_feature     1..88
                 note = Description of sequence: Sequence Name: SG-3 #8;
                  Source: FIG: 7E
SEQUENCE: 272
atcggaaccc ttaatgtcga cgagatcgag tgccgcataa gagcacaaga ggaagagaga   60
gaccctcact gctggggagt ccctgcca                                       88

SEQ ID NO: 273   moltype = DNA  length = 86
FEATURE          Location/Qualifiers
misc_feature     1..86
                 note = Description of sequence: Sequence Name: SG-3 #9;
                  Source: FIG: 7E
source           1..86
                 mol_type = other DNA
                 organism = synthetic construct
SEQUENCE: 273
atcggaaccc ttaatgtcga cgagatcgag tgccgcatga gcacaagagg aagagagaga   60
ccctcactgc tggggagtcc ctgcca                                         86

SEQ ID NO: 274   moltype = DNA  length = 88
FEATURE          Location/Qualifiers
source           1..88
                 mol_type = other DNA
                 organism = synthetic construct
misc_feature     1..88
                 note = Description of sequence: Sequence Name: SG-3 #10;
                  Source: FIG: 7E
SEQUENCE: 274
```

```
atcggaaccc ttaatgtcga cgagatcgag tgccgcataa gagcacaaga ggaagagaga  60
gaccctcact gctggggagt ccctgcca                                     88

SEQ ID NO: 275         moltype = DNA   length = 88
FEATURE                Location/Qualifiers
misc_feature           1..88
                       note = Description of sequence: Sequence Name: SG-3 #11;
                        Source: FIG: 7E
source                 1..88
                       mol_type = other DNA
                       organism = synthetic construct
SEQUENCE: 275
atcggaaccc ttaatgtcga cgagatcgag tgccgcataa gagcacaaga ggaagagaga  60
gaccctcact gctggggagt ccctgcca                                     88

SEQ ID NO: 276         moltype = DNA   length = 88
FEATURE                Location/Qualifiers
misc_feature           1..88
                       note = Description of sequence: Sequence Name: SG-3 #12;
                        Source: FIG: 7E
source                 1..88
                       mol_type = other DNA
                       organism = synthetic construct
SEQUENCE: 276
atcggaaccc ttaatgtcga cgagatcgag tgccgcataa gagcacaaga ggaagagaga  60
gaccctcact gctggggagt ccctgcca                                     88

SEQ ID NO: 277         moltype = DNA   length = 54
FEATURE                Location/Qualifiers
misc_feature           1..54
                       note = Description of sequence: Sequence Name: SG-3 #13;
                        Source: FIG: 7E
source                 1..54
                       mol_type = other DNA
                       organism = synthetic construct
SEQUENCE: 277
atcggaaccc ttaatgggaa gagagagacc ctcactgctg gggagtccct gcca          54

SEQ ID NO: 278         moltype = DNA   length = 88
FEATURE                Location/Qualifiers
source                 1..88
                       mol_type = other DNA
                       organism = synthetic construct
misc_feature           1..88
                       note = Description of sequence: Sequence Name: SG-3 #14;
                        Source: FIG: 7E
SEQUENCE: 278
atcggaaccc ttaatgtcga cgagatcgag tgccgcataa gagcacaaga ggaagagaga  60
gaccctcact gctggggagt ccctgcca                                     88

SEQ ID NO: 279         moltype = DNA   length = 88
FEATURE                Location/Qualifiers
source                 1..88
                       mol_type = other DNA
                       organism = synthetic construct
misc_feature           1..88
                       note = Description of sequence: Sequence Name: SG-3 #15;
                        Source: FIG: 7E
SEQUENCE: 279
atcggaaccc ttaatgtcga cgagatcgag tgccgcataa gagcacaaga ggaagagaga  60
gaccctcact gctggggagt ccctgcca                                     88

SEQ ID NO: 280         moltype = DNA   length = 88
FEATURE                Location/Qualifiers
source                 1..88
                       mol_type = other DNA
                       organism = synthetic construct
misc_feature           1..88
                       note = Description of sequence: Sequence Name: SG-3 #16;
                        Source: FIG: 7E
SEQUENCE: 280
atcggaaccc ttaatgtcga cgagatcgag tgccgcataa gagcacaaga ggaagagaga  60
gaccctcact gctggggagt ccctgcca                                     88

SEQ ID NO: 281         moltype = DNA   length = 65
FEATURE                Location/Qualifiers
misc_feature           1..65
                       note = Description of sequence: Sequence Name: SG-3 #17;
                        Source: FIG: 7E
```

```
source                   1..65
                         mol_type = other DNA
                         organism = synthetic construct
SEQUENCE: 281
atcggaaccc ttaataagag cacaagagga agagagagac cctcactgct ggggagtccc   60
tgcca                                                                65

SEQ ID NO: 282           moltype = DNA   length = 88
FEATURE                  Location/Qualifiers
misc_feature             1..88
                         note = Description of sequence: Sequence Name: SG-3 #18;
                          Source: FIG: 7E
source                   1..88
                         mol_type = other DNA
                         organism = synthetic construct
SEQUENCE: 282
atcggaaccc ttaatgtcga cgagatcgag tgccgcataa gagcacaaga ggaagagaga   60
gaccctcact gctggggagt ccctgcca                                      88

SEQ ID NO: 283           moltype = DNA   length = 100
FEATURE                  Location/Qualifiers
source                   1..100
                         mol_type = other DNA
                         organism = synthetic construct
misc_feature             1..100
                         note = Description of sequence: Target Name: 5' homology
                          arm; Source: FIG: 9A
SEQUENCE: 283
atggcctcca aggagtaaga cccctggacc accagcccca gcaagagcac aagaggaaga   60
gagagaccct cactgctggg gagtccctgc cacactcagt                         100

SEQ ID NO: 284           moltype = AA   length = 5
FEATURE                  Location/Qualifiers
REGION                   1..5
                         note = Description of sequence: Target Name: 5' homology
                          arm peptide; Source: FIG: 9A
source                   1..5
                         mol_type = protein
                         organism = synthetic construct
SEQUENCE: 284
MASKE                                                                5

SEQ ID NO: 285           moltype = DNA   length = 100
FEATURE                  Location/Qualifiers
misc_feature             1..100
                         note = Description of sequence: Target Name: 3' homology
                          arm; Source: FIG: 9A
source                   1..100
                         mol_type = other DNA
                         organism = synthetic construct
SEQUENCE: 285
cccccaccac actgaatctc ccctcctcac agttgccatg tagacccctt gaagagggga   60
ggggcctagg gagccgcacc ttgtcatgta ccatcaataa                         100

SEQ ID NO: 286           moltype = DNA   length = 85
FEATURE                  Location/Qualifiers
source                   1..85
                         mol_type = other DNA
                         organism = synthetic construct
misc_feature             1..85
                         note = Description of sequence: Sequence Name: Ref Seq ;
                          Source: FIG: 9E
SEQUENCE: 286
atggcctcca aggagtaaga cccctggacc accagcccca gcaagagcac aagaggaaca   60
attgacgcgt gctcctctcc ctccc                                         85

SEQ ID NO: 287           moltype = DNA   length = 85
FEATURE                  Location/Qualifiers
misc_feature             1..85
                         note = Description of sequence: Sequence Name: SG-1 #1;
                          Source: FIG: 9E
source                   1..85
                         mol_type = other DNA
                         organism = synthetic construct
SEQUENCE: 287
atggcctcca aggagtaaga cccctggacc accagcccca gcaagagcac aagaggaaca   60
attgacgcgt gctcctctcc ctccc                                         85

SEQ ID NO: 288           moltype = DNA   length = 85
```

-continued

```
FEATURE              Location/Qualifiers
misc_feature         1..85
                     note = Description of sequence: Sequence Name: SG-1 #2;
                      Source: FIG: 9E
source               1..85
                     mol_type = other DNA
                     organism = synthetic construct
SEQUENCE: 288
atggcctcca aggagtaaga cccctggacc accagcccca gcaagagcac aagaggaaca  60
attgacgcgt gctcctctcc ctccc                                         85

SEQ ID NO: 289       moltype = DNA  length = 85
FEATURE              Location/Qualifiers
misc_feature         1..85
                     note = Description of sequence: Sequence Name: SG-1 #3;
                      Source: FIG: 9E
source               1..85
                     mol_type = other DNA
                     organism = synthetic construct
SEQUENCE: 289
atggcctcca aggagtaaga cccctggacc accagcccca gcaagagcac aagaggaaca  60
attgacgcgt gctcctctcc ctccc                                         85

SEQ ID NO: 290       moltype = DNA  length = 93
FEATURE              Location/Qualifiers
misc_feature         1..93
                     note = Description of sequence: Sequence Name: HDR-Donor.2;
                      Source: FIG: 9E
source               1..93
                     mol_type = other DNA
                     organism = synthetic construct
SEQUENCE: 290
atggcctcca aggagtaaga cccctggacc accagcccca gcaagagcac aagaggaaca  60
attgacgcgt gctcctctcc ctccccccc cct                                 93

SEQ ID NO: 291       moltype = AA  length = 5
FEATURE              Location/Qualifiers
source               1..5
                     mol_type = protein
                     organism = synthetic construct
REGION               1..5
                     note = Description of sequence: Sequence Name: HDR-Donor.2
                      peptide; Source: FIG: 9E
SEQUENCE: 291
MASKE                                                                5

SEQ ID NO: 292       moltype = DNA  length = 100
FEATURE              Location/Qualifiers
misc_feature         1..100
                     note = Description of sequence: Sequence Name: GAPDH locus;
                      Source: FIG: 9E
source               1..100
                     mol_type = other DNA
                     organism = synthetic construct
SEQUENCE: 292
atggcctcca aggagtaaga cccctggacc accagcccca gcaagagcac aagaggaaga  60
gagagaccct cactgctggg gagtccctgc cacactcagt                        100

SEQ ID NO: 293       moltype = AA  length = 5
FEATURE              Location/Qualifiers
REGION               1..5
                     note = Description of sequence: Sequence Name: GAPDH locus
                      peptide; Source: FIG: 9E
source               1..5
                     mol_type = protein
                     organism = synthetic construct
SEQUENCE: 293
MASKE                                                                5

SEQ ID NO: 294       moltype = DNA  length = 86
FEATURE              Location/Qualifiers
source               1..86
                     mol_type = other DNA
                     organism = synthetic construct
misc_feature         1..86
                     note = Description of sequence: Sequence Name: SG-2 #1;
                      Source: FIG: 9E
SEQUENCE: 294
atggcctcca aggagtaaga cccctggacc accagcccca gcaagagcac caagaggaac  60
```

-continued

```
aattgacgcg tgctcctctc cctccc                                       86

SEQ ID NO: 295          moltype = DNA   length = 86
FEATURE                 Location/Qualifiers
misc_feature            1..86
                        note = Description of sequence: Sequence Name: SG-2 #2;
                         Source: FIG: 9E
source                  1..86
                        mol_type = other DNA
                        organism = synthetic construct
SEQUENCE: 295
atggcctcca aggagtaaga cccctggacc accagcccca gcaagagcac caagaggaac  60
aattgacgcg tgctcctctc cctccc                                       86

SEQ ID NO: 296          moltype = DNA   length = 86
FEATURE                 Location/Qualifiers
source                  1..86
                        mol_type = other DNA
                        organism = synthetic construct
misc_feature            1..86
                        note = Description of sequence: Sequence Name: SG-2 #3;
                         Source: FIG: 9E
SEQUENCE: 296
atggcctcca aggagtaaga cccctggacc accagcccca gcaagagcac caagaggaac  60
aattgacgcg tgctcctctc cctccc                                       86

SEQ ID NO: 297          moltype = DNA   length = 86
FEATURE                 Location/Qualifiers
source                  1..86
                        mol_type = other DNA
                        organism = synthetic construct
misc_feature            1..86
                        note = Description of sequence: Sequence Name: SG-2 #4;
                         Source: FIG: 9E
SEQUENCE: 297
atggcctcca aggagtaaga cccctggacc accagcccca gcaagagcac caagaggaac  60
aattgacgcg tgctcctctc cctccc                                       86

SEQ ID NO: 298          moltype = DNA   length = 103
FEATURE                 Location/Qualifiers
source                  1..103
                        mol_type = other DNA
                        organism = synthetic construct
misc_feature            1..103
                        note = Description of sequence: Sequence Name: SG-2 #5;
                         Source: FIG: 9E
SEQUENCE: 298
atggcctcca aggagtaaga cccctggacc accagcccca gcaagagcag aagacagcaa  60
gagacagcaa gaggaacaat tgacgcgtgc tcctctccct ccc                   103

SEQ ID NO: 299          moltype = DNA   length = 85
FEATURE                 Location/Qualifiers
source                  1..85
                        mol_type = other DNA
                        organism = synthetic construct
misc_feature            1..85
                        note = Description of sequence: Sequence Name: SG-2 #6;
                         Source: FIG: 9E
SEQUENCE: 299
atggcctcca aggagtaaga cccctggacc accagcccca gcaagagcac ttgaggaaca  60
attgacgcgt gctcctctcc ctccc                                        85

SEQ ID NO: 300          moltype = DNA   length = 86
FEATURE                 Location/Qualifiers
source                  1..86
                        mol_type = other DNA
                        organism = synthetic construct
misc_feature            1..86
                        note = Description of sequence: Sequence Name: SG-2 #7;
                         Source: FIG: 9E
SEQUENCE: 300
atggcctcca aggagtaaga cccctggacc accagcccca gcaagagcac caagaggaac  60
aattgacgcg tgctcctctc cctccc                                       86

SEQ ID NO: 301          moltype = DNA   length = 83
FEATURE                 Location/Qualifiers
source                  1..83
                        mol_type = other DNA
                        organism = synthetic construct
```

-continued

```
misc_feature           1..83
                       note = Description of sequence: Sequence Name: SG-2 #8;
                        Source: FIG: 9E
SEQUENCE: 301
atggcctcca aggagtaaga cccctggacc accagcccca gcaagagcaa gaggaacaat  60
tgacgcgtgc tcctctccct ccc                                          83

SEQ ID NO: 302        moltype = DNA   length = 69
FEATURE               Location/Qualifiers
source                1..69
                       mol_type = other DNA
                       organism = synthetic construct
misc_feature          1..69
                       note = Description of sequence: Sequence Name: SG-3 #1;
                        Source: FIG: 9E
SEQUENCE: 302
atggcctcca aggagtaaga cccctggacc accagcccca gcaaattgac gcgtgctcct  60
ctccctccc                                                          69

SEQ ID NO: 303        moltype = DNA   length = 87
FEATURE               Location/Qualifiers
source                1..87
                       mol_type = other DNA
                       organism = synthetic construct
misc_feature          1..87
                       note = Description of sequence: Sequence Name: SG-3 #2;
                        Source: FIG: 9E
SEQUENCE: 303
atggcctcca aggagtaaga cccctggacc accagcccca gcaaaagagc acaagaggaa  60
caattgacgc gtgctcctct ccctccc                                      87

SEQ ID NO: 304        moltype = DNA   length = 83
FEATURE               Location/Qualifiers
misc_feature          1..83
                       note = Description of sequence: Sequence Name: SG-3 #3;
                        Source: FIG: 9E
source                1..83
                       mol_type = other DNA
                       organism = synthetic construct
SEQUENCE: 304
atggcctcca aggagtaaga cccctggacc accagcccca aagagcacaa gaggaacaat  60
tgacgcgtgc tcctctccct ccc                                          83

SEQ ID NO: 305        moltype = DNA   length = 86
FEATURE               Location/Qualifiers
source                1..86
                       mol_type = other DNA
                       organism = synthetic construct
misc_feature          1..86
                       note = Description of sequence: Sequence Name: SG-3 #4;
                        Source: FIG: 9E
SEQUENCE: 305
atggcctcca agaagtaaga cccctggacc accagcccca gcaaagagca caagaggaac  60
aattgacgcg tgctcctctc cctccc                                       86

SEQ ID NO: 306        moltype = DNA   length = 67
FEATURE               Location/Qualifiers
source                1..67
                       mol_type = other DNA
                       organism = synthetic construct
misc_feature          1..67
                       note = Description of sequence: Sequence Name: SG-3 #5;
                        Source: FIG: 9E
SEQUENCE: 306
atggcctcca aggagtaaga cccctggagc acaagaggaa caattgacgc gtgctcctct  60
ccctccc                                                            67

SEQ ID NO: 307        moltype = DNA   length = 74
FEATURE               Location/Qualifiers
misc_feature          1..74
                       note = Description of sequence: Sequence Name: SG-3 #6;
                        Source: FIG: 9E
source                1..74
                       mol_type = other DNA
                       organism = synthetic construct
SEQUENCE: 307
atggcctcca aggagtaaga cccctggacc accagccaca agaggaacaa ttgacgcgtg  60
ctcctctccc tccc                                                    74
```

```
SEQ ID NO: 308          moltype = DNA   length = 59
FEATURE                 Location/Qualifiers
source                  1..59
                        mol_type = other DNA
                        organism = synthetic construct
misc_feature            1..59
                        note = Description of sequence: Sequence Name: SG-3 #7;
                         Source: FIG: 9E
SEQUENCE: 308
atggcctcca aggagtaaga gcacaagagg aacaattgac gcgtgctcct ctccctccc   59

SEQ ID NO: 309          moltype = DNA   length = 86
FEATURE                 Location/Qualifiers
misc_feature            1..86
                        note = Description of sequence: Sequence Name: SG-3 #8;
                         Source: FIG: 9E
source                  1..86
                        mol_type = other DNA
                        organism = synthetic construct
SEQUENCE: 309
atggcctcca aggagtaaga cccctggacc accagcccca gccaagagca caagaggaac   60
aattgacgcg tgctcctctc cctccc                                       86

SEQ ID NO: 310          moltype = DNA   length = 86
FEATURE                 Location/Qualifiers
misc_feature            1..86
                        note = Description of sequence: Sequence Name: SG-3 #9;
                         Source: FIG: 9E
source                  1..86
                        mol_type = other DNA
                        organism = synthetic construct
SEQUENCE: 310
atggcctcca aggagtaaga cccctggacc accagcccca gcaaagagca caagaggaac   60
aattgacgcg tgctcctctc cctccc                                       86

SEQ ID NO: 311          moltype = DNA   length = 83
FEATURE                 Location/Qualifiers
misc_feature            1..83
                        note = Description of sequence: Sequence Name: sgOCT4;
                         Source: FIG: 10C
source                  1..83
                        mol_type = other DNA
                        organism = synthetic construct
SEQUENCE: 311
accactctgg gctctcccat gcattcaaac tgaggtgcct gcccttctag gaatgggga   60
caggggagg ggaggagcta ggg                                           83

SEQ ID NO: 312          moltype = AA   length = 10
FEATURE                 Location/Qualifiers
source                  1..10
                        mol_type = protein
                        organism = synthetic construct
REGION                  1..10
                        note = Description of sequence: Sequence Name: sgOCT4
                         peptide; Source: FIG: 10C
SEQUENCE: 312
TTLGSPMHSN                                                          10

SEQ ID NO: 313          moltype = DNA   length = 80
FEATURE                 Location/Qualifiers
misc_feature            1..80
                        note = Description of sequence: Sequence Name:
                         NHEJ-Donor.1; Source: FIG: 10E
source                  1..80
                        mol_type = other DNA
                        organism = synthetic construct
SEQUENCE: 313
tagaactagt ggatccgaga tcgagtgccg catcaccggc aattgacgcg tgctcctctc   60
cctcccccc ccctaacgtt                                               80

SEQ ID NO: 314          moltype = DNA   length = 83
FEATURE                 Location/Qualifiers
source                  1..83
                        mol_type = other DNA
                        organism = synthetic construct
misc_feature            1..83
                        note = Description of sequence: Sequence Name: OCT4 locus;
                         Source: FIG: 10E
SEQUENCE: 314
```

```
tctcccatgc attcaaactg aggtgcctgc ccttctagga atgggggaca gggggagggg   60
aggagctagg gaaagaaaac ctg                                          83

SEQ ID NO: 315           moltype = AA  length = 6
FEATURE                  Location/Qualifiers
REGION                   1..6
                         note = Description of sequence: Sequence Name: OCT4 locus
                          peptide; Source: FIG: 10E
source                   1..6
                         mol_type = protein
                         organism = synthetic construct
SEQUENCE: 315
SPMHSN                                                              6

SEQ ID NO: 316           moltype = DNA  length = 90
FEATURE                  Location/Qualifiers
misc_feature             1..90
                         note = Description of sequence: Sequence Name: 5'-Junction
                          #1; Source: FIG: 10E
source                   1..90
                         mol_type = other DNA
                         organism = synthetic construct
SEQUENCE: 316
tctcccatgc attcaaactg aggtgcctgc ccttctatcc tgtccccggc aattgacgcg   60
tgctcctctc cctcccccccc ccctaacgtt                                  90

SEQ ID NO: 317           moltype = DNA  length = 42
FEATURE                  Location/Qualifiers
source                   1..42
                         mol_type = other DNA
                         organism = synthetic construct
misc_feature             1..42
                         note = Description of sequence: Sequence Name: 5'-Junction
                          #2; Source: FIG: 10E
SEQUENCE: 317
tctcccatgc attcaaactg aggtgcctgc ccttctaacg tt                     42

SEQ ID NO: 318           moltype = DNA  length = 42
FEATURE                  Location/Qualifiers
misc_feature             1..42
                         note = Description of sequence: Sequence Name: 5'-Junction
                          #3; Source: FIG: 10E
source                   1..42
                         mol_type = other DNA
                         organism = synthetic construct
SEQUENCE: 318
tctcccatgc attcaaactg aggtgcctgc ccttctaacg tt                     42

SEQ ID NO: 319           moltype = DNA  length = 80
FEATURE                  Location/Qualifiers
source                   1..80
                         mol_type = other DNA
                         organism = synthetic construct
misc_feature             1..80
                         note = Description of sequence: Sequence Name: 5'-Junction
                          #4; Source: FIG: 10E
SEQUENCE: 319
tctcccatgc attcaaactg aggtgcctgc ccctctaggc aattgacgcg tgctcctctc   60
cctcccccccc ccctaacgtt                                             80

SEQ ID NO: 320           moltype = DNA  length = 42
FEATURE                  Location/Qualifiers
misc_feature             1..42
                         note = Description of sequence: Sequence Name: 5'-Junction
                          #5; Source: FIG: 10E
source                   1..42
                         mol_type = other DNA
                         organism = synthetic construct
SEQUENCE: 320
tctcccatgc attcaaactg aggtgcctgc ccttctaacg tt                     42

SEQ ID NO: 321           moltype = DNA  length = 92
FEATURE                  Location/Qualifiers
source                   1..92
                         mol_type = other DNA
                         organism = synthetic construct
misc_feature             1..92
                         note = Description of sequence: Sequence Name: 3' Junction
                          #1; Source: FIG: 10E
```

-continued

```
SEQUENCE: 321
ccgctctaga actagtggat ccgagatcga gtgccgcata atgggggaca gggggagggg    60
aggagctagg gaaagaaaac ctggagtttg tg                                  92

SEQ ID NO: 322          moltype = DNA   length = 92
FEATURE                 Location/Qualifiers
source                  1..92
                        mol_type = other DNA
                        organism = synthetic construct
misc_feature            1..92
                        note = Description of sequence: Sequence Name: 3' Junction
                        #2; Source: FIG: 10E
SEQUENCE: 322
ccgctctaga actagtggat ccgagatcga gtgccgcata atgggggaca ggggaagggg     60
aggagctagg gaaagaaaac ctggagtttg tg                                  92

SEQ ID NO: 323          moltype = DNA   length = 80
FEATURE                 Location/Qualifiers
misc_feature            1..80
                        note = Description of sequence: Sequence Name: 3' Junction
                        #3; Source: FIG: 10E
source                  1..80
                        mol_type = other DNA
                        organism = synthetic construct
SEQUENCE: 323
ccgctctaga actagtggat ccgagatcga gtgccgcagg gggaggggag gagctaggga     60
aagaaaacct ggagtttgtg                                                80

SEQ ID NO: 324          moltype = DNA   length = 86
FEATURE                 Location/Qualifiers
source                  1..86
                        mol_type = other DNA
                        organism = synthetic construct
misc_feature            1..86
                        note = Description of sequence: Sequence Name: 3' Junction
                        #4; Source: FIG: 10E
SEQUENCE: 324
ccgctctaga actagtggat ccgagatcga gtgcctgggg gacagggggga ggggaggagc    60
tagggaaaga aaacctggag tttgtg                                         86

SEQ ID NO: 325          moltype = DNA   length = 80
FEATURE                 Location/Qualifiers
source                  1..80
                        mol_type = other DNA
                        organism = synthetic construct
misc_feature            1..80
                        note = Description of sequence: Sequence Name: 3' Junction
                        #5; Source: FIG: 10E
SEQUENCE: 325
ccgctctaga actagtggat ccgagatcga gtgccgcagg gggaggggag gagctaggga     60
aagaaaacct ggagtttgtg                                                80
```

1

METHODS AND SYSTEMS FOR TARGETED GENE MANIPULATION

CROSS-REFERENCE TO RELATED APPLICATIONS

This application is a continuation of U.S. patent application Ser. No. 15/354,329, filed Nov. 17, 2016, which claims the benefit of U.S. Provisional Application No. 62/256,514, filed Nov. 17, 2015, and claims the benefit of U.S. Provisional Application No. 62/288,974 filed Jan. 29, 2016, contents of all of the above are incorporated by reference herein in their entirety for all purposes.

REFERENCE TO BIOLOGICAL SEQUENCE DISCLOSURE

The instant application contains a Sequence Listing which has been submitted in .txt format via EFS-Web, in accordance with 37 C.F.R. §§ 1.831- to 1.835, and is hereby incorporated by reference in its entirety. The Sequence Listing created on Aug. 15, 2025, is named "080015-1420947-017430US_ST26.xml", and is 438,461 bytes in size.

BACKGROUND OF THE INVENTION

The development of efficient and reliable tools to make precise, targeted changes to the genome of living cells is a long-standing goal for biomedical researchers. Recently, a new technology based on a bacterial CRISPR-associated protein-9 nuclease (Cas9) from *Streptococcus pyogenes* has generated considerable excitement and interest, see, e.g., Cong et al. (2013) Science, 339, 819-823. Various attempts have followed over the past two years to manipulate genomic sequence and gene function in a highly target-specific fashion utilizing this CRISPR/Cas9 system.

On the other hand, studies have made efforts to improve the efficiency of homology-directed repair (HDR) of CRISPR/Cas9 induced DNA cleavages for achieving precise targeted DNA insertion into genome: Yu et al. in 2015 successfully identified several small chemical molecules to enhance HDR efficiency [24]; Maruyama et al. in 2015 inhibited non-homologous end joining (NHEJ) pathway to increase the HDR efficiency of genome editing [25]; Zhu et al. in 2015 developed iCRISPR system to optimize the laborious strategy and escape the drug selection step for gene knock-in in human pluripotent stem cells (hPSC) [26]; Merkle et al. in 2015 designed a strategy to physically separate CRISPR target sites at the targeted allele with bioinformatics identifications to improve the precision of gene knock-in [15]. Yet in these studies it is still inefficient in mediating knock-in of large DNA fragment, especially in human pluripotent stem cells (hPSCs). More recently, Li et al. in 2015 and Hisano et al. in 2015 have developed Cas9-mediated donor vectors, which showed high efficiency DNA insertion in zebrafish, and the systems were confirmed to be heritable [27,28]. However, the systems were not designed and examined in human cells, thus an optimized system for human cells including hPSC is still in critical demand.

RNA-guided genome engineering has been widely used in cell biology research. Original CRISPR/Cas9 system has shown market potential and been granted as several US patents in last two years [29-34]. Some of them have been in commercial development stage. Our previous invention, U.S. Provisional patent No. 62/256,514, provides optimized CRISPR/Cas9 systems, which include flexible donor vectors and promising procedures, have significant potential of user-friendly tool kit products for biological researchers. In addition, potential applications of this invention include various uses in clinical context such as disease diagnosis and gene correction.

In particular, the Cas9-mediated genome editing systems of the present invention are suitable for use in human cells and has several advantages. For example, these improved systems successfully fulfill the requirements of high HR efficiency in human cells, including human embryonic stem cells (ESCs) and induced pluripotent stem cells (iPSCs). The HR efficiency has been increased up to 5-folds in human ESCs compared to previously known methods. Furthermore, that present invention presents universal genomic editing systems, which have the potential to be used in low vertebrate as well. In addition, the systems are user-friendly, including several designs of donor constructs, making these systems highly valuable to many different applications in research and clinical contexts.

In the present invention, further evidence is provided for the application of the Cas9-mediated genome editing system in various genomic loci and conditions. The molecular basis and efficiency of homology-independent reporter integrations were further demonstrated; and additional methods and systems for NHEJ-induced efficient knock-in at silenced gene loci are provided. Additionally, off-target effects by a NHEJ-induced knock-in system are investigated.

Furthermore, an additional method and system of homology-independent knock-in of reporter genes into CPF1-induced DSBs at 3'-UTR of GAPDH locus is disclosed that demonstrates a preference for directional integration. Thus, the instant application discloses a method and system for unidirection-preferred knock-in induced by NHEJ using CRISPR/CPF1.

The instant application also discloses an additional method and system of homology-independent dual color insertion knock-in of reporter genes. Thus, the instant application discloses a method and system for bidirectional knock-in induced by NHEJ using CRISPR/Cas9.

Additionally, a method and system of homology-independent knock-in of multiple reporter genes into one target gene on multiple genomic alleles is disclosed that demonstrates the production of single or double positive cell populations. Accordingly, the instant application discloses a construct, method, and system of NHEJ-induced knock-in with multiple color fluorescent reporter genes into multiple alleles.

BRIEF SUMMARY OF THE INVENTION

This invention provides new cell lines, polynucleotide constructs, compositions, kits, and systems for CRISPR/Cas9 and CRISPR/Cpf1-based gene editing, which allow one to carry out studies for the mechanism and regulation of genomic sequence as well as to identify compounds that can modulate such genomic editing events.

The gene-editing systems as disclosed herein include two general types: the first is one involving two insertion events, whereas the second involves just one insertion event. For the first type, the present invention provides an integration construct, a donor construct, a transformed host cell, a composition, a kit, as well as various methods of using this gene-editing system. More specifically, in integration construct typically includes a promoter operably linked to, from 5' to 3', a first non-functional coding segment for a reporter gene, an interrupter segment, and a second non-functional coding segment for the reporter gene, such that no functional reporter protein is expressed from the promoter. In some embodiments, the integration construct further comprises two genomic homology sequences, one located at the 5' end of the promoter and the other located at the 3' end of the second non-functional coding segment for the reporter gene. The two genomic homology sequences are homologous to two segments of genomic sequence at a pre-determined genetic locus of a cell, such that the presence of the two genomic homology sequences permits homologous recombination between the integration construct and the genomic sequence of the cell at the pre-determined genetic locus. In some embodiments, the integration construct is a circular construct, e.g., a plasmid. In some embodiments, the reporter gene encoding for a green fluorescent protein (GFP). In some embodiments, each of the two genomic homology sequences is about 100-5000, 200-2500, or 500-1500 nucleotides in length, preferably 1000 nucleotides in length. In some embodiments, the promoter in the integration construct is heterologous to the reporter gene (i.e., taken from two different species or having been recombinantly modified). In some embodiments, the first and second non-functional coding segments for the reporter gene, when joined together without the interrupter segment, encode a functional reporter gene protein. The interrupter segment can be of any length, so long as it interrupts expression of the reporter gene. In some embodiments, the interrupter segment is about 10-2000, 15-1000, 20-500, or 25-100 nucleotides in length, preferably 30 nucleotides in length. In some embodiments, the interrupter segment comprises three termination codons, each in a different reading frame, to completely abolish expression of the reporter gene. In some embodiments, the pre-determined genetic locus comprises a house-keeping gene.

Also provided for the first type of gene-editing system is a donor construct, which comprises, from 5' to 3', a first reporter gene homology segment, an interval segment, and a second reporter gene homology segment. The first and second reporter gene homology segments are homologous to the first and second non-functional coding segments for the reporter gene in the integration construct, such that the presence of the two reporter gene homology segments permits homologous recombination between the integration construct and the donor construct to form a coding sequence for a functional reporter gene. In some embodiments, each of the first and second reporter gene homology segments is about 100-1000, 200-800, or 250-500 nucleotides in length, preferably 250, 500, or 800 nucleotides in length. In some embodiments, the interval segment is about 10-2000, 15-1000, 20-500, or 25-100 nucleotides in length, for example, 30 nucleotides or 726 nucleotides in length. In some embodiments, the interval segment encodes a functional reporter gene protein.

Another aspect of the disclosure is a host cell comprising the integration construct described above and also in the various sections of this application. The cell may be a stem cell or a somatic cell, and the cell may be a human cell or an animal cell. In some embodiments, the cell is a human stem cell. In some embodiments, the integration construct has been incorporated into the genome of the cell. In some embodiments, the cell further comprises the donor construct. In one embodiment, the host cell comprises a LO2 cell line having a large deletion in all LIG4 gene loci as determined by a lack of expression of DNA ligase IV protein. In one embodiment, the lack of expression of the DNA ligase IV protein can be determined by one of more methods routinely used in the art, for example, Western blot. In one embodiment, the host cell can comprise a human somatic cell.

Further disclosed is a composition comprising the cell comprising the integration construct, the donor construct, a DNA molecule encoding a sgRNA capable of hybridizing to a target site sequence (a segment typically about 20 nucleotides in length but may vary from about 10-50, 15-45, or 20-40 nucleotides, e.g., about 20, 25, or 30 nucleotides) within the non-functional coding segments for the reporter gene or the interrupter segment, and a DNA molecule encoding a Cas9 protein.

A kit is in addition disclosed for testing CRISPR-mediated homology-directed repair pathway. It typically includes these components: (1) the integration construct; (2) the donor construct; (3) a DNA molecule encoding a sgRNA capable of hybridizing to a target site sequence within the non-functional coding segments for the reporter gene or the interrupter segment; and (4) a DNA molecule encoding a Cas9 protein.

Methods are also disclosed for using the first type of gene-editing system. A method for testing CRISPR-mediated homology-directed repair pathway is disclosed. The method includes the steps of: (i) contacting the cell comprising the integration construct with the donor construct, a DNA molecule encoding a sgRNA capable of hybridizing to a target sequence site (e.g., a segment of about 20 nucleotides) within the non-functional coding segments for the reporter gene or the interrupter segment, and a DNA molecule encoding a Cas9 protein; and (ii) detecting a signal generated by the reporter gene protein.

Another method disclosed is for identifying an enhancer for CRISPR-mediated homology-directed repair pathway, comprising the steps of: (i) contacting, in the presence and absence of a candidate compound, the cell described herein with the donor construct described herein, a DNA molecule encoding a sgRNA capable of hybridizing to a segment of about 20) nucleotides within the non-functional coding segments for the reporter gene or the interrupter segment, and a DNA molecule encoding a Cas9 protein; and (ii) detecting signals generated by the reporter gene protein; and (iii) determining the compound as an enhancer of CRISPR-mediated homology-directed repair pathway when a higher reporter gene protein signal is detected in the presence of the compound than in the absence of the compound.

For the second type of gene-editing system, where only one integration event takes place, the invention provides a donor construct comprising (1) a coding sequence for a reporter gene; (2) a first genomic homology segment located at the 5' end of the reporter gene coding sequence; and (3) a second genomic homology segments located at the 3' end of the reporter gene coding sequence, wherein the first and second genomic homology segments are homologous to a pre-determined genomic sequence. In some embodiments, the first and second genomic homology segments are homologous to two segments of genomic sequence at the pre-determined genetic locus of a cell, such that the presence of the two genomic homology segments permits homologous recombination between the donor construct and the genomic sequence of the cell at the pre-determined genetic locus. In some embodiments, the donor construct is a circular construct, e.g., a plasmid. In some embodiments, the reporter gene encodes for a green fluorescent protein (GFP) or a drug resistance gene. In some embodiments, each of the two genomic homology segments is about 100-5000, 200-2500, or 500-1500 nucleotides in length, preferably 1000 nucleotides in length. In some embodiments, the pre-determined genetic locus comprises a house-keeping gene.

Another aspect of the disclosure is a host cell comprising the donor construct described above and also in the various sections of this application. The cell may be a stem cell or a somatic cell, and the cell may be a human cell or an animal cell. In some embodiments, the cell is a human cell. In a preferred embodiment, the donor construct has been incorporated into the genome of the cell. In one embodiment, the host cell comprises a LO2 cell line having a large deletion in all LIG4 gene loci as determined by a lack of expression of DNA ligase IV protein. In one embodiment, the lack of expression of the DNA ligase IV protein can be determined by one of more methods routinely used in the art, for example, Western blot. In one embodiment, the host cell can comprise a human somatic cell.

Further disclosed is a composition comprising a cell, a donor construct, a DNA molecule encoding a sgRNA capable of hybridizing to a segment (typically, a target site sequence of about 20 nucleotides in length but may vary from about 10-50, 15-45, or 20-40 nucleotides, e.g., about 20, 25, or 30 nucleotides) within the upstream or downstream non-coding sequence of the pre-determined genomic sequence; and a DNA molecule encoding a Cas9 protein.

A kit is in addition disclosed for testing CRISPR-mediated homology-directed repair pathway. It typically includes these components: (1) a donor construct; (2) a DNA molecule encoding a sgRNA capable of hybridizing to a segment within the upstream or downstream non-coding sequence of the pre-determined genomic sequence; and (3) a DNA molecule encoding a Cas9 protein.

A method for testing CRISPR-mediated homology-directed repair pathway is also provided by way of using the donor construct. The method includes the steps of: (i) contacting a cell with a donor construct, a DNA molecule encoding a sgRNA capable of hybridizing to a segment (i.e., target sequence site) within the upstream or downstream non-coding sequence of the pre-determined genomic sequence, and a DNA molecule encoding a Cas9 protein; and (ii) detecting a signal generated by the reporter gene protein.

Additionally disclosed is a method for identifying an enhancer for CRISPR-induced homology-directed repair pathway, comprising the steps of: (i) contacting, in the presence and absence of a candidate compound, a cell with the donor construct, a DNA molecule encoding a sgRNA capable of hybridizing to a segment within the upstream or downstream non-coding sequence of the pre-determined genomic sequence, and a DNA molecule encoding a Cas9 protein; and (ii) detecting signals generated by the reporter gene protein; and (iii) determining the compound as an enhancer of CRISPR-induced homology-directed repair pathway when a higher reporter gene protein signal is detected in the presence of the compound than in the absence of the compound, and determining the compound as an inhibiter of CRISPR-induced homology-directed repair pathway when a lower reporter gene protein signal is detected in the presence of the compound than in the absence of the compound.

As a variation of the second type of gene-editing system, a donor construct is disclosed as comprising (1) a coding sequence for a reporter gene; (2) a bicistronic element at the 5' end of the reporter gene coding sequence; (3) a poly A segment at the 3' end of the reporter gene coding sequence, (4) optionally with one sg-A target sequence site located at the 5' end of the reporter gene coding sequence or 3' end of the poly A segment, or with two sgA target sequence sites one located at the 5' end of the reporter gene coding sequence and the other located at the 3' end of the poly A segment; and (5) optionally with a sequence containing multiple stop codons inserted at the 5' end of the bicistronic element. A preferred form of the construct is a circular form such as a plasmid. In some embodiments, the reporter gene encodes for a green fluorescent protein (GFP) or a drug resistance gene.

Another aspect of the disclosure is a host cell comprising the donor construct described above and also in the various sections of this application. The cell may be a stem cell or a somatic cell, and the cell may be a human cell or an animal cell. In some embodiments, the cell is a human stem cell. In a preferred embodiment, the donor construct has been incorporated into the genome of the cell. In one embodiment, the host cell comprises a LO2 cell line having a large deletion in all LIG4 gene loci as determined by a lack of expression of DNA ligase IV protein. In one embodiment, the lack of expression of the DNA ligase IV protein can be determined by one of more methods routinely used in the art, for example, Western blot. In one embodiment, the host cell can comprise a human somatic cell.

Further disclosed is a composition comprising a cell, a donor construct, a DNA molecule encoding a sgRNA capable of hybridizing to a target sequence site; and a DNA molecule encoding a Cas9 protein.

A kit is in addition disclosed for testing CRISPR-induced homology-directed repair. It typically includes these components: (1) a donor construct; (2) a DNA molecule encoding a sgRNA capable of hybridizing to a target sequence site; and (3) a DNA molecule encoding a Cas9 protein.

A method of using this type of construct is disclosed for testing CRISPR-induced non-homologous end joining. The method comprises the steps of: (i) contacting a cell with the donor construct of this variation, one or two DNA molecules encoding one or two sgRNAs each capable of hybridizing to one of the target sequence sites, and a DNA molecule encoding a Cas9 protein; and (ii) detecting a signal generated by the reporter gene protein.

Additionally disclosed is a method for identifying an enhancer for CRISPR-induced non-homologous end joining repair using this variation of the donor construction. The method includes the steps of: (i) contacting, in the presence and absence of a candidate compound, a cell with the donor construct, one or two DNA molecules encoding one or two sgRNAs each capable of hybridizing to one of the target sequence sites, and a DNA molecule encoding a Cas9 protein; and (ii) detecting signals generated by the reporter gene protein; and (iii) determining the compound as an enhancer of CRISPR-induced homology-directed repair when a higher reporter gene protein signal is detected in the presence of the compound than in the absence of the compound, and determining the compound as an inhibitor of CRISPR-induced non-homologous end joining repair when a lower reporter gene protein signal is detected in the presence of the compound than in the absence of the compound. In some embodiments, the cell in step (i) is contacted with two DNA molecules encoding two sgRNAs, one capable of hybridizing to the target sequence site(s) within the donor construct and the other capable of hybridizing to the non-coding sequences in a pre-determined genomic region.

As another variation of the second type of gene-editing system, a donor construct is disclosed as comprising (1) a coding sequence for a reporter gene; (2) a bicistronic element at the 5' end of the reporter gene coding sequence; (3) a polyA segment at the 3' end of the reporter gene coding sequence; (4) a first genomic homology segment located at the 5' end of the bicistronic element; and (5) a second genomic homology segment located at the 3' end of the polyA segment, wherein the first and second genomic homology segments are homologous to a pre-determined genomic sequence. In one embodiment, the donor construct further comprises a target sequence site at the 5' end of the first genomic homology segment or at the 3' end of the second genomic homology segment. A preferred form of the construct is a circular form such as a plasmid. In some embodiments, the reporter gene encodes for a green fluorescent protein (GFP) or a drug resistance gene. In some embodiments, the bicistronic element is heterologous to the reporter gene. In some embodiments, the pre-determined genomic sequence comprises a house-keeping gene. In some embodiments, the pre-determined genomic sequence comprises a silenced gene. In some embodiments, each of the first and second genomic homology segments is about 100-5000, 200-2500, 500-1500, or preferably about 1000 nucleotides in length. In one embodiment, the donor construct can include one or more reporter genes. In one embodiment, the donor construct can include two coding sequences that encode for two distinct reporter genes. In another embodiment, the donor construct can include two reporter genes. In another embodiment, the donor construct can include two copies a reporter gene, preferably in different orientations within the donor construct (i.e., a two directional donor construct). In another embodiment, the donor construct can comprise a single cut linearized donor plasmid. In yet another embodiment, the donor construct can comprise a double cut linearized donor plasmid. In one embodiment, the donor construct can further include a first LoxP sequence at the 5' end of the bicistronic element and a second LoxP sequence at the 3' end of the poly A segment.

Another aspect of the disclosure is a host cell comprising the donor construct described above and also in the various sections of this application. The cell may be a stem cell or a somatic cell, and the cell may be a human cell or an animal cell. In some embodiments, the cell is a human stem cell. In a preferred embodiment, the donor construct has been incorporated into the genome of the cell. In one embodiment, the donor construct can further comprise a target sequence site at the 5' end of the first genomic homology segment or at the 3' end of the second genomic homology segment. In one embodiment, the host cell comprises a LO2 cell line having a large deletion in all LIG4 gene loci as determined by a lack of expression of DNA ligase IV protein. In one embodiment, the lack of expression of the DNA ligase IV protein can be determined by one of more methods routinely used in the art, for example, Western blot. In one embodiment, the host cell can comprise a human somatic cell.

Further disclosed is a composition comprising a cell, a donor construct, a DNA molecule encoding a sgRNA capable of hybridizing to a segment within the upstream or downstream non-coding sequence of the pre-determined genomic sequence; and a DNA molecule encoding a Cas9 protein.

A kit is in addition disclosed for testing CRISPR-induced homology-directed repair. It typically includes these components: (1) a donor construct; (2) a DNA molecule encoding a sgRNA capable of hybridizing to a segment within the upstream or downstream non-coding sequence of the pre-determined genomic sequence; and (3) a DNA molecule encoding a Cas9 protein.

A method of using this type of construct is disclosed for testing CRISPR-induced non-homologous end joining. The method comprises the steps of: (i) contacting a cell with the donor construct of this variation, one or two DNA molecules encoding one or two sgRNAs each capable of hybridizing to one of the target sequence sites, and a DNA molecule encoding a Cas9 protein; and (ii) detecting a signal generated by the reporter gene protein.

A method of using this type of construct is disclosed for testing CRISPR-induced homology-directed repair and non-homology end joining in parallel, comprising the steps of: (i) contacting a cell with the donor construct described above, a DNA molecule encoding a sgRNA capable of hybridizing to a segment within the upstream or downstream non-coding sequence of the pre-determined genomic sequence and the donor construct, and a DNA molecule encoding a Cas9 protein; wherein an absence of the DNA molecule encoding the sgRNA capable of hybridizing to the donor construct pertains to homology-directed repair, and inclusion of the DNA molecule encoding the sgRNA capable of hybridizing to the donor construct pertains to non-homology end joining repair; and (ii) detecting a signal generated by the reporter gene protein.

A method of using this type of construct is disclosed for identifying an enhancer for CRISPR-induced homology-directed repair, comprising the steps of: (i) contacting, in the presence and absence of a candidate compound, a cell with the donor construct described above, a DNA molecule encoding a sgRNA capable of hybridizing to a segment within the upstream or downstream non-coding sequence of the pre-determined genomic sequence, and a DNA molecule encoding a Cas9 protein; and (ii) detecting signals generated by the reporter gene protein; and (iii) determining the compound as an enhancer of CRISPR-induced homology-directed repair when a higher reporter gene protein signal is detected in the presence of the compound than in the absence of the compound, and determining the compound as an inhibiter of CRISPR-induced homology-directed repair when a lower reporter gene protein signal is detected in the presence of the compound than in the absence of the compound.

As yet another variation of the second type of gene-editing system, a donor construct is disclosed as comprising (1) a coding sequence for a reporter gene; (2) a universal and constitutive promoter at the 5' end of the reporter gene coding sequence; (3) a poly A segment at the 3' end of the reporter gene coding sequence; (4) a first genomic homology segment located at the 5' end of the universal and constitutive promoter; and (5) a second genomic homology segment located at the 3' end of the polyA segment, wherein the first and second genomic homology segments are homologous to a pre-determined genomic sequence. In one embodiment, the donor construct further comprises a target sequence site at the 5' end of the first genomic homology segment or at the 3' end of the second genomic homology segment. A preferred form of the construct is a circular form such as a plasmid. In some embodiments, the reporter gene encodes for a green fluorescent protein (GFP) or a drug resistance gene. In some embodiments, the universal and constitutive promoter is heterologous to the reporter gene. In some embodiments, the pre-determined genomic sequence comprises a house-keeping gene. In some embodiments, the pre-determined genomic sequence comprises a silenced gene. In some embodiments, each of the first and second genomic homology segments is about 100-5000, 200-2500, 500-1500, or preferably about 1000 nucleotides in length.

Another aspect of the disclosure is a host cell comprising the donor construct described above and also in the various sections of this application. The cell may be a stem cell or a somatic cell, and the cell may be a human cell or an animal cell. In some embodiments, the cell is a human stem cell. In a preferred embodiment, the donor construct has been incorporated into the genome of the cell. In one embodiment, the donor construct can further comprise a target sequence site at the 5' end of the first genomic homology segment or at the 3' end of the second genomic homology segment. In one embodiment, the host cell comprises a LO2 cell line having a large deletion in all LIG4 gene loci as determined by a lack of expression of DNA ligase IV protein. In one embodiment, the lack of expression of the DNA ligase IV protein can be determined by one of more methods routinely used in the art, for example, Western blot. In one embodiment, the host cell can comprise a human somatic cell.

Further disclosed is a composition comprising a cell, a donor construct, a DNA molecule encoding a sgRNA capable of hybridizing to a segment within the upstream or downstream non-coding sequence of the pre-determined genomic sequence; and a DNA molecule encoding a Cas9 protein.

A kit is in addition disclosed for testing CRISPR-induced homology-directed repair. It typically includes these components: (1) a donor construct; (2) a DNA molecule encoding a sgRNA capable of hybridizing to a segment within the upstream or downstream non-coding sequence of the pre-determined genomic sequence; and (3) a DNA molecule encoding a Cas9 protein.

A method for inserting the reporter to an active gene locus via CRISPR-induced homology directed repair is disclosed. The method comprises the steps of: (i) contacting a cell with the donor construct of this variation, a DNA molecule encoding a sgRNA capable of hybridizing to a segment within the upstream or downstream non-coding sequence of the pre-determined genomic, and a DNA molecule encoding a Cas9 protein; and (ii) detecting a signal generated by the reporter gene protein.

A method for inserting the reporter to a silenced genome locus via CRISPR-induced homology-directed repair is disclosed. The method comprises the steps of: (i) contacting a cell with the donor construct described above, one or two DNA molecules encoding one or two sgRNAs each capable of hybridizing to one of the target sequence sites, and a DNA molecule encoding a Cas9 protein; and (ii) detecting a signal generated by the reporter gene protein. In one embodiment, the method comprises multiple passages to avoid detection of transient expression. In one embodiment, multiple passages refers to not less than 5 passages.

A method of using this type of construct is disclosed for CRISPR-induced homology-directed repair, comprising the steps of: (i) contacting, in the presence and absence of a candidate compound, a cell with a donor construct as described above, a DNA molecule encoding a sgRNA capable of hybridizing to a segment within the upstream or downstream non-coding sequence of the pre-determined genomic sequence, and a DNA molecule encoding a Cas9 protein; and (ii) detecting signals generated by the reporter gene protein; and (iii) determining the compound as an enhancer of CRISPR-induced homology-directed repair when a higher reporter gene protein signal is detected in the presence of the compound than in the absence of the compound, and determining the compound as an inhibiter of CRISPR-induced homology-directed repair when a lower reporter gene protein signal is detected in the presence of the compound than in the absence of the compound.

As a further variation of the second type of gene-editing system, a donor construct is disclosed as comprising (1) a coding sequence for a reporter gene; (2) a bicistronic element at the 5' end of the reporter gene coding sequence; and (3) a polyA segment at the 3' end of the reporter gene coding sequence, optionally with a target sequence site located at the 5' end of the reporter gene coding sequence, or with two target sequence sites one located at the 5' end of the reporter gene coding sequence and the other located at the 3' end of the poly A segment. A preferred form of the construct is a circular form such as a plasmid. In some embodiments, the reporter gene encodes for a green fluorescent protein (GFP) or a drug resistance gene. In some embodiments, the bicistronic element is heterologous to the reporter gene. In one embodiment, the donor construct further comprises a first genomic homology segment located at the 5' end of the bicistronic element; and a second genomic homology segment located at the 3' end of the reporter gene, wherein the first and second genomic homology segments are homologous to a pre-determined genomic sequence. In some embodiments, the pre-determined genomic sequence comprises a house-keeping gene. In some embodiments, the pre-determined genomic sequence comprises a silenced gene. In some embodiments, each of the first and second genomic homology segments is about 100-5000, 200-2500, 500-1500, or preferably about 1000 nucleotides in length. In one embodiment, the donor construct can include one or more reporter genes. In one embodiment, the donor construct can include two coding sequences that encode for two distinct reporter genes. In another embodiment, the donor construct can include two reporter genes. In another embodiment, the donor construct can include two copies a reporter gene, preferably in different orientations within the donor construct (i.e., a two directional donor construct). In another embodiment, the donor construct can comprise a single cut linearized donor plasmid. In yet another embodiment, the donor construct can comprise a double cut linearized donor plasmid. In one embodiment, the donor construct can further include a first LoxP sequence at the 5' end of the bicistronic element and a second LoxP sequence at the 3' end of the poly A segment.

Another aspect of the disclosure is a host cell comprising the donor construct described above and also in the various sections of this application. The cell may be a stem cell or a somatic cell, and the cell may be a human cell or an animal cell. In some embodiments, the cell is a human stem cell. In a preferred embodiment, the donor construct has been incorporated into the genome of the cell. In one embodiment, the donor construct further comprises two target sequence sites one located at the 5' end of the reporter gene coding sequence and the other located at the 3' end of the poly A segment. In one embodiment, the host cell comprises a LO2 cell line having a large deletion in all LIG4 gene loci as determined by a lack of expression of DNA ligase IV protein. In one embodiment, the lack of expression of the DNA ligase IV protein can be determined by one of more methods routinely used in the art, for example, Western blot. In one embodiment, the host cell can comprise a human somatic cell.

Further disclosed is a composition comprising a cell, a donor construct, one or two DNA molecules encoding one or two sgRNAs each capable of hybridizing to one of the target sequence sites; and a DNA molecule encoding a Cas9 protein.

A kit is in addition disclosed for testing CRISPR-induced homology-directed repair. It typically includes these components: (1) a donor construct; (2) one or two DNA molecules encoding one or two sgRNAs each capable of hybridizing to one of the target sequence sites; and (3) a DNA molecule encoding a Cas9 protein.

A method of using this type of construct is disclosed for testing CRISPR-induced non-homologous end joining. The method comprises the steps of: (i) contacting a cell with the donor construct of this variation, one or two DNA molecules encoding one or two sgRNAs each capable of hybridizing to one of the target sequence sites, and a DNA molecule encoding a Cas9 protein; and (ii) detecting a signal generated by the reporter gene protein.

A method of using this type of construct is disclosed for identifying an enhancer for CRISPR-induced non-homologous end joining repair, comprising the steps of: (i) contacting, in the presence and absence of a candidate compound, a cell with a donor construct as described above, one or two DNA molecules encoding one or two sgRNAs each capable of hybridizing to one of the target sequence sites, and a DNA molecule encoding a Cas9 protein; and (ii) detecting signals generated by the reporter gene protein; and (iii) determining the compound as an enhancer of CRISPR-induced homology-directed repair when a higher reporter gene protein signal is detected in the presence of the compound than in the absence of the compound, and determining the compound as an inhibitor of CRISPR-induced homology-directed repair when a lower reporter gene protein signal is detected in the presence of the compound than in the absence of the compound.

In yet a further variation of the second type of gene-editing system, a donor construct is disclosed as comprising (1) a coding sequence for a reporter gene; (2) a universal and constitutive promoter at the 5' end of the reporter gene coding sequence; and (3) a polyA segment at the 3' end of the reporter gene coding sequence, optionally with a target sequence site located at the 5' end of the reporter gene coding sequence, or with two target sequence sites one located at the 5' end of the reporter gene coding sequence and the other located at the 3' end of the poly A segment. A preferred form of the construct is a circular form such as a plasmid. In some embodiments, the reporter gene encodes for a green fluorescent protein (GFP) or a drug resistance gene. In some embodiments, the universal and constitutive promoter is heterologous to the reporter gene. In one embodiment, the donor construct further comprises a first genomic homology segment located at the 5' end of the universal and constitutive promoter; and a second genomic homology segment located at the 3' end of the reporter gene, wherein the first and second genomic homology segments are homologous to a pre-determined genomic sequence. In some embodiments, the pre-determined genomic sequence comprises a house-keeping gene. In some embodiments, the pre-determined genomic sequence comprises a silenced gene. In some embodiments, each of the first and second genomic homology segments is about 100-5000, 200-2500, 500-1500, or preferably about 1000 nucleotides in length. In one embodiment, the donor construct is a constant expression construct such CE NH-donor.

Another aspect of the disclosure is a host cell comprising the donor construct described above and also in the various sections of this application. The cell may be a stem cell or a somatic cell, and the cell may be a human cell or an animal cell. In some embodiments, the cell is a human stem cell. In a preferred embodiment, the donor construct has been incorporated into the genome of the cell. In one embodiment, the donor construct further comprises two target sequence sites one located at the 5' end of the reporter gene coding sequence and the other located at the 3' end of the poly A segment.

Further disclosed is a composition comprising a cell, a donor construct, one or two DNA molecules encoding one or two sgRNAs each capable of hybridizing to one of the target sequence sites; and a DNA molecule encoding a Cas9 protein.

A kit is in addition disclosed for testing CRISPR-induced homology-directed repair. It typically includes these components: (1) a donor construct; (2) one or two DNA molecules encoding one or two sgRNAs each capable of hybridizing to one of the target sequence sites; and (3) a DNA molecule encoding a Cas9 protein.

A method of using this type of construct is disclosed for testing CRISPR-induced non-homologous end joining. The method comprises the steps of: (i) contacting a cell with the donor construct of this variation, one or two DNA molecules encoding one or two sgRNAs each capable of hybridizing to one of the target sequence sites, and a DNA molecule encoding a Cas9 protein; and (ii) detecting a signal generated by the reporter gene protein. In one embodiment, the cell in step (i) is contacted with two DNA molecules encoding two sgRNAs, wherein one sgRNA is capable of hybridizing to a target sequence site within the donor construct and the second sgRNA is capable of hybridizing to a non-coding sequence in a pre-determined genomic region A method of using this type of construct is disclosed for identifying an enhancer for CRISPR-induced non-homologous end joining repair, comprising the steps of: (i) contacting, in the presence and absence of a candidate compound, a cell with a donor construct as described above, one or two DNA molecules encoding one or two sgRNAs each capable of hybridizing to one of the target sequence sites, and a DNA molecule encoding a Cas9 protein; and (ii) detecting signals generated by the reporter gene protein; and (iii) determining the compound as an enhancer of CRISPR-induced homology-directed repair when a higher reporter gene protein signal is detected in the presence of the compound than in the absence of the compound, and determining the compound as an inhibitor of CRISPR-induced homology-directed repair when a lower reporter gene protein signal is detected in the presence of the compound than in the absence of the compound.

As a further variation of the second type of gene-editing system, a donor construct is disclosed as comprising (1) a coding sequence for a first reporter gene; (2) a coding sequence for a second reporter gene; (3) a PolyA segment located at the 3' end of the first reporter gene coding sequence; (4) a PolyA segment located at the 3' end of the second reporter; wherein the first and second coding sequences for the first and second reporter genes are in different orientations; and (5) a target sequence site located at the 5' end of the second reporter gene. In one embodiment, the donor construct as described above, comprises a dual color donor construct that is capable of expressing the first or second reporter gene upon non-directional integration. In one embodiment, the reporter gene expressed by the donor construct is dependent on the orientation of the donor construct upon integration.

A method of using this type of construct is disclosed for testing CRISPR-induced non-homologous end joining. The method comprises the steps of: (i) contacting a cell with the donor construct described above, a DNA molecule encoding a sgRNA capable of hybridizing to the target sequence site; and a DNA molecule encoding a Cas9 protein; and (ii) detecting a signal generated by the reporter gene protein.

As a further variation of the second type of gene-editing system, a donor construct is disclosed as comprising (1) a coding sequence for a first reporter gene; (2) a coding sequence for a second reporter gene; (3) a Poly A segment located at the 3' end of the first reporter gene coding sequence; (4) a PolyA segment located at the 3' end of the second reporter; wherein the first and second coding sequences for the first and second reporter genes are in different orientations; and (5) a target sequence site located at the 5' end of the second reporter gene. In one embodiment, the donor construct as described above, comprises a dual color donor construct that is capable of expressing the first or second reporter gene upon non-directional integration. In one embodiment, the reporter gene expressed by the donor construct is dependent on the orientation of the donor construct upon integration.

A method of using this type of construct is disclosed for testing CRISPR-induced non-homologous end joining. The method comprises the steps of: (i) contacting a cell with the donor construct described above, a DNA molecule encoding a sgRNA capable of hybridizing to the target sequence site; and a DNA molecule encoding a Cas9 protein; and (ii) detecting a signal generated by the reporter gene protein.

According to one aspect, a donor construct, method and system is provided for unidirection-preferred knock-in induced by non-homologous end joining using CRISPR/Cpf1. In one embodiment, a CRISPR/Cpf1 donor construct is disclosed comprising a (1) a coding sequence for a reporter gene; (2) a bicistronic element at the 5' end of the reporter gene coding sequence; (3) a polyA segment at the 3' end of the reporter gene coding sequence; and (4) a target sequence site located at the 5' end of the bicistronic element; wherein the target sequence site at the 5' end of the bicistronic element is capable of producing a staggered DNA double stranded break when subjected to Cpf1.

In one embodiment, the invention further provides a method for testing CRISPR/Cpf1-induced NHEJ repair, comprising the steps of: (i) contacting a cell with the donor construct described above, a DNA molecule encoding a sgRNA capable of hybridizing to the target sequence site; and a DNA molecule encoding a Cpf1 protein; and (ii) detecting a signal generated by the reporter gene.

According to one aspect, a construct, method and system is provided for non-homologous end joining integration of multiple reporter genes into multiple genomic alleles. In one embodiment, a donor construct is disclosed comprising a plurality of donor constructs each having a coding sequence for a different reporter gene; (2) a target sequence site located at the 5' end of each reporter gene coding sequence; and (3) a polyA segment located at the 3' end of the reporter gene coding sequence. In one embodiment, the donor construct further comprises a different fluorescent reporter gene in each of the plurality of donor constructs. In another embodiment, the donor construct further comprises a different drug resistance reporter gene in each of the plurality of donor constructs. In another embodiment, tandem repeats of human insulator sequences serves a blocking element to reduce the expression of target gene at the 5' end of the sg-A target sequence site located at the 5' end of the reporter gene coding sequence.

As a further variation, a donor construct is disclosed as comprising (1) a coding sequence for a reporter gene; (2) a poly A segment at the 3' end of the reporter gene coding sequence; (3) with a sg-A target sequence site located at the 5' end of the reporter gene coding sequence, or with two target sequence sites one located at the 5' end of the reporter gene coding sequence and the other located at the 3' end of the polyA segment; and (4) tandem repeats of human insulator sequences at the 5' end of the sg-A target sequence site located at the 5' end of the reporter gene coding sequence.

A donor construct comprising a first and second reporter, wherein the first reporter is under the control of a bicistronic element and the second reporter is under the control of a universal and constitutive promoter, wherein the donor construct comprises: (1) a reporter cassette of the construct described herein, comprising a coding sequence for a reporter gene, a bicistronic element at the 5' end of the reporter gene coding sequence, a poly A segment at the 3' end of the reporter gene coding sequence; (2) a sg-A target sequence site located at the 5' end of bicistronic element of the first reporter gene coding sequence; (3) a reporter cassette of the construct described herein, comprising a coding sequence for a reporter gene, a universal and constitutive promoter at the 5' end of the reporter gene coding sequence, a poly A segment at the 3' end of the reporter gene coding sequence; (4) two LoxP sites, one located at the 5' end of the sg-A target sequence and one located at the 3' end of the poly A segment following the first reporter gene coding sequence.

As a further variation, a donor construct is disclosed as comprising (1) a coding sequence fora first reporter gene, followed by a poly A segment located at its 3' end; (2) a sg-A target sequence site located at the 5' end of the first reporter gene coding sequence; (3) a coding sequence for a second reporter gene followed by a poly A segment located at its 3' end, located at the 5' end of the sg-A target sequence in a head-to-head manner to the first reporter gene coding sequence.

As a further variation, a donor construct is disclosed as comprising (1) a coding sequence for a reporter gene; (2) a bicistronic element at the 5' end of the reporter gene coding sequence; (3) a poly A segment at the 3' end of the reporter gene coding sequence; and (4) a sgRNA sequence site located at the 5' end of the bicistronic element; wherein the sgRNA sequence site at the 5' end of the bicistronic element is capable of producing a targeted DNA double stranded break when subjected to Cpf1 induced cleavage.

As a further variation, a donor construct is disclosed as comprising (1) a coding sequence for a reporter gene; (2) a universal and constitutive promoter at the 5' end of the reporter gene coding sequence; (3) a poly A segment at the 3' end of the reporter gene coding sequence; and (4) optionally with a sg-A target sequence site located at the 5' end of the reporter gene coding sequence, or with two target sequence sites one located at the 5' end of the reporter gene coding sequence and the other located at the 3' end of the poly A segment. In some embodiments, the constructs do not comprise segments homologous to a pre-determined genomic sequence.

In one embodiment, a method for inserting a reporter gene at an active gene locus to generate reporter cells via CRISPR-induced non-homologous end joining repair, comprising the steps of: (i) contacting a cell with the donor construct described herein, one or two DNA molecules encoding one or two sgRNAs each capable of hybridizing to one of the target sequence sites, and a DNA molecule encoding a Cas9 protein; (ii) detecting a signal generated by the reporter gene protein; and (iii) collecting cells that showing co-occurrence of more than two reporter signals.

In one embodiment, a method for inserting the reporter to an active gene locus to trace its expression change via CRISPR-induced non-homologous end joining repair is disclosed as comprising (1) contacting a cell with the donor construct described herein, one or two DNA molecules encoding one or two sgRNAs each capable of hybridizing to one of the target sequence sites, and a DNA molecule encoding a Cas9 protein; and (2) detecting a signal generated by the reporter gene protein.

In one embodiment, method for inserting the reporter to a silenced gene locus via CRISPR-induced non-homologous end joining repair, comprising the steps of: (i) contacting a cell with the donor construct described herein, one or two DNA molecules encoding one or two sgRNAs each capable of hybridizing to one of the target sequence sites, and a DNA molecule encoding a Cas9 protein; and (ii) detecting a signal generated by the reporter gene protein.

In one embodiment, a method for inserting the reporter to simultaneously disrupt multiple copies of a target gene in a genome thus generating loss-of-function (knock-out) cells via CRISPR-induced non-homologous end joining repair, comprising the steps of (i) contacting a cell with a plurality of donor constructs described herein, each having a coding sequence for a different reporter gene, one or two DNA molecule encoding a sgRNA capable of hybridizing to the target sequence site and a DNA molecule encoding a Cas9 protein; (ii) detecting signals generated by the reporter gene proteins; and (iii) collecting cells that showing co-occurrence of more than two reporter signals.

In one embodiment, a method for inserting the reporter to a silenced gene locus, for the purpose of tracing the activation of target gene, via CRISPR-induced non-homologous end joining repair, comprising the steps of: (i) contacting a cell with the donor constructs described herein, one or two DNA molecules encoding a sgRNA capable of hybridizing to the target sequence site and a DNA molecule encoding a Cas9 protein; (ii) detecting a signal generated by the second reporter gene protein; (iii) collecting cells that showing signal generated by the second reporter gene protein; and (iv) contacting collected reporter cells with a DNA molecule encoding CRE endonuclease to remove extra parts of the inserted donor.

In one embodiment, a method of inserting the reporter to an active gene via CRISPR-induced non-homologous end joining repair, comprising the steps of: (i) contacting a cell with the donor construct described herein, one or two DNA molecules encoding one or two sgRNAs each capable of hybridizing to one of the sg-A target sequence sites, and a DNA molecule encoding a Cas9 protein; and (ii) detecting signals generated by the first and the second reporters.

In one embodiment, a method for inserting the reporter gene in a more precise way via CRISPR-induced non-homologous end joining repair, comprising the steps of: (i) contacting a cell with the donor construct described herein, one or two DNA molecules encoding one or two sgRNAs each capable of hybridizing to one of the sgRNA sequence sites; and a DNA molecule encoding a Cpf1 protein; and (ii) detecting a signal generated by the reporter gene.

In one embodiment, a method for testing CRISPR-induced non-homologous end joining is provided, the method comprising the steps of: (i) contacting a cell with a donor construct, wherein the donor construct includes a plurality of donor constructs each having a coding sequence for a different reporter gene, a target sequence site located at the 5' end of each reporter gene coding sequence, and a poly A segment located at the 3' end of the reporter gene coding sequence, a DNA molecule encoding a sgRNA capable of hybridizing to the target sequence site and a DNA molecule encoding a Cas9 protein; and (ii) detecting a signal generated by the reporter gene protein.

BRIEF DESCRIPTION OF THE DRAWINGS

FIG. 1 Schematics of broken GFP reporter plasmids design and targeting strategy for HDR-mediated knock-in of PGK-Puro2a(B)cGFP at target gene locus.

FIG. 2 Schematics of the donor plasmids design and targeting strategy at knock-in broken GFP reporter locus on genome.

FIG. 3 HDR-mediated gene targeting induced by Cas9 system in HEK293T-AAVS1(b)GFP reporter cell line.

FIG. 4 Genome integration of reporter vector into H1-(b) GFP reporter line and DSB induced by Cas9 system. (FIG. 4A) PCR with genomic DNA confirming Piggy Bac_(B) cGFP reporter vector knock-in at the AAVS1 locus on genome. (FIG. 4B) T7E1 assays showing the efficiency of genome DSB by Cas9/sg-X.

FIG. 5 Design of a system to directly detect CRISPR/ Cas9-induced HDR-mediated reporter insertion at the GAPDH 3'-UTR.

FIG. 6 Varied frequency of HDR-mediated gene targeting of GAPDHdonor-HDR, 1 in different human cell lines. (FIG. 6C) Sequencing results of the PCR fragments amplified from the junctions. Expected modifications in both 5' and 3-junctions were detected, indicating precise integration of 2a-copGFP through HDR-mediated repair of the Cas9/sg-1-induced DSBs (SEQ ID NOs: 147-166, top to bottom, respectively). (FIG. 6D) FACS analysis of H1 human ESCs and different human somatic cell lines, showing HDR-mediated integration of 2a-copGFP in the presence of wt or D10A Cas9 and sg-1. Cell samples were co-transfected with Cas9/sgRNAs and donor plasmids, and analyzed four days after transfection.

FIG. 8 Genome PCR detected re-joining of genome and donor fragments in non-GFP expressing integrations. (FIG. 8B) PCR with genomic DNA detected the junction fragments that represent non-GFP expressing integrations of the donors and fragments.

FIG. 9 Comparison of NHEJ and HDR-targeting in different human cell lines. (FIG. 9E) Top panel shows the sequencing results of the 5'-juctions in the HDR-targeting induced with Cas9/sg-1. Second panel shows schematics of sg-2 and sg-3 target sites in genome and GAPDHdonor-HDR.2, as well as the positions of cleavage and re-joining during integrations induced with Cas9/sg-2 or sg-3 via NHEJ repair. Third panel shows sequencing results of the 5-junctions. Fourth panel shows sequencing results in the 5'-junctions of integrations induced with Cas9/sg-4. Bottom panel shows sequencing results in the 5'-junctions of integrations induced by co-transfection with Cas9/sg-3 and sg-4 (SEQ ID NOs: 286-310, top to bottom. respectively).

FIG. 10 CRISPR/Cas9-induced NHEJ-mediated knock-in of ires-eGFP reporter at OCT4 and ACTB 3'-UTR in H1 human ESCs. (FIG. 10E) Sequences of the integration junctions amplified in B. The 5'- and 3'-junctions were analyzed individually. For each junction multiple sequences are shown. Nucleotides of different sgRNA target sites and PAMs are color-coded. Sequences from donor templates are shown in grey, and genomic DNA flanking the integration junctions are shown in black (SEQ ID NOs: 313-325, top to bottom, respectively).

FIG. 11 Selection-free generation of knock-in clones via the homology-independent knock-in approach.

FIG. 12 Conventional NHEJ repair mediates efficient knock-in of large reporter genes.

FIG. 13 Comparison between HDR- and NHEJ-mediated reporter knock-in. (FIG. 13C) FACS analysis showing HDR-mediated knock-in with circular and linear donor templates. The ires-eGFP(+HAs) Donor-2, 2.A or 2.B were transfected together with Cas9/sg-1 or Cas9/sg-2. The Donor-2.A and 2.B were both examined in the presence of sg-A (linear) as well as in the absence of sg-A (circular). Cas9/sg-A cleaves the Donor-2.A at 3' of the ires-eGFP(+HAs) cassette and the linearized Donor 2.A produced GFP+ cells via HDR-mediated knock-in. Distinctly, Cas9/sg-A cleaves the Donor-2.B at 5' of the ires-eGFP(+HAs) cassette, and the linearized Donor 2.B produced high proportion of GFP+ cells via both NHEJ- and HDR-mediated knock-in.

FIG. 14 NHEJ-mediated reporter knock-in at silenced genome loci.

FIG. 15 Homology-independent knock-in at silent gene loci with loxp sites. (FIG. 15A) Schematic view of Cas9 induced homology-independent knock-in at silent gene loci. Endogenous sgRNA induce genomic DSBs, and sg-A induce cleavage on donor plasmid. NH-S donor 4 for silent gene targeting contains PGK-eGFP-pA cassette for knock-in selection, ires-td Tomato-pA for reporter application and LoxP sites for the deletion of unnecessary part after florescent selection. NH-S donor 1, 2 and 3 have similar functional purposes. (FIG. 15B) NH-S donor 4 was used for the reporter knock-in at GADPH 3'-UTR loci. The flow detection showed positive signal for the td-Tomato expression, which represented successful knock-in and suggested the functional role of this type of donors. (FIG. 15C) Flow analysis of NH-S donor 4 was carried out for the detection of knock-in at 3'-UTR of Sox1 and Foxa2 sites. The much higher GFP positive ratios compared with control group indicated successfully knock-in at this sites.

(FIG. 16A) Schematic view of Cas9 induced NHEJ-mediated two directional florescence knock-in. Endogenous sgRNA induces genomic DSBs, and sg-A induce cleavage on donor plasmid. Two directional florescence donor contains eGFP-pA cassette and TD tomato-pA cassette for reporter application. NHEJ-mediated non directional integration induced two directional knock-in. With this new donor, one directional integration could produce eGFP expression (FIG. 16A, left side), and the other directional integration could produce TD tomato expression (FIG. 16A, right side). (FIG. 16B) SgGAPDH targeting GAPDH 5'-UTR was used to mediate the non-directional integration. Flow analysis was used for the knock-in detection. With the two directional florescence donor, Cas9/sg-A/sgGAPDH mediated-knock-in produced GFP+/TD−, GFP−/Td+ and GFP+/TD+ cell populations, suggesting the functional role of this new donor for non-directional integration.

(FIG. 17A) Schematic view of CPF1 induced homology-independent knock-in at 3'-UTR of GAPDH locus. sgGAPDH targets to endogenous GAPDH locus, and sg-A induces cleavage on donor plasmid. Two donors were used, namely complementary donor (C donor) and non-complementary donor (NC donor). (FIG. 17B) FACS analysis showing the reporter integration mediated by CPF1-induced DSBs. spCas9 induced NHEJ mediated knock-in serves as a positive control. CPF1 with C donor produce a much higher knock-in efficiency (7.04%) than that mediated with NC donor (2.69%), indicating a preferred directional integration.

FIG. 18 Homology-independent knock-in of multiple reporter genes into one target gene on multiple genomic alleles. (FIG. 18A) Schematic view of multiple allele knock-out strategy by Cas9 induced NHEJ-mediated knock-in. Endogenous sgRNA induces genomic DSBs at 5'-UTR of endogenous gene locus, and sg-A induces cleavage of donor plasmid. Multiple donor plasmids are provided for knock-in at the same time. With different reporters integrated, the targeted cell shows different fluorescent color or drug resistance. That means NH-insulator donor eGFP knock-in expresses GFP, NH-insulator donor TD Tomato knock-in expresses TD tomato, NH-insulator donor puro and NH-insulator donor Hygro show puromycin and hygromycin resistance, respectively. (FIG. 18B) Flow analysis for the targeting result at MRE11 locus, which employed both NH-insulator donor eGFP and NH-insulator donor tdTomato. Either GFP or tdTomato (single)-positive cells represent at least one allele was modified (FIG. 18, right panel). Double positive cell population represents those cells carrying knock-in at two alleles.

Figure 1A:
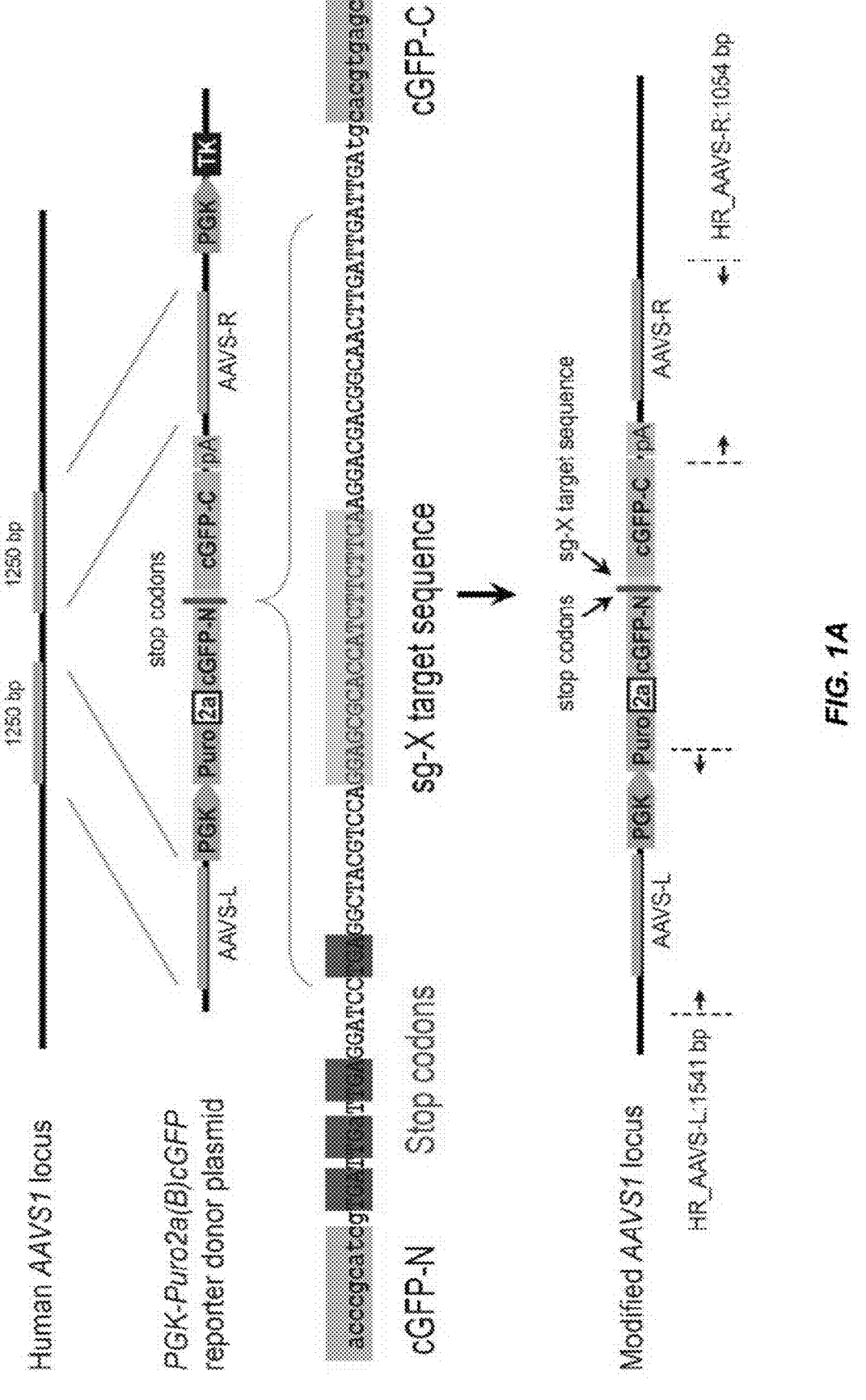
(FIG. 1A) Targeting to human AAVS1 genome locus in HEK293T-AAVS1 (b)GFP and H1-(b)GFP reporter cell lines (SEQ ID NO.

Table 1 DNA sequences bound by sgRNAs.

Table 2 Potential off-target sites for sgRNAs targeting GAPDH locus.

Table 3 Primers used for cloning and integration detections.

DETAILED DESCRIPTION OF THE INVENTION

I. Introduction

Gene targeting enables replacement of endogenous genome DNA segment in living cells with designed donor templates, allowing introducing a wide range of designed alterations [1]. Since 1980s, this technology has been widely used in generating genetically modified mice, becoming a fundamental and ultimate tool in analysing gene functions in living mammals [2]. Extensive studies of a large number of genes based on this technology have revolutionized our understanding on many aspects of gene regulations involved in mammalian development, metabolism and genetic diseases [3].

Genome editing tool has long been desired for studying human cells, especially after the advert of recent technologies for generating human pluripotent stem cells (hPSCs), including human embryonic stem cells (ESCs) and human induced pluripotent stem cells (iPSCs) [4,5]. These cells can robustly self-renew while remaining to be pluripotent in culture. Thus, they hold great potentials in providing unlimited and autologous sources for generating almost any functional cell type required for clinical transplantations [6]. However, harnessing the full potential of these cells requires efficient gene targeting, which is currently not available but is essential to understanding the gene regulations involved in lineage commitment, correcting disease-causative mutations in patient iPSCs, or eliminating potential immuno-stimulating antigens in human ESCs before further consideration of clinical applications [7,8].

In last two years, a novel endonuclease system, the clustered regularly interspaced short palindromic repeat (CRISPR) and CRISPR associated 9 (Cas9), has been established to mediate precise homologous recombination (HR) and applied for reporter knock-in, gene knockout, and gene correction [9-11]. In CRISPR/Cas9 system, small guide RNA (sgRNA) associates to Cas9 nuclease via a scaffold structure at its 3' terminus. sgRNA anneals to a target sequence (typically about 20 nucleotides) in genomic DNA in a base-pairing manner, which is adjacent to 5'-NGG-3' protospacer adjacent motifs (PAM). Subsequently double strand DNA break (DSB) is introduced at the target DNA which occurs at 3-bp upstream of the PAM. Similar to other DSBs, CRISPR/Cas9 system triggers DNA repair process via two distinct mechanisms, including non-homologous end joining (NHEJ) and homology-directed repair (HDR).

NHEJ pathway repairs DNA DSBs by joining the broken ends through a mechanistically flexible process. It often results in random small insertion or deletion (indels), thus it is error-prone [12]. CRISPR/Cas9-introduced DNA cleavage followed by NHEJ repair has been exploited to generate loss-of-function allele in protein-coding genes [13], but it is thought to have limited potential when targeted insertion of large fragments is desired. On the other hand, HDR pathway mediates a strand-exchange process to repair DNA damage accurately based on an existing template [14]. It provides a route to precisely replace a DNA segment in endogenous genome with donor templates carrying homologous arms, thus allowing introduction of a wide range of designed genetic modifications to living cells [1].

However, low HDR efficiency is acknowledged as the main challenge for clinical applications of CRISPR/Cas9 system in hPSCs. Studies showed that the HR in human ESC/iPSC present at a low efficiency, around 10E-5 [15]. The reasons behind are not fully understood. In addition, although the safety concerns caused by off-target mutations is another challenge of CRISPR/Cas9 system, several studies has investigated and concluded that the off-target mutations are very low in hPSC and thus it is not a significant concern for further research and clinical applications [2-4]. To date, it is critical and urgent to improve the efficiency of precise CRISPR-mediated gene editing in hPSC to meet the clinical requirement.

In the previous disclosure, U.S. Provisional patent No. 62/256,514, the inventors constructed universal reporter systems to detect CRISPR-mediated genomic integration of large DNA fragments in human ESCs and somatic cells lines. The system of this invention targets the genome locus encoding house-keeping gene GAPDH, which is constantly and universally expressed in almost all cell types. Combinatory use of this targeting locus with fluorescence protein (copGFP or eGFP) reporters would allow one to observe the gene targeting events directly and in a real time, in any human cell type used. The data showed that this reporter system can robustly detect HDR-mediated gene targeting directly within 4-5 days after transfection, which can serve as a superior universal platform for drug screening or mechanistic studies for improving the HDR efficiency as well as HDR-based gene targeting.

On the other hand, by targeting the same locus, the inventors construct another system to detect NHEJ mediated gene targeting. It was found that the system and targeting strategy described herein establish a novel method for gene targeting, through NHEJ. The efficiency of NHEJ targeting is much higher, reaching up to 20% in somatic cell lines and to 1.7% in human ESCs, without any pre-selection or enrichment procedures. The associated method and vector construction provide a promising and user-friendly tool to achieve high-efficiency gene targeting in human cells, especially in human ESCs/iPSCs. More importantly, the system in present invention can be universal, thus has potential to apply in many other human cell types, as well as other species including low vertebrate such as zebrafish and frog (*Xenopus*), with minor modification in the sgRNA construction.

In the present invention, further evidence is provided by inventors for the application of the Cas9-mediated genome editing system in various genomic loci and conditions. The molecular basis and efficiency of homology-independent reporter integrations were further demonstrated; and additional methods and systems for NHEJ-mediated efficient knock-in at silenced gene loci are provided. Additionally, off-target effects by a NHEJ-mediated knock-in system are investigated.

Furthermore, the present application discloses an additional method and system of homology-independent knock-in of reporter genes into CPF1-induced DSBs at 3'-UTR of GAPDH locus that demonstrates a preference for directional integration. Thus, the instant application discloses a construct, method and system for unidirection-preferred knock-in mediated by NHEJ using CRISPR/CPF1.

The instant application also discloses an additional method, construct, and system of homology-independent dual color insertion knock-in of reporter genes. Thus, the instant application discloses a method, construct, and system for bidirectional knock-in mediated by NHEJ using CRISPR/Cas9.

Additionally, the present application discloses a method and system of homology-independent knock-in of multiple reporter genes into one target gene on multiple genomic alleles that demonstrates the production of single or double positive cell populations. Accordingly, the instant application discloses a construct, method, and system of NHEJ-mediated knock-in with multiple color fluorescent reporter genes into multiple alleles.

II. Definitions

As used herein, a "reporter gene" refers to a polynucleotide sequence encoding a protein product that can generate, under appropriate conditions, a detectable signal that allows detection for indicating the presence and/or quantity of the reporter gene protein product.

As used herein, a "homology sequence" or "sequence homologous" to a reference gene/sequence describes a polynucleotide sequence that has a substantial sequence identity to a corresponding segment of the reference gene/sequence, e.g., at least 80, 85, 90, 91, 92, 93, 94, 95, 96, 97, 98, 99% identical or even 100% identical, to the nucleotide sequence of the reference gene/sequence, such that, when placed under appropriate conditions, homologous recombination can take place between a pair of "homologous sequences" and their reference gene/sequence.

The term "target sequence" or "target DNA sequence," when used to refer to a pre-determined segment of a genomic sequence or polynucleotide construct of this invention (e.g., a donor plasmid), is similarly defined in regard to the percentage sequence identity between the target sequence and its corresponding sgRNA. On the other hand, a "homology sequence" or "target sequence" is of the appropriate length that ensures its purpose. Typically, a "homology sequence" is in the size range of about 100-1000, 200-800, or 250-500 nucleotides (e.g., about 250, 500, or 800 nucleotides in length); whereas a "target sequence" is shorter and may vary in the size range of about 10-50, 15-45, or 20-40 (e.g., about 20, 25, or 30) nucleotides. In some embodiments, the target sequence contains a sequence that is suitable as a substrate for Cas9 nuclease (i.e., a nuclease target sequence site). In some embodiments, the target sequence contains a sequence that is suitable as a substrate for Cfp1 endonuclease (i.e., a endonuclease target sequence site).

The term "heterologous," when used to describe the relationship between two polynucleotide sequences or two polypeptide sequences present adjacent to each other in a recombinant polynucleotide or polypeptide construct, indicates that these two sequences are not found together in nature.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

The term "operably linked" refers to a functional relationship between two or more polynucleotide (e.g., DNA) segments. Typically, it refers to the functional relationship of a transcriptional regulatory sequence to a transcribed sequence. For example, a promoter is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, an "interrupter segment" refers to a polynucleotide sequence that interrupts expression of the reporter gene. In some embodiments, the interrupter segment is about 10-2000, 15-1000, 20-500, or 25-100 nucleotides in length, preferably 30 nucleotides in length. In some embodiments, the interrupter segment comprises three termination codons, each in a different reading frame, to completely abolish expression of the reporter gene.

As used herein, an "interval segment" refers to a polynucleotide sequence that interrupts expression of the reporter gene. In some embodiments, the interval segment is about 10-2000, 15-1000, 20-500, or 25-100 nucleotides in length, for example, 30 nucleotides or 726 nucleotides in length. In some embodiments, the interval segment can encode a functional reporter gene that is different from the functional reporter gene belonging to the donor construct.

As used herein, a "house-keeping gene" is any gene that continuously expresses its encoded protein at a stable and detectable level in an appropriate cell line. Preferably, a "house-keeping gene" is continuously expressed in multiple cell lines.

As used herein, a "non-essential gene" is any gene that is not indispensable for a living organism. Non-essential genes do not lead to a lethal phenotype when inactivated. In contrast, an essential gene must be activated for an organism to survive, such as genes encoding metabolism or DNA replication.

As used herein, the word "about," when used in the context of describing approximation of a specified value, defines a range encompassing ±10% of the value.

As used herein, a "constitutive promoter" refers to an unregulated promoter that allows for continual transcription of its associated gene in any suitable host cell or organism.

As used herein, a "universal promoter" refers to a promoter that can be fused upstream of any target gene enabling transcription of its associated gene in any suitable host cell or organism.

As used herein, a "bicistronic element" or an "internal ribosome entry site (ires) element" refers to a genetic element or a segment of polynucleotide sequence that permits co-expression of two coding sequences. In some aspects, a bicistronic element enables coordinated expression of two genes with the same vector. For example, a bicistronic element can allow for the monitoring of the delivery of one gene by using a second gene with a fluorescent tag, or express a protein of interest and simultaneously biotinylate it with the same vector. In one aspect, a bicistronic element allows for the translation of a reporter gene and an antibiotic resistance marker. In one aspect, a bicistronic element allows for the translation of a reporter gene and a fluorescent protein.

The term "expression cassette", "cassette", "construct", "vector" or "donor plasmid" refers to a nucleic acid construct that, when introduced into a host cell, results in transcription and/or translation of an RNA or polypeptide, respectively. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" or "cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

"Cas9" or (CRISPR associated protein 9) is an RNA-guided DNA endonuclease enzyme associated with the CRISPR (Clustered Regularly Interspersed Palindromic Repeats) adaptive immunity system in *Streptococcus pyogenes*, among other bacteria. *S. pyogenes* utilizes Cas9 to memorize and later interrogate and cleave foreign DNA, such as the DNA of an invading bacteriophage. Cas9, complexed with a small guide RNA (sgRNA), performs this interrogation by unwinding foreign DNA and checking whether the DNA contains any sequence segment complementary to a 20 bp spacer region of the sgRNA. If the sgRNA finds sequence complementarity in the DNA, it is cleaved by Cas9.

"Cpf1" or "CRISPR/Cpf1" is a DNA editing technology analogous to the CRISPR/Cas9 system. Cpf1 is an RNA-guided DNA endonuclease enzyme associated with the CRISPR adaptive immunity system in *Prevotella* and *Francisella*, among other bacteria. Cpf1 is a smaller and simpler endonuclease as compared to Cas9 because Cpf1 only requires one RNA molecule to cut DNA while Cas9 requires two. Cpf1 is a Type V CRISPR/Cas system containing a 1,300 amino acid protein.

As used herein, "sgRNA" or "small guide RNA" refers to a short RNA molecule that is capable of forming a complex with Cas9 protein and contains a segment of about 20 nucleotides complementary to a target DNA sequence, such that the Cas9-sgRNA complex directs Cas9 cleavage of a target DNA sequence upon the sgRNA recognizing the complementary sequence in the target DNA sequence. Accordingly, a sgRNA is approximately a 20-base sequence (ranging from about 10-50, 15-45, or 20-40, for example, 15, 20, 25, or 30 bases) specific to the target DNA 5' of a non-variable scaffold sequence.

As used herein the term "GAPDH" is a term of the art understood by skilled persons and means a housekeeping gene which produces Glyceraldehyde 3-phosphate dehydrogenase. GAPDH gene is often stably and constitutively expressed at high levels in most human tissues and cells. Thus, GAPDH is commonly used as control for western blot to check protein expression levels or for qPCR to check mRNA expression levels.

As used herein the term "AAVS1" is a term of the art understood by skilled persons and means a genome locus termed Adeno-associated virus integration site 1 (also known as PPP1R12C locus) in human genome. It exhibits open chromatin structure and has been suggested as potential target regions for integration as its disruption has no functional consequence [16].

As used herein the term "ACTB" is a term of the art understood by skilled persons and means a genome locus termed beta-actin in human genome. The gene produces highly conserved proteins that are involved in cell motility, structure, and integrity.

As used herein the term "SOX17" is a term of the art understood by skilled persons and means a genome locus termed SOX (SRY-related HMG-box) family member 17 in human genome. The gene produces transcription factors involved in the regulation of embryonic development and in the determination of the cell fate.

As used herein the term "T" is a term of the art understood by skilled persons and means a genome locus in human genome termed T brachyury transcription factor (also known as TFT or SAVA locus). The protein encoded by this gene is an embryonic nuclear transcription factor that binds to a specific DNA element, the palindromic T-site.

As used herein the term "OCT4" is a term of the art understood by skilled persons and means a genome locus termed POU class 5 homeobox 1 (POU5F1) in human genome which produces protein as a transcription factor containing a POU homeodomain that plays a key role in embryonic development and stem cell pluripotency.

As used herein the term "NANOG" is a term of the art understood by skilled persons and means a genome locus termed Nanog homeobox in human genome which produces protein as a DNA binding homeobox transcription factor involved in embryonic stem (ES) cell proliferation, renewal, and pluripotency.

As used herein the term "PAX6" is a term of the art understood by skilled persons and means a genome locus termed paired box 6 in human genome which produces a homeobox and paired domain-containing protein that binds DNA and functions as a regulator of transcription.

As used herein the term "SOX1" is a term of the art understood by skilled persons and means a genome locus termed SRY-related HMG-box 1 in the human genome which produces a homeobox transcription factor involved in the regulation of embryonic development and the determination of cell fate.

As used herein the term "FOXA2" is a term of the art understood by skilled persons and means a genome locus termed forkhead box protein A2 or transcription factor 3B or hepatocyte nuclear factor 3-beta in the human genome which encodes a protein that binds DNA and functions as a regulator of transcription.

As used herein the term "LoxP" is a term of the art understood by skilled persons and means a genome locus termed LoxP1. The Cre-Lox recombination system is a site-specific recombinase method used to perform deletions, insertions, translocations and inversions at specific sites in the DNA. It is implemented in both eukaryotic and prokaryotic systems. The Cre-Lox system consists of an enzyme, Cre recombinase, that recombines a pair of short target sequences called the LoxP sequences. LoxP is a site on the bacteriophage P1 consisting of 34 bp. The site includes an asymmetric 8 bp sequence, variable except for the middle two bases, in between two sets of palinodromic, 13 bp sequences.

As used herein the term "PGK" is a term of the art understood by skilled persons and means the promoter of Phosphoglycerate Kinase 1, which is constantly active in most human and mouse cells.

As used herein the term "puro" is a term of the art understood by skilled persons and means the gene encoding puromycin N-acetyl-transferase that was found in a *Streptomyces* producer strain, and can confer host cells a resistance against antibiotic puromycin supplemented in culture medium.

As used herein the term "hygro" is a term of the art understood by skilled persons and means the gene encoding hygromycin B phosphotransferase that was found in a *Streptomyces* producer strain, and can confer host cells a resistance against antibiotic hygromycin supplemented in culture medium.

As used herein the term "2a" is a term of the art understood by skilled persons and means DNA sequence that encodes a short self-cleaving peptide originally identified in Picornavirus (F2a) [17].

As used herein the term "Rosa26" is a term of the art understood by skilled persons and means a gene used for constitutive, ubiquitous gene expression in mice [18].

As used herein the term "copGFP" is a term of the art understood by skilled persons and means a green fluorescent protein (GFP) cloned from copepod *Pontellina plumata*. copGFP is characterized by superbright green fluorescence (excitation/emission max=482/502 nm) and fast maturation rate at a wide range of temperatures, leading to the successful performance in cold-blooded animals.

As used herein the term "eGFP" is a term of the art understood by skilled persons and means enhanced green fluorescent protein with F64L point mutation which folds the efficiency at 37° C. Thus, eGFP leads to the significant performance of GFPs in mammalian cells.

As used herein the term "ires" is a term of the art understood by skilled persons and means internal ribosome entry site segments which are known to attract eukaryotic ribosomal translation initiation complex and thus promote translation initiation independently of the presence of the commonly utilized 5'-terminal 7 mG cap structure.

As used herein the term "H1" is a term of the art understood by skilled persons and means a popular human embryonic stem cell line established from the inner cell mass of human blastocyst.

As used herein the term "E14" is a term of the art understood by skilled persons and means a popular mouse embryonic stem cell line in naïve state established from the inbred mouse strain 129/Ola.

As used herein the term "LO2" is a term of the art understood by skilled persons and means a somatic immortalized cell line established from human hepatic tissue.

As used herein the term "HK2" is a term of the art understood by skilled persons and means a somatic immortalized cell line established from human epithelial tissue.

As used herein the term "HEK293T" is a term of the art understood by skilled persons and means a variant of human embryonic kidney 293 cells (HEK293) that contains the SV40 large T-antigen. The antigen allows episomal replication of transfected plasmids containing the SV40 origin of replication, which leads to the amplification of transfected plasmids and extended temporal expression of the desired gene products.

As used herein the term "BEL-7402" is a term of the art understood by skilled persons and means a hepatocellular carcinoma cell line established from human hepatoma tissue.

As used herein the term "BEL-7404" is a term of the art understood by skilled persons and means a hepatocellular carcinoma cell line established from human hepatoma tissue.

As used herein the term "SMMC-7721" is a term of the art understood by skilled persons and means a hepatocellular carcinoma cell line established from human hepatoma tissue.

As used herein the term "H1299" is a term of the art understood by skilled persons and means a human non-small cell lung carcinoma cell line derived from the lymph node.

As used herein the term "HCT116" is a term of the art understood by skilled persons and means a human colon carcinoma cell line established from human colon carcinoma tissue.

As used herein the term "human insulator" is a term of the art understood by skilled persons and means a certain type of blocking sequences in the human genome which prevent interference between different regulatory elements of different chromatin domains.

III. Targeted Genomic Manipulation Systems

The CRISPR/Cas9 genomic sequence manipulation systems of this invention are intended for universally targeting essentially any gene in essentially any cell type derived from essentially any living organism. These systems include a gene targeting system that requires a first insertion event in the host cell genome in which an integration construct containing a non-functional reporter gene is first introduced into the target genomic locus. Subsequently, the second insertion event takes place to replace the non-functional reporter gene with a full functional one, thus allowing immediate detection of the reporter gene protein product and the completion of the second insertion event. Both insertion events are based on nucleotide sequence homology between a polynucleotide construct and its insertion site.

The second gene targeting system does not require a prior integration event before a reporter gene is integrated into a pre-determined genomic locus and its expression product is detected. There are two variations in this gene targeting system: the first utilizes homology-based integration of the reporter gene at the chosen integration site, whereas the second utilizes non-homologous end joining mechanism for integration of the reporter gene.

The recombinant polynucleotide constructs, cells, compositions, and kits useful for practicing these two systems, as well as various applications of these systems, are described in details below.

A. Cells

The present invention can be practiced in essentially any eukaryotic cell types for the purpose of manipulating a genomic sequence at a pre-selected genomic locus. For example, the gene targeting systems of this invention may be used in various human cells, including stem cells (e.g., embryonic stem cells, pluripotent stem cells, adult stem cells) or somatic cells. Cells originated from other animal species, especially from other mammals including primates, can be similarly used for genetic manipulation.

B. Gene-Targeting System Involving Two Integration Events

One gene-targeting system of this invention involves two integration events: first, an integration construct comprising a non-functional reporter gene, typically resulted from an interrupter sequence segment being placed in the middle of a normal functional reporter gene coding sequence, is inserted into a pre-selected genomic locus by way of homologous recombination. Second, the host cell containing the integration construct is targeted in a CRISPR/Cas9-based method to replace the non-functional reporter gene with a functional reporter gene supplied by a donor construct, allowing the functional reporter gene to express its protein product and therefore detection of successful integration.

The integration construct used in the first integration event is a recombinant polynucleotide construct comprising a promoter operably linked to, from 5' to 3', a first non-functional coding segment for a reporter gene, an interrupter segment, and a second non-functional coding segment for the reporter gene. Due to the presence of the interrupter segment, no functional reporter protein is expressed from the promoter. The interrupter segment can be of any nucleotide sequence of any length, typically about 10-200, 20-100, or 20-50 nucleotides in length. In one example, to ensure no functional reporter gene protein is expressed, the interrupter segment used in this invention is 30 nucleotides in length, which was engineered to include three termination codons, each in a different reading frame, followed by a sgRNA (sg-X) target sequence.

The reporter gene is a nucleic acid sequence encoding a protein that allows a cell to present a detectable signal. Examples of such a protein capable of generating a detectable signal include a protein that generates a fluorescence signal or a phosphorescence signal, a protein that is detectable in an assay, a protein exhibiting an enzyme activity, and an antigen that is detectable on a cell or in a cell. Examples of a protein encoded by such a reporter gene include fluorescent proteins such as a green fluorescent protein (GFP), a humanized *Renilla* green fluorescent protein (hrGEP), an enhanced green fluorescent protein (eGFP), an enhanced blue fluorescent protein (eBFP), an enhanced cyan fluorescent protein (eCFP), an enhanced yellow fluorescent protein (eYFP), and a red fluorescent protein (RFP or DsRed). More examples of a protein encoded by such a reporter gene include bioluminescent proteins such as firefly luciferase and *Renilla* luciferase. Further examples of a protein encoded by such a reporter gene include enzymes for converting chemiluminescent substrates, such as alkaline phosphatase, peroxidase, chloramphenicol acetyltransferase, and β-galactosidase. In the present invention, when a reporter gene detected by a light signal such as a fluorescence signal or a phosphorescence signal is used, the expression level of the reporter gene can be observed in a state in which a cell is maintained, and a cell used for evaluation can be easily selected, while the cell is alive. In addition, in such a case, the reporter gene can be used in an experiment in which a test substance is continuously administered, and a change over time in the expression level of the reporter gene can be pursued in a real time. As such, a reporter gene using a light signal as a label can be preferably used as the reporter gene of the present invention.

The integration construct can be present in various forms. One embodiment of such a construct is a circular polynucleotide vector, such as a plasmid, where the vector further comprises two genomic homology sequences, one of which is located at the 5' end of the promoter and the other is located at the 3' end of the second non-functional coding segment for the reporter gene. These two genomic homology sequences are designed to be homologous to two segments of the genomic sequence at a pre-determined genetic locus of a host or recipient cell, such that the presence of the two genomic homology sequences permits homologous recombination between the integration construct and the genomic sequence of the cell at the pre-determined genetic locus. The resultant host cell therefore contains in its genome the promoter operably linked to the non-functional reporter gene coding sequence (i.e., from 5' to 3', a first non-functional coding segment for a reporter gene, an interrupter segment, and a second non-functional coding segment for the reporter gene).

The second integration event relies on a second recombinant polynucleotide construct, a donor construct. The donor construct comprises, from 5' to 3', a first reporter gene homology segment, an interval segment, and a second reporter gene homology segment. The first and second reporter gene homology sequences are homologous to the first and second non-functional coding segments for the reporter gene, respectively, such that the presence of the two reporter gene homology sequences permits homologous recombination between the integration construct, now incorporated into the host cell genome, and the donor construct to form a coding sequence for a functional reporter gene. The functional reporter gene can then be expressed under the promoter, allow detection of the completion of the second insertion event. The donor construct is typically also a circular vector, such as a plasmid. Each of the first and second reporter gene homology segments may vary in length but is typically about 100-1000, 200-800, or 250-500 nucleotides in length, for example, about 250, 500, or 800 nucleotides in length. The interval segment can also vary in its length, typically it may be about 20-1000, 50-750, 100-500, or 200-400 nucleotides in length, in accordance of the targeting strategy used. In some examples, it may be about 30 or 726 nucleotides in length. In some cases, it may encode a functional reporter gene protein.

To successfully achieve the second integration event, the host cell harboring the integration construct is transfected with the donor construct described above, a DNA molecule encoding a sgRNA capable of hybridizing to a segment of about 20 nucleotides within the non-functional coding segments for the reporter gene or the interrupter segment, and a DNA molecule encoding a Cas9 protein (nuclease). The sgRNA/Cas9 complex will recognize and cleave the DNA at the target site within the non-functional coding segment for the reporter gene; which will then promote the homologous recombination between the integration construct, now incorporated into the host cell genome, and the donor construct to form a coding sequence for a functional reporter gene. The present invention is therefore also provides a composition comprising these components.

This gene-targeting system is not only useful for one to study the mechanism and process involved in the CRISPR-induced homology-directed repair, it also allows one to screen for compounds that are potential modulators of such repair pathways. For example, if the presence of a candidate compound leads to an increased rate of successful integration, the compound is identified as a potential enhancer of the CRISPR-induced homology-directed repair and can be further tested and verified for this activity. On the other hand, if the presence of a candidate compound leads to a decreased rate of successful integration, the compound is identified as a potential inhibiter of the CRISPR-induced homology-directed repair, and it can be further tested and verified for this activity. Given the importance of the CRISPR/Cas9-mediated gene manipulation, such testing methods can prove to be useful tools for identifying compounds of interesting potentials.

C. Gene-Targeting System Involving One Integration Event

Another gene-targeting system of this invention requires only one genomic integration event and may be further divided into the first type, or homology-directed repair, and the second type, or the non-homology end joining type. The donor construct in the first type of such gene-targeting system comprises (1) a coding sequence for a reporter gene; (2) a first genomic homology segment located at the 5' end of the reporter gene coding sequence; and (3) a second genomic homology segments located at the 3' end of the reporter gene coding sequence. The first and second genomic homology segments are homologous to a pre-determined genomic sequence, which is preferably an actively expressed gene, such as a house-keeping gene. Under suitable conditions, the presence of these genomic homology segments allows homologous recombination between the donor construct and the pre-determined genomic sequence. As described above, the donor construct is often a circular vector such as a plasmid.

To achieve genomic integration of the reporter gene and its subsequent expression, a host or recipient cell is contacted with the donor construct, a DNA molecule encoding a sgRNA capable of hybridizing to a segment within the coding sequence or the upstream or downstream non-coding sequence of the pre-determined genomic sequence, and a DNA molecule encoding a Cas9 protein (nuclease). The sgRNA/Cas9 complex will recognize and cleave the DNA at the target site within the upstream or downstream non-coding sequence of the pre-determined genomic sequence; which will then promote the reporter integration via either the homology-directed repair, in the presence of the donor construct. Successful integration results in the reporter gene being expressed and detectable by a suitable detection means.

In contrast, the donor construct in the second type of the gene-targeting system requiring only one integration event has rather different components. The construct comprises (1) a coding sequence for a reporter gene; and (2) a polyA segment at the 3' end of the reporter gene coding sequence, optionally with one target sequence site located at the 5' end of the reporter gene coding sequence or 3' end of the poly A segment, or with two target sequence sites one located at the 5' end of the reporter gene coding sequence and the other located at the 3' end of the poly A segment. The nucleotide sequence at the target sequence site, sometimes referred to as "sg-A target site," correspond to a pre-determined segment of a pre-selected genomic sequence, or the intended integration site, typically in the upstream or downstream non-coding regions of a house-keeping gene, while in some cases may be within the coding region of the gene as well. When two of such target sequence sites are used, they may have the same or different nucleotide sequence. By careful selection of the nucleotide sequences of such target sites, for instance, by choosing nucleotide sequences of prokaryotic origin (e.g., bacterial or viral origin) that may be found in multiple genomic loci in multiple eukaryotic species as target site sequences, one can use the gene manipulation system of this invention as a universal tool for introducing the reporter into any genomic locus in a eukaryotic cell. This donor construct does not contain any homology-based element, since it is intended for use in a non-homology end joining manner. Circular vector (such as a plasmid) is also a preferred form of the donor construct.

Using this type of system for genomic manipulation, a cell is contacted with the donor construct, one or two DNA molecules encoding one or two sgRNAs (whose nucleotide sequence may be the same or different) each capable of hybridizing to one of the target sequence sites, and a DNA molecule encoding a Cas9 protein (nuclease). The one or two sgRNAs include one capable of hybridizing to the sg-A target sequence sites in the donor constructs and one capable of hybridizing to a pre-determined genomic sequence typically within the downstream non-coding sequence (although in some case within the coding sequence or upstream non-coding sequence). The sgRNAs will recruit Cas9 nuclease to cleave the DNA at the target sites, in the donor constructs and in the pre-determined genomic region; which will then promote the reporter integration via either the non-homology end joining. Successful integration results in the reporter gene being expressed and detectable by a suitable detection means.

Aside from the use of these gene-targeting systems for studying the mechanism and process involved in the CRISPR-induced homology-directed or non-homology end-joining repair, these systems can similarly allow one to screen for compounds that are potential modulators of such repair pathways. For example, if the presence of a candidate compound leads to an increased rate of successful integration, the compound is identified as a potential enhancer of the CRISPR-induced homology-directed or non-homology repair and can be further tested and verified for this activity. On the other hand, if the presence of a candidate compound leads to a decreased rate of successful integration, the compound is identified as a potential inhibiter of the CRISPR-induced homology-directed or non-homology repair, and it can be further tested and verified for this activity.

D. Efficient Knock-In Via CRISPR/Cas9-Coupled NHEJ

Figures 11A, 11B:
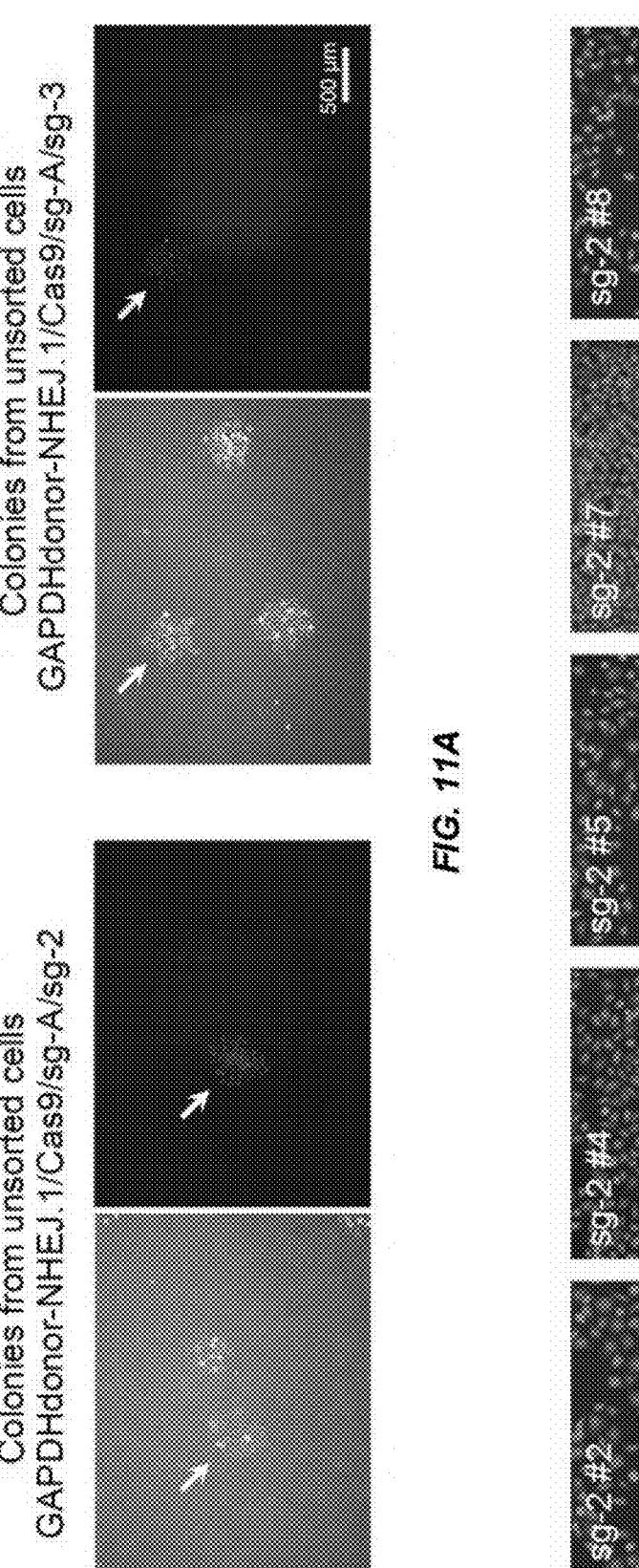
(FIG. 11A) Bright field and fluorescence images of single-cell colonies, observed at 10 days after seeding the cells transfected with single-cut NH-donor/Cas9/sg-A/sg-2 or sg-3 (unsorted) at low density. GFP+ (white arrows) and GFP-colonies (unlabeled) were seen in both samples.
(FIG. 11B) Fluorescence images showing GFP expression in selected individual clones, which were isolated from cells transfected with single-cut NH-donor/Cas9/sg-A/sg-2.
Figure 11C:
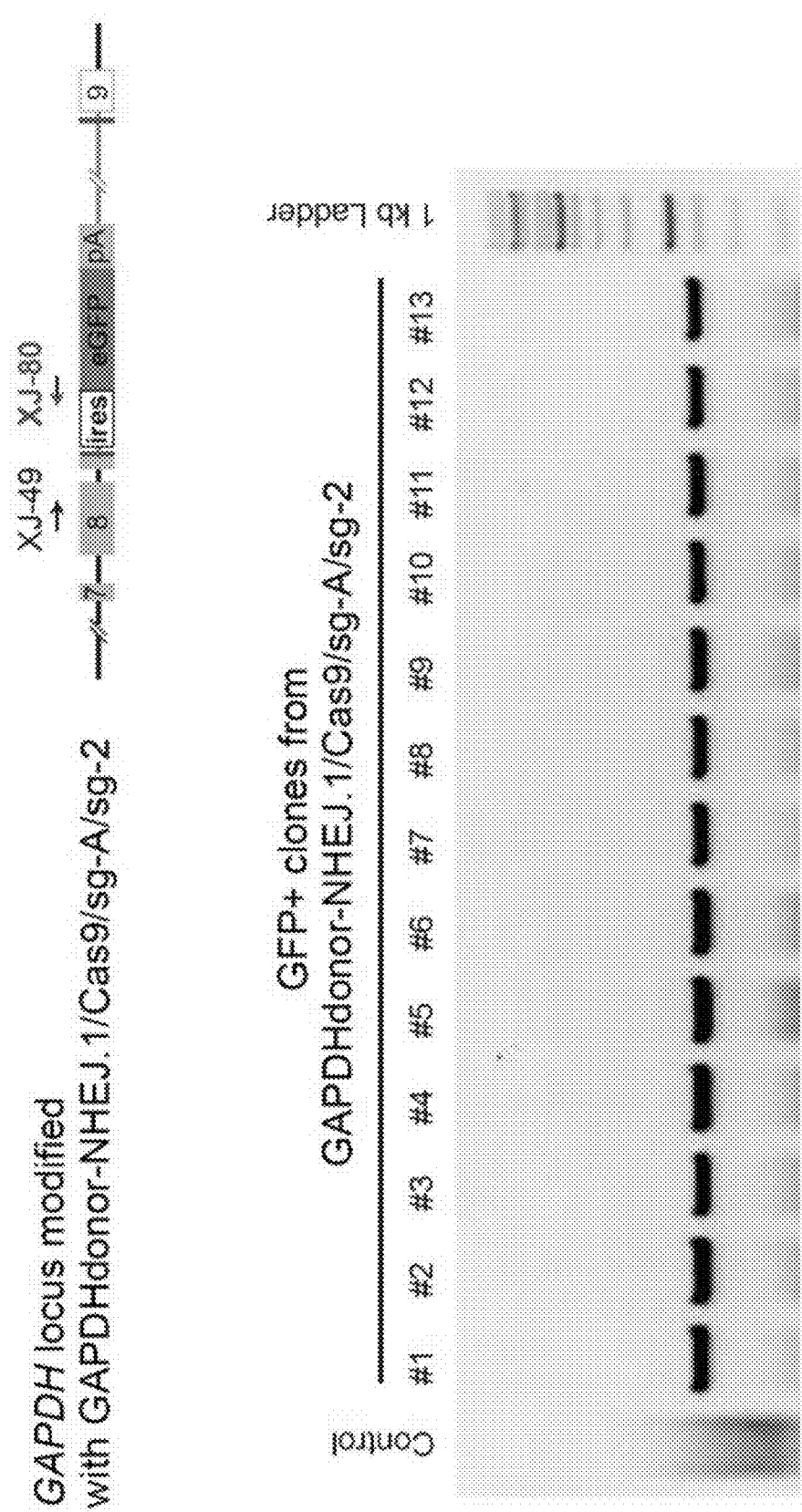
(FIG. 11C) PCR of the 13 GFP+ clones isolated from the cells transfected with single-cut NH-donor/Cas9/sg-A/sg-2. Primers F3/R3* was used to detect the 5'-integration junction; and their positions are indicated in the schematics (upper panel). Primer R3* was used instead of primer R3 here to obtain optimal amplification. PCR amplifications showed DNA fragments at expected sizes, indicating correct integration of the ires-eGFP reporter at the GAPDH 3'-UTR.

According to one aspect, we examined the efficiency of genomic integration using a single cut NH-donor (GAPDH-donor-NHEJ.1) which was cotransfected with Cas-9, sg-A, sg-2 or sg-3 into LO cells. To explore whether a non-homology (NH)-targeting approach could produce stable knock-in clones at high efficiency, the LO cells were transfected with single-cut NH-donor (GAPDHdonor-NHEJ.1)/Cas9/sg-A/sg-2 and sg-3 were expanded at a low density. Among the colonies raised from the unsorted cells, pure GFP+ clones were observed (FIG. 11A). Among 90 clones randomly isolated from the cells transfected with sg-2, 13 were found to be GFP+ (14.44%). PCR and sequencing analysis confirmed that these clones indeed carried the correct reporter knock-in in their genomes (FIG. 11C), suggesting success in generating stable knock-in clones without any pre-selection.

Figure 12A:
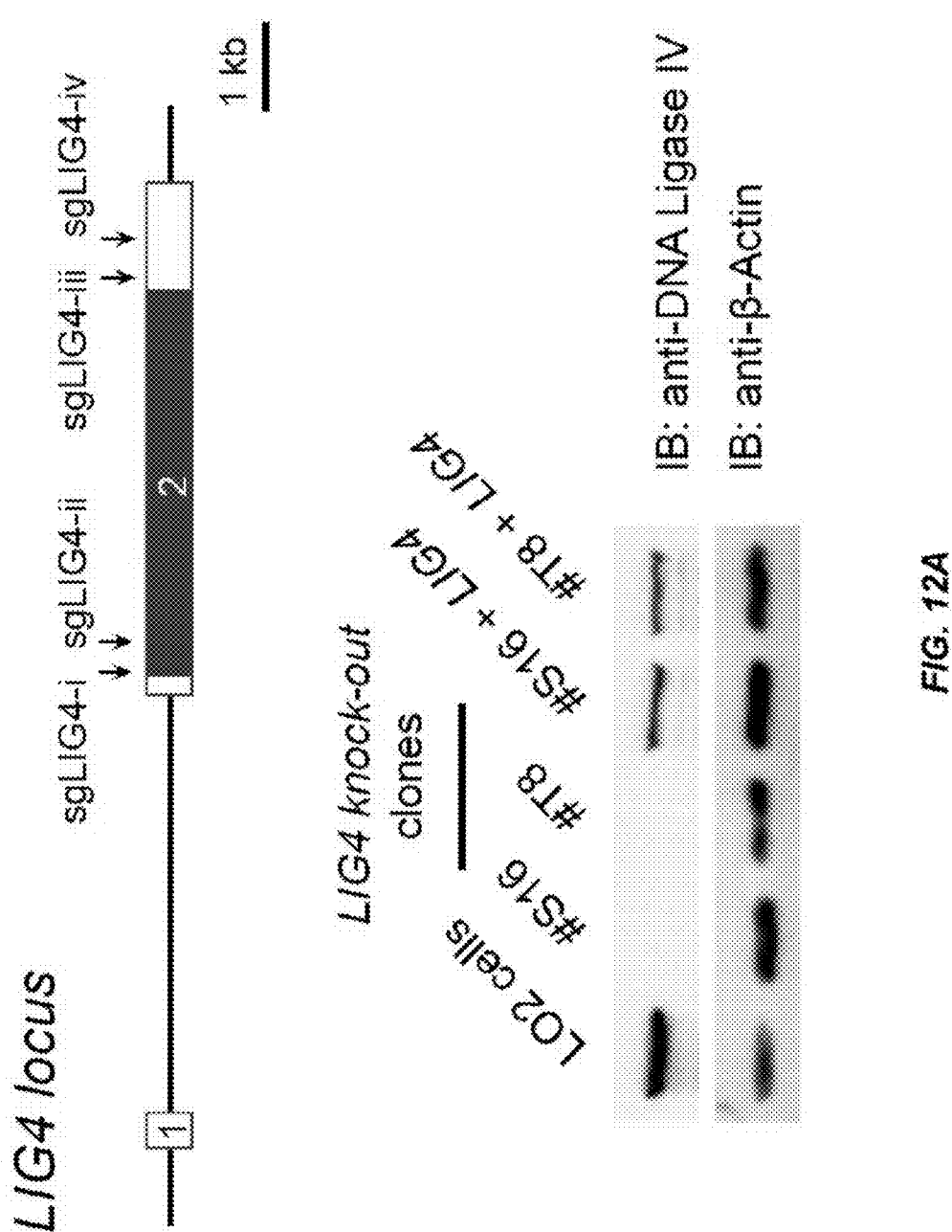
(FIG. 12A) Upper panel shows the schematics of the sgLIG4-i-iv target positions at the LIG4 locus. These sgRNAs were combined and co-transfected with Cas9 into LO2 cells to generate LIG4 knock-out clones. Lower panel is the western blot, showing the loss of DNA ligase IV in the obtained LIG4 null clones, and LIG4 expression introduced by transfection of LIG4 cDNA construct into these cells.
Figure 12B:
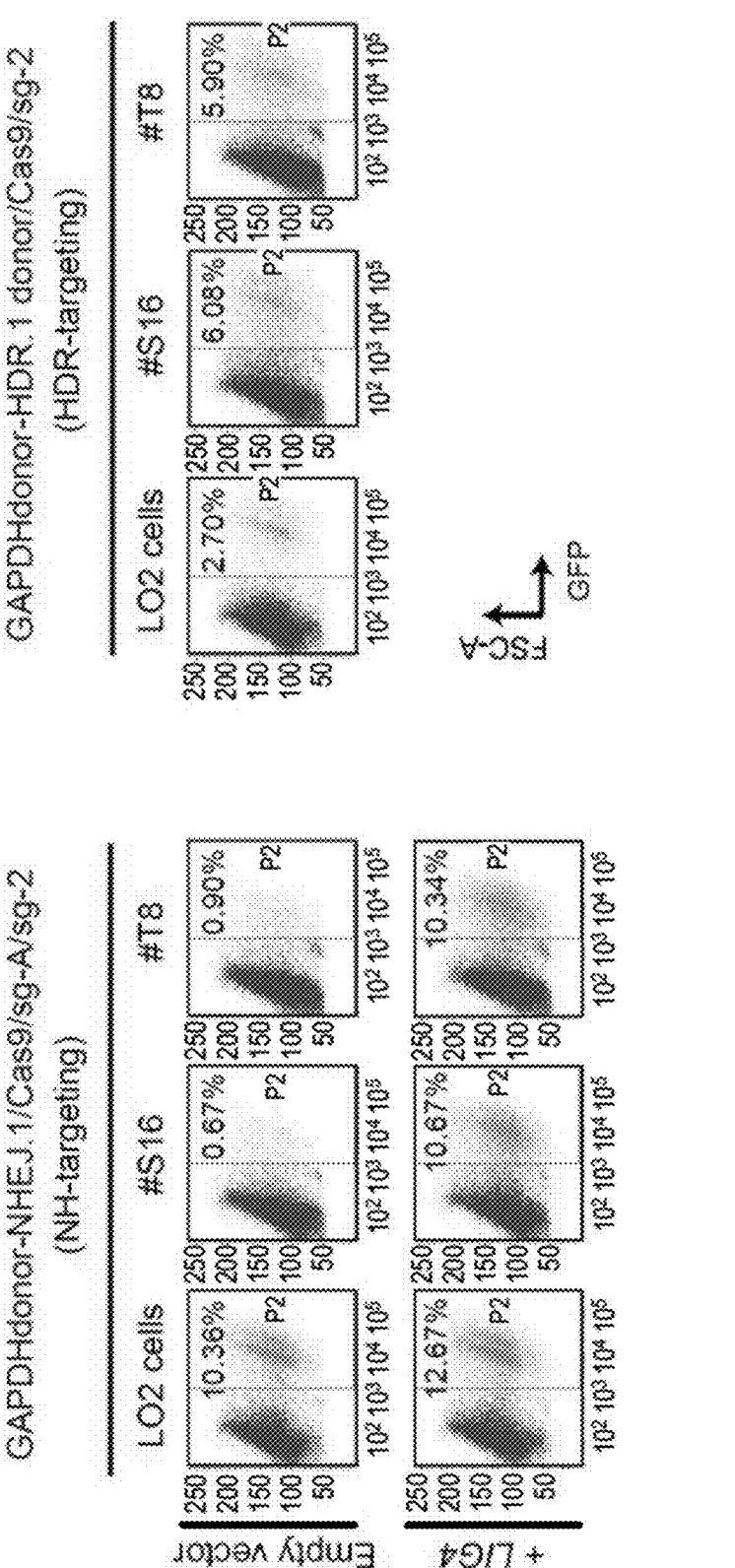
(FIG. 12B) FACS analysis of the LIG4 knock-out LO2 cells. Homology-independent knock-in was induced by single-cut NH-donor/Cas9/sg-A/sg-2, and HDR-based knock-in was introduced using 2a-copGFP (+HAs) donor/Cas9/sg-2, in both wild type as well as LIG4 knock-out LO2 cells. Drastic decrease of NH-targeting and rescue by LIG4 overexpression were observed in both LIG4 null clone #S16 and #T8 (left panel). Significant increase of HDR knock-in was also observed in LIG4 null cells (right panel).

1. Molecular Basis Underlies Homology-Independent Reporter Integrations were Mediated by the Conventional DNA Ligase IV-Dependent NHEJ Pathway According to one aspect, we examined the molecular basis of genomic integration using DNA ligase IV (LIG4) knock-out LO2 cells after transfection with the single-cut NH-donor (GAPDHdonor-NHEJ.1)/Cas9/sg-A/sg-2. To uncover the molecular basis underlying these homology-independent reporter integrations, DNA ligase IV (LIG4) knock-out LO2 cells were generated by deleting large pieces of the LIG4 CDS using Cas9/sgRNAs (FIG. 12A). In the two LIG4 knock-out clones examined (#S16 and #T8), a drastic decrease of reporter knock-in was observed after transfection with the single-cut NH-donor (GAPDHdonor-NHEJ.1)/Cas9/sg-A/sg-2, as compared to that in wild type LO2 cells (FIG. 12B, left panel, top row). Moreover, the decrease of NH-targeting in these LIG4 null cells could be rescued by a plasmid carrying LIG4 overexpression cassette (FIG. 12B, left panel, bottom row). Consistent with the recent studies by Maruyama et al. [1] and Chu et al. [2], a significant increase of the HDR-based knock-in of 2a-copGFP (GAPDHdonor-HDR. 1) reporter was also observed in these LIG4 null cells (FIG. 12B, right panel), which correlated with the loss of NHEJ activity. Collectively, these data showed that the homology-independent reporter integrations observed were indeed largely mediated by the conventional DNA ligase IV-dependent NHEJ pathway.

2. NHEJ-Mediated Knock-In can Accommodate Larger Insert

Figure 12C:
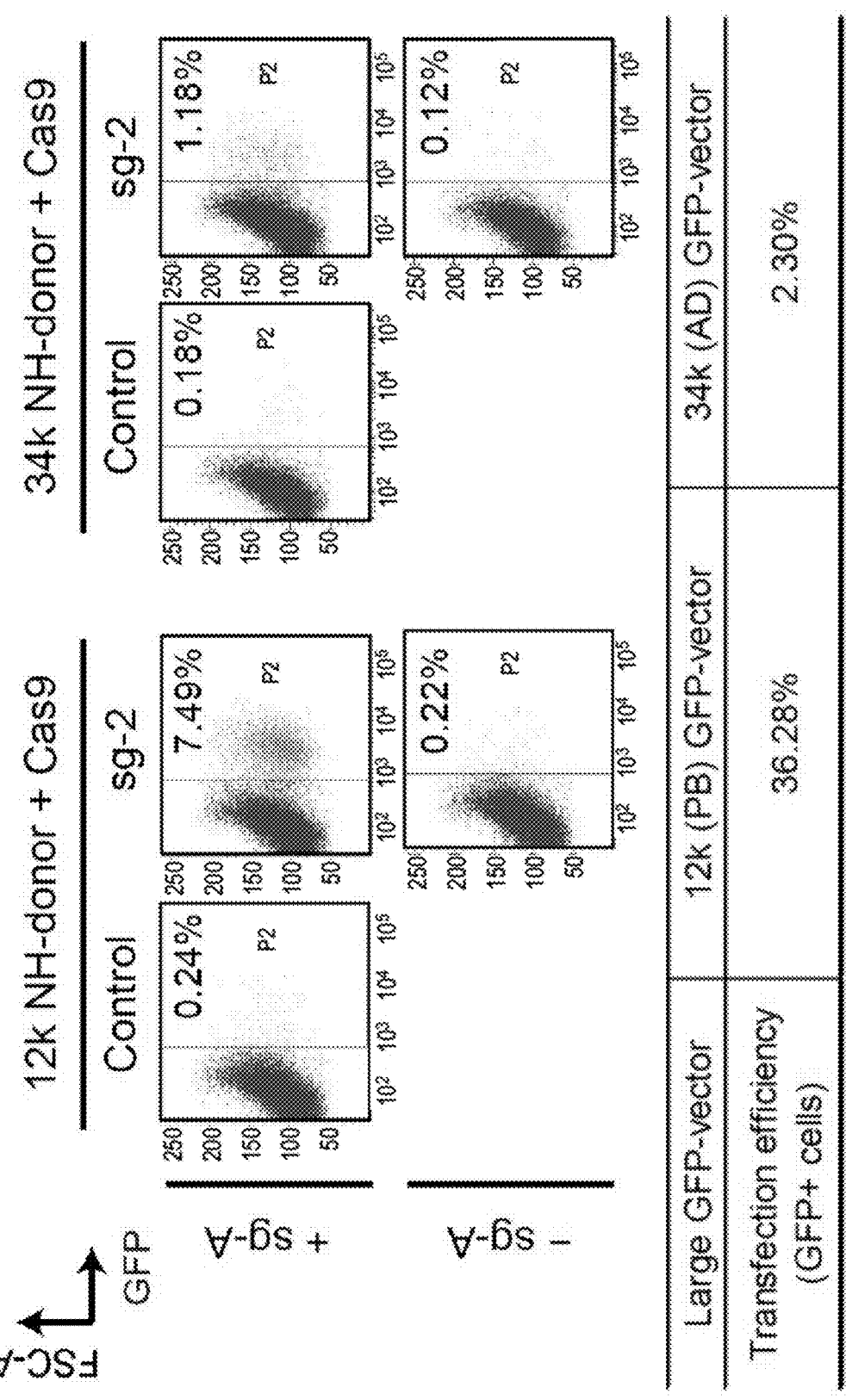
(FIG. 12C) FACS results showing NHEJ-mediated knock-in with large size donors. 12k and 34k NH-donors were co-transfected with Cas9/sg-A/sg-2 into wild type LO2 cells. Controls were transfected without sg-2 or sg-A. GFP+ cells are gated to the right of the dashed line in each panel. At the same time, constant GFP-expressing 12k (PB) and 34k (AD) GFP-vectors were transfected in parallel; and the transfection efficiencies examined at day 2 by FACS are shown at the lower panel.
Figure 12C:
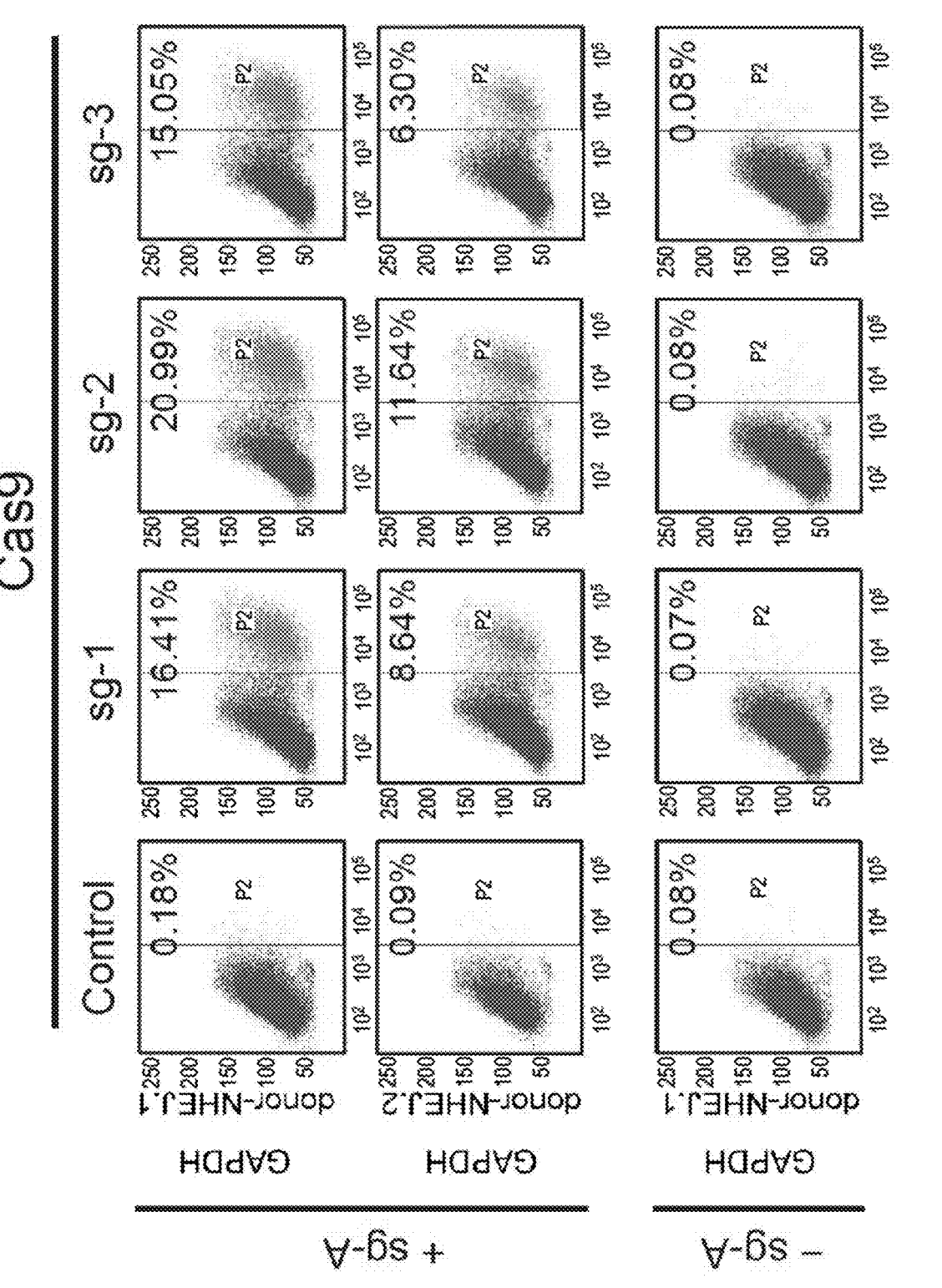
Figure 12D:
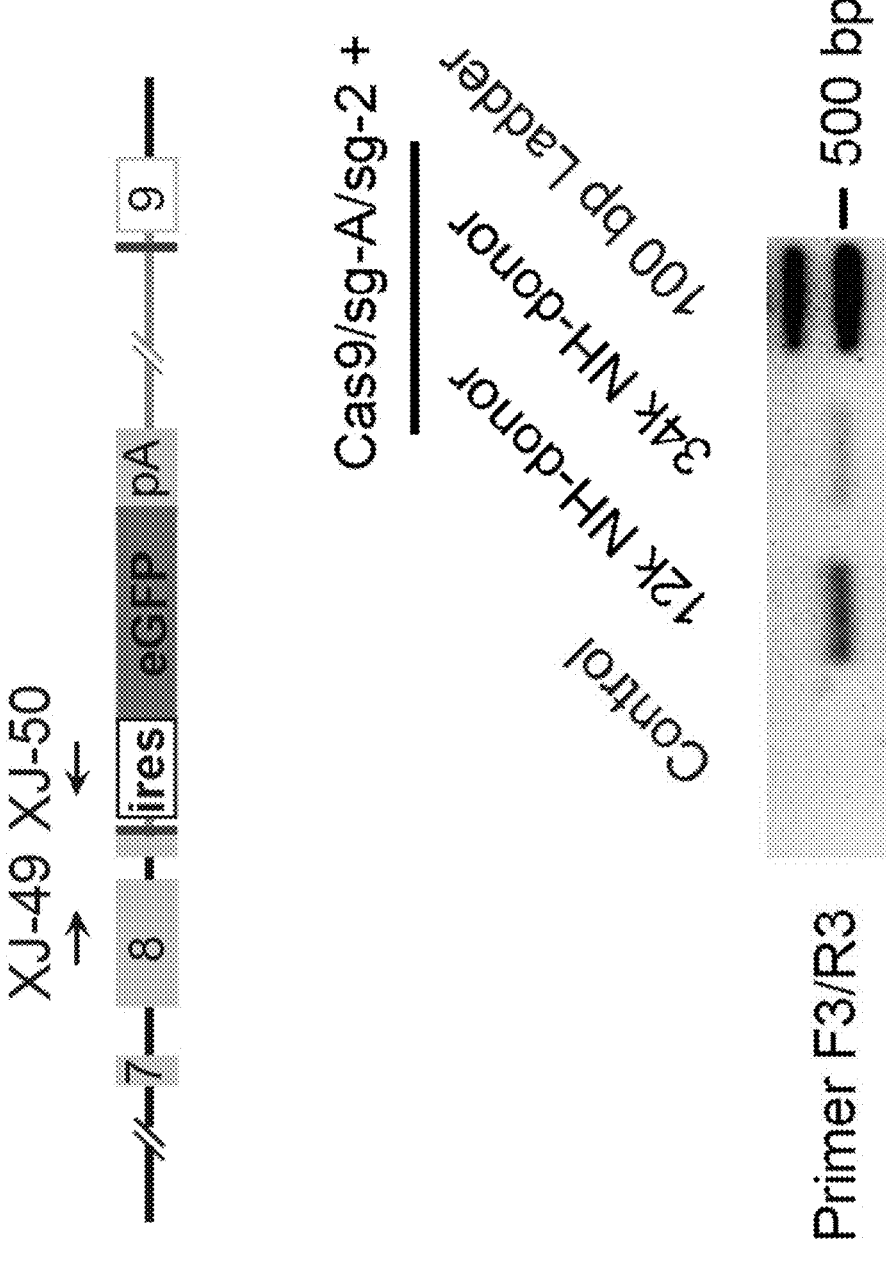
(FIG. 12D) PCR detection of the reporter integration in the transfected cells (unsorted) in C. Primer pair F3/R3 detected the 5'-junctions of the 12k and 34k NH-donors integrated at GAPDH 3'-UTR. PCR amplifications showed DNA fragments at expected sizes.

According to one aspect, a method is provided for insertion of large inserts using a 12 kb or 34 kb NH-donor upon co-transfection with Cas9/sg-A/sg-2. To examine whether the NHEJ-mediated knock-in could accommodate a larger insert, plasmids named 12k and 34k NH-donors were constructed, by inserting the promoterless ires-eGFP reporter together with the 5' sg-A target sequence into a large Piggy Bac vector (12 kb) and an adenoviral vector (34 kb), respectively. These donors can be cleaved at the sg-A target sequence upon the co-transfection with Cas9/sg-A, thus providing linear donors that carry the ires-eGFP in a 12 kb or 34 kb backbone for NHEJ-based knock-in. After co-transfection with the Cas9/sg-A/sg-2, 7.49% GFP+ cells were detected with the 12k NH-donor, and 1.18% with the 34k NH-donor (FIG. 12C, left panel). Together with the 20.99% GFP+ cells observed using the single-cut NH-donor (GAPDHdonor-NHEJ.1)/Cas9/sg-A/sg-2 (4.6 kb) (FIG. 12C, right panel), it was apparent that the knock-in frequencies decreased when larger donors were used. This might be caused, at least partially, by the reduced transfection efficiencies of the larger plasmids (FIG. 12C, left panel). PCR analysis of the transfected cells further confirmed the correct knock-in of these large donors at the GAPDH locus (FIG. 12D).

Figure 13A:
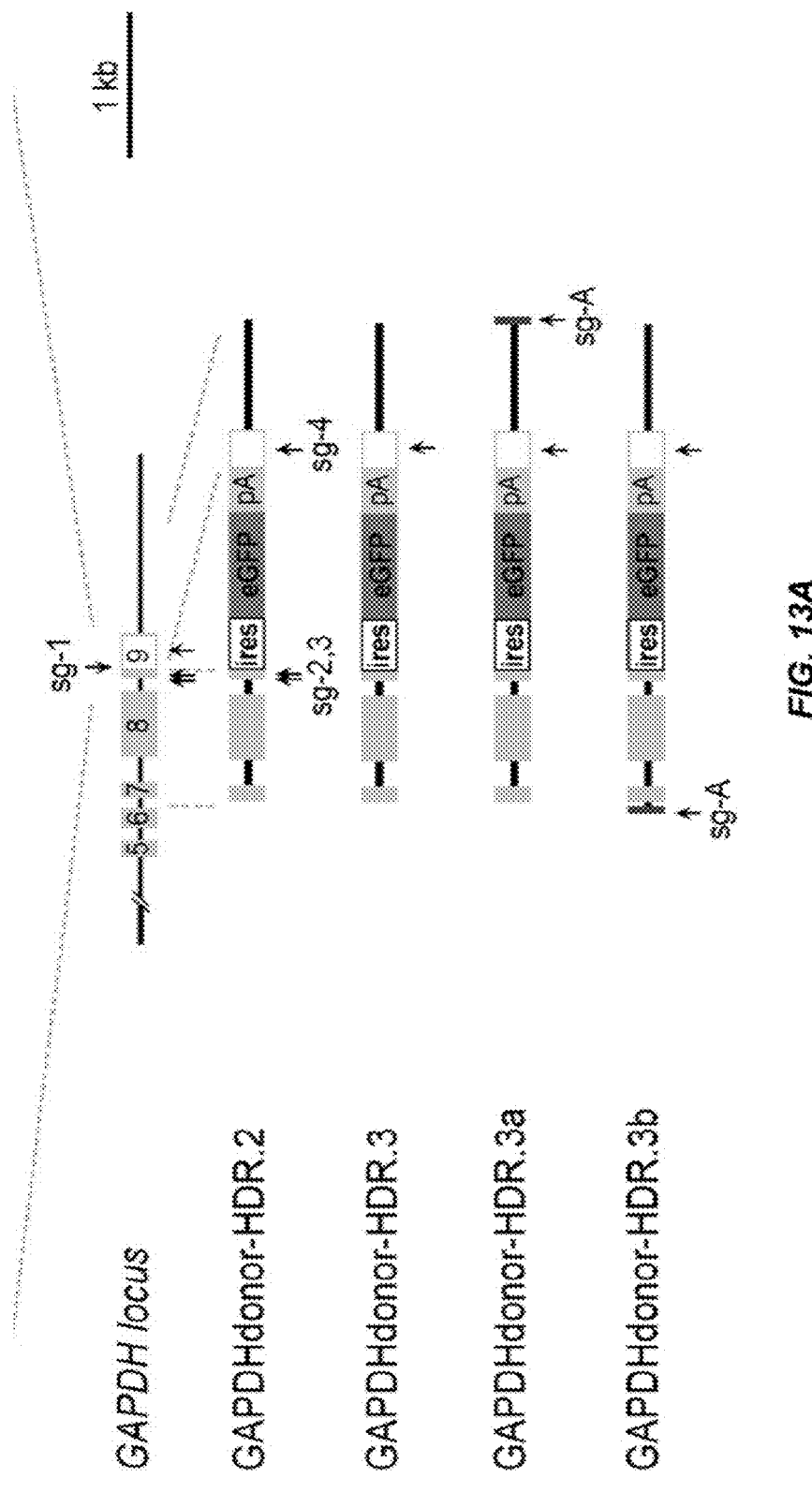
(FIG. 13A) Schematics showing a zoomed-in view of the sg-1-4 target sites and their positions on the genomic GAPDH locus, as well as the design of ires-eGFP(+HAs) Donor-1, 2, 2.A and 2.B plasmids. Homology arm (HA) regions used in the ires-eGFP(+HAs) donor-1 are highlighted in grey, and the HAs used in donor-2, 2.A and 2.B are highlighted in purple. Donor-2.A carries a single sg-A target site at the 3', and Donor-2.B carries a sg-A target site at the 5' of the ires-eGFP(+HAs) cassette.
Figure 13B:
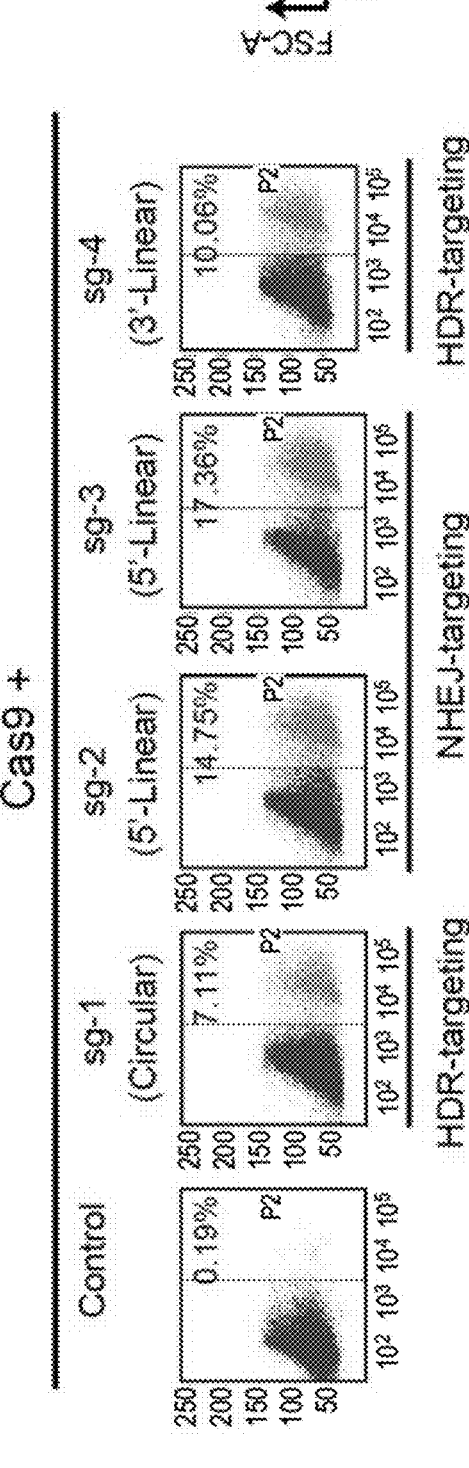
(FIG. 13B) FACS analysis of LO2 cells transfected with the ires-eGFP(+HAs) donor-1/Cas9 and sg-1, 2, 3, or 4. Due to the different target positions on the genome and the donor, sg-1 induced HDR-mediated knock-in; sg-2 and sg-3 induced NHEJ-based knock-in; and sg-4 mainly produced GFP+ cells via the HDR-based knock-in through the intact 5' homology arm.
Figure 13C:
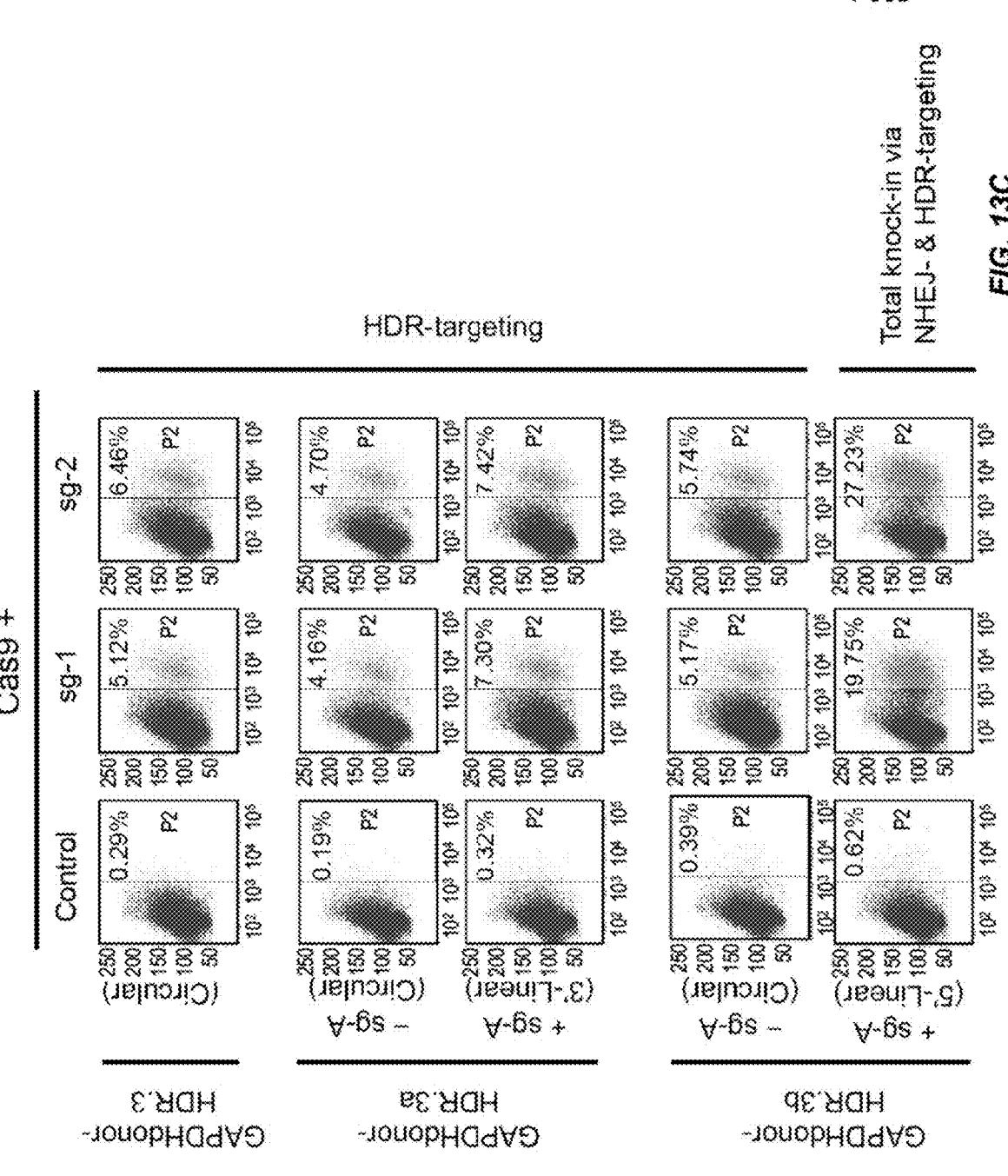
Figure 13D:
(FIG. 13D) FACS results showing NHEJ- and HDR-mediated reporter knock-in at ACTB, SOX17 and T gene loci. Upper panel shows the schematics of ires-eGFP and PGK-eGFP reporters used for knock-in at ACTB and SOX17 or T gene loci, respectively. Single-cut NH-donor was co-transfected with Cas9/sg-A/sgACTB-i or sgACTB-ii to target the ACTB locus (lower left panel, top two rows); while the CE NH-donor was co-transfected with Cas9/sg-A/sgSOX17-i, sgSOX17-ii or sgT-i to target the SOX17 or T gene loci (lower right panel, top two rows). ACTB HDR-donor carrying ires-eGFP, and SOX17 and T HDR-donors containing PGK-eGFP, were co-transfected with Cas9 and corresponding sgRNAs to examine the HDR-based knock-in (lower panel, bottom row). Control samples were transfected without gene-specific sgRNA or sg-A. FACS analysis for the tests at ACTB locus was performed at day 5 after transfection. Cells transfected with PGK-eGFP containing donors for the tests at SOX17 and T loci, were maintained for five passages before FACS analysis. GFP+ cells are gated to the right of the dashed line in each panel.
Figure 13D:
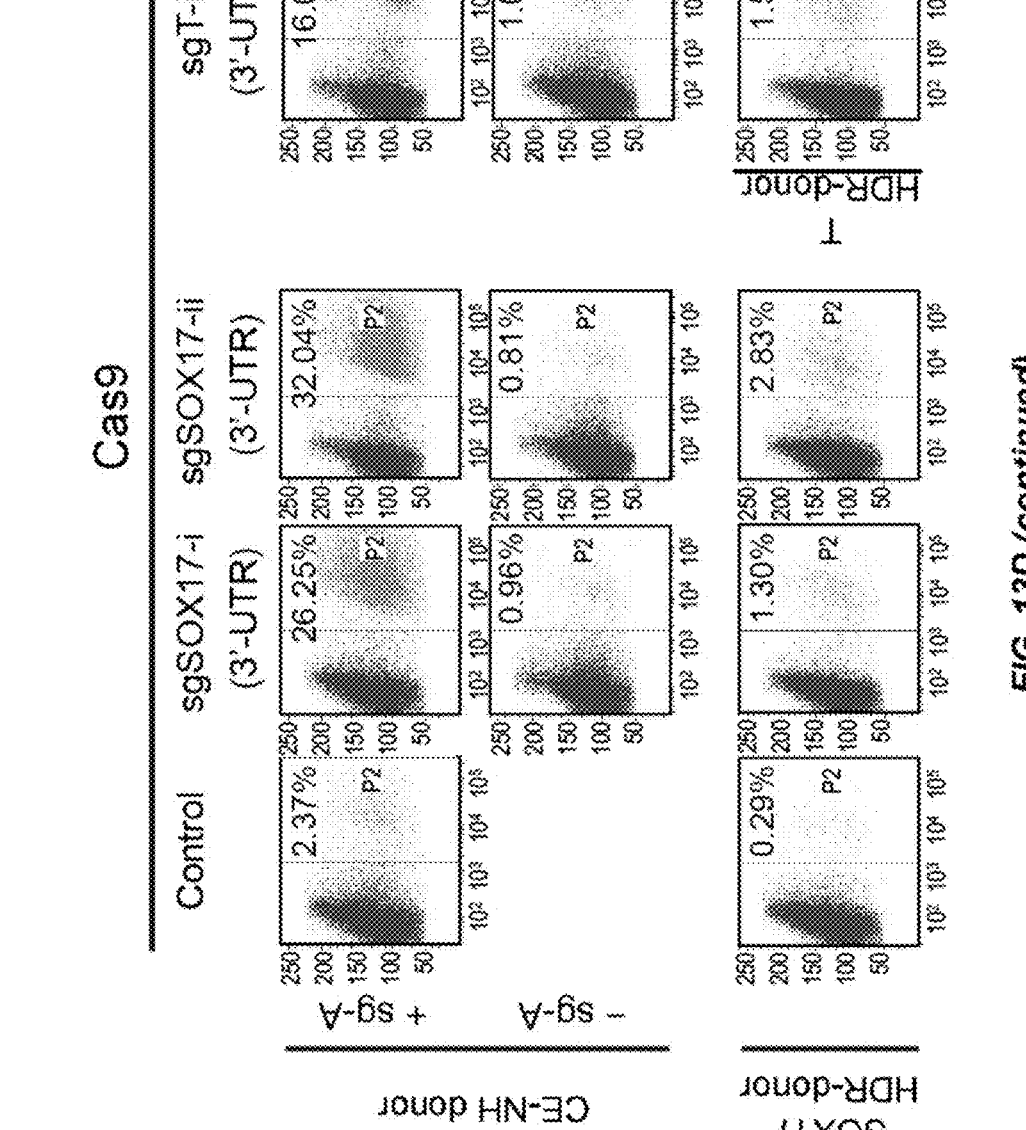
Figure 13E:
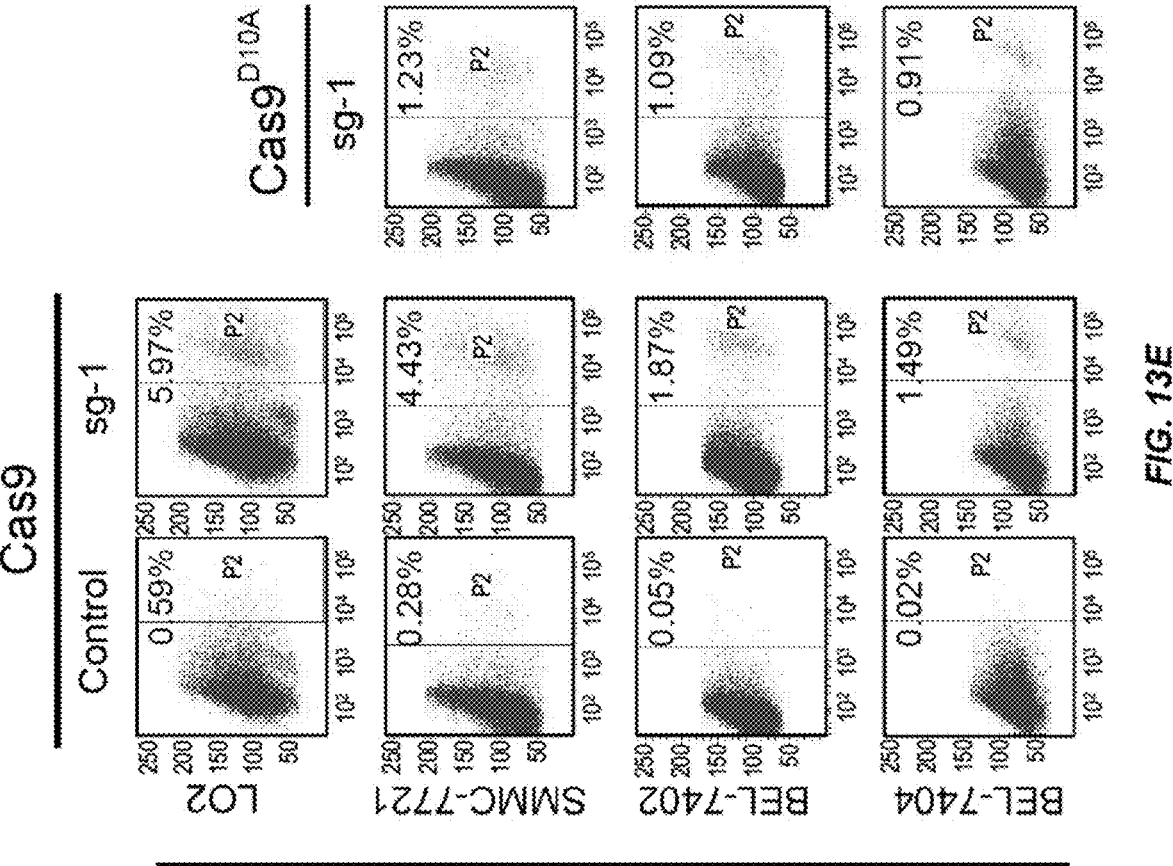
(FIG. 13E). FACS results showing Cas9/sg-1 induced HDR-mediated reporter knock-in in various somatic cell lines examined. Both wild type and nickase Cas9 carrying D10A mutation were examined.
Figure 13E:
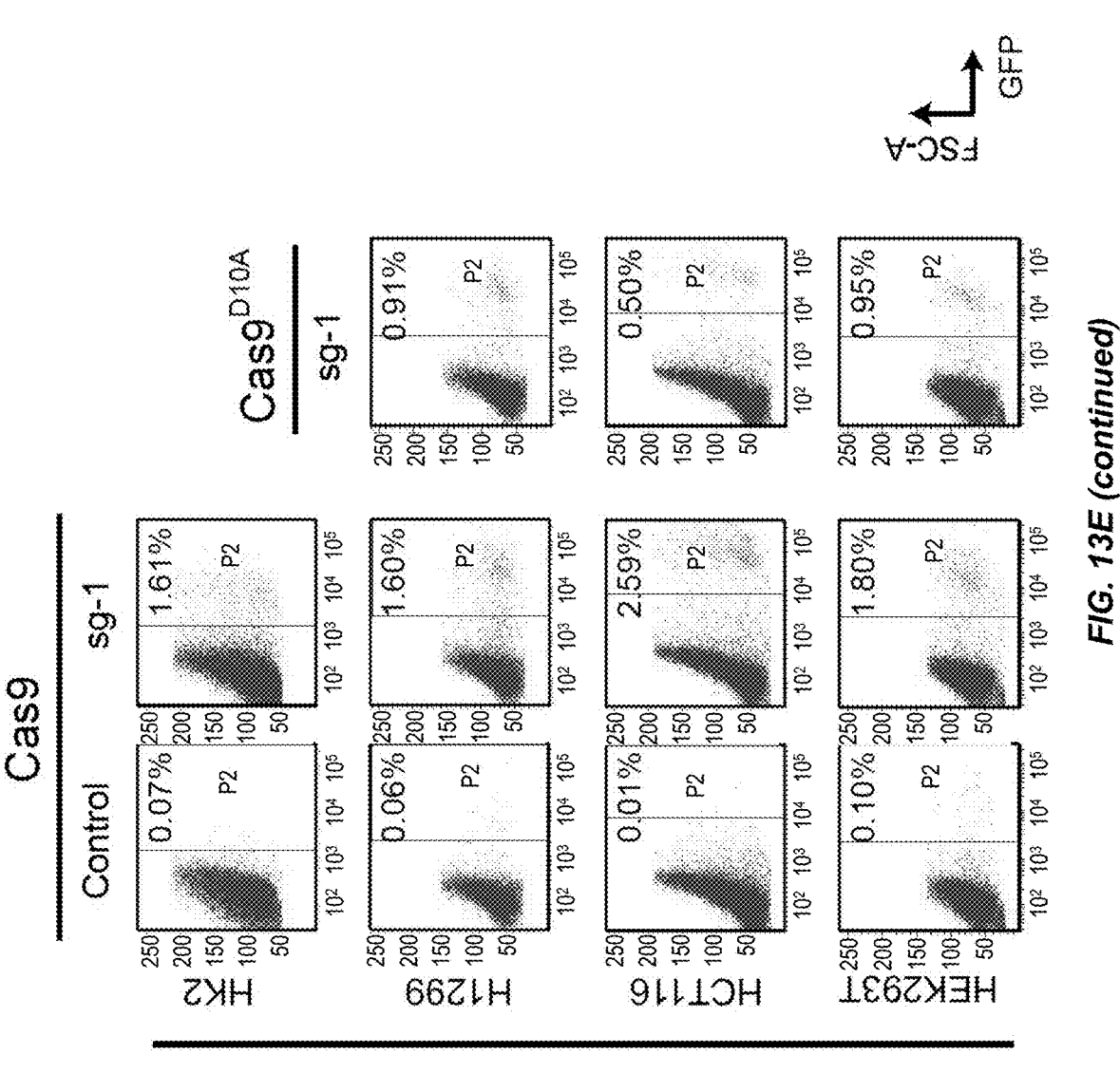

E. NHEJ Knock-In Approach has Higher Efficacy than HDR Approach Under Identical Conditions Using Linearized Donors According to one aspect, we examined the efficiency of NHEJ knock-in compared to HDR knock-in using various HDR and NHEJ constructs co-transfected with Cas9/sg-1 or sg-2. The GAPDHdonor-HDR.3 was constructed by using a shortened 5' homology arm that does not contain the sg-2 and sg-3 target sites (FIG. 13A, upper panel). This plasmid will not be cleaved by Cas9/sg-2 or sg-3 and can only serve as donor for HDR-based knock-in. Indeed, co-transfection of Cas9/sg-2 with this new donor yielded 6.46% GFP+ cells (FIG. 13C, top row). This frequency was much lower than the NHEJ-based knock-in introduced with ires-eGFP(+HAs) donor-1/Cas9/sg-2 (FIG. 13B), while it was comparable to the HDR-mediated reporter integrations produced using Cas9/sg-1 together with either type of the (HAs+) donors (FIG. 13B, 13C and FIG. 13E).

To compare the NHEJ- and HDR-based knock-in under identical conditions, HDR-mediated reporter insertion was further examined using a linearized donor. The GAPDHdonor-HDR.3a and GAPDHdonor-HDR.3b were constructed, by inserting a sg-A target sequence at the 3' or 5' of the ires-eGFP(+HAs) cassette, respectively (FIG. 13A). These donors thus can be cleaved at the sg-A target site by Cas9/sg-A to provide linear templates carrying homology arms. Using the GAPDHdonor-HDR.3a in presence of sg-A, 7.30% GFP+ cells with sg-1, and 7.42% with sg-2 were observed (FIG. 13C, third row), which were indeed higher than the results obtained using circular donors (Donor-2, or Donor-2.A and 2.B without sg-A) (FIG. 13C, top, second and fourth rows). These frequencies, however, were still much lower than that produced through NHEJ-based reporter knock-in (FIG. 12C, right panel; and FIG. 13B, with sg-2 and sg-3). Interestingly, using the GAPDHdonor-HDR.3b and Cas9/sg-A, we observed 19.75% GFP+ cells with sg-1, and 27.23% with sg-2 (FIG. 13C, bottom row). Indicating that the linearized donor-2.B enabled NHEJ-based knock-in, and the high proportion of GFP+ cells likely represented a combinatory result of both NHEJ- and HDR-mediated GFP+ knock-in events.

F. Off-Target Effect of NHEJ-Mediated Knock-In

According to one aspect, a method is provided for determining the off-target effect of NHEJ-mediated knock-in. Off-target effect is a general concern to all CRISPR/Cas9-based technology [30]. Because of the homology-independent and non-directional nature, NHEJ-mediated knock-in approach faces a higher chance of introducing a DNA insertion at an off-target site than the HDR approach. To evaluate the off-target effect, potential off-target sites that contain ≤2 mismatches in the used sgRNAs were searched, throughout the entire human genome (hg19). No strong off-target site was found for sg-A. For sg-1, sg-2, and sg-3 targeting GAPDH, 15, 14, and 6 potential off-target sites were identified respectively, and none of these off-targets are located in an exon of a known transcript (Table 2). The top 3 off-targets of sg-2 were further selected, and performed PCR analysis on off-target integrations with primers XJ-77/XJ-78/XJ-79 respectively. Among the 90 single-cell clones that were expanded previously, none were found to carry reporter integration at the off-target site #1, while integration at off-target site #2 and #3 were found in two and three clones, respectively. Compared with the number of correct knock-in clones obtained (13 out of 90) (FIG. 11), these results indicated that off-target integrations might occur during the NHEJ-mediated knock-in, but at a much lower frequency than the on-target insertion.

G. CRISPR/Cas9-Coupled NHEJ Introduces Efficient Knock-In at Both Active and Silenced Gene Loci According to one aspect, a method is provided to establish reporter sytems that allow the measuring of gene targeting efficiency in both active and silenced gene loci. To examine whether the chromatin architecture in a local genomic context influences the efficiency of NHEJ-mediated reporter knock-in, another actively transcribed locus ACTB and several silenced gene loci were targeted, including SOX17. T. OCT4. NANOG and PAX6.

Two sgRNAs (sgACTB-i and sgACTB-ii) targeting ACTB 3'-UTR were designed to examine the HDR- and NHEJ-mediated knock-in at the ACTB locus. By co-transfecting the single-cut NH-donor/Cas9/sg-A together with sgACTB-i or sgACTB-ii, GFP+ cells were observed at 10.25% and 15.27%, respectively (FIG. 13D, left panel, top row). Using the newly constructed ACTB HDR-donor, which carried the ires-eGFP flanked by homology arms to ACTB gene locus, the HDR-based knock-in were observed at 2.38% with sgACTB-i, and 8.60% with sgACTB-ii (FIG. 13D, left panel, bottom row). Both the NHEJ- and HDR-based knock-in frequencies were comparable to that observed at the GAPDH locus.

Figure 14A:
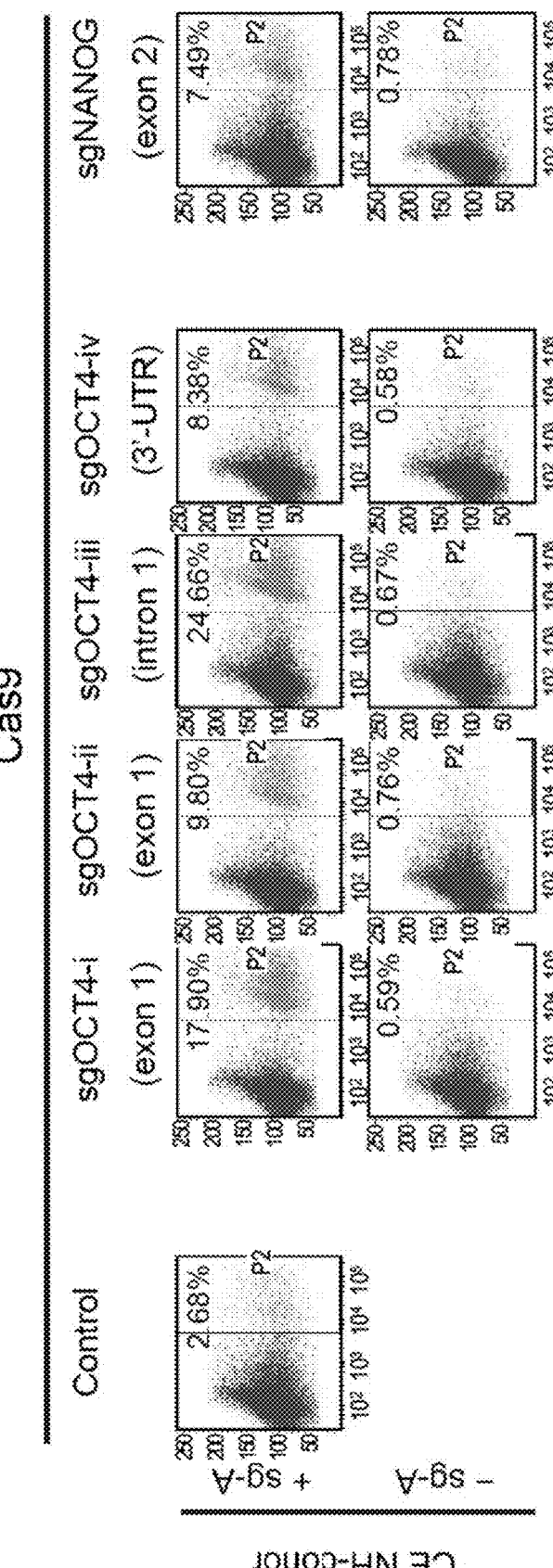
(FIG. 14A) FACS results showing NHEJ-mediated knock-in of PGK-eGFP reporter at various locations in the OCT4, NANOG, T and PAX6 gene loci. The CE NH-donor was co-transfected with Cas9 and corresponding sgRNAs, with or without sg-A, into LO2 cells. Transfected cells were maintained for five passages before FACS analysis. GFP+ cells are gated to the right of the dashed line in each panel.
Figure 14B:
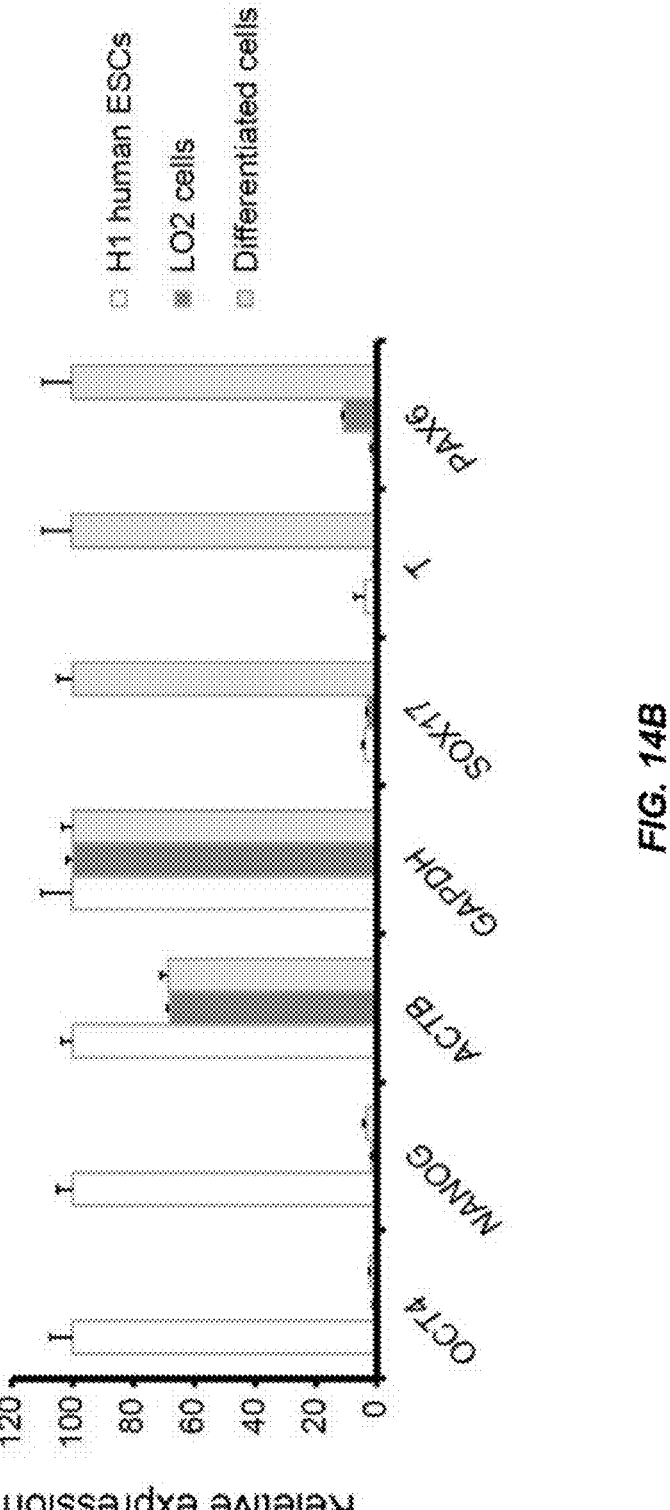
(FIG. 14B) qRT-PCR analysis of the expression of OCT4, NANOG, ACTB, GAPDH, SOX17, T and PAX6 genes in LO2 cells. H1 human ESCs which express OCT4 and NANOG, and differentiated cells that expressed SOX17, T and PAX6, were included as references. Data shown are the mean±s.d., n=3.

In order to examine knock-in at a silenced gene locus directly by FACS analysis, PGK-eGFP reporter was employed (FIG. 13D, upper right panel), which will express GFP after integration regardless whether the target locus is actively transcribed or not. A constant expression (CE) NH-donor was constructed which carries the sg-A target sequence at 5' of the PGK-eGFP cassette; meanwhile, sgRNAs targeting the SOX17 and T 3'-UTRs were generated. Noteworthy, because the expression of PGK-eGFP reporter is independent from integration orientations, the GFP+ cells observed in these assays represent knock-in events in either orientation. After transfection with the CE NH-donor/Cas9/sg-A and one of the gene-specific sgRNAs, the LO2 cells were maintained for five passages to eliminate the transient GFP expression before FACS analysis. Indeed, 26.25% and 32.04% GFP+ cells were detected for sgSOX17-i and sgSOX17-ii respectively, and 16.00% GFP+ cells were observed with sgT-i (FIG. 13D, right panel, top row). In contrast, only around 2-3% GFP+ cells were observed in the absence of gene-specific sgRNA; and approximately 1% GFP+ cells were detected in the absence of sg-A. Using this CE NH-donor, the NHEJ-mediated knock-in were also examined at various positions of OCT4. NANOG. T and PAX6 gene loci, which are largely silenced in LO2 cells. Indeed, varied knock-in frequencies were observed, which correlated neither with the target positions in a gene, nor the transcriptional status of the target loci (FIG. 14A and FIG. 14B), suggesting that the actual targeting efficiency was largely determined by the intrinsic properties of a sgRNA.

Furthermore, the HDR-based knock-in at the SOX17 and T genomic loci were examined, using donor plasmids carrying PGK-eGFP flanked by homology arms to SOX17 or T genomic regions respectively. Similarly, the transfected cells were passaged for five times before FACS analysis. By transfecting the SOX17 HDR-donor together with Cas9/sgSOX17-i or sgSOX17-ii, 1.30% and 2.83% GFP+ cells were observed, which indicated the HDR-mediated knock-in at SOX17 locus; while usage of T HDR-donor together with Cas9/sgT-i produced 1.59% GFP+ cells (FIG. 13D, right panel, bottom row). These frequencies were indeed much lower than that produced by the NHEJ-based knock-in at the same target sites (FIG. 13D, right panel, top two rows). Moreover, they were also lower than the HDR-based knock-in observed in actively transcribed ACTB and GAPDH loci (FIG. 13B, FIG. 13C and FIG. 13D, left panel, bottom row), which is consistent with previous studies showing that active transcription enhances homologous recombination [31,32]. Collectively, these results indicated that CRISPR/Cas9-coupled NHEJ can mediate efficient knock-in at both active and silenced gene loci, and the efficiencies were higher than that produced by a HDR-based approach.

H. Additional System for CRISPR/Cas9 Coupled NHEJ-Mediated Knock-In at Silent Gene Locus According to one aspect, a method and system is provided to establish reporter sytems that allow the measuring of gene targeting efficiency in a silenced gene loci. In order to examine knock-in at silenced gene locus (Sox1 and Foxa2 3' UTR loci) directly by FACS analysis, a PGK-eGFP-PA cassette for knock-in selection and an ires-td-Tomato-PA for reporter application and two LoxP sites for the deletion of unnecessary parts after fluorescent detection was employed (FIG. 15A). A NH-donor (NH-S donor 4) was constructed which carries the sg-A target sequence 5' of the ires-td-Tomato-PA; meanwhile, sgRNAs targeting the Sox1 and Foxa2 3'-UTR were generated. After transfection with the NH-S donor 4/Cas9/sg-A and one of the gene-specific sgRNAs, the LO2 cells were maintained for five passages to eliminate the transient GFP expression before FACS analysis. Indeed, 2.8% and 2.48% GFP+ cells were detected for sgSox1-i and sgSox1-ii respectively (FIG. 15C), and 1.36 and 1.56% GFP+ cells were observed for sgFoxa2-i and Foxa2-ii (FIG. 15C). In contrast, less than 1% GFP+ cells were observed in the absence of gene-specific sgRNA. Flow detection demonstrated a positive signal for td-Tomato expression, which represented a successful knock-in via the the NH-S donor 4 construct (FIG. 15B). Collectively, these results indicated CRISPR/Cas9-coupled NHEJ can mediate efficient knock-in at silent gene locus.

I. Two-Directional NHEJ-Mediated Knock-In of Reporter Genes

Figure 16:
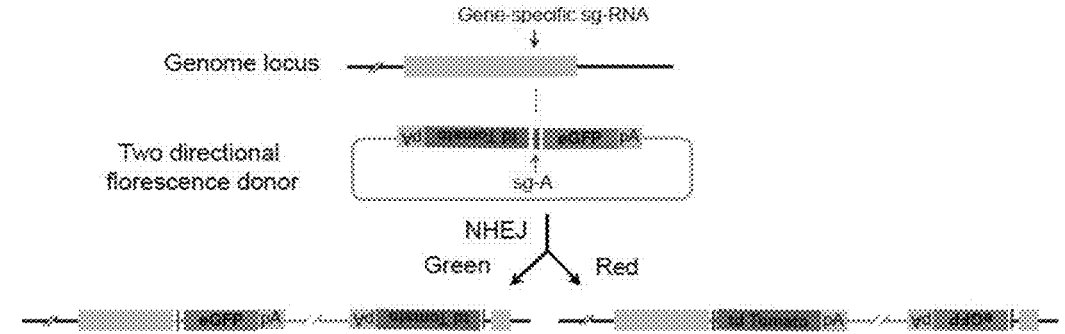
FIG. 16 Homology-independent dual color-insertion knock-in of reporter genes.
Figure 16:
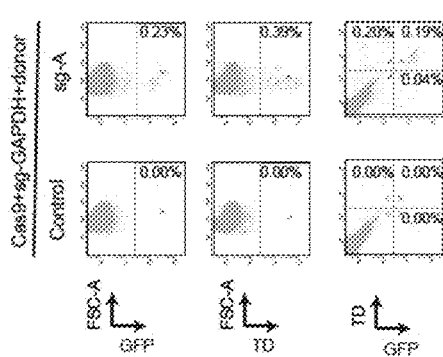

According to one aspect, a method and system is provided to establish a reporter system that allows for two directional (dual color) NHEJ-mediated knock-in. In order to examine bidirectional knock-in at a gene locus (GADPH 3' UTR loci) directly by FACS analysis, a single cut NH-donor (GAP- DHdonor-NHEJ.1) was used as the backbone; ires were deleted using enzyme cutting sites Mlu1 and Msc1 and then the TD-PA were cloned in to Sac2 site to obtain the dual reporter. As outlined in FIG. 16A, an eGFP-PA cassette for knock-in selection and an td-Tomato-PA for reporter application were employed. A sgGAPDH targeting GAPDH 5'-UTR was used to mediate non-directional integration, and sg-A induced cleavage of the NH-donor plasmid. Using this donor, one directional integration could produce eGFP expression (FIG. 16A, left side) and the other directional integration could produce TD tomato expression (FIG. 16A, right side). Flow analysis demonstrated that using the two directional fluorescence donor, Cas9/sg-A/sgGAPDH mediated knock-in produced GFP+/TD−, GFP−/Td+ and GFP+/TD+ cell populations. Collectively, these results indicated a functional role for this donor in non-directional integration.

J. Unidirection-Preferred Knock-In Method Mediated by CRISPR/Cpf1

CRISPR/Cpf1 (CRISPR from *Prevotella* and *Francisella* 1) is type V CRISPR-Cas systems containing ~1,300 amino acids. Unlike Cas9 systems (also referred as type II CRISPR-Cas systems), Cpf1-sgRNA complexes efficiently cleave target DNA proceeded by processing into mature crRNAs without the requirement of an additional trans-activating crRNA (tracrRNA) with a short T-rich proto-spacer-adjacent motif (PAM), in contrast to the G-rich PAM following the target DNA for Cas9 systems. More importantly, instead of blunt ends produced by Cas9, Cpf1 introduces a staggered DNA double-stranded break with a 4 or 5-nt 5' overhang [35]. Consequently, Cpf1 has the potential to enhance the efficiency of genetic insertions and specificity compared to Cas9.

Figure 17:
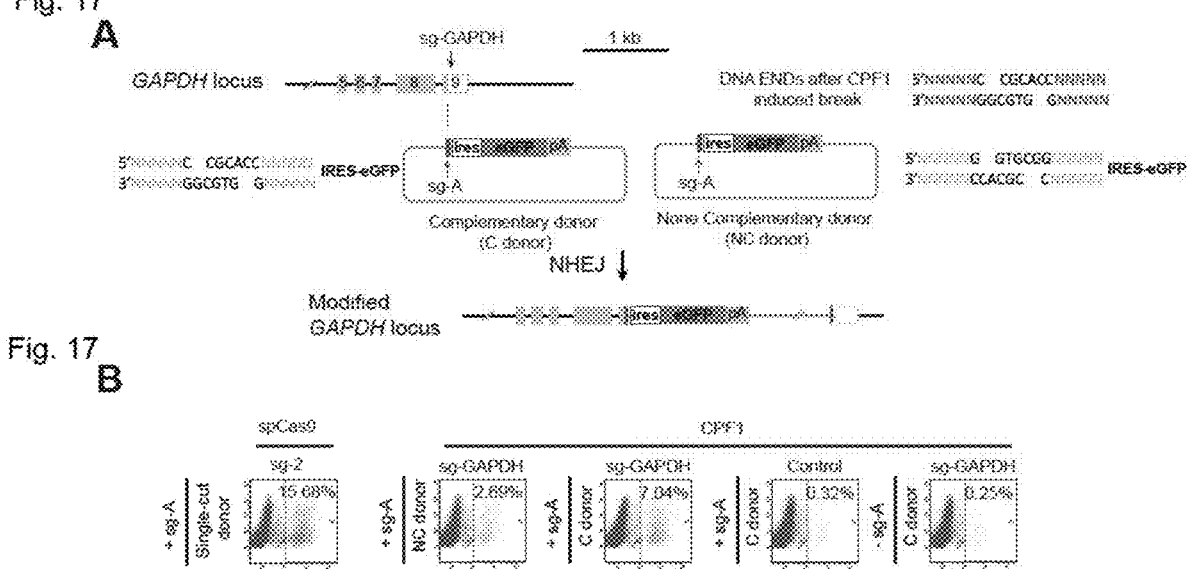
FIG. 17 Homology-independent knock-in of reporter genes into CPF1-induced DSBs in genome.

According to one aspect, a method and system is provided for unidirection-preferred knock-in mediated by NHEJ using a CRISPR/Cpf1 system. A plasmid of CRISPR/Cpf1 pY016 (pcDNA3.1-hLbCpf1) was obtained from Addgene (plasmid #69988), and sgRNAs were designed according to reference and cloned into the sgRNA backbone. Two donor plasmids were prepared, one donor plasmid was a complementary donor (C donor) and the other donor plasmid was a non-complementary donor (NC donor) (FIG. 17A). To explore whether a non-homology (NH)-targeting approach could produce stable knock-in clones using the CRISPR/Cpf1 system, cells were transfected with single-cut NH-donor (C and NC donors)/Cpf1/sg-A and sg-GADPH. The spCas9 induced NHEJ-mediated knock-in (FIG. 17B, left panel) efficiency serves as a positive control (15.68%) (FIG. 17B, left panel). The complementary donor produced a substantially higher knock-in efficiency (C donor=7.04%) than that mediated with the non-complementary donor (NC donor=2.69%). Collectively, these results indicated that a unidirection-preferred knock-in method mediated by NHEJ using CRISPR/Cpf1 can be achieved.

K. NHEJ-Mediated Knock-In of Multiple-Color Fluorescent Reporter Genes into Multiple Alleles According to one aspect, a method is provided to establish a reporter system that allows for a multiple allele knock-out strategy using CRISPR/Cas9 induced NHEJ-mediated knock-in (FIG. 18). In essence, multiple donor plasmids are provided for knock-in at the same time. The donor plasmids each include a different reporter gene, and the reporter gene can include, but is not limited to, a different fluorescent color or drug resistance. With each plasmid containing a different reporter, the targeted cell will show different colors and/or drug resistance upon successful NHEJ-mediated knock-in. With human insulator sequences included, the donors insert at the 5' end of a target gene and therefore disrupt its expression. With multiple donor plasmids inserted simultaneously into multiple alleles, the target gene will be completely disrupted and produce a knock-out genotype.

According to one aspect, multiple color fluorescent reporter donors were prepared essentially as follows:

(a) NH-donor-in-eGFP: A single-cut NH-donor (GAPDH-donor-NHEJ.1) was used as the backbone; and ires was deleted using enzyme cutting sites Mlu1 and Msc1 to obtain the NH donor eGFP; and tandem repeats of human insulator sequences was inserted at the 5' end of the sg-A target sequence.

(b) NH-donor-in-td-Tomato: A single-cut NH-donor (GAPDHdonor-NHEJ.1) was used as the backbone; and ires was deleted using enzyme cutting sites Mlu1 and Msc1: after which td-Tomato was used to replace eGFP; and tandem repeats of human insulator sequences was inserted at the 5' end of the sg-A target sequence.

(c) NH-donor-in-puro: A single-cut NH-donor (GAPDH-donor-NHEJ.1) was used as the backbone; and ires was deleted using enzyme cutting sites Mlu1 and Msc1: after which puromycin ("puro") was used to replace eGFP, and tandem repeats of human insulator sequences was inserted at the 5' end of the sg-A target sequence.

(d) NH-donor-in-hygro: A single-cut NH-donor (GAP-DHdonor-NHEJ.1) was used as the backbone; and ires was deleted using enzyme cutting sites Mlu1 and Msc1: after which hygromycin ("hygro") was used to replace eGFP, and tandem repeats of human insulator sequences was inserted at the 5' end of the sg-A target sequence.

After transfection with the respective NH-in-donors, Cas9, sg-A, and one of the gene-specific sgRNAs (sgMRE11), the cells were subjected to FACS analysis. Here, flow analysis for the targeting result at the MRE11 locus, which employed both the NH-donor-in-eGFP and NH-dono-in-td-Tomato, showed single positive cells (1.18% and 1.01%, respectively), representing at least one allele was modified. Additionally, a double positive cell population was also noted, representing those cells carrying a knock-in at two alleles (0.08%). In contrast, no positive cells were observed in the absence of the gene-specific sgRNA.

Below are some exemplary systems of the present invention:

1. (b) GFP Reporter System
pSuper_AAVS1(B)cGFP reporter plasmid
PiggyBac_(B)cGFP reporter plasmid
pSuper_Rosa26(B)cGFP reporter plasmid
sgRNA-X
Three donor plasmids (B)cGFPdonor-HDR.1-3, carrying 30-bp insert and homology arms at 250 bp, 500 bp and 800 bp, respectively
Three donor plasmids (B)cGFPdonor-HDR.A and B, carrying 726-bp insert and homology arms at 250 bp and 500 bp, respectively According to one aspect, a method is provide to allow direct assessment of the HDR-mediated gene targeting efficiency using fluorescence activated cell sorting (FACS) analysis. A broken copGFP ((B)cGFP) reporter system was generated.

According to one aspect, a reporter gene was designed to contain a PGK promoter-driven Puro-2a-broken copGFP fusion coding sequence (CDS) (PGK-Puro2a(B)cGFP), and it was built into pSuper-puro plasmid (See FIG. 1A). The broken copGFP fragment consists of two non-functional copGFP fragments (copGFP-N and copGFP-C) separated by a 77-bp synthesized segment. Within the 77-bp, three stop codons are included in different reading frames to prevent the restoration of copGFP expression by NHEJ-mediated repair, and target sequence of sgRNA (named sg-X and sg-Y) are included for introducing site-specific DSB in genome.

According to one aspect, we cloned two genome DNA fragments from human AAVS1 genome locus (also known as PPP1R12C locus) and inserted at 5' and 3' of the PGK-Puro2a(B)cGFP fragment into the pSuper-puro plasmids, to generate the pSuper_AAVS1(B)cGFP reporter plasmids (See FIG. 1A). This plasmid can be used to insert the (b) GFP reporter into the AAVS1 locus in any human cell line (See FIG. 1A), and thus allow direct analysis of HDR in the target cell line.

According to one aspect, we inserted the PGK-Puro2a-(B)cGFP reporter fragment into the Piggy Bac plasmid [19], to obtain the Piggy Bac_(B)cGFP reporter plasmid.

Figure 1B:
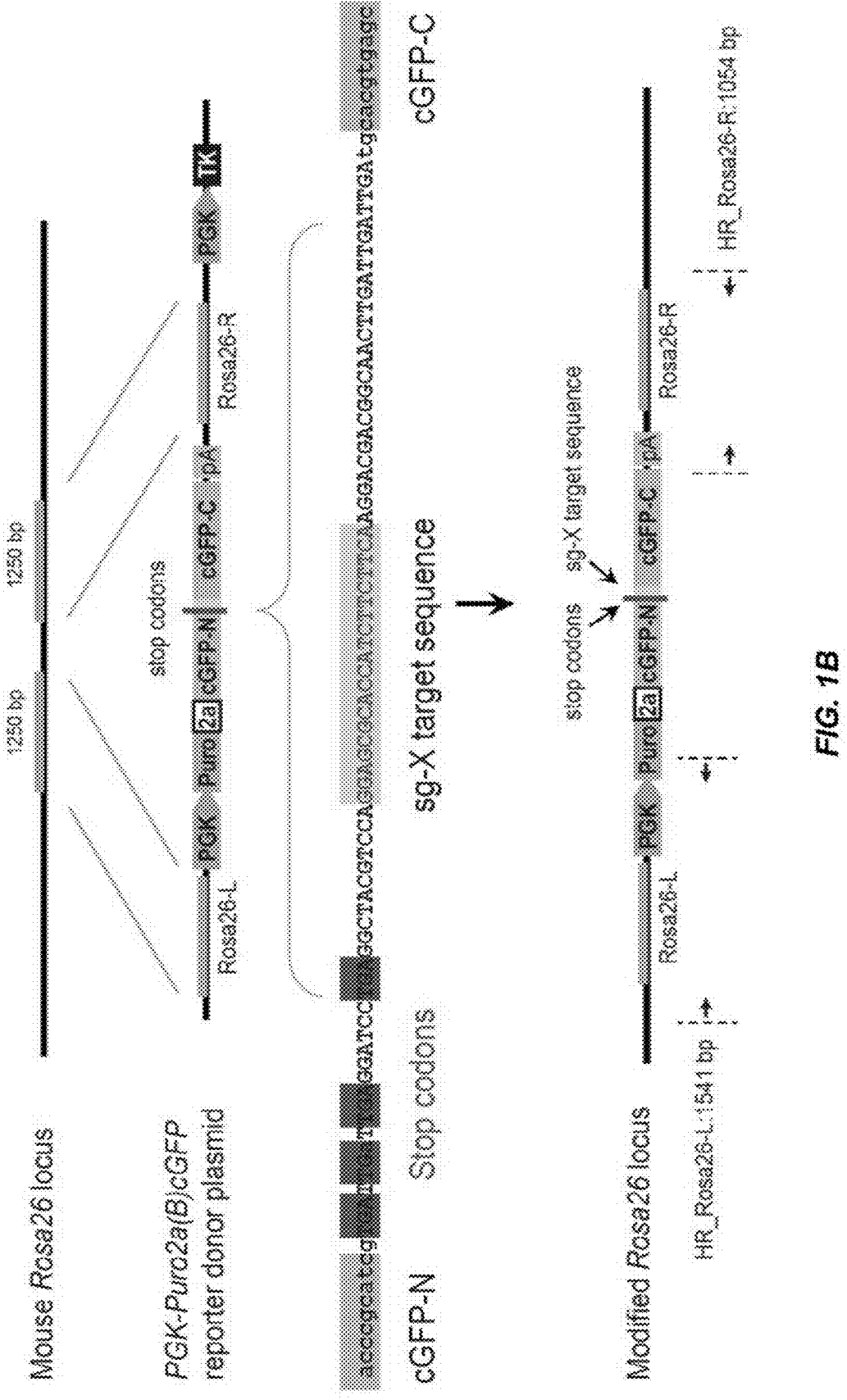
(FIG. 1B) Targeting to mouse Rosa26 gene locus in E14-Rosa26(B)cGFP reporter cell line (SEQ ID NO: 144).

According to one aspect, we cloned two genome DNA fragments from mouse Rosa26 genome locus and inserted at 5' and 3' of the PGK-Puro2a-(B)cGFP fragment in to pSuper-puro plasmid, to generate the pSuper_Rosa26(B)cGFP reporter plasmid (See FIG. 1B). This plasmid can be used to insert the (B)cGFP reporter into the Rosa26 locus in any mouse cell line, and thus allow direct analysis of HDR efficiency in the target cell line.

According to one aspect, two sgRNAs (sg-X and sg-Y) were constructed using previous described scaffold plasmid to target the designed target site within the 77-bp fragment, or to target a selected site within copGFP-N, respectively.

Figure 2A:
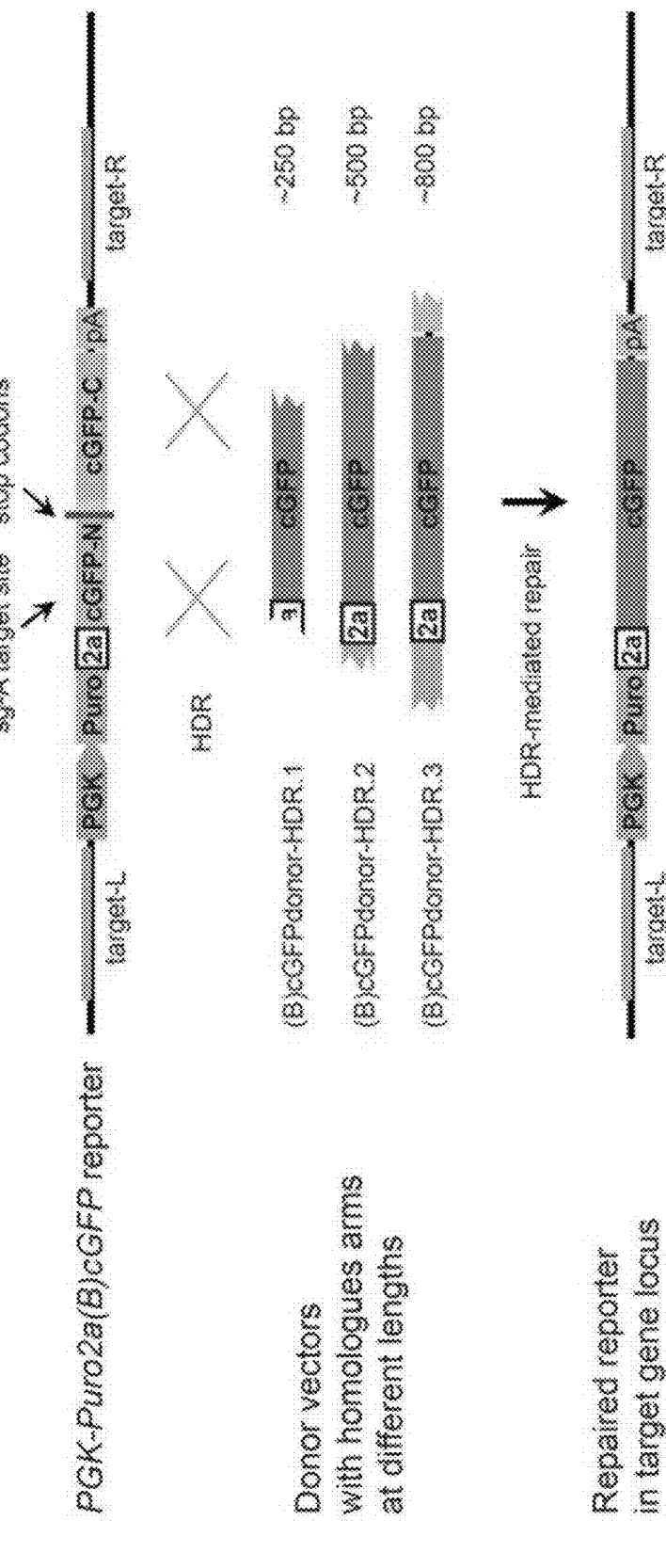
(FIG. 2A) (B)cGFPdonor-HDR.1-3.

According to one aspect, three donor plasmids were constructed (named (B)cGFPdonor-HDR.1-3), each containing a pair of homologous arms at different length (250 bp, 500 bp or 800 bp, respectively) to the Puro2a-(B)cGFP reporter gene (See FIG. 2A). These donor plasmids can serve as templates for replacing the disrupting 77-bp segment with functional copGFP fragments, thus restoring the copGFP expression via HDR. The insertion involved is a 24-bp sequence that was deleted for constructing the broken copGFP reporter. Three donor plasmids carrying varied homology arms allow quantifying the effect of homology length on HDR efficiency.

Figure 2B:
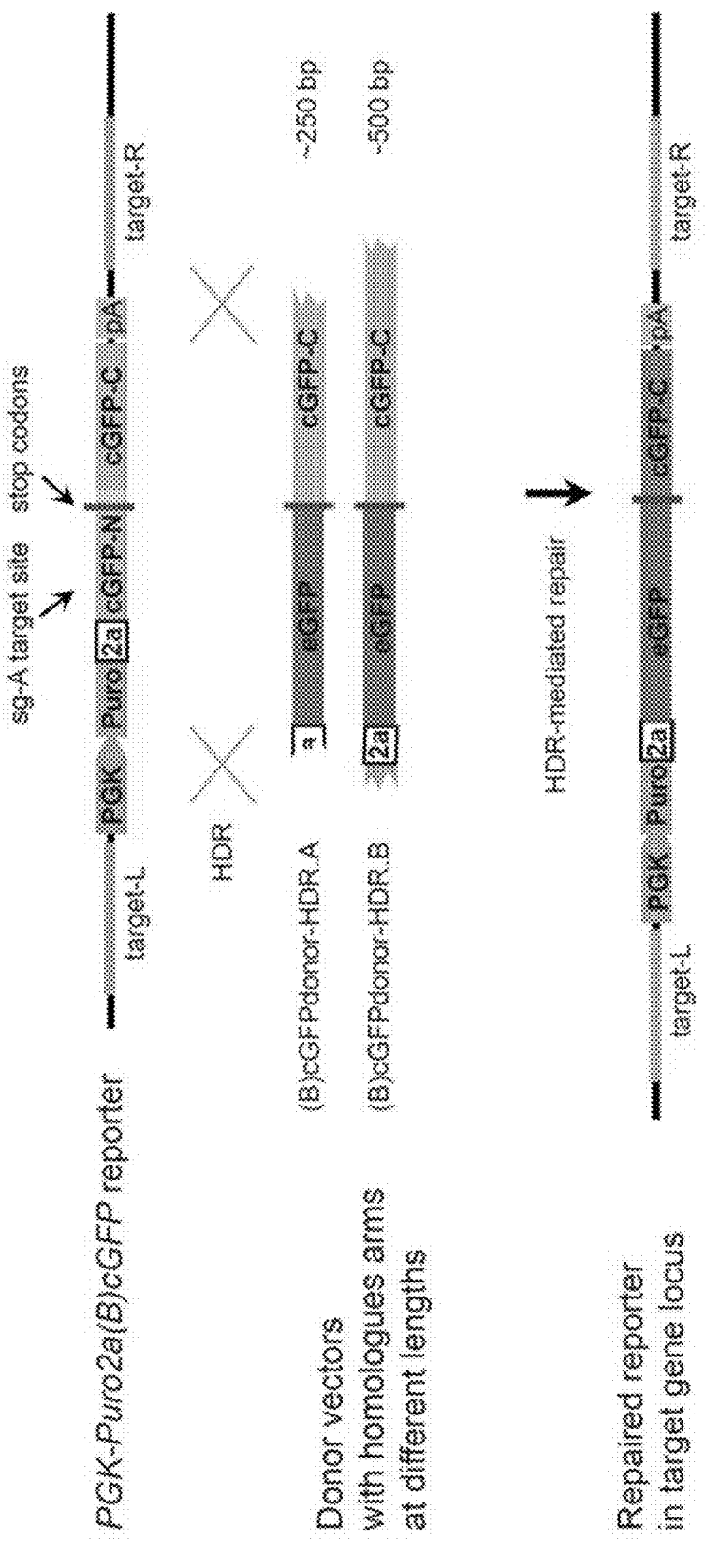
(FIG. 2B) (B)cGFPdonor-HDR.A-B.

According to one aspect, to examine whether a larger insert can be efficiently targeted to genome via CRISPR/Cas9-induced HDR, we construct donor plasmids carrying the full eGFP CDS in-between the homology arms to Puro2a-(B)cGFP (See FIG. 2B). Similarly, two donor plasmids were constructed to carry the eGFP insert flanked with homology arms of 250 bp or 500 bp (named (B)cGFPdonor-HDR.A and B, respectively).

2. HEK293T-AAVS1 (B)cGFP Reporter Line

Figure 3A:
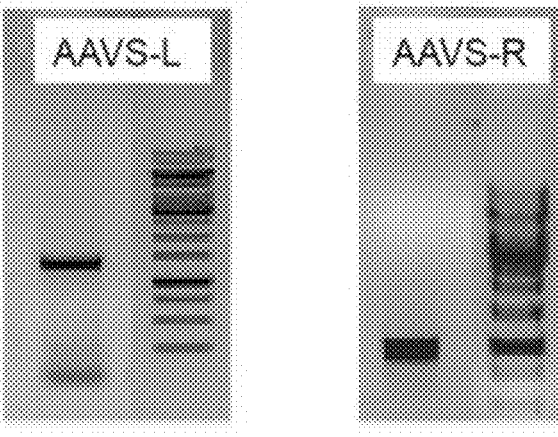
(FIG. 3A) PCR with genomic DNA confirming PGK-Puro2a(B) cGFP reporter vector knock-in at the AAVS1 locus on genome.
Figure 3B:
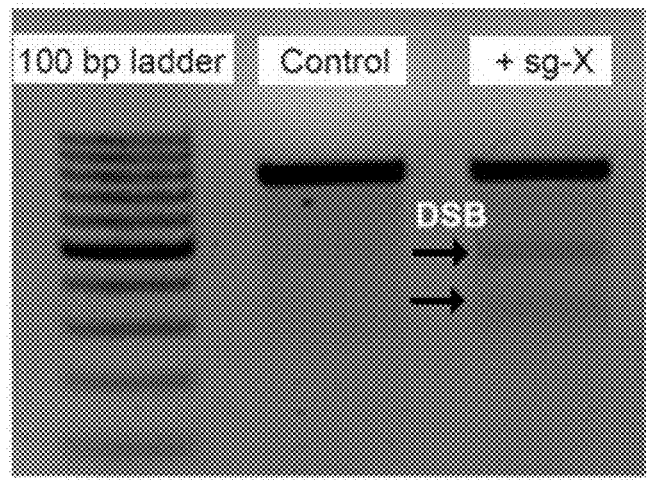
(FIG. 3B) T7E1 assay's showing the efficiency of genome targeting by Cas9/sg-X.

According to one aspect, we generated a stable cell line using HEK293T cells to measure the efficiency of HDR-mediated gene targeting in human somatic cells. We choose to insert the (B)cGFP reporter in the AAVS1 locus in human genome, which exhibits open chromatin structure and has been suggested as potential target regions for integration as its disruption has no functional consequence. According to one aspect, one HEK293T (B)cGFP reporter cell line was generated in present disclosure and confirmed by genome PCR to carry the desired PGK-Puro2a-(B)cGFP reporter in AAVS1 locus (named HEK293T-AAVS1(B)cGFP reporter line) (See FIG. 3A). According to one aspect, DSBs introduced by Cas9/sg-X in the reporter cell line can be detected by T7E1 assay (See FIG. 3B). To assess the HDR efficiency induced by CRISPR/Cas9, plasmids (B)cGFPdonor- HDR.1-3 were transfected individually with plasmids encoding Cas9 and sg-X into the HEK293T-AAVS1(B) cGFP reporter cells. According to one aspect, GFP expressions representing HDR efficiency was detected using FACS analysis at day 3, 5, 7 and 9 after transfection (see FIG. 3C). Our results showed that HDR efficiency at AAVS1 locus induced by Cas9/sg-X in presence of (B)cGFPdonor-HDR.1-3 were around 0.11%, 1.00% and 3.45% respectively. whereas no GFP+ wells were observed in control group which were transfected without sg-X plasmids. The most efficient targeting was obtained using the (B)cGFPdonor-HDR.3 that carry 800 bp homology arm, which was increased to ~3.45%. According to these data, higher Cas9 induced HDR could be induced when longer homology arms were provided.

Figure 3C:
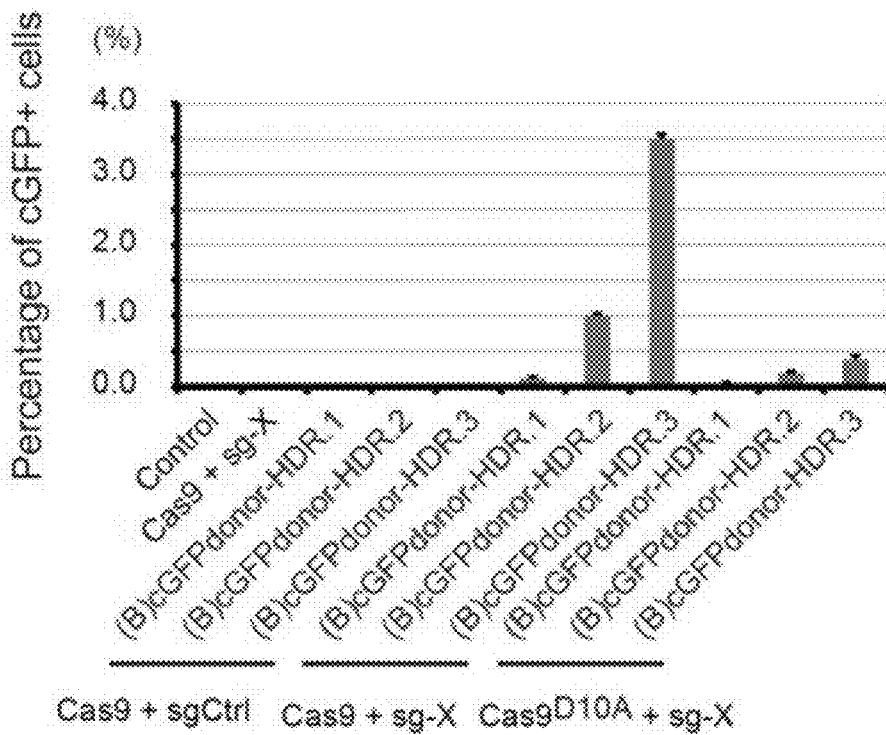
(FIG. 3C) FACS results showing HDR-mediated knock-in of (B)cGFPdonor-HDR.1-3, induced by nickase Cas9D10A and wild type Cas9 (wtCas9) in combination with sg-X.

According to one aspect, when D10A mutant Cas9 was used instead of wild type Cas9, we observed the targeting efficiency at ~0.11%, 0.21% and 0.35% in the presence of (B)cGFPdonor-HDR.1-3 respectively (See FIG. 3C). According to one aspect, HDR frequency was about ten times lower when D10A mutant Cas9 was used, compared to WT Cas9. The data indicates the limitation of using nickase Cas9 for gene targeting.

Figure 3D:
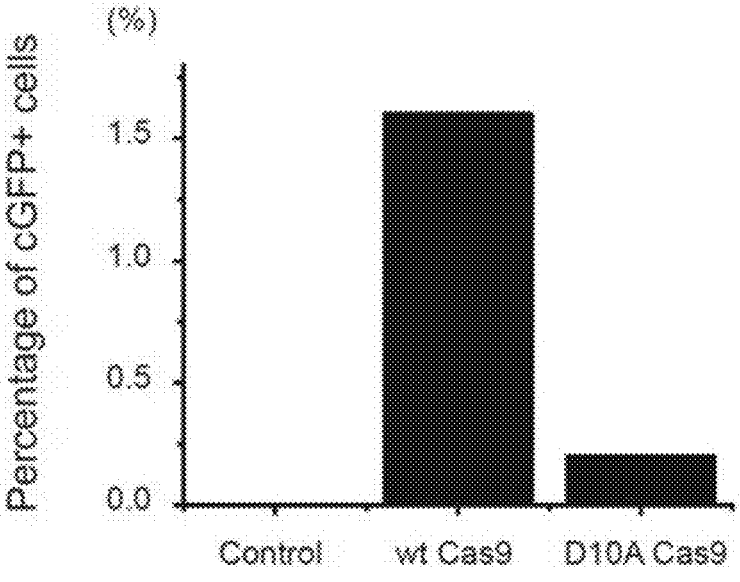
(FIG. 3D) FACS results showing HDR-mediated knock-in of (B)cGFPdonor-HDR.B, induced by nickase Cas9D10A and wild type Cas9 (wtCas9) in combination with sg-Y.

According to one aspect, to examine whether a larger insert can be efficiently targeted to genome, we co-transfected donor plasmid (B)cGFPdonor-HDR.B together with Cas9/sg-Y into the HEK293T-AAVS1(B)cGFP reporter cell line. HDR efficiency detected using FACS analysis at 9 days after transfection was around 1.6% (see FIG. 3D). Similarly, lower HDR frequency (0.2%) was observed when D10A mutant Cas9 was used.

3. H1-AAVS1(B)cGFP Reporter Line

According to one aspect, one stable human embryonic stem cell (ESC) reporter line was generated through co-transfection of Piggy Bac_(B)cGFP reporter plasmid together with transposase, to measure the HDR gene targeting efficiency in genome. This cell line was confirmed to carry the (B)cGFP reporter integrated into the genome (see FIG. 4). To assess the HDR efficiency induced by CRISPR/Cas9, plasmid (B)cGFPdonor-HDR.3 that carries 800 bp homology arms were transfected with Cas9 and sg-X into the H1-(b)GFP reporter cells. According to one aspect, GFP expression representing HDR efficiency was detected using FACS analysis at day 5 after transfection. A control group was transfected with the donor and Cas9, but without sg-X. HDR efficiency induced by Cas9/sg-X in presence of (B)cGFPdonor-HDR.3 were detected stably at 0.02%, whereas control group showed no GFP-positive cells within 10E5 cells. This data showed that our H1-(B)cGFP reporter line can be used for assessing the HDR-mediated gene targeting, with provided donor plasmid/Cas9/sg-X.

4. E14-Rosa26(B)cGFP Reporter Line

According to one aspect, we generated a stable mouse ESC (E14) reporter line to measure the efficiency of HDR-mediated gene targeting in mouse ESCs. We choose to insert the (B)cGFP reporter in the Rosa26 locus in mouse genome, which also exhibits open chromatin structure and has been suggested as potential target regions for integration as its disruption has no functional consequence. According to one aspect, one E14 (B)cGFP reporter cell line was generated in present disclosure carrying the desired PGK-Puro2a-(B) cGFP reporter in the Rosa26 locus (named E14-Rosa26(B) cGFP reporter line). To assess the HDR efficiency induced by CRISPR/Cas9, plasmids (B)cGFPdonor-HDR.3 was transfected with plasmids encoding Cas9 and sg-X into the E14-Rosa26(B)cGFP reporter cells. According to one aspect, GFP expressions representing HDR efficiency was detected using FACS analysis at day 3, 5, 7 and 9 after transfection. A control group was transfected with the donor and Cas9, but without sg-X. HDR efficiency at Rosa26 locus induced by Cas9/sg-X in presence of (B)cGFPdonor-HDR.3 was detected stably at 0.08%, which is ~40 folds higher than control group. According to these data, E14-Rosa26(B) cGFP reporter cell line provides a reliable and convenient tool for analyzing HR frequency in stalely cultured mouse ESCs.

Figure 5A:
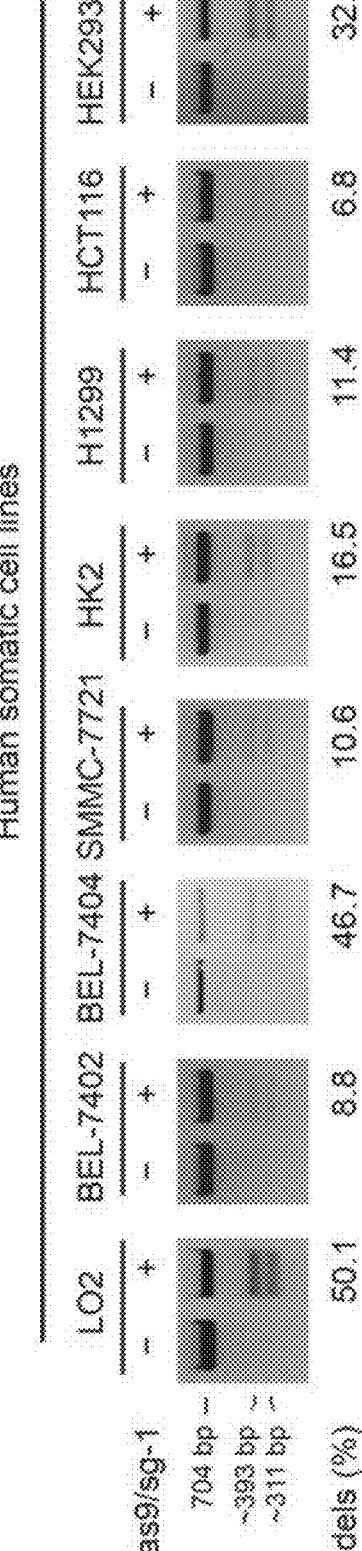
(FIG. 5A) Upper panel shows the schematics of sg-1-4 targeting sites, primer pair used for T7E1 assay and predicted cutting patterns with different sgRNAs in T7E1 assay. Middle panel shows H1 human ESCs cultured on Matrigel in mTeSR1 medium, and T7E1 assays showing the efficiency of genome targeting by Cas9/sg-1, 2 or 3 in human H1 ESC (top panel) and selected somatic cell lines (bottom panel). Lower panel: the T7E1 assays showing the efficiency of genome targeting by Cas9/sg-1 in selected human somatic cell lines.

5. Polynucleotide Constructs for GAPDH HDR-Reporter System sg-1, 2, 3 and 4 (sgRNA targeting GAPDH 3'-UTR) plasmids GAPDHdonor-HDR.1 plasmid According to one aspect, a method is provided to establish reporter systems that allow measuring the gene targeting efficiency directly in all human cell types (lines). We choose to target the GAPDH locus in human genome, which encode a constantly and universally expressed house-keeping gene. Promoterless GFP reporter inserted in this locus can be actively transcribed and then translated into fluorescence proteins, which can be observed in live cells, and the efficiency of successful targeted insertions can be examined directly by fluorescence activated cell sorting (FACS). To avoid disturbing the GAPDH protein function, which may happen during the CRISPR/Cas9-mediated gene targeting, we choose to target GAPDH 3'-UTR. In total, we designed and constructed four sgRNAs (sg-1-4), they were driven by a U6 promoter in the previously used scaffold vector [20]. The activity and effectiveness of individual sgRNAs to induce DSB were examined using T7E1 assays (see FIG. 5A, sg-1-3 as examples).

Figure 5B:
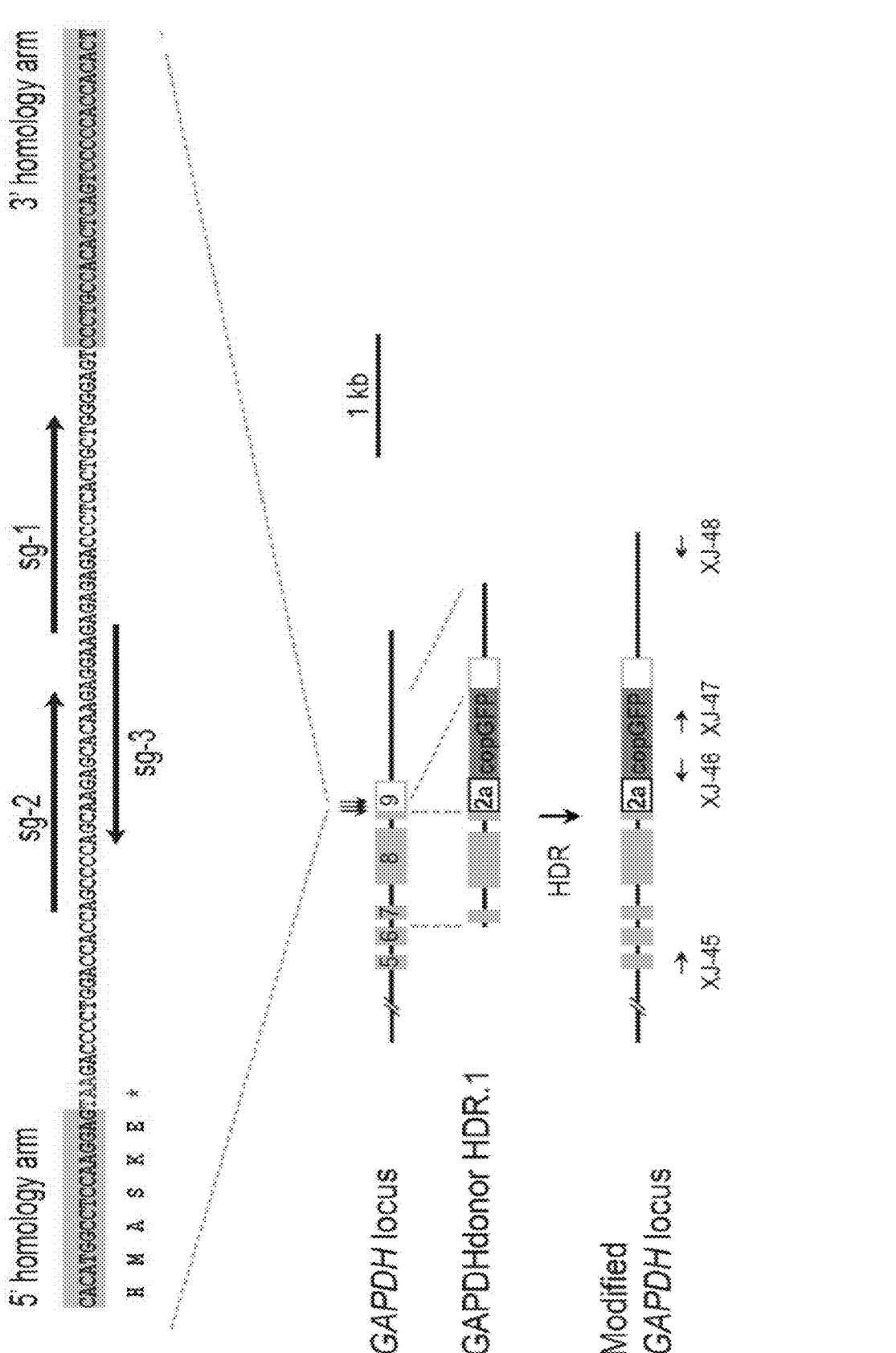
(FIG. 5B) Schematics of the sg-1-3 targeting sites, the donor plasmid design and targeting strategy for HDR-mediated knock-in of 2a-copGFP reporter at GAPDH exon 9. Dashed lines indicate sections of homology between the genomic locus and plasmid DNA. Positions of PCR primers used for detection of reporter knock-in are shown (SEQ ID NOs: 145-146).

According to one aspect, a method is provided to directly quantify and compare the efficiency of CRISPR/Cas9-induced HDR-based gene targeting in human ESCs and somatic cells. We construct a donor plasmid (named GAPDHdonor-HDR.1) to carry P2a-copGFP CDS flanked by two DNA fragment arms that share homology to the GAPDH locus in human genome (see FIG. 5B, 5C). The 5'-arm contains 903 bp sequences at the upstream and 3'-arm contains 967 bp at the downstream of sg-1-4 target sites. They were cloned from genome and inserted in the 5' and 3' side of the promoterless P2a-copGFP fragment that was cloned into pSuper-puro vector. To assess the efficiency of CRISPR/Cas9-induced HDR-mediated gene targeting. wild type (WT) Cas9, a sgRNA from sg-1-4, and the GAPDHdonor-HDR.1 are co-transfected together. The Cas9/sgRNA-induced DSBs will then stimulate DNA repair via HDR pathway in the presence of the GAPDHdonor-HDR.1 template. When successful recombination happens to both homology arms, the P2a-copGFP fragment from the donor will be inserted in frame with GAPDH CDS in genome, transcribed together with GAPDH, but translated as separate GFP proteins (FIG. 5B). The GFP expression representing precise genomic integration could be directly detected using FACS analysis after transfection (see FIG. 5D). The donor vector has been confirmed for not expressing GFP without integration into GAPDH locus correctly.

Figures 6A, 6B:
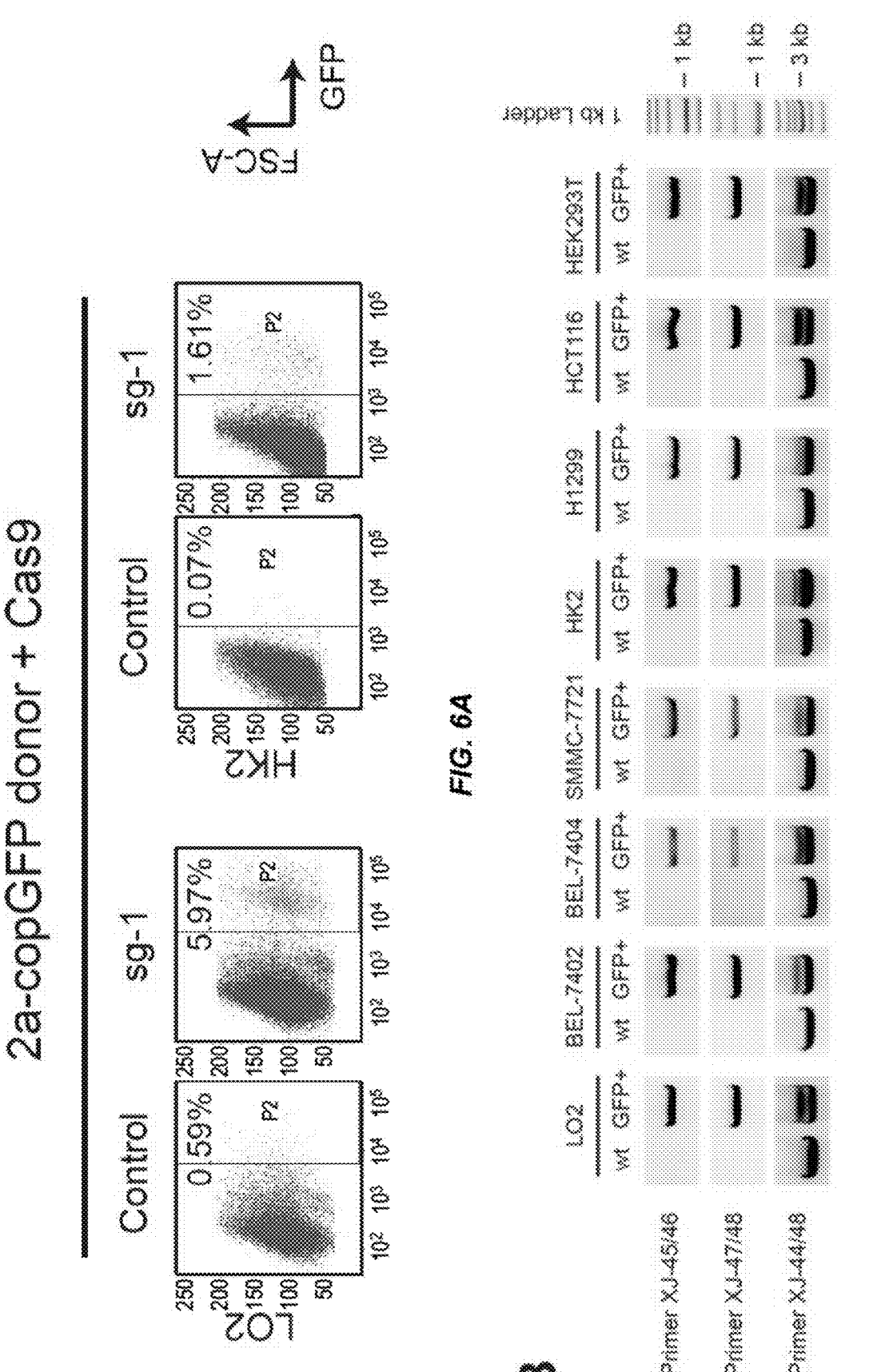
(FIG. 6A) FACS results showing varied frequency of HDR-mediated 2a-copGFP knock-in in human cell line LO2 and HK2, with or without sg-1. Donor plasmid and wild type Cas9 were transfected in all samples. GFP+ cells from the Cas9/sg-1 targeted cells (green signals gated to the right of the dashed line in each panel) were sorted for further analysis.
(FIG. 6B) PCR with genomic DNA isolated from GFP+ cells obtained in a. Primers binding sites were indicated in a. Primer pair XJ-45/46 amplified the 5'-junctions (1350) bp) and XJ-47/48 detected 3-junctions (1473 bp), after 2a-copGFP was integrated into genome via HDR. Primers XJ-45/48 amplified two DNA fragments that represent wild type (2480 bp) and modified alleles (3241 bp). All PCR analyses amplified DNA fragments at expected sizes, indicating correct integration of 2a-copGFP via HDR into genome.
Figure 6C:
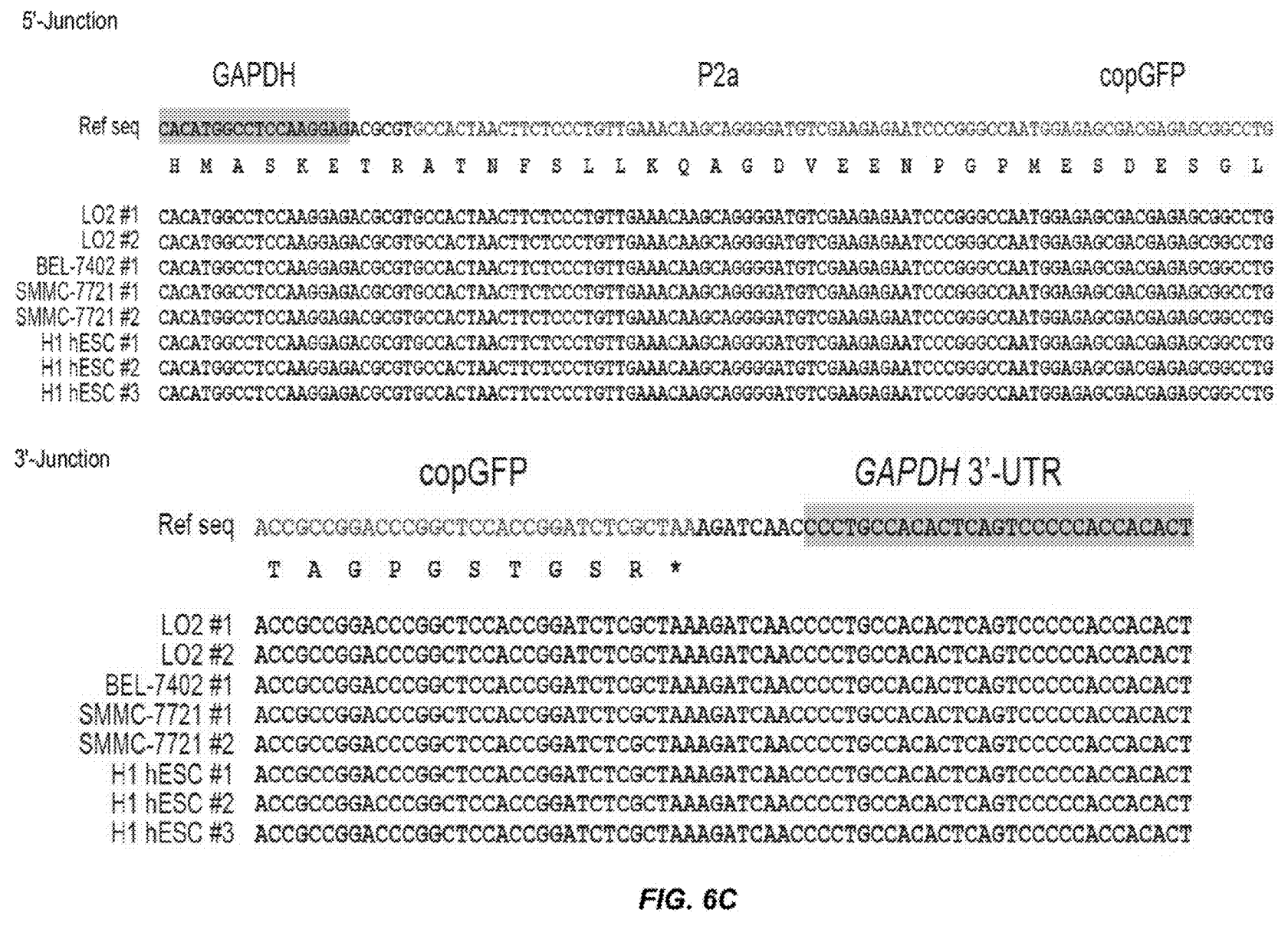

According to one aspect, genome PCR and sequencing analysis were applied to confirm that 2a-cGFP fragment has been precisely inserted into the 3' end of GAPDH CDS in genome (See FIGS. 6A and 6B), suggesting that the targeting indeed was induced by HDR repair. According to one aspect, HDR-based targeting efficiencies were examined in various human cell lines. Consistent with results from reference [15], HDR-based targeting was observed at low frequency in human ESCs. In the absence of CRISPR/Cas9, no GFP+ cells could be detected within $10^5$ cells examined; when Cas9 and sgRNAs were co-transfected with the donor plasmid, targeted insertions indicated by GFP+ cells appeared around 0.2-0.4% (See FIG. 6C). On the other hand, varied but higher frequencies of HDR-based gene targeting were detected in somatic cell lines. LO2 and HK2 cells showed 5.970% and 1.608% targeting efficiency respectively, while human HEK293T cells showed the targeting efficiency at 1.655%. Among the tumor cell lines examined, BEL-7402, BEL-7404 and SMMC-7721 exhibited targeting frequency at 1.907%, 1.492% and 4.429% respectively, while H1299 showed 1.177% and HCT116 showed 2.139% targeting efficiency (See FIG. 6C). According to one aspect, in all cell lines, when Cas9 and sgRNAs were omitted, GFP+ cells that represented basal HDR-targeting occurred in the absence of site-specific DSBs, appeared at a much lower frequency (See FIG. 6C, control groups). The enhancement of HDR targeting induced by CRISPR/Cas9 (as examined using Cas9/sg-1) was around 4-70 folds. According to one aspect, D10A mutant Cas9 (nickase)-induced HDR-targeting occurred at an efficiency 1.5-3-fold lower than that was induced by wild type Cas9 (See FIG. 6C). According to these data, our reporter system (including GAPDHdonor-HDR.1 and relevant sgRNAs targeting GAPDH 3'-UTR) provides a reliable and convenient tool for analyzing HDR frequency in any human cells, through commonly used transfection methods.

Figure 7A:
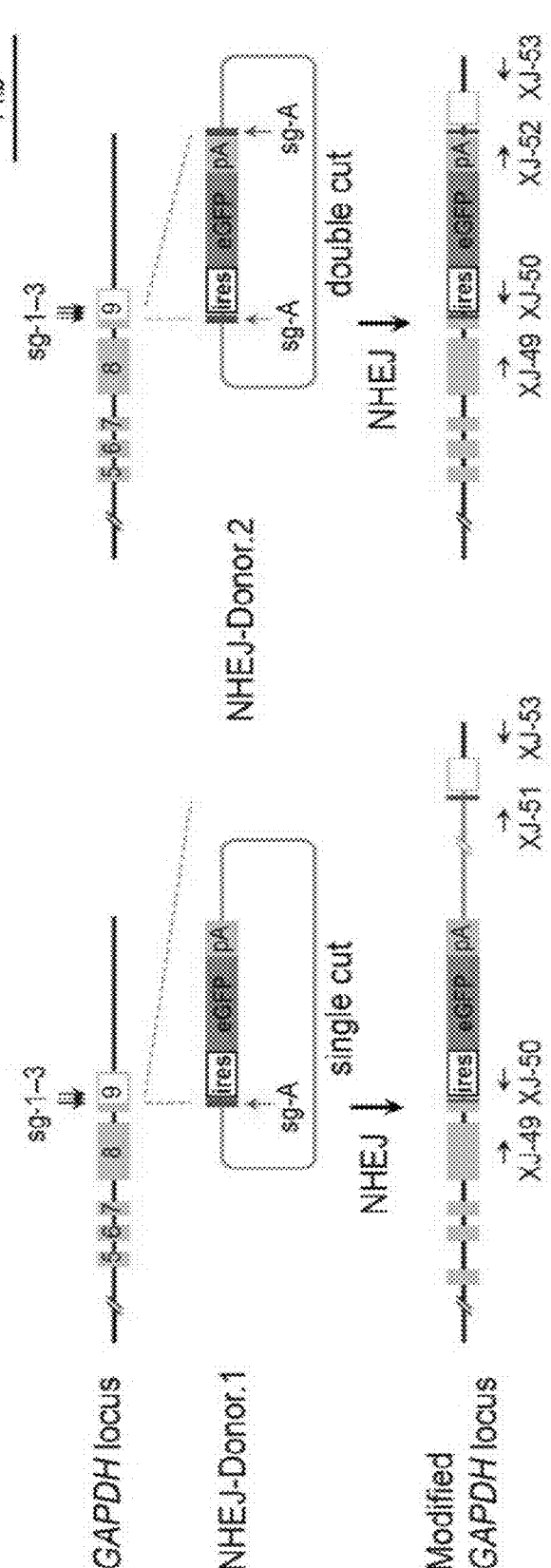
(FIG. 7A) Schematics of the donor plasmid design and targeting strategy for NHEJ mediated insertion of ires-eGFP reporter at GAPDH 3'-UTR. Two NHEJ-donor plasmids were generated. One plasmid carries a single sg-A target site at the 5' of ires-eGFP reporter (GAPDHdonor-NHEJ.1), and the other plasmid carries two sg-A target sites at both the 5' and 3' sides of ires-eGFP (GAPDHdonor-NHEJ.2).

6. Polynucleotide Constructs for GAPDH NHEJ-Reporter System sg-1, 2, 3, and 4 (sgRNA targeting GAPDH 3'-UTR) plasmids sg-A plasmid NHEJ-Donor.1 plasmid NHEJ-Donor.2 plasmid According to one aspect, a method is provided to directly quantify and compare the efficiency of CRISPR-induced NHEJ-based gene targeting in human ESCs and somatic cells. For this purpose, we constructed two donor plasmids (named GAPDHdonor-NHEJ.1 and GAPDHdonor-NHEJ.2) carrying promoterless ires-eGFP followed by poly A signal sequence, but no homologous sequences to the GAPDH locus in human genome. According to one aspect, we inserted one synthesized sg-A target site at the 5' of ires-eGFP in GAPDHdonor-NHEJ.1 plasmid, or two sg-A sites at both sides of ires-eGFP in GAPDHdonor-NHEJ.2 plasmid. These sg-A target sites will allow introduction of DSB in the donor plasmids in the presence of Cas9/sg-A, thus generate desired ires-eGFP reporter fragments for integration into GAPDH 3'-UTR in genome (see FIG. 7A). One and two sg-A target sites were used in these two donors for the purpose of generating ires-eGFP reporter fragments in different lengths, thus allowing examine the effect of different insert length during the targeted integration. According to one aspect, to ensure GFP expression after the reporter was inserted into GAPDH 3'-UTR, the ires element was used to bypass the frameshift caused by NHEJ-introduced indels. Collectively, when the Cas9/sgRNA induced DSBs in genome and transfected donors, it will stimulate DNA repair via NHEJ pathway in the absence of the homologous donor template. When desired end-joining happens, ires-eGFP fragment will be inserted at GAPDH 3'-UTR in genome, transcribed together with GAPDH, but translated as separate eGFP proteins. The GFP expression representing desired integration was detected using FACS analysis at 4-5 days after transfection.

According to one aspect, we examined the efficiency of genomic integration using GAPDHdonor-NHEJ.1 and GAPDHdonor-NHEJ.2 which were co-transfected with Cas9, sg-A and sg-1, 2, 3 into LO2 cells. Intriguingly, up to 20% GFP+ cells was detected when GAPDHdonor-NHEJ.1 was used (See FIG. 7B); and the efficiency was lower when GAPDHdonor-NHEJ.2 was used (See FIG. 7B). According to one aspect, in the absence of either sg-1-3 or sg-A (See FIG. 7B), or when nickase Cas9 D10A mutant was used to introduce single strand breaks (SSBs) (See FIG. 7B), no obvious targeting could be detected. According to these data, site-specific DSBs are necessary for the NHEJ-induced gene targeting to a selected genomic locus.

Figure 7D:
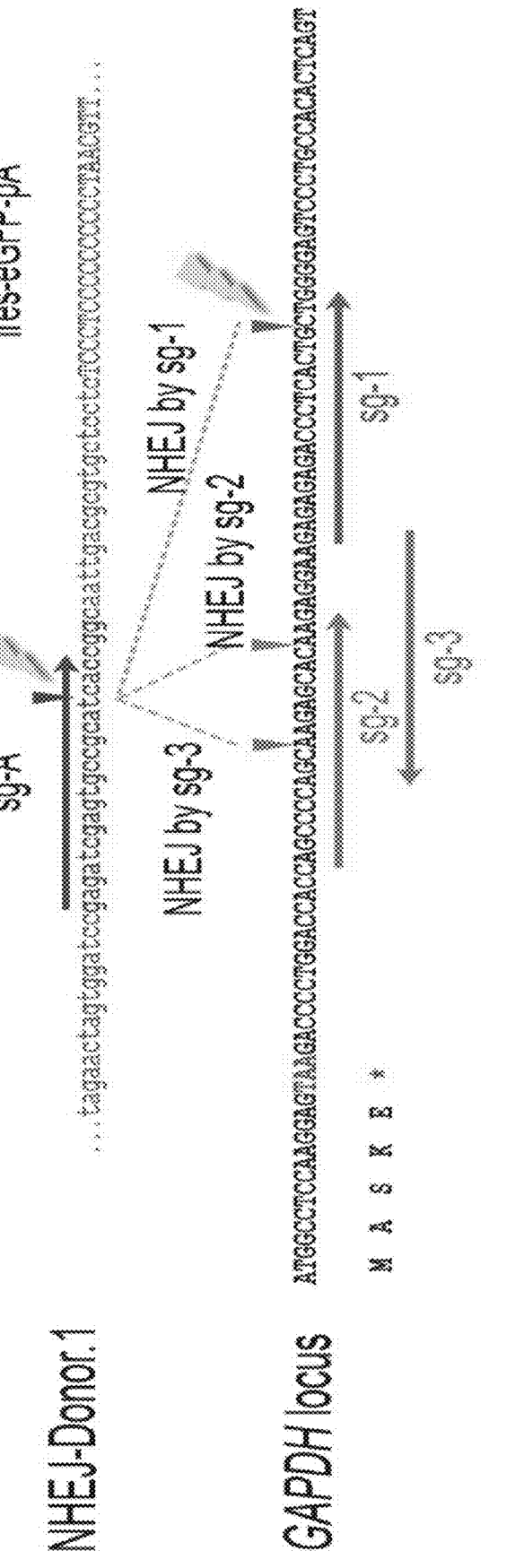
(FIG. 7D) Upper panel shows the schematics of sg-1, 2 and 3 target sites in GAPDH genomic locus, sg-A target site in single-cut donor GAPDHdonor-NHEJ.1, and positions of cleavage and re-joining between the genome and donor DNA. Lower panel shows sequencing results of the junction PCRs from GFP+ cells produced by GAPDHdonor-NHEJ.1 (in C, top panel). 5'- and 3'-junctions of Cas9/sg-A/sg-1, 2 or 3 induced integrations were analyzed individually. In each junction, multiple sequencing results are shown. In the junction sequences, nucleotides of different sgRNA target sites and PAMs are indicated in different colors: green for sg-1, blue for sg-2, orange for sg-3 and purple for sg-A. Sequences from donor templates are shown in grey, and genomic DNA are indicated in black. These results show the insertions of donors at expected sgRNA target sites as well as frequent indels in both 5' and 3'-junctions (SEQ ID NOs: 167-199, top to bottom, respectively). (E) Top panel shows the schematics of sg-1, 2 and 3 target sites in GAPDH genomic locus, sg-A target sites in double-cut donor, and positions of cleavage and re-joining between the genome and donors. Bottom panel shows sequencing results of the junction PCRs from GFP+ cells produced with GAPDHdonor-NHEJ.2 (in C, bottom panel). 5'- and 3'-junctions of Cas9/sg-A/sg-1, 2 or 3 induced integrations were analyzed individually. In each junction, multiple sequencing results are shown. In the junction sequences, nucleotides of different sgRNA target sites and PAMs are indicated in different colors: green for sg-1, blue for sg-2, orange for sg-3 and purple for sg-A. Sequences from donor templates are shown in grey, and DNA from genome are in black. These results confirmed the insertions of donors at expected sgRNA target sites, and frequent indels were found in both 5' and 3'-junctions (SEQ ID NOs: 200-282, left to right and top to bottom, respectively).
Figure 7D:
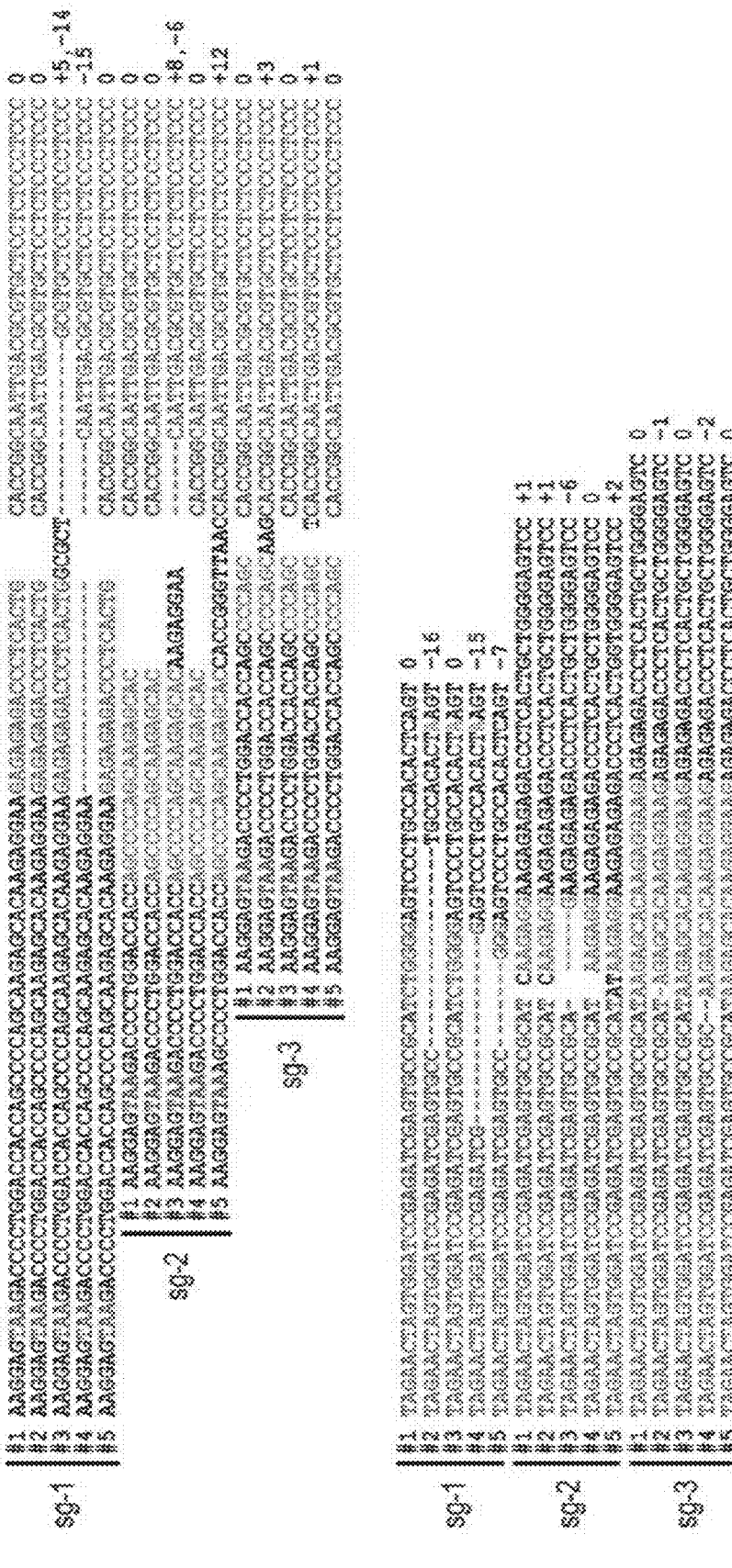
Figure 7E:
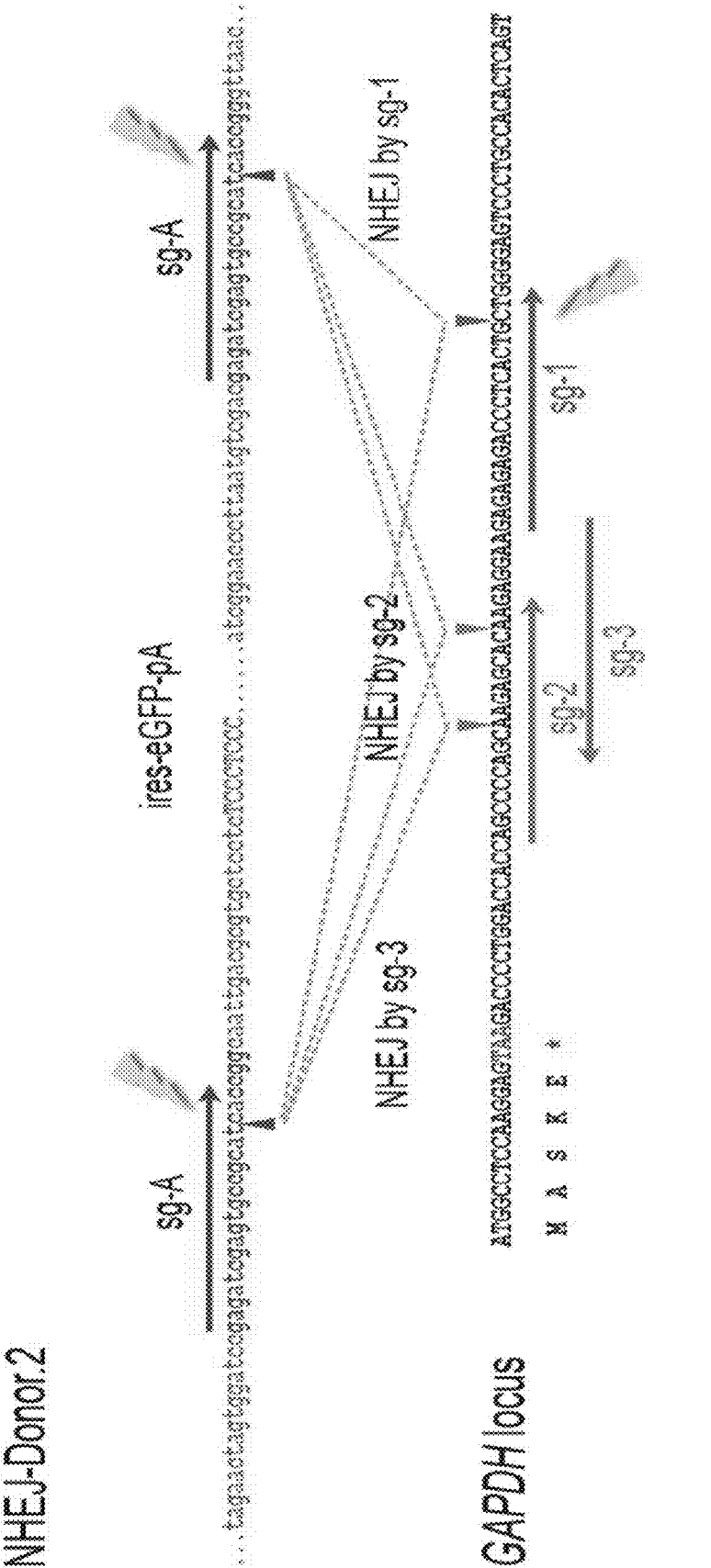
FIG. 7 NHEJ repair mediates efficient insertion of reporter genes into CRISPR/Cas9)-induced DSBs.
(FIG. 7B) FACS analysis in LO2 cells, showing NHEJ-mediated insertion of ires-eGFP reporter, induced by different combinations of donors and sgRNAs in the presence of wild type or nickase D10A Cas9.
(FIG. 7C) Genomic PCR for GFP+ cells transfected with sg1, sg-2 or sg-3, with either GAPDHdonor-NHEJ.1 or GAPDHdonor-NHEJ.2, were all analyzed. Primer pairs used for junction detection were indicated in (A) PCR amplifications showed DNA fragments at expected sizes, indicating correct integration of ires-eGFP donors at GAPDH 3'-UTR.
Figure 7E:
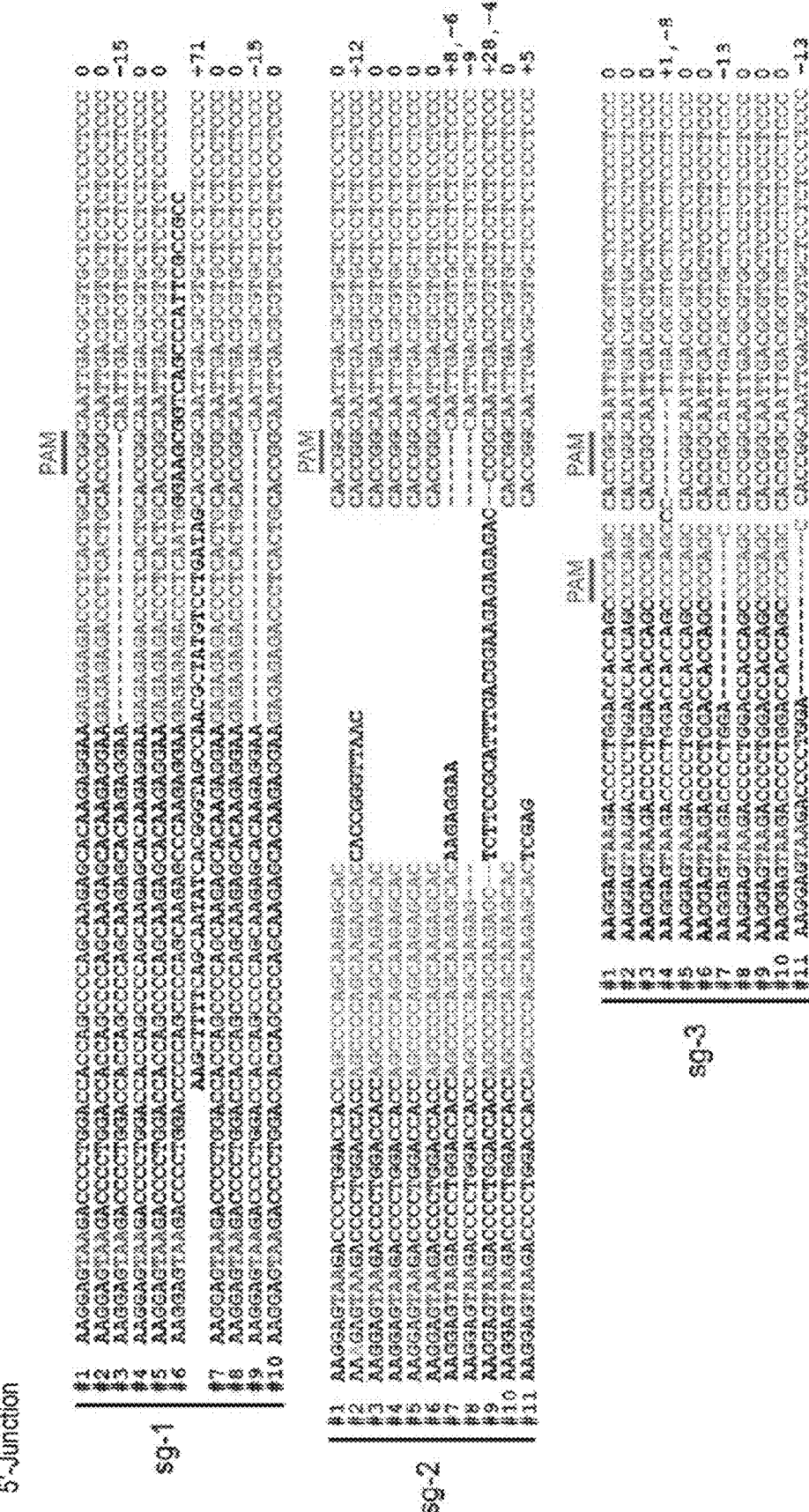
Figure 7E:
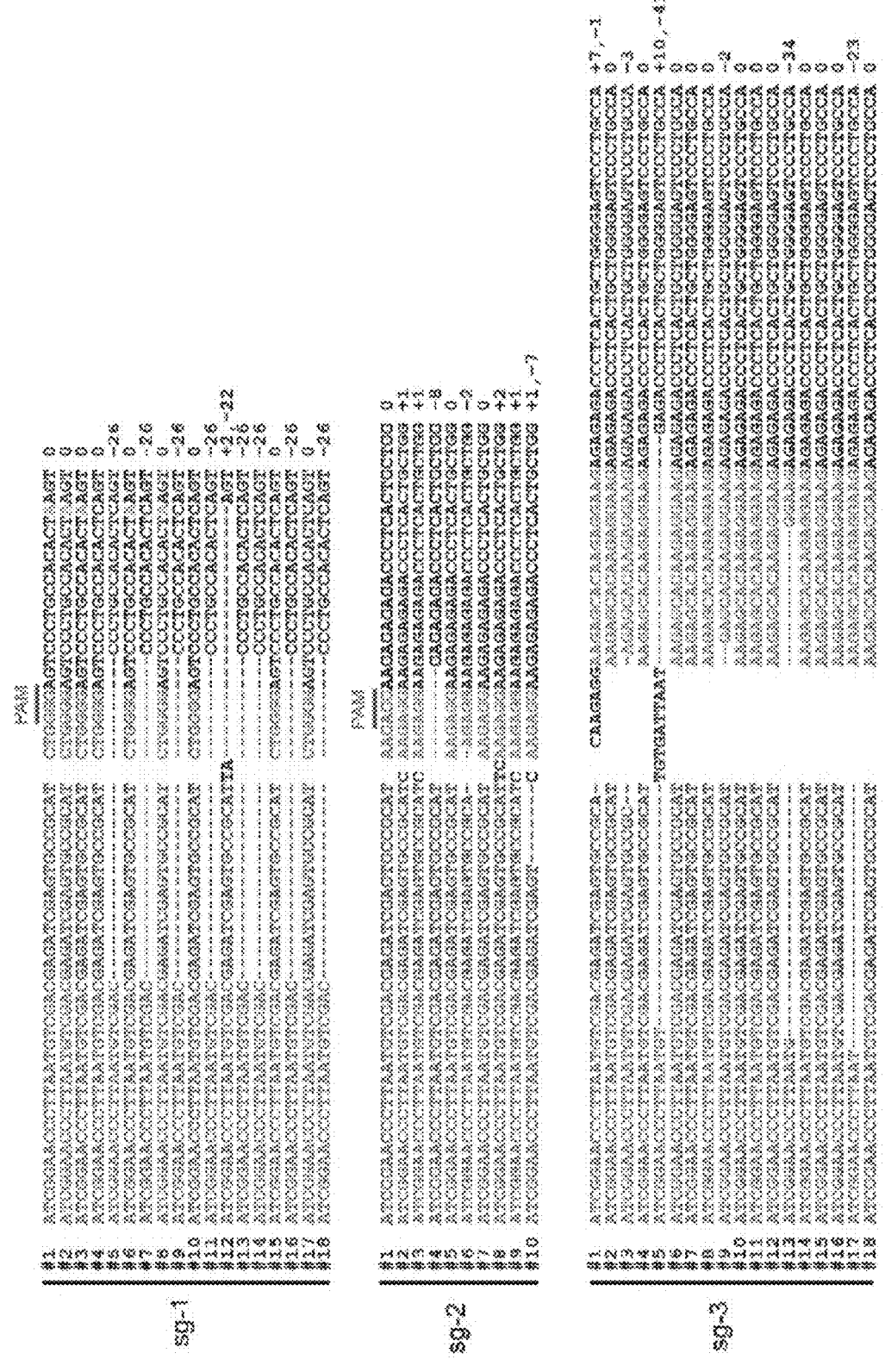
Figure 8A:
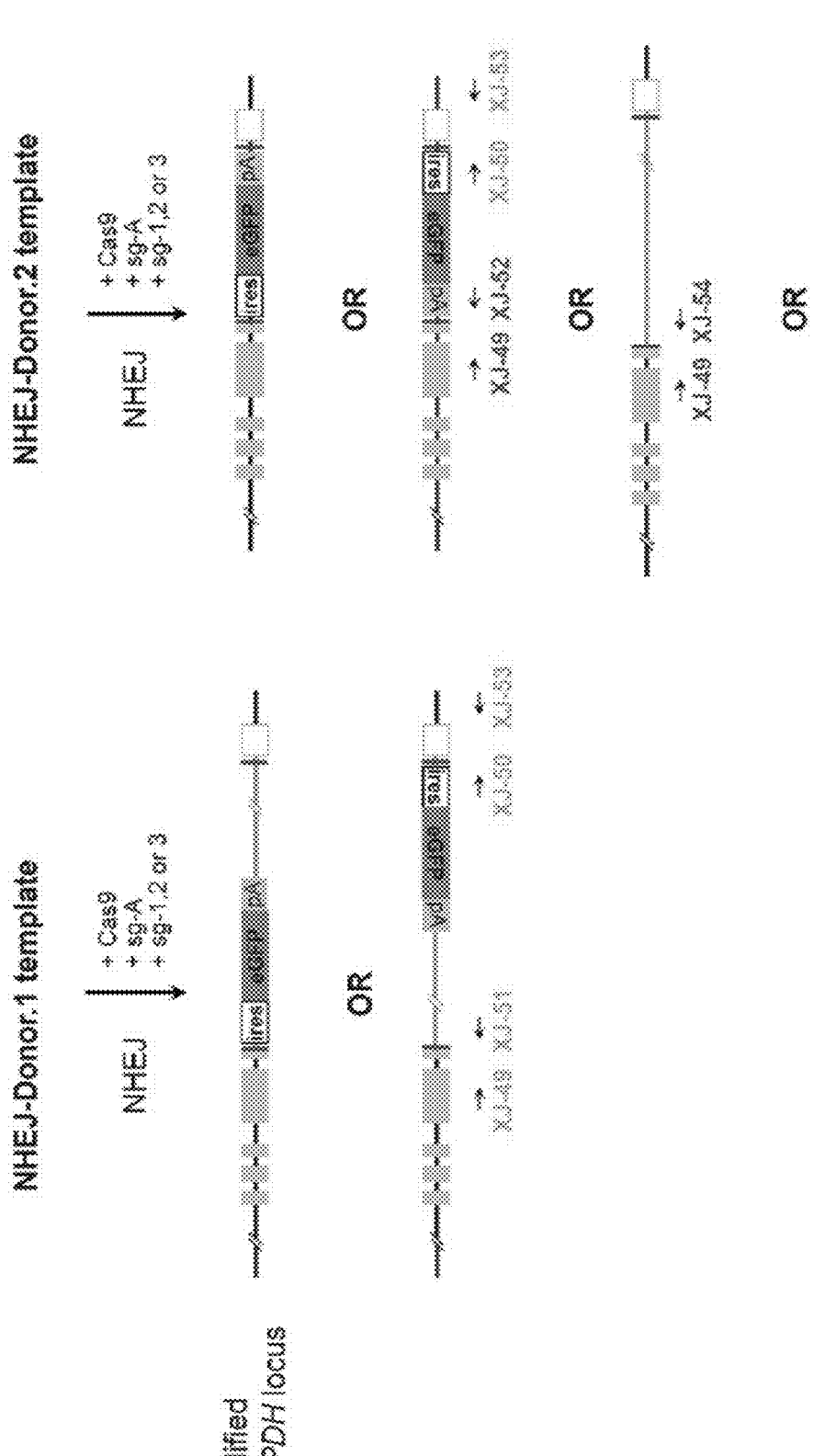
(FIG. 8A) Schematics showing different types of integrations that may occur during NHEJ mediated knock-in of ires-eGFP reporter, either with single-cut donor GAPDHdonor-NHEJ.1 (left panel) or with double-cut donor GAPDHdonor-NHEJ.2 (right panel).

According to one aspect, the GFP+ cells generated with GAPDHdonor-NHEJ.1 were analyzed by genome PCR. The insertion of ires-eGFP fragment and connected vector backbone at the 3' of GAPDH CDS in genome was detected (See FIG. 7C, top panel). Whereas, when GAPDHdonor-NHEJ.2 was used, PCR analysis only detected the insertion of ires-eGFP fragment between the two sg-A target sites in genome (See FIG. 7C, bottom panel). This indicated that the double-cut donor templates indeed had been cleaved at both target sites by sg-A/Cas9. Junction sequencing analysis of the GFP+ cells produced with either single- or double-cut donor revealed expected cleavage by specific sgRNAs, and error-prone re-joining between genome and donor templates at the cleavage sites (FIGS. 7D and 7E), suggesting that these targeting were indeed induced by Cas9/sgRNA-induced NHEJ repair. In total, the integration induced by NHEJ in LO2 cells may reach up to ~40% given that NHEJ repair also occurred in a reverse direction of CRISPR-induced DSB but lead to no GFP expression, which was confirmed by genomic PCR (See FIG. 8). According to these data, our reporter system has provided a convenient tool for enabled direct measurement of the NHEJ-mediated gene targeting in any human cells, and allowed direct comparison of the targeting efficiency among them.

7. Polynucleotide Constructs for GAPDH HDR-Reporter System 2 sg-1, 2, 3, and 4 (sgRNA targeting GAPDH 3'-UTR) plasmids

GAPDHdonor-HDR.2 plasmid

Figure 9A:
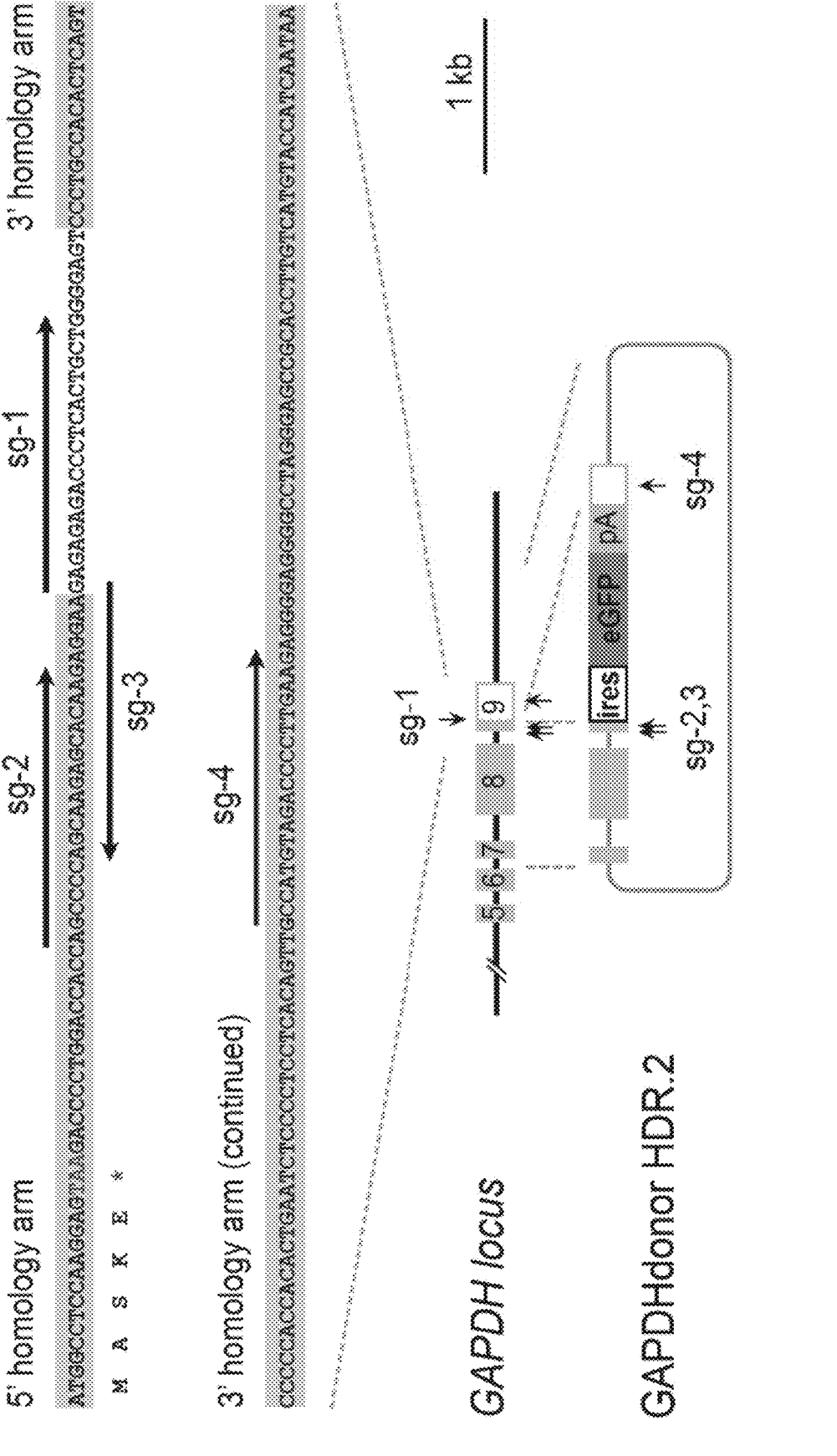
(FIG. 9A) Schematics showing sg-1-4 targeting sites and their locations in GAPDHdonor- HDR.2 and genome. Homology arm regions at GAPDH exon 9 in genome are highlighted in brown (SEQ ID NOs: 283-285, top to bottom, respectively).
Figure 9C:
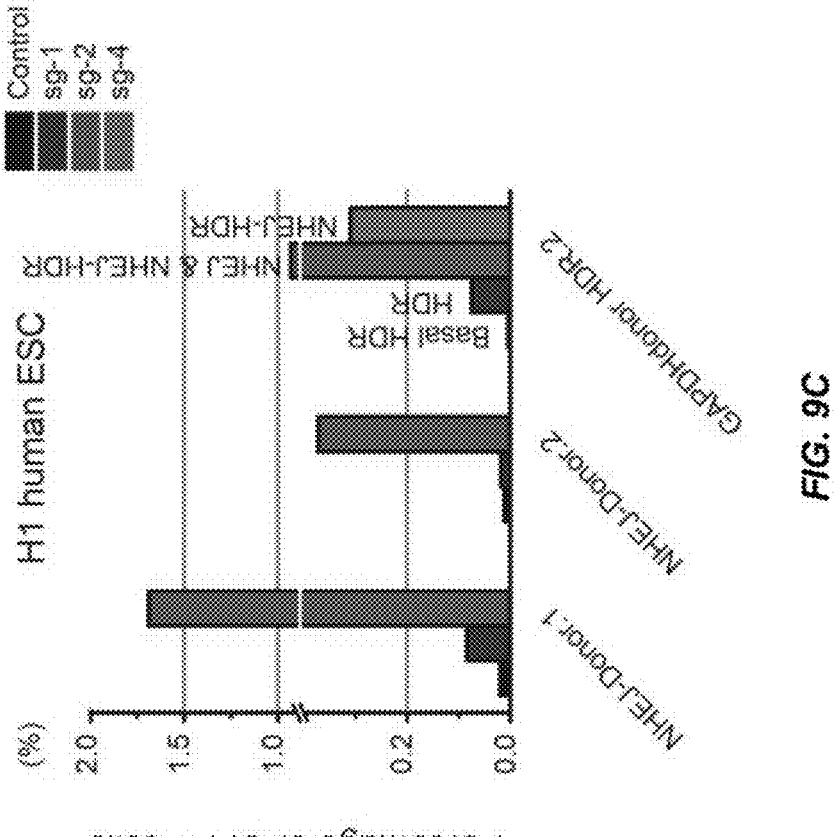
(FIG. 9C) FACS results showing CRISPR/Cas9-induced HDR or NHEJ-mediated integration of GAPDHdonor-NHEJ.1, GAPDHdonor-NHEJ.2 or GAPDHdonor-HDR.2 reporter in H1 human ESCs. Both GAPDHdonor-NHEJ.1 and GAPDHdonor-NHEJ.2 templates were examined in combination with sg-1 or sg-2. The GAPDHdonor-HDR.2 was examined in combination with Cas9/sg-1, 2 or 4. FACS analysis was performed four days after nucleofection.
Figure 9B:
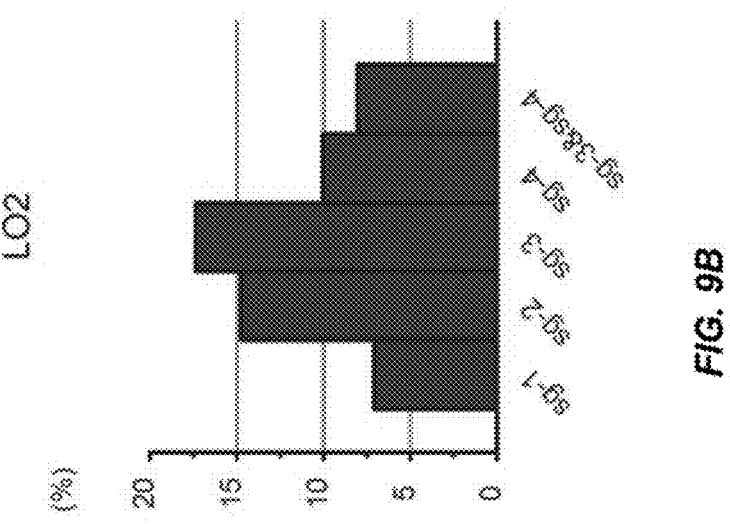
(FIG. 9B) FACS results of HDR or NHEJ-mediated insertion induced by GAPDHdonor-HDR.2 co-transfected with Cas9 and sg-1, 2, 3, 4 or 3 & 4 obtained in LO2 cells.

According to one aspect, a method is provided to clarify whether NHEJ indeed mediates large fragment targeting at a higher efficiency compared to HDR. A HDR donor was constructed carrying the ires-eGFP flanked by homologous arms to GAPDH locus (named GAPDHdonor-HDR.2). The 5' homologous arm in GAPDHdonor-HDR.2 was longer than the one used in GAPDHdonor-HDR.1, to cover the stop codon and an extended sequence harboring sg-2-4 target sites (See FIG. 9). HDR mediated efficiency was detected at 7.114% in LO2 cells when GAPDHdonor-HDR.2 was co-transfected with Cas9 and sg-1 (See FIG. 9B). The efficiency was lower than the NHEJ-mediated targeting with the sg-1, but it was similar to HDR-mediated targeting detected using GAPDHdonor-HDR.1. According to one aspect, when GAPDHdonor-HDR.2 was co-transfected the with Cas9/sg-2 or sg-3, which target to the 5' homology arm in both genome and donor plasmid, GFP+ cells increased to 14.75% and 17.36% respectively (See FIG. 9B), which were similar to NHEJ-targeting with single-cut donor (GAPDHdonor-NHEJ.1). Genome PCR confirmed end-joining between genome and donor plasmids beyond the 3' homology arm, and sequencing analysis detected frequent indels in the 5'-junctions. These data suggested that Cas9/sg-2 or 3 cleaved both genomic and donor DNAs and induced NHEJ-mediated integration of reporters. According to one aspect, when Cas9/sg-4 was used to target the 3' homology arm, GFP+ cells decreased to 10.06% (See FIG. 9B). Sequencing analysis detected no indel in the 5'-junctions (See FIG. 9E), suggesting that intact 5' homology arms mediated HDR targeting. Cleavage on both 5' and 3' homology arms, as shown by co-transfection of Cas9/sg-3 together with sg-4, induced NHEJ-targeting on both sides.

According to one aspect, NHEJ-mediated targeting efficiency in human ESCs and other somatic cell lines were examined and compared to HDR-mediated targeting. In H1 human ESCs, co-transfection of Cas9/sg-1/sg-A and GAPDHdonor-NHEJ.1 produced 0.84% GFP+ cells, and the proportion of GFP+ cells increased to 1.69% when the more active sg-2 was used (See FIG. 9C). Compared to HDR-targeting induced by Cas9/sg-2 in presence of GAPDHdonor-HDR.1, the efficiency of NHEJ-targeting with Cas9/sg-A/sg-2/GAPDHdonor-NHEJ.1 was approximately five-fold higher; whereas, the increase between Cas9/sg-1-induced NHEJ and HDR-targeting (with GAPDHdonor-HDR.2) is around ten-fold. Consistently, the efficiency of NHEJ-targeting was also higher than HDR-targeting in human somatic cell lines, ranging from 2.76% in HCT116 cells to 18.42% in SMMC-7721 cells, when single-cut donor/Cas9/sg-A/sg-1 were used (See FIG. 9D). According to these data, the GAPDHdonor-HDR.2 plasmid allowed us to directly compare and prove that NHEJ-mediated gene targeting occurred at higher frequency than HDR-mediated gene targeting in selected cell lines.

8. Polynucleotide Constructs for Targeting OCT4 and ACTB NHEJ-Reporter System

Figure 9D:
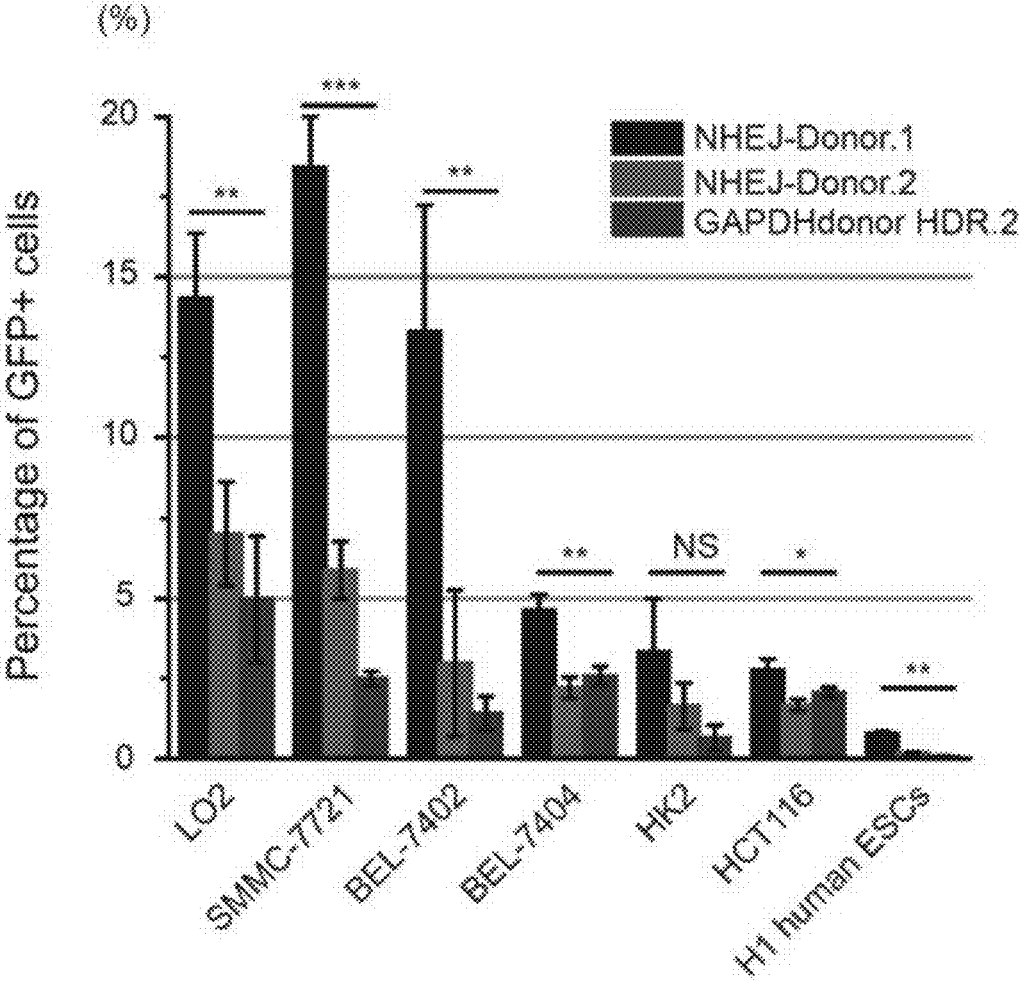
(FIG. 9D) Summary of Cas9/sg-1-induced NHEJ and HDR-targeting in examined human ESCs and somatic cell lines. Data shown are percentages of GFP+ cells, presented as the mean±s.e.m. and derived from independent experiments (n=3). Data from human ESCs were derived from two independent experiments (n=2). *: p<0.001; : p<0.01; *: p<0.05; ns: not significant p>0.05.
Figure 9E:
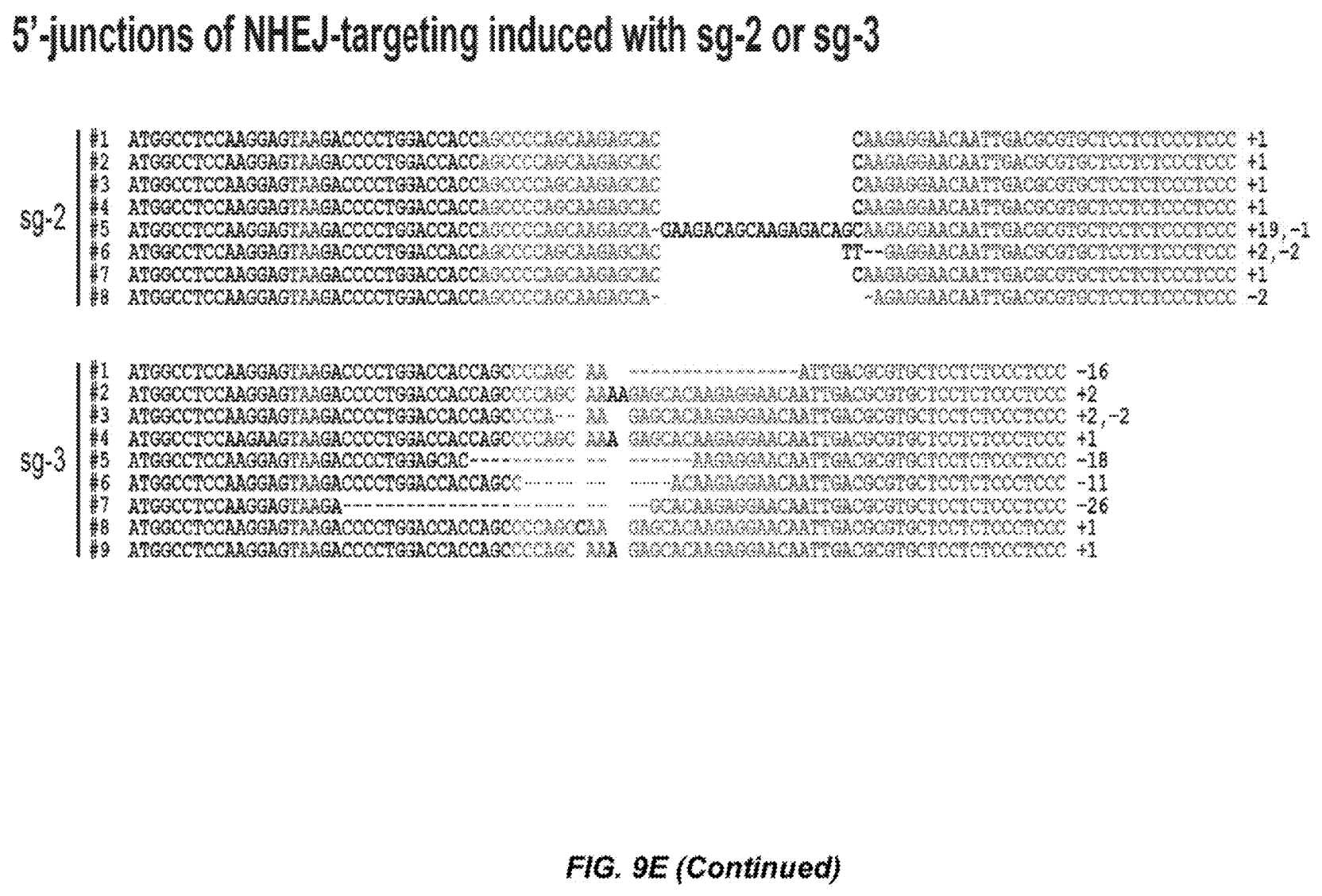
Figures 10A, 10B:
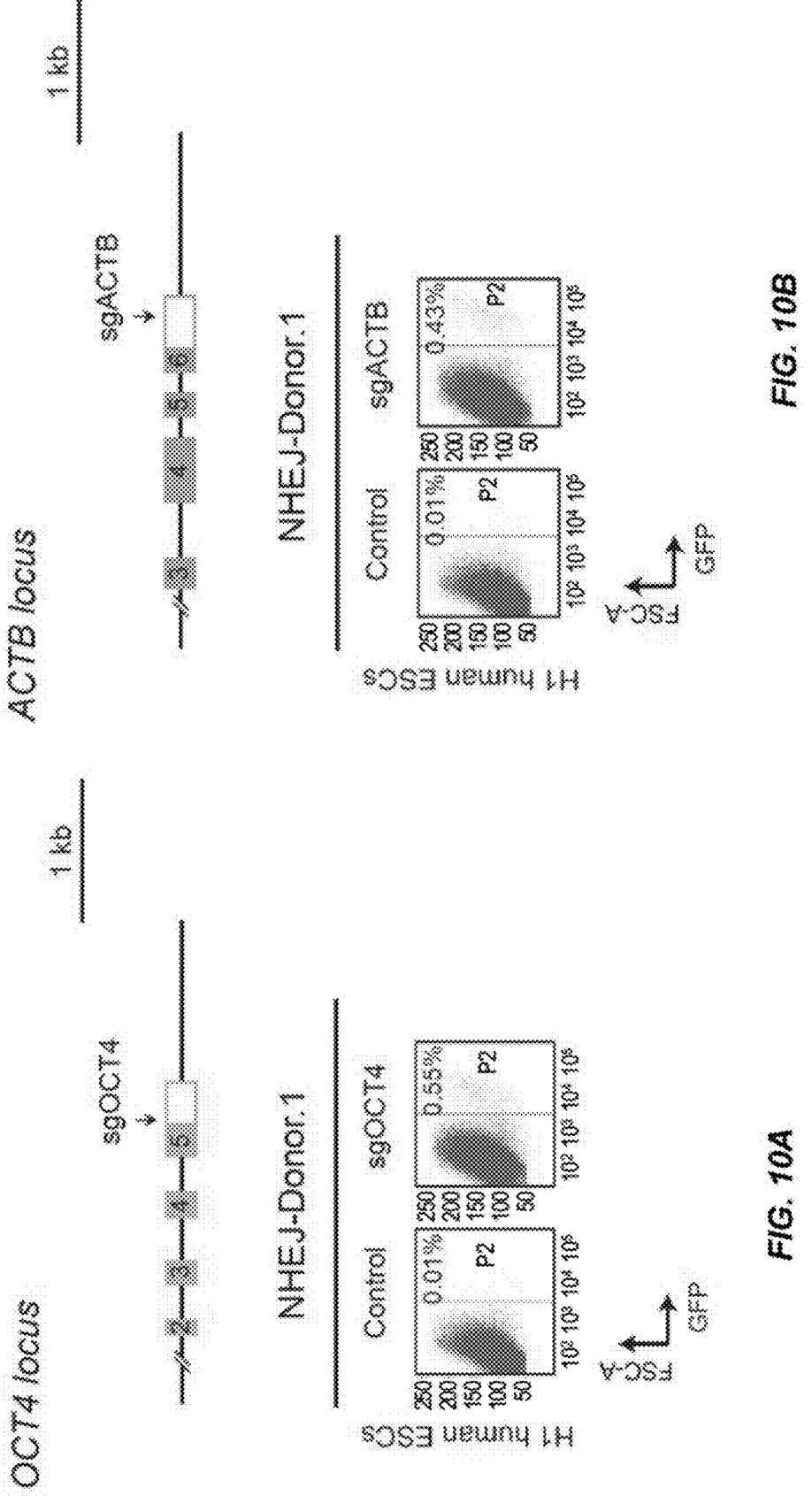
(FIG. 10A) FACS results showing CRISPR/Cas9-coupled NHEJ-mediated integration of ires-eGFP reporter at OCT4 3'-UTR in H1 human ESCs. The single-cut NHEJ donor was co-transfected with Cas9/sgOCT4 (SEQ ID NOs: 311-312, top to bottom, respectively).
(FIG. 10B) FACS results showing CRISPR/Cas9-coupled NHEJ-mediated integration of ires-eGFP reporter at ACTB 3'-UTR in H1 human ESCs. The single-cut NHEJ-donor was co-transfected with Cas9/sgACTB. FACS analyses were performed four days after nucleofection. GFP+ cells are gated to the right of the dashed line in each panel.
Figure 10C:
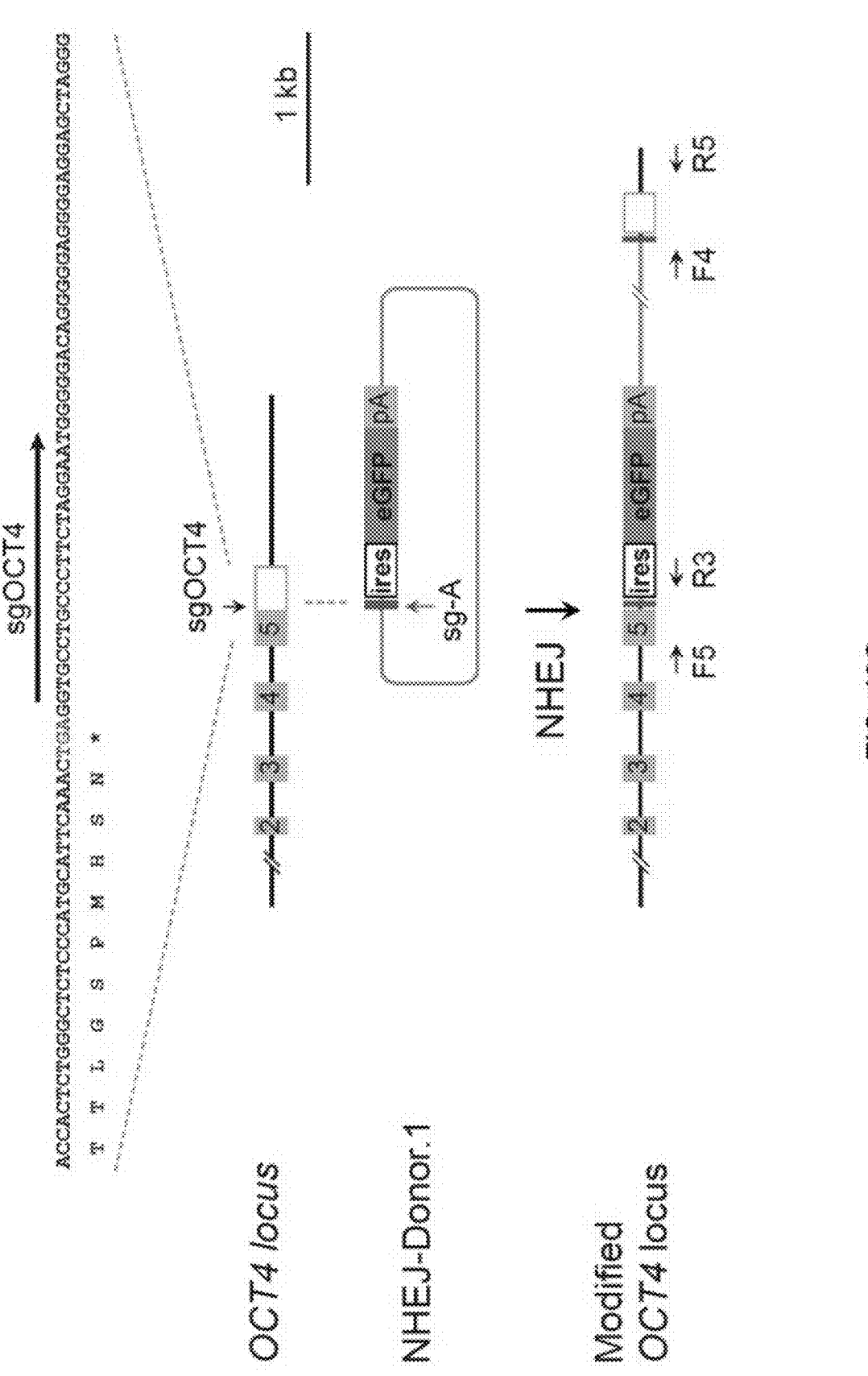
(FIG. 10C) Schematics showing a zoomed-in view of the sgOCT4 target site in the OCT4 genomic locus and the CRISPR/Cas9-coupled NHEJ-based targeting strategy using the single-cut donor.
Figure 10D:
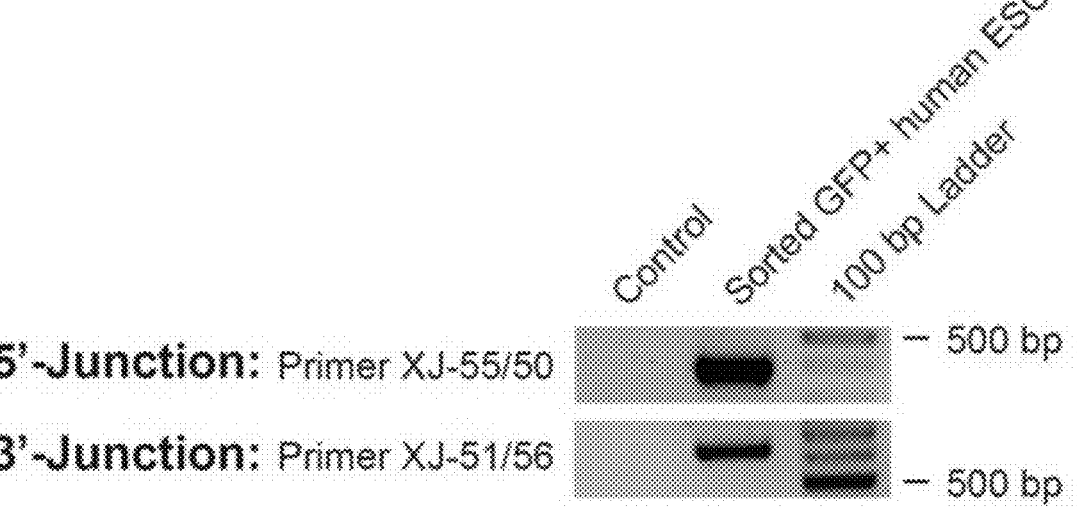
(FIG. 10D) Genomic PCR for integration junctions in the sorted GFP+ cells produced in the transfection with single-cut NHEJ donor/Cas9/sgOCT4 (FIG. 3C). PCR with primers F5/R3 detected the 5'-junctions, while amplification with primers F4/R5 detected the 3'-junctions of NHEJ-mediated integration of the single-cut donor at the OCT4 3'-UTR.
Figure 10E:
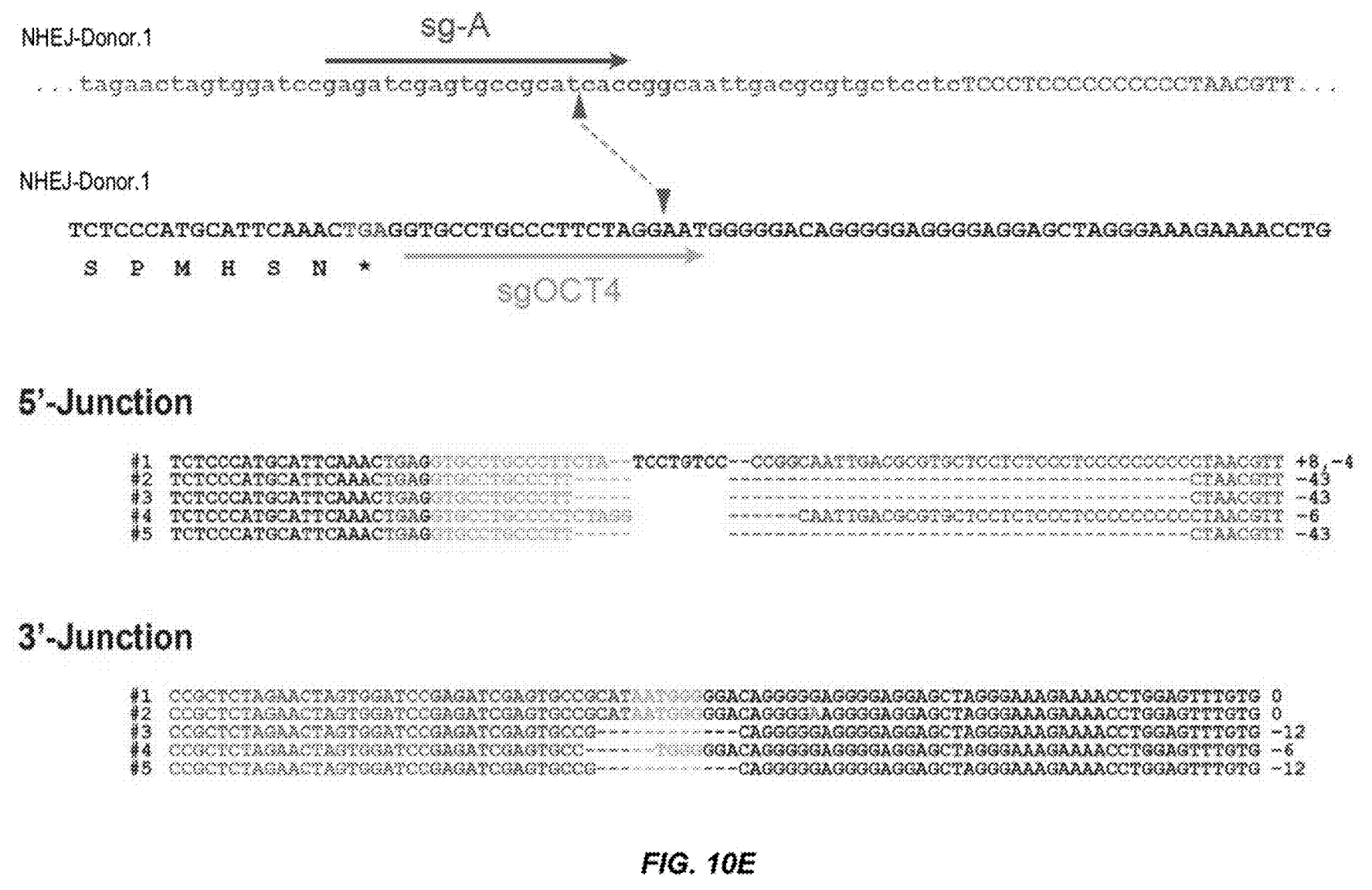

According to one aspect, a method is provided to clarify whether CRISPR/Cas9-induced NHEJ can mediate reporter gene integration into the OCT4 and ACTB genomic loci at a high efficiency comparable to that in GAPDH locus. For this purpose, we constructed two sgRNAs (sgOCT4 or sgACTB) targeting the OCT4 and ACTB genes respectively at the 3'-UTR. OCT4 gene encodes the pluripotency-associated transcription factor OCT4, while ACTB gene encodes the housekeeping protein β-Actin. Hence, knock-in of ires-eGFP reporter at the OCT4 and ACTB 3'-UTRs will result in active transcription and reporter expression. Indeed, co-transfection of the NHEJ-Donor.1/Cas9/sg-A with sgOCT4 or sgACTB into H1 human ESCs produced 0.55% and 0.43% GFP+ cells, respectively (FIGS. 10A and 10B). These are comparable to the efficiency of reporter integration into GAPDH locus (FIG. 9D). PCR and sequencing analysis fully confirmed the integration of single-cut donor at the OCT4 3'-UTR in the genome (FIG. 10C-E). Collectively, these data showed that CRISPR/Cas9-coupled NHEJ repair can mediate efficient knock-in of large reporter genes into any selected genomic locus in human ESCs.

EXAMPLES

The following examples are provided by way of illustration only and not by way of limitation. Those of skill in the art will readily recognize a variety of non-critical parameters that could be changed or modified to yield essentially the same or similar results.

Example I: Type II CRISPR System

Three classes of CRISPR systems are generally known and are referred to as Type I, Type II or Type III. According to one aspect, a particular useful enzyme according to the present disclosure to cleave dsDNA is the single effector enzyme, Cas9, common to Type II. As a consequence, Type II systems are more likely to function in alternative contexts such as eukaryotic cells. The Type II effector system consists of a long pre-crRNA transcribed from the spacer-containing CRISPR locus, the multifunctional Cas9 protein, and a tracrRNA important for gRNA processing. According to one aspect, Cas9 enzyme of the present disclosure unwinds the DNA duplex and searches for sequences matching the crRNA to cleave. Target recognition occurs upon detection of about 20 bp sequence in the target DNA which can match the sequence in the crRNA. Importantly, Cas9 cuts the DNA only if a correct PAM is also present at the 3' end. In the present disclosure, type II CRISPR system, originally from *Streptococcus pyogenes*, requires a 5'-NGG-3' sequence, where N can be any nucleotide. Bioinformatic analyses have generated extensive databases of CRISPR loci in a variety of bacteria that may serve to identify additional useful PAMs and expand the set of CRISPR-targetable sequences [21]. In *S. pyogenes* type II CRISPR system, DNA double strand break (DSB) formation occurs both towards the 5' and 3' ends of the protospacer. If one of the two nuclease domains is inactivated, Cas9 will function as a nickase in vitro and in human cells.

The specificity of gRNA-directed Cas9 cleavage is used as a mechanism for genome engineering eukaryotic cells. Hybridization of gRNA/DNA need not be 100 percent matching for the enzyme to recognize and cleavage. Thus off-target activity could occur. In the present disclosure, the type II CRISPR system from *S. pyogenes* tolerates mismatches in the first 6 bases out of the 20 bp mature spacer sequence in vitro.

Example II: Plasmid Construction

According to one aspect, a vector of Type II CRISPR system was constructed. The Cas9 gene sequence was human codon optimized from Addgene (#41815). Nickase hCas9D10A was similarly from Addgene (#41816).

According to one aspect, a vector of Type V CRISPR system was constructed. Plasmid of CRISPR/Cpf1 pY016 (pcDNA3.1-hLbCpf1) was obtained from Addgene (plasmid #69988), and sgRNAs were designed according to reference and cloned into sgRNA backbone.

sg-1, 2, 3 and 4 (sgRNA targeting GAPDH 3'-UTR)
        plasmids
    sgOCT4
    sgACTB
    sgSOX17
    sgT
    sgNANOG
    sgPAX6
    sgMRE11
    sg-X
    sg-A According to one aspect, sgRNA were designed according to reference [22]. To generate sgRNA, a pair of 26-mer oligos containing sgRNA target sequences were synthesized. They were annealed and then inserted into the BsmBI site in the sgRNA expression vector MLM3636 (Addgene #43860). The sg-1-4 target sequences (20-bp) preceding the PAM motif (5'-NGG-3') were obtained from the GAPDH exon 9 region, at 3' of the GAPDH CDS; while sgOCT4, sgSOX17, sgT, sgNANOG, sgPAX6, sgMRE11 and sgACTB target sequences were selected from OCT4 3'-UTR, SOX17 3'-UTR, T 3'-UTR, NANOG 3'-UTR, PAX6 3'-UTR, MRE11 3'-UTR and ACTB 3'-UTR respectively. sg-X and sg-A target sequence was selected from fluorescence protein eGFP and copGFP, respectively. Potential off-target effects of guide sequence were predicted using NCBI Nucleotide BLAST. The target sequences of sgRNAs used are shown in Table 1.

pSuper-MSC (modified pSuper-puro vector)

According to one aspect, pSuper-puro vector was modified in our previous work (unpublished) to carry two clusters of multiple restriction enzyme cutting sites (including SalI, MfeI, Mlu1, Bamh1, Nhe1, Hpa1, Afl2, EcoR1 Avr2, Pml1 and Xho1) at each side of a few expression cassettes (which were removed in the subsequent construction procedures).

pSuper-PGK-puro (without stop codon)
    pSuper_AAVS1(B)cGFP reporter plasmid

According to one aspect, DNA fragment containing PGK-puro (without stop codon) was amplified by PCR using primers XJ-1/XJ-2 and subcloned into the previously modified pSuper-based vector (unpublished) at MfeI and MluI sites to obtain pSuper-PGK-puro. Primer XJ-3 harboring P2a sequence were used together primer XJ-4 for amplification of copGFP N-terminal fragment, which was then inserted into the above pSuper-PGK-puro plasmid to get pSuper-PGK-puro-p2a-cGFP (N). Another pair of primer (XJ-5/XJ-6) containing sg-X target sequence and repetitive stop codons (total 77 bp) were synthesized and used to amplify the C-terminal of copGFP. This fragment was then inserted into pSuper-PGK-puro-p2a-cGFP (N) plasmid to obtain the pSuper-PGK-puro-p2a-broken cGFP (the N- and C-terminals of the cGFP was separated by repetitive stop codons and sg-X target sequence). This plasmid was named in a short form later as pSuper_(B)cGFP. Next, 5' homology arm from AAVS1 was amplified using primers XJ-7/XJ-8 and inserted at SalI and MfeI sites, whereas 3' homology arm from AAVS1 was amplified using primers XJ-9/XJ-10 and inserted at HpaI and EcoRI sites of the pSuper_(B)cGFP plasmid. The new constructed plasmid is pSuper_AAVS1 (B)cGFP reporter.

pSuper_Rosa26(B)cGFP reporter plasmid

According to one aspect, 5' homology arm from mouse Rosa26 genome locus was amplified using primers Xj-11/XJ-12 and inserted at SalI and MfeI sites, whereas 3' homology arm from mouse Rosa26 genome locus was amplified using primers Xj-13/XJ-14 and inserted at AflII and EcoRI sites of the pSuper_(B)cGFP plasmid. The new constructed plasmid is pSuper_Rosa26(B)cGFP reporter.

PiggyBac_AAVS1(B)cGFP reporter plasmid

According to one aspect, PGK-Puro2a(B)cGFP DNA fragment was obtained through MfeI and EcoRI double digestion of the pSuper_(B)cGFP plasmid; and it was then subcloned into Piggy Bac vector pCy150 (Sanger Center in United Kingdom) at EcoRI. Forwarded insertion was selected, and named as PiggyBac_AAVS1(B)cGFP reporter plasmid.

Three donor plasmids (B)cGFPdonor-HDR.1-3, carrying 30-bp insert and homology arms at 250 bp, 500 bp and 800 bp, respectively According to one aspect, we constructed donor plasmids containing full copGFP which will repair of the broken cGFP in above reporters, for assessing the HDR-mediated targeted DNA insertion. First, a complete and function P2a-copGFP-poly A DNA fragment was obtained by PCR using primers XJ-3/XJ-6, and inserted into the above intermediate plasmid pSuper-PGK-puro (no stop codon) at MluI and BamHI sites. Next, three pairs of primers (XJ-15/XJ-16, XJ-17/XJ-18, and XJ-19/XJ-20) were used to amplify puro-P2a-copGFP fragment at different lengths. The three fragments carrying different homology arms (250 bp, 500 bp or 800 bp, respectively) to the Puro2a(B)cGFP were then cloned into pGEM-T easy vector via TA-ligation. The obtained plasmids are donor plasmids (B)cGFPdonor-HDR.1-3.

Two donor plasmid (B)cGFPdonor-HDR.A, B, carrying 726-bp insert and homology arms around 250 bp, 500 bp, respectively According to one aspect, we constructed donor plasmids containing functional eGFP, which could replace the broken cGFP in above reporters, for assessing the HDR-mediated targeted DNA insertion. eGFP DNA fragment was amplified using primers XJ-21/XJ-22, and then inserted into the pSuper_(B)cGFP plasmid at BamHI and MluI sites. The BamHI and MluI digestion at the same time removed the broken cGFP fragment. In order to provide 3' homology sequence to the broken cGFP reporter, the C-terminal cGFP fragment was amplified by PCR using primers XJ-23/XJ-6 and inserted back to the above plasmid. Next, two pairs of primers (XJ-4/XJ-24 and XJ-25/XJ-16) were used to amplify puro-P2a-copGFP fragment at different lengths. The two fragments carrying different homology arms (250 bp or 500 bp respectively) to the Puro2a(B)cGFP were then cloned into pGEM-T easy vector via TA-ligation. The obtained plasmids are donor plasmids (B)cGFPdonor-HDR.A and B.

GAPDHdonor-HDR.1 plasmid
GAPDHdonor-HDR.2 plasmid
GAPDHdonor-HDR.3 plasmid
GAPDHdonor-HDR.3a plasmid
GAPDHdonor-HDR.3b plasmid According to one aspect, five vectors targeting GAPDH were constructed for the HDR-mediated gene targeting reporter assay: (1) A 2a-copGFP donor was constructed (GAPDHdonor-HDR.1, see FIG. 5). Primers XJ-3/XJ-26 carrying Picornavirus "self-cleaving" P2a sequence and cloning sites were synthesized, and used for amplifying DNA fragment carrying P2a-copGFP joint-CDS via two-step PCR from PCDH-CMV-MCS-EF1-copGFP (SBI, CD511B-1). The fragment obtained was inserted into BamHI and XhoI sites in the modified pSuper-puro vector [23]. Two homology arms were amplified from the upstream (903 bp, with primers XJ-27/XJ-28) and downstream (967 bp, with primer XJ-29/XJ-30) of sg-1-3 target sites in GAPDH genomic locus, and inserted into MfeI and MluI sites at 5' and HpaI and XhoI sites at 3' of the 2a-copGFP fragment in the above plasmid. (2) A ires-eGFP HDR-donor was constructed (GAPDHdonor-HDR.2, see FIG. 9). DNA fragment carrying ires-eGFP was amplified from pLenti6.3-MCS-IRES2-EGFP (Invitogen) using primers XJ-31/XJ-32 and inserted into MluI and HpaI sites to replace 2a-copGFP in the aforementioned pSuper-puro plasmid. 5' homology arm was amplified with another pair of primers XJ-33/XJ-34 to cover the GAPDH stop codon and sg-2, 3 target sites, while the 3' homology arm remained the same. (3) The 5' homology arm in GAPDHdonor-HDR.2 was replaced with a shortened fragment amplified using primers GADPH 5'-arm XJ-33/XJ-57 (Table 3), to cover the GAPDH stop codon but not sg-2 and sg-3 target sites. The 3' homology arm remained the same. Two complementary oligonucleotides containing the sg-A target sequence were synthesized, annealed and inserted at 3' (XhoI site) or 5' (NotI and BamHI sites) of the homology arm-flanked ires-eGFP cassette, to construct the GAPDHdonor-HDR.3a and GAPDHdonor-HDR.3b, respectively.

NHEJ-Donor. 1 plasmid
NHEJ-Donor.2 plasmid

According to one aspect, two vectors for the NHEJ reporter assay involving a broken GFP were constructed: Two ires-eGFP NHEJ-donor was constructed (GAPDHdonor-NHEJ. 1 and GAPDHdonor-NHEJ.2, see FIG. 7). A pair of oligos (XJ-35/XJ-36) carrying sg-A target site (5'-GAGATCGAGTGCCGCATCACCGG-3') was synthesized, annealed and inserted into the pSuper-puro carrying ires-eGFP to build sgRNA target sites to linearize the donor vector. For the single-cut NHEJ-donor (GAPDHdonor-NHEJ.1), a single sg-A target site was inserted into MfeI and MluI site at 5' of ires-eGFP: whereas, for double-cut NHEJ-donor (GAPDHdonor-NHEJ.2), two sg-A target sites were inserted into MfeI and MluI site at 5', and SalI and HpaI at 3' of ires-eGFP separately.

12k NH-donor plasmid
34k NH-donor plasmid

A DNA fragment containing the sg-A target sequence followed by ires-eGFP cassette from the single-cut NH-donor was subcloned into a large Piggy Bac vector (3) at AfeI site to generate the PB-ires-eGFP(12,458 bp), namely 12k NH-donor. The same sg-A-ires-eGFP fragment was also inserted into AdTrack vector (4) at HpaI and MfeI sites, which was then co-transformed with AdEasy-1 plasmid into E. Coli BJ5183 (4) to generate the recombinant AdEasy-ires-eGFP(34,457 bp), named 34k NH-donor. At the same time, PGK-GFP fragment was inserted at AfeI site in the PiggyBac vector to generate 12k (PB) GFP-vector; while the original AdTrack vector, which contains CMV-eGFP, was co-transformed with AdEasy-1 plasmid to generate the recombinant 34k (AD) GFP-vector. These large plasmids express GFP constantly, and were used to monitor the transfection efficiency.

Constant expression (CE) NH-donor plasmid

The DNA fragment containing the sg-A target sequence followed by a 500 bp space sequence was amplified from the single-cut NH-donor by PCR and inserted into BamHI and MscI sites of the pSuper-puro plasmid that carries PGK-eGFP cassette. The obtained plasmid was named CE NH-donor.

ACTB HDR-donor plasmid
SOX17 HDR-donor plasmid
T HDR-donor plasmid

One 5'- and one 3'-homology arm were amplified from ACTB, locus, to replace the GAPDH homology sequences in the GAPDHdonor-HDR.2 plasmid for generating ACTB HDR-donor. Similarly, one 5'- and one 3'-homology arm were amplified from each of SOX17 and T genomic loci, and inserted at 5' and 3' of the PGK-eGFP in the CE NH-donor-, to generate the SOX17 and T HDR-donors. Primers used are listed in the Table 3. XJ-58/XJ-59 and XJ-60/XJ-61 are for 5'-homology arms and 3'-homology arms of ACTB respectively. XJ-62/XJ-63 and XJ-64/XJ-65 are for 5'-homology arms and 3'-homology arms of SOX17 respectively. XJ-66/XJ-67 and XJ-68/XJ-69 are for 5'-homology arms and 3'-homology arms of T respectively.

NH-donor-in-eGFP plasmid
NH-donor-in-td-Tomato plasmid
NH-donor-in-puro plasmid
NH-donor-in-hygro plasmid The single-cut NH-donor (GAPDHdonor-NHEJ.1) previously described herein was used as the backbone for all four vectors; ires was deleted using enzyme cutting sites MluI and Msc1 to obtain the NH-donor-eGFP plasmid. To create the NH-donor-td-Tomato plasmid, td-Tomato was used to replace eGFP. To create the NH-donor-puro plasmid, puro-mycin ("puro") was used to replace eGFP. To create the NH-donor-hygro plasmid, hygromycin ("hygro") was used to replace eGFP. Tandem repeats of human insulator sequences were inserted at the 5' end of the sg-A using enzyme cutting site BamHI to obtain NH-donor-in-eGFP, NH-donor-td-in-Tomato, NH-donor-in-puro, as well as NH-donor-in-hygro, respectively. Human insulator sequences in the present disclose were discovered in Liu et al's report

[36]. Tandem repeats of two types of human insulator sequences (A2 and A4 in Liu et al's report) were applied.

Dual color fluorescence plasmid

The single-cut NH-donor (GAPDHdonor-NHEJ.1) previously described herein was used as the backbone for the dual color vector; ires was deleted using enzyme cutting sites MluI and Msc1. Subsequently, td-pA was cloned into the SacII site to create the dual reporter.

Loxp-sgA-ires-eGFP-PA-LoxP-PGK-eGFP-pa donor plasmid

Loxp-sgA-ires-eGFP-PA-LoxP-PGK-td Tomato-pa donor plasmid

Loxp-sgA-ires-td Tomato-PA-LoxP-PGK-eGFP-pa donor plasmid

Loxp-sgA-ires-td Tomato-PA-LoxP-PGK-td Tomato-pa donor plasmid

According to one aspect, four vectors targeting silent gene loci were constructed for the NHEJ-mediated gene targeting reporter assay. The single-cut NH-donor (GAPDHdonor-NHEJ. 1) previously described herein was used as the backbone for the Loxp-sgA-ires-eGFP-PA-LoxP-PGK-eGFP-pa donor. Enzyme cutting sites HpaI and XhoI were used for the insertion of PGK-GFP-PA cassette. Then, the LoxP site on the 5' side were synthesized as oligonucleotides and inserted at SacII site. Additionally, the single-cut NH-donor (GAPDHdonor-NHEJ.1) previously described herein was used as the backbone for the Loxp-sgA-ires-eGFP-PA-LoxP-PGK-td Tomato-pa donor. Enzyme cutting enzyme sites HpaI and XhoI were used for the insertion of PGK-td Tomato-pa cassette. Then, the LoxP site on the 5' side were synthesized as oligonucleotides and inserted at SacII site. For the Loxp-sgA-ires-td Tomato-PA-LoxP-PGK-eGFP-pa donor, the Loxp-sga-ires-eGFP-PA-LoxP-PGK-eGFP-pa donor was used as the backbone. Enzyme cutting sites BamHI and HpaI were used to delete ires-eGFP-pa and insert the ires-td Tomato-pa cassette. Finally, for the Loxp-sgA-ires-td Tomato-PA-LoxP-PGK-td Tomato-pa donor, the Loxp-sga-ires-eGFP-PA-LoxP-PGK-td Tomato-pa donor was used as the backbone. Enzyme cutting sites BamHI and HpaI were used for deletion of ires-eGFP-pa and to insert the PGK-td Tomato-pa cassette.

Example III: Cell Culture

H1 human ESCs (WiCell Research Institute) were maintained feeder-free on Matrigel (BD Biosciences) in mTeSR1 medium (Stemcell Technologies). Medium was changed daily and cells were sub-cultured every 3 days with 0.5 mM ethylenediaminetetraacetic acid (EDTA, Life Technologies). TrypLE (Life technologies) was applied to dissociate H1 cells to prepare single cells for FACS analysis.

Human somatic cell lines were obtained from ATCC (American Type Culture Collection). LO2 and HEK293T cells were cultured in Dulbecco's modified Eagle's medium (DMEM, Life Technologies) supplemented with 10% fetal bovine serum (FBS, Life Technologies); SMMC-7721, BEL-7402, BEL-7404 and H1299 cells were culture in Roswell 30) Park Memorial Institute 1640) (RPMI, Life Technologies) supplemented with 10% FBS; HK2 cells were culture in 1:1 F-12/DMEM medium (Life Technologies) supplemented with 10% FBS; and HCT116 cells were cultured in McCoy 5A medium (Life Technologies) supplemented with 10% FBS. Cultures were passaged every 3 or 4 days with standard trypsin/EDTA.

All cells were maintained at 37° C. and 5% $CO_2$ in a humidified incubator.

Example IV: Generation of HEK293T-AAVS1 (B)cGFP Reporter Line

According to one aspect, pSuper_AAVS1(B)cGFP reporter plasmid was transfected into HEK293T cells using Lipofectamine 2000 (Life Technologies) in accordance with the manufacture's instruction. Cells were dissociated into single cells and seed in low density at day 2 after transfection. Puromycin was added into the culture medium at 0.8 μg/ml, and the cells were cultured for 7-10 days until individual puromycin-resistant clones emerged. Single clones were picked and expanded. Genome DNA were then analyzed by PCR using primers XJ-37/XJ-38 for the 5' integration junction, and XJ-39/XJ-40 for the 3' integration junction. Positive clones were used for HDR assays by FACS. One clone was identified to carry the (B)cGFP reporter in correct target site in genome, which can be repaired by both donor plasmids (B)cGFPdonor-HDR.1-3 and (B)cGFPdonor-HDR.A-B.

Example V: Generation of Human ESC H1-(B)cGFP Reporter Line

According to one aspect. Piggy Bac_(B)cGFP reporter plasmid was transfected into human ESCs H1 cells using Fugene HD (promega) in accordance with the manufacture's instruction. Cells were dissociated into single cells and seed in low density in the presence of 20) Rock inhibitor at day 3 after transfection. Puromycin was added into the culture medium at 0.4 ug/ml, and the cells were cultured for 7-10 days until individual puromycin-resistant clones emerged. Single clones were picked, expanded, and then screened by HDR assays using FACS analysis. One clone was identified to carry the (B)cGFP reporter in genome, and it can be repaired by both donor plasmids (B)cGFPdonor-HDR.3.

Example VI: Generation of Mouse ESC E14-Rosa26(B)cGFP Reporter Line

According to one aspect, pSuper_Rosa26(B)cGFP reporter plasmid was transfected into mouse ESCs E14 cells using Lipofectamine 2000 (Life Technologies) in accordance with the manufacture's instruction. Cells were dissociated into single cells and seed in low density at day 2 after transfection. Puromycin was added into the culture medium at 0.8 μg/ml, and the cells were cultured for 7-10 days until individual puromycin-resistant clones emerged. Single clones were picked and expanded. Genome DNA were then analyzed by PCR using primers XJ-41/XJ-42 (for the 3' integration junction only). Positive clones were used for HDR assays by FACS. One clone was identified to carry the (B)cGFP reporter in correct target site in genome, which can be repaired by both donor plasmids (B)cGFPdonor-HDR.1-3 and (B)cGFPdonor-HDR.A and B.

Example VII: Gene Targeting of Human ESCs (H1)

Human ESCs (H1) were cultured in mTeSR1 medium and passaged every 3 days using 1 mg/ml collagenase IV or 0.5 mM EDTA. For nucleofection, cells were dissociated using TrypLE into single cells, and transfected using Amaxa nucleofection (Lonza) following the manufacturer's instruction. Briefly, for each transfection, $5 \times 10^6$ cells were mixed with 100 μl nucleofection reagent (82 μl solution-1+18 μl solution-B) and prewarmed in 37° C. for 30) min. The cell suspension was then mixed with 16 μg DNA (6 μg Cas9 plasmid, 4 μg gRNA and/or 6 μg DNA donor plasmid) and electroporated using program A-023 according to manufacturer's instruction (Lonza). Electroporated H1 human ESCs were cultured on mitomycin-C inactivated MEF feeder, in 1:1 F-12/DMEM medium supplemented with 20% knockout serum replacement, 1 mM L-glutamine, 1% non-essential amino acids, 0.1 mM β-mercaptoethanol and 4 ng/ml basic fibroblast growth factor (bFGF) (Life technologies). Medium was conditioned by mouse embryonic fibroblast. Additional 8 ng/ml bFGF was added freshly to conditioned medium for culturing freshly transfected human ESC. Medium was changed daily for 4-5 days and cells were dissociated using TrypLE (Life technologies) to prepare single cells for FACS analysis. The estimated transfection efficiency was around 53.5% using 16 μg pEGFP-NI plasmid.

Example VIII: Gene Targeting of LO2, HEK293T and HCT116 Cells

LO2, HEK293T and HCT116 cells were seeded into 12-well plates at a density of $5 \times 10^5$ cells per well 5-8 hrs before transfection. Cells were transfected using Lipofectamine 2000 (Life Technologies) 1.6 μg plasmids (0.6 μg donor DNA plasmid, 0.6 μg Cas9 plasmid and 0.4 μg sgRNA plasmid) were used into each well and 4 μl Lipofectamine 2000 (Life Technologies) following the manufacturer's instruction (Life Technologies). When more than one sgRNA was used, the total amount was kept the same and each sgRNA plasmid equaled to 0.4 μg divided equally by the numbers of plasmids. LO2 cells were passaged once in bulk and grown for four days before examined by FACS analysis (BD LSRFortessa Cell Analyzer); while, due to high background GFP expression from transfected plasmids, HEK293T and HCT116 cells were maintained for one week before gene targeting efficiency was analyzed by FACS. Transfection efficiency in each cell line was estimated by transfection of 1.6 μg pEGFP-NI plasmid followed by FACS analysis after 48 hrs.

Example IX: Gene Targeting of SMMC-7721, BEL-7402, BEL-7404, H1299 and HK2 Cells SMMC-7721, BEL-7402, BEL-7404, H1299 and HK2 cells were transfected using FuGENE HD (Promega). Cells were seeded into 12-well plates at a density of $5 \times 10^5$ cells/well 16 hrs before transfection. 0.6 μg donor plasmid, 1.6 μg DNA (0.6 μg Cas9 plasmid, 0.4 μg sgRNA plasmid) and 4.5 μl FuGENE HD (Promega) were used for transfection into each well following the manufacturer's instruction (Promega). When multiple sgRNAs were used, each sgRNA plasmids equaled to 0.4 μg divided equally by the numbers of plasmids. The transfected cells were passaged once or twice in bulk before examined using FACS (BD LSR-Fortessa Cell Analyzer). Transfection efficiency in each cell line was estimated by transfection of 1.6 μg pEGFP-NI plasmid followed by FACS analysis after 48 hrs.

Example X: Genomic DNA Extraction and PCR Detection of Genomic Integrations

Genome DNA from cultured cells was extracted using Genome DNA extraction Kit (Tiangen) following the manufacturer's instruction. 200 ng genomic DNA were generally used for PCR reaction using Phusion High-Fidelity DNA Polymerase (New England Biolabs), following the manufacturer's instruction. Primers used for detection of HDR or NHEJ-mediated genomic integration are shown in Table 3.

Example XI: T7E1 Assays

According to one aspect, genome PCR were performed to amplify sgRNAs target region (704 bp, with primer XJ-43/XJ-44) in genome. The PCR products were then purified using Gel Extraction Kit (Tiangen) after electrophoresis. Purified genomic DNA samples were subjected to the T7 endonuclease I. 300 ng purified PCR products were denatured and annealed in 20 μl NE Buffer 2 (NEB) using a thermocycler. Hybridized PCR products were then digested with T7 endonuclease 1 (NEB, M0302L) for 60 mins at 37° C. and subjected to 2% agarose gel electrophoresis. T7E1 cleavage efficiency was quantified using ImageJ. All PCR primer sequences are listed in Table 3.

Example XII: TA-Ligation Sequencing

According to one aspect, PCR fragment amplified from extracted genomic DNA was sequenced. Primers used for homology arm amplification and integration detection (XJ-45-XJ-54) are listed in Table 3. Genome PCR fragments were incubated with dATP and Taq DNA polymerase (Dream taq, TAKARA) for adding A at the end. These products were then purified using MEGAquick-spin Total Fragment DNA Purification Kit (iNtRON), and ligated into pGEM T easy vector (Promega) following the manufacturer's instruction. Positive clones were then sequenced by BGI with standard M13-forward and M13-reverse primers (Table 3).

Example XIII: Fluorescence-Activated Cell Sorting Analysis

Fluorescence Activated Cell Sorting (FACS) analyzer (BD LSRFortessa Cell Analyzer) was configured with a single 488 nm argon ion laser (200 mW). The laser is used to induce light scattering by either the excitation of cellular fluorescent proteins (copGFP or eGFP) or the granularity within the cell. The SSC (Side Scatter Collector) light detection from the cell is collected through a microscope objective, transmitted via fiber light guide to an array of photo-multiplier tubes (PMT's), and the FSC (Forward Scatter Collector) was constructed of a photo-diode, in accordance with the default settings recommended by the manufacture.

The data obtained for the FACS samples included several different plot windows; which included dot plots for FSC-A vs. SSC-A. FSC-A vs. FITC-A (GFP), SSC-A vs. FITC-A (GFP) and histograms for SSC-A, FSC-A, and FITC-A (GFP) (width×height) for the particular channel ("A" is the computed area; "FS" is forward scatter; and "SS" is side scatter). During the recording of each sample, a gate was set on the plots for FSC-A vs. SSC-A. and/or on the FITC-A (GFP) histogram between the $10^3$ and $10^4$ (log scale) to monitor and observe the GFP expression level and efficiency. The recorded events within the gate on the FITC-A (GFP) log scale provided a good indication of the GFP expression level and the counts indicate the number of GFP-positive cells. The ration of GFP-positive cells over the total counts in the gated area is defined as targeting efficiency.

Example XIV: Generation of LIG4 Overexpression Construct

Human LIG4 cDNA was amplified by RT-PCR from the RNA extracted from wild type LO2 cells, and cloned into pCAG-ires-Hyg vector at the BglII and XhoI sites [9]. Primers used were listed as XJ-70 and XJ-71 in the Table 3.

Example XV: Generation of LIG4 Null LO2 Cells

Wild type LO2 cells were co-transfected twice with Cas9 together with combined sgLIG4-i-iv. The transfected cells were dissociated into single cells and seeded at low density (2000 cells/10 cm dish) for clonal expansion. Individual clones were then isolated and analyzed by genome PCR and western blot. Primers used are shown as XJ-72 to XJ-76 in Table 3.

Example XVI: Gene Targeting of LO2

LO2 cells were seeded into 12-well plates at a density of $5 \times 10^5$ cells per well 5-8 hrs before transfection. Cells were transfected using Lipofectamine 2000 (Life Technologies) 1.6 μg plasmids (0.6 μg donor DNA plasmid, 0.6 μg Cas9 plasmid and 0.4 μg sgRNA plasmid) were used into each well and 4 μl Lipofectamine 2000 (Life Technologies) following the manufacturer's instruction (Life Technologies). When more than one sgRNA was used, the total amount was kept the same and each sgRNA plasmid equaled to 0.4 ug divided equally by the numbers of plasmids. LO2 cells were passaged once in bulk and grown for four days before examined by FACS analysis (BD LSRFortessa Cell Analyzer); while, due to high background GFP expression from transfected plasmids. Transfection efficiency in each cell line was estimated by transfection of 1.6 μg pEGFP-NI plasmid followed by FACS analysis after 48 hrs.

Example XVII: LIG4 Rescue Assay

To perform the LIG4 rescue assays, an additional 0.6 μg LIG4 cDNA overexpression plasmid was combined with 0.6 μg donor, 0.6 μg Cas9, 0.4 μg sgRNA in each well, and 5.5 μl Lipofectamine 2000 (Life Technologies) following the manufacturer's instruction (Life Technologies) for transfection. LO2 cells were passaged once in bulk and grown for four days before examined by FACS analysis (BD LSR-Fortessa Cell Analyzer).

Example XVIII: Western Blot

Cells were trypsinized, and washed with PBS, and lysed in buffer containing 50 mM Tris, 0.5% NP40, 1 mM EDTA, 1 mM DTT, 10% glycerol, 400 mM sodium chloride and Protease Inhibitor Cocktail (Roche) on ice for 20 min, followed by centrifugation at 4° C. for 15 min. 10 μg protein from each sample was resolved by SDS/PAGE and subsequently transferred to polyvinylidene difluoride membranes (Bio-Rad). Membranes were blocked with 5% non-fat dry milk in PBST buffer for 1 hr at room temperature and then incubated with anti-DNA Ligase IV (Abcam) or anti-β-actin (Santa Cruz) antibodies for overnight. Membrane was washed three times with PBST buffer and incubated with HRP-conjogated goat anti-mouse (Life-Technologies) or goat anti-rabbit (Santa Cruz) antibodies. Signals were detected using Amersham ECL select western blotting detection kit (GE Health Care Life Sciences) and exposed to Super RX-N film (Fuji).

Example XIX: Immunofluorescence

Immunofluorescence was performed as previously described [9]. Basically, cells were fixed using 4% paraformaldehyde (Sigma) in PBS. Cell membrane was permeabilized using 1% Triton X-100/PBS and non-specific binding was blocked with 8% FBS in 0.1% Tween-20/PBS. The samples were then incubated with primary antibody diluted in blocking solution at 4° C. overnight, followed by incubation with Alexafluor 546-conjugated secondary antibodies at room temperature for 2-4 hours. Nuclei were counterstained by Hoechst dye 1:5000 (Life Technologies). Primary antibodies used were OCT4 (1:100, Santa Cruz), TRA-1-60 (1:100, Santa Cruz).

All patents, patent applications, and other publications, including GenBank Accession Numbers, cited in this application are incorporated by reference in the entirety for all purposes.

TABLE 1

| sgRNA | Target sequences | SEQ ID NO: | PAM | Gene locus |
|---|---|---|---|---|
| sg-1 | GAGAGAGACCCTCACTGCTG | 1 | GGG | GAPDH 3'-UTR |
| sg-2 | AGCCCCAGCAAGAGCACAAG | 2 | AGG | GAPDH 3'-UTR |
| sg-3 | CTTCCTCTTGTGCTCTTGCT | 3 | GGG | GAPDH 3'-UTR |
| sg-4 | GCCATGTAGACCCCTTGAAG | 4 | AGG | GAPDH 3'-UTR |
| sg-A | GAGATCGAGTGCCGCATCAC | 5 | CGG | — |
| sgLIG4-i | AAGATTCATCACCGCTTTGA | 6 | TGG | LIG4 5'-UTR |
| sgLIG4-ii | TTAAACTACAGAACACCCAC | 7 | TGG | LIG4 CDS |
| sgLIG4-iii | TCTGGCAGACTCATTGCAGC | 8 | AGG | LIG4 3'-UTR |
| sgLIG4-iv | TAGGGTAGAATTGTTACAGC | 9 | TGG | LIG4 3'-UTR |
| sgACTB-i | AATATGAGATGCGTTGTTAC | 10 | AGG | ACTB 3'-UTR |
| sgACTB-ii | GTAACAACGCATCTCATATT | 11 | TGG | ACTB 3'-UTR |

TABLE 1-continued

| sgRNA | Target sequences | SEQ ID NO: | PAM | Gene locus |
|---|---|---|---|---|
| sgSOX17-i | CTGCAGGCTGGGGCGGATCA | 12 | GGG | SOX17 3'-UTR |
| sgSOX17-ii | GAAGTGTGTAACACTGCTTC | 13 | TGG | SOX17 3'-UTR |
| sgT-i | CACTGCATCTTTCGGGACCT | 14 | GGG | T 3'-UTR |
| sgT-ii | GGAGAATGAGCTGCAGG | 15 | CGG | T exon 2 |
| sgT-iii | GCTCTTTCCCGCGCTCT | 16 | CGG | T exon 2 |
| sgT-iv | CAAAAAGTCACTGCATCTTT | 17 | CGG | T 3'-UTR |
| sgOCT4-i | GCCTTCTCGCCCCCTCCAGG | 18 | TGG | OCT4 exon 1 |
| sgOCT4-ii | GGTGGTGGAGGTGATGGGCC | 19 | AGG | OCT4 exon 1 |
| sgOCT4-iii | GGTGAATGACATTTGTGGGT | 20 | AGG | OCT4 intron 1 |
| sgOCT4-iv | GTGCCTGCCCTTCTAGGAAT | 21 | GGG | OCT4 3'-UTR |
| sgNANOG | GGCCCACAAATCACAGGCAT | 22 | AGG | NANOG exon 2 |
| sgPAX6-i | GCCGACCGACTGAGGCC | 23 | CGG | PAX6 intron 5 |
| sgPAX6-ii | GCTGCCGGGCGCGGAGC | 24 | GGG | PAX6 intron 5 |
| sgPAX6-iii | GTTAATTCAGTCAGTGACTA | 25 | TGG | PAX6 3'-UTR |

TABLE 2

| ID | SEQ ID NO: | Target sequences | Score | Mismatch | Target gene | Genome locations (hg19) | Strand |
|---|---|---|---|---|---|---|---|
| | | | Off-target sites of sg-1 | | | | |
| sg-1 | 26 | GAGAGAGACCCTCACTGCTG GGG | 100 | 0 | GAPDH (3'UTR) | chr12:6647376-6647399 | + |
| 1 | 27 | GAGAGAGACCCTCACTGCTG GGG | 100 | 0 | — | chr5:173941350-173941373 | + |
| 2 | 28 | GAGAGAGACCCTCACTGCTG GGG | 100 | 0 | — | chrX:39646322-39646345 | - |
| 3 | 29 | GAGAGAGACCCTCACTGCTG GGG | 100 | 0 | — | chrX:46299077-46299100 | - |
| 4 | 30 | GAGAGAGGCCCTCACTGCTG GGG | 100 | 1 | — | chr16:28250946-28250969 | - |
| 5 | 31 | GAGAGAGGCCCTCACTGCTG GGG | 100 | 1 | — | chr1:117256391-117256414 | - |
| 6 | 32 | GAGAGAGACCCTCAATGCTG GGG | 26.8 | 1 | GTF2F (intron) | chr13:45698083-45698106 | - |
| 7 | 33 | GAGAGAGGCCCTCACTGCTG GGA | NA | 1 | PPM1H (intron) | chr12:63150053-63150076 | + |
| 8 | 34 | AAGAGAGGCCCTCACTGCTG GGG | 7.1 | 2 | — | chr6:166478828-166478851 | + |
| 9 | 35 | GAGAGAGGCTCTCACTGCTG CGG | 5 | 2 | — | chr10:15135195-15135218 | - |
| 10 | 36 | TAGAGAGAGCCTCACTGCTG CAG | 4.6 | 2 | — | chr9:82834458-82834481 | + |
| 11 | 37 | GAGAGCGGCCCTCACTGCTG GAG | 3.3 | 2 | ME1 (intron) | chr6:84103168-84103191 | + |

TABLE 2-continued

| ID | SEQ ID NO: | Target sequences | Score | Mismatch | Target gene | Genome locations (hg19) | Strand |
|---|---|---|---|---|---|---|---|
| 12 | 38 | CAGAGAGACCCTCAGTGCTG GAG | 3.3 | 2 | PON2 (intron) | chr7:95052806-95052829 | + |
| 13 | 39 | GAGAGAGGCCTTCACTGCTG GGG | 3.2 | 2 | MTUS2 (intron) | chr13:29881962-29881985 | + |
| 14 | 40 | GAGAGAGGCCTTCACTGCTG GGG | 3.2 | 2 | — | chr11:88141283-88141306 | - |
| 15 | 41 | GAGAGAGGCCCTCACTCCTG GGG | 3.1 | 2 | — | chrX:86680522-86680545 | - |
| | | Off-target sites of sg 2 | | | | | |
| sg-2 | 42 | AGCCCCAGCAAGAGCACAAG AGG | 100 | 0 | GAPDH (3'UTR) | chr12:6647351-6647374 | + |
| 1 | 43 | AGCCCCAGCAAGAGCACAAG AAG | 100 | 0 | ALLC (intron) | chr2:3735539-3735562 | - |
| 2 | 44 | AGCCCCAGCAAGAGCACAAG AGG | 92.1 | 1 | DLGAP1 (intron) | chr18:3977604-3977627 | - |
| 3 | 45 | AGCCCCAG AAGAGCACAAG AGG | 61.1 | 1 | — | chrX:39646347-39646370 | - |
| 4 | 46 | AGCCCCAGCAAGAGCACAAC AGG | 41.7 | 1 | LMBRD1 (intron) | chr6:70456759-70456782 | + |
| 5 | 47 | AGCCCCAGCAAGAGCACGAG AGG | 19.6 | 1 | — | chr1:69652240-69652263 | + |
| 6 | 48 | AGCCCCAGCAAGAGCACGAG AGG | 19.6 | 1 | CALCRL (intron) | chr2:188280588-188280611 | + |
| 7 | 49 | AGCCCCAGCAAGAGCACGAG AGG | 19.6 | 1 | — | chrX:135160806-135160829 | + |
| 8 | 50 | AGCCCCAGTGAGAGCACAAG AGG | 2.9 | 2 | — | chr13:29881937-29881960 | + |
| 9 | 51 | AGCCCCAGTGAGAGCACAAG AGG | 2.9 | 2 | ANKRD46 (intron) | chr8:101562913-101562936 | - |
| 10 | 52 | AGCCCCAGTCAGAGCACAAG AGG | 2.9 | 2 | TMEM132E (intron) | chr17:32942729-32942752 | + |
| 11 | 53 | AGCCCAAGCAACAGCACAAG AGG | 2 | 2 | — | chr22:17954910-17954933 | - |
| 12 | 54 | AGCCCCAGGAAGAGCACAGG GGG | 1.7 | 2 | CACNA1B (intron) | chr9:140945417-140945440 | + |
| 13 | 55 | AGCCCCAGCGAGAGCACGAG AGG | 1.4 | 2 | LINCOO189 (intron) | chr21:30595603-30595603 | + |
| 14 | 56 | AGCCCCAGCGAGAGCACCAG AGG | 1.4 | 2 | — | chr5:173941325-173941348 | + |
| | | Off-target sites of sg-3 | | | | | |
| sg-3 | 57 | GTTCCTCTTGTGCTCTTGCT GGG | 100 | 1 | GAPDH (3'UTR) | chr12:6647354-6647377 | + |
| 1 | 58 | CTTCCTCTTGTGCTCTCGCT GGG | 5.9 | 2 | — | chr18:3977601-3977624 | + |
| 2 | 59 | CTTCCTCTCGTGCTCTTGCT GGG | 4.6 | 2 | — | chrX:135160809-135160832 | - |
| 3 | 60 | CTTCCTCTCGTGCTCTTGCT GGG | 4.6 | 2 | — | chr2:188280591-188280614 | - |
| 4 | 61 | TTTCCTCTCGTGCTCTTGCT GGG | 4.6 | 2 | — | chr1:69652243-69652266 | - |

TABLE 2-continued

| ID | SEQ ID NO: | Target sequences | Score | Mismatch | Target gene | Genome locations (hg19) | Strand |
|---|---|---|---|---|---|---|---|
| 5 | 62 | CTTCCTCTTGTGCTCTTACG GGG | 3.4 | 2 | — | chrX:39646344-39646367 | + |
| 6 | 63 | CTTCCTCTTGTGCTGTTGCT TGG | 3.3 | 2 | — | chr22:17954906-17954929 | + |
| Off-target sites of sg-4 | | | | | | | |
| sg-4 | 64 | GCCATGTAGACCCCTTGAAG AGG | 100 | 0 | GAPDH (3' UTR) | chr12:6647452-6647475 | + |
| 1 | 65 | TCCATGTAGACCCCTTGAAG AGG | 100 | 1 | — | chrX:39646246-39646269 | - |

TABLE 3

| Primer | Sequences | SEQ ID NO: |
|---|---|---|
| XJ-1 | AGAGA CAATTG CGCACACATTCCACATCCAC | 66 |
| XJ-2 | AGAGA ACGCGT GGCACCGGGCTTGCG | 67 |
| XJ-3 | AGAGAACGCGTGCCACTAACTTCTCCCTGTTGAAACAAGCAGGGGATG TCGAAGAGAATCCCGGGCCAATGGAGAGCGACGAGAGCG | 68 |
| XJ-4 | AGAGA GGATCCTCAATCAATCACGATGCGGGTGTTGGTGTAG | 69 |
| XJ-5 | AGAGAGGATCCTGAGGCTACGTCCAGGAGCGCACCATCTTCTTCAAGG ACGACGGCAACTTGATTGATTGATGCACGTGAGCTTCAGCTACC | 70 |
| XJ-6 | AGAGA AGATCT CCATAGAGCCCACCGCATC | 71 |
| XJ-7 | AGAGA GTCGAC CGGAACTCTGCCCTCTAACG | 72 |
| XJ-8 | AGAGA CAATTG CCCAGAACCAGAGCCACATT | 73 |
| XJ-9 | AGAGA GTTAAC CCCCCACCTCCTGTTAGGCAGA | 74 |
| XJ-10 | AGAGA GAATTC AGAGCAGAGCCAGGAACCC | 75 |
| XJ-11 | AGAGA GTCGAC GTGGAGCCGTTCTGTGAGAC | 76 |
| XJ-12 | AGAGA CAATTG AACTCCCAGAAAGGTATTGCAAC | 77 |
| XJ-13 | AGAGA CTTAAG TTCTGGGCAGGCTTAAAGGC | 78 |
| XJ-14 | AGAGA GAATTC AGCTTGGCAAAATCACATTTAGACC | 79 |
| XJ-17 | ACCGAGCTGCAAGAACTCTTCC | 80 |
| XJ-18 | CCTAAGCTTGGCTGGACGTAAACTC | 81 |
| XJ-19 | CCGCAACCTCCCCTTCTACGAG | 82 |
| XJ-20 | CTGGCAACTAGAAGGCACAGTCG | 83 |
| XJ-21 | AGAGAACGCGTGCCACTAACTTCTCCCTGTTGAAACAAGCAGGGGATG TCGAAGAGAATCCCGGGCCAATGGTGAGCAAGGGCGAG | 84 |
| XJ-22 | AGAGA GGATCC TTACTTGTACAGCTCGTCCATGC | 85 |
| XJ-23 | AGAGA GGATCC CACCCTGAACGGCGTGGA | 86 |
| XJ-24 | CCCGCAACCTCCCCTTCTACGAG | 87 |
| XJ-25 | CTGCAAGAACTCTTCCTCACG | 88 |
| XJ-26 | AGAGA AGATCT TTAGCGAGATCCGGTGGAGC | 89 |
| XJ-27 | AGAGA CAATTG GACACGCTCCCCTGACTTGC | 90 |
| XJ-28 | AGAGA ACGCGT CTCCTTGGAGGCCATGTGG | 91 |

TABLE 3-continued

| Primer | Sequences | SEQ ID NO: |
|--------|-----------|------------|
| XJ-29 | AGAGA GTTAAC CCCTGCCACACTCAGTCCCC | 92 |
| XJ-30 | AGAGA CTCGAG CTGGGGTTACAGGCGTGCG | 93 |
| XJ-31 | AGAGAGAATTCCAATTG ACGCGT GCTCCTCTCCCTCCCCCC | 94 |
| XJ-32 | AGAGA AGATCT ACTTACCTG TTACTTGTACAGCTCGTCCATGCCG | 95 |
| XJ-33 | AGAGA GGATCC GACACGCTCCCCTGACTTGC | 96 |
| XJ-34 | AGAGA CAATTG TTCCTCTTGTGCTCTTGCTGG | 97 |
| XJ-35 | GATCC GAGATCGAGTGCCGCATCACCGGC | 98 |
| XJ-36 | AATTG CCG GTGATGCGGCACTCGATCTCG | 99 |
| XJ-37 | CGTGGGCTTGTACTCGGTCATGG | 100 |
| XJ-38 | GACCTGCATCCATCTAGATCTCTCG | 101 |
| XJ-39 | GATACCCCGAAGAGTGAGTTTGCC | 102 |
| XJ-40 | GTTCTAATTCCATCAGAAGCTGGTCG | 103 |
| XJ-41 | ATTGTTTTGCCAAGTTCTAATTCCATC | 104 |
| XJ-42 | CAAGTCAAGCAAAATTATAGGTCCTG | 105 |
| XJ-43 | GAAGGTGGTGAAGCAGGCG | 106 |
| XJ-44 | GAGCGGGAAGCAAATGGTT | 107 |
| XJ-45 | GGAGTCCACTGGCGTCTTCA | 108 |
| XJ-46 | GCCCACCAGCTCGAACTCC | 109 |
| XJ-47 | GCGGCTACTACAGCTTCGTGGTG | 110 |
| XJ-48 | GATGGAGTCTCATACTCTGTTGCCT | 111 |
| XJ-49 | GAAGGTGGTGAAGCAGGCG | 112 |
| XJ-50 | CCTCACATTGCCAAAAGACG | 113 |
| XJ-51 | CGCCAGGGTTTTCCCAGTCACGAC | 114 |
| XJ-52 | ACTCCCACTGTCCTTTCCTAAT | 115 |
| XJ-53 | GAGCGGGAAGCAAATGGTT | 116 |
| XJ-54 | CAGGAAACAGCTATGAC | 117 |
| XJ-55 | TTGAGGCTGCTGGGTCTC | 118 |
| XJ-56 | GCTCTGAACAGGTAACAGCTACA | 119 |
| XJ-57 | agaga caattg TTACTCCTTGGAGGCCATGTGG | 120 |
| XJ-58 | agaga ggatcc ACATTAAGGAGAAGCTGTGCTACGTC | 121 |
| XJ-59 | agaga caattg ACAACAATGTGCAATCAAAGTCCTCG | 122 |
| XJ-60 | agaga gtcgac TCTAAGGAGAATGGCCCAGTCCTC | 123 |
| XJ-61 | agaga gttaac CAGACCTCAGCCCATAGCTAACCAG | 124 |
| XJ-62 | agaga caattg CCTTTAGAGGACGGGTGTTC | 125 |
| XJ-63 | agaga acgcgt CACGTCAGGATAGTTGCAGTAAT | 126 |
| XJ-64 | agaga gaattc GTTTTTGTTGTTGCTGTTGTTG | 127 |
| XJ-65 | agaga ctcgag CCATCTTTTACTCACAACCCTG | 128 |
| XJ-66 | agaga caattg GGTGCTTTTCTTGCTGCTGG | 129 |

TABLE 3-continued

| Primer | Sequences | SEQ ID NO: |
|--------|-----------|------------|
| XJ-67 | agaga acgcgt CATGGAAGGTGGCGACACAG | 130 |
| XJ-68 | agaga gttaac TGGCAGTCTCAGGTTAAGAAGGA | 131 |
| XJ-69 | agaga gaattc ATAATGCCGCTTTGACACTCC | 132 |
| XJ-70 | agaga ggatcc ATGGCTGCCTCACAAACTTCAC | 133 |
| XJ-71 | agaga ctcgag GCAATGAGTCTGCCAGATCAGAG | 134 |
| XJ-72 | CTTCAAATTAGGGTTGGAGCAAAACAG | 135 |
| XJ-73 | ATCGACAGGGTTTTATTGTTACATTTGG | 136 |
| XJ-74 | TCCTTTCTGTAAACATCTTGGCTTCAACAC | 137 |
| XJ-75 | CTCCCCTCAGGACATTTTACGTTTG | 138 |
| XJ-76 | ACACATAGTATCGCATGGATCAAATTCCG | 139 |
| XJ-77 | TCATTTTGGACCTGACTTGCCATC | 140 |
| XJ-78 | CATCCCTGCATCTACTGGTGCTAC | 141 |
| XJ-79 | GGAAAAACCTGCCAAATATGATGACACC | 142 |
| XJ-80 | TCAGCCCCTTGTTGAATACGCTTG | 143 |

REFERENCES

1. Vasquez. KM. Marburger K. Intody Z & Wilson JH. Manipulating the mammalian genome by homologous recombination. *Proc Natl Acad Sci USA* 98, 8403-10 (2001).
2. Koller B H. Hagemann L J. Doctschman T. Hagaman J R. Huang S. Williams P J. First N L. Maeda N & Smithies O. Germ-line transmission of a planned alteration made in a hypoxanthine phosphoribosyltransferase gene by homologous recombination in embryonic stem cells. *Proc Natl Acad Sci USA* 86, 8927-31 (1989).
3. Capecchi M R. Gene targeting in mice: functional analysis of the mammalian genome for the twenty-first century. *Nat Rev Genet* 6, 507-12 (2005).
4. Thomson J A. Itskovitz-Eldor J. Shapiro S S. Waknitz M A. Swiergiel J J. Marshall V S & Jones J M. Embryonic stem cell lines derived from human blastocysts. *Science* 282, 1145-7 (1998).
5. Takahashi K. Tanabe K. Ohnuki M. Narita M. Ichisaka T. Tomoda K & Yamanaka S. Induction of pluripotent stem cells from adult human fibroblasts by defined factors. *Cell* 131, 861-72 (2007).
6. Sterneckert J L. Reinhardt P & Scholer H R. Investigating human disease using stem cell models. *Nat Rev Genet* 15, 625-39 (2014).
7. Nakayama M. Homologous recombination in human iPS and E S cells for use in gene correction therapy. *Drug Discov Today* 15, 198-202 (2010).
8. Musunuru K. Genome editing of human pluripotent stem cells to generate human cellular disease models. *Dis Model Mech* 6, 896-904 (2013).
9. Jiang W. Bikard D. Cox D. Zhang F & Marraffini L A. RNA-guided editing of bacterial genomes using CRISPR-Cas systems. *Nat Biotech* 31, 233-239 (2013).
10. Hsu P D. Lander E S & Zhang F. Development and applications of CRISPR-Cas9 for genome engineering. *Cell* 157, 1262-78 (2014).
11. Kearns N A. Genga R M. Enuamch M S. Garber M. Wolfe S A & Machr R. Cas9 effector-mediated regulation of transcription and differentiation in human pluripotent stem cells. *Development* 141, 219-23 (2014).
12. Lieber M R. The mechanism of double-strand DNA break repair by the nonhomologous DNA cnd-joining pathway. *Annu Rev Biochem* 79, 181-211 (2010). 30) 13. Wang H. Yang H. Shivalila C S. Dawlaty M M. Cheng A W. Zhang F & Jaenisch R. One-step generation of mice carrying mutations in multiple genes by CRISPR/Cas-mediated genome engineering. *Cell* 153, 910-8 (2013).
14. Heyer W D. Ehmsen K T & Liu J. Regulation of homologous recombination in eukaryotes. *Annu Rev Genet* 44, 113-39 (2010).
15. Merkle F T. Neuhausser W M. Santos D. Valen E. Gagnon J A. Maas K. Sandoc J. Schier A F & Eggan K. Efficient CRISPR-Cas9-Mediated Generation of Knockin Human Pluripotent Stem Cells Lacking Undesired Mutations at the Targeted Locus. *Cell Rep* 11, 875-83 (2015).
16. van Rensburg R. Beyer I. Yao X Y. Wang H. Denisenko O. Li Z Y. Russell D W. Miller D G. Gregory P. Holmes M. Bomsztyk K & Lieber A. Chromatin structure of two genomic sites for targeted transgene integration in induced pluripotent stem cells and hematopoietic stem cells. *Gene Ther* 20, 201-14 (2013).
17. Szymczak A L. Workman C J. Wang Y. Vignali K M. Dilioglou S. Vanin E F & Vignali D A. Correction of multi-gene deficiency in vivo using a single 'self-cleaving' 2A peptide-based retroviral vector. *Nat Biotechnol* 22, 589-94 (2004).
18. Casola S. Mouse models for miRNA expression: the ROSA26 locus. *Methods Mol Biol* 667, 145-63 (2010).
19. Woltjen K. Michacl I P. Mohseni P. Desai R. Milcikovsky M. Hamalainen R. Cowling R. Wang W. Liu P. Gertsenstein M. Kaji K. Sung H K & Nagy A. piggy Bac transposition reprograms fibroblasts to induced pluripotent stem cells. *Nature* 458, 766-70 (2009).

20. Hwang W Y. Fu Y. Reyon D. Maeder M L. Tsai S Q. Sander J D. Peterson R T. Yeh J R & Joung J K. Efficient genome editing in zebrafish using a CRISPR-Cas system. *Nat Biotechnol* 31, 227-9 (2013).

21. Jiang W. Bikard D. Cox D. Zhang F & Marraffini L A. RNA-guided editing of bacterial genomes using CRISPR-Cas systems. *Nat Biotechnol* 31, 233-9 (2013).

22. Hu J. Lei Y. Wong W-K. Liu S. Lee K-C. He X. You W. Zhou R. Guo J-T. Chen X. Peng X. Sun H. Huang H. Zhao H & Feng B. Direct activation of human and mouse Oct4 genes using engineered TALE and Cas9 transcription factors. *Nucleic Acids Research* 42, 4375-4390 (2014).

23. Feng B. Jiang J. Kraus P. Ng J H. Heng J C. Chan Y S. Yaw L P. Zhang W. Loh Y H. Han J. Vega V B. Cacheux-Rataboul V. Lim B. Lufkin T & Ng H H. Reprogramming of fibroblasts into induced pluripotent stem cells with orphan nuclear receptor Esrrb. *Nat Cell Biol* 11, 197-203 (2009).

24. Yu C. Liu Y. Ma T. Liu K. Xu S. Zhang Y. Liu H. La Russa M. Xie M. Ding S & Qi L S. Small molecules enhance CRISPR genome editing in pluripotent stem cells. *Cell Stem Cell* 16, 142-7 (2015).

25. Maruyama T. Dougan S K. Truttmann M C. Bilate A M. Ingram J R & Ploegh H L. Increasing the efficiency of precise genome editing with CRISPR-Cas9 by inhibition of nonhomologous end joining. *Nat Biotechnol* 33, 538-42 (2015).

26. Zhu Z. Verma N. Gonzalez F. Shi Z D & Huangfu D. A CRISPR/Cas-Mediated Selection-free Knockin Strategy in Human Embryonic Stem Cells. *Stem Cell Reports* 4, 1103-11 (2015).

27. Li J. Zhang B B. Ren Y G. Gu S Y. Xiang Y H & Du J L. Intron targeting-mediated and endogenous gene integrity-maintaining knockin in zebrafish using the CRISPR/Cas9 system. *Cell Res* 25, 634-7 (2015).

28. Hisano Y. Sakuma T. Nakade S. Ohga R. Ota S. Okamoto H. Yamamoto T & Kawahara A. Precise in-frame integration of exogenous DNA mediated by CRISPR/Cas9 system in zebrafish. *Sci Rep* 5, 8841 (2015).

29. MALI P G. Church G M & Yang L. RNA-Guided Human Genome Engineering. (Google Patents. 2014).

30. Wu F. Crispr/cas systems for genomic modification and gene modulation. (Google Patents. 2014).

31. Zhang F & RAN F. Delivery. engineering and optimization of systems, methods and compositions for sequence manipulation and therapeutic applications. (Google Patents. 2014). Cong L & Zhang F. CRISPR-Cas component systems, methods and compositions for 32. sequence manipulation. (Google Patents. 2014).

33. Chen F. Davis G D. KANG Q & KNIGHT S W. Crispr-based genome modification and regulation. (Google Patents. 2014).

34. Zhang F. Crispr-cas component systems, methods and compositions for sequence manipulation. (Google Patents. 2015).

35. Zetsche. B., et al., *Cpf1 Is a Single RNA-Guided Endonuclease of a Class 2 CRISPR-Cas System.* Cell. 163 (3): p. 759-771.

36. Liu, M., et al., *Genomic discovery of potent chromatin insulators for human gene therapy.* Nat Biotech, 2015, 33 (2): p. 198-203.

What is claimed is:

1. A composition comprising:

(1) a donor construct for gene integration into a target locus within a mammalian host cell genome, comprising (a) a coding sequence for at least one gene; (b) a polyA segment at the 3' end of the at least one gene coding sequence; (c) an internal ribosome entry site (ires) at the 5' end of the at least one gene coding sequence; (d) two copies of a first sgRNA target sequence, one copy located at the 5' end of the ires and the other copy located at the 3' end of the polyA segment, wherein the first sgRNA target sequence is about 20 to about 40 nucleotides in length and comprises the nucleotide sequence of SEQ ID NO:5 or its reverse complementary sequence; (e) tandem repeats of human insulator sequences located at the 5' end of the first sgRNA target sequence site located at the 5' end of the ires; and (f) a nucleotide sequence containing multiple stop codons inserted at the 5' end of the ires element;

wherein the donor construct is a promoterless construct; and wherein the donor construct does not comprise substantial sequence identity to the target locus within the mammalian host cell genome; and (2) two sgRNAs targeting different target sequences and/or one or two DNA molecules encoding the two sgRNAs, wherein one of the sgRNAs targets the first sgRNA target sequence on the donor construct, and the other sgRNA targets a second sgRNA target sequence within a 3' untranslated region (UTR) of the target locus within the mammalian host cell genome.

2. The composition of claim 1, further comprising a Cas9 protein or a Cpf1 protein, or a DNA molecule encoding a Cas9 protein or a Cpf1 protein.

3. The composition of claim 1, wherein the mammalian host cell is a human cell.

4. The composition of claim 1, wherein the mammalian host cell is a human embryonic stem cell.

5. The composition of claim 1, further comprising a Cas9 protein or a DNA molecule encoding a Cas9 protein.

6. The composition of claim 5, comprising a DNA molecule encoding a Cas9 protein.

7. An isolated mammalian host cell comprising:

(1) a donor construct for gene integration into a target locus within a mammalian host cell genome, comprising (a) a coding sequence for at least one gene; (b) a polyA segment at the 3' end of the at least one gene coding sequence; (c) an internal ribosome entry site (ires) at the 5' end of the at least one gene coding sequence; (d) two copies of a first sgRNA target sequence, one copy located at the 5' end of the ires and the other copy located at the 3' end of the polyA segment, wherein the first sgRNA target sequence is about 20 to about 40 nucleotides in length and comprises the nucleotide sequence of SEQ ID NO:5 or its reverse complementary sequence; (e) tandem repeats of human insulator sequences located at the 5' end of the first sgRNA target sequence site located at the 5' end of the ires; and (f) a nucleotide sequence containing multiple stop codons inserted at the 5' end of the ires element;

wherein the donor construct is a promoterless construct;

and wherein the donor construct does not comprise substantial sequence identity to the target locus within the mammalian host cell genome; and (2) two sgRNAs targeting different target sequences and/ or one or two DNA molecules encoding the two sgR-NAs, wherein one of the sgRNAs targets the first sgRNA target sequence on the donor construct, and the other sgRNA targets a second sgRNA target sequence within a 3' UTR of the target locus within the mammalian host cell genome.

8. The isolated mammalian host cell of claim 7, further comprising a Cas9 protein or a Cpf1 protein, or a DNA molecule encoding a Cas9 protein or a Cpf1 protein.

9. The isolated mammalian host cell of claim 7, which is a human cell.

10. The isolated mammalian host cell of claim 7, which is a human embryonic stem cell.

11. The isolated mammalian host cell of claim 7, further comprising a Cas9 protein or a DNA molecule encoding a Cas9 protein.

12. The isolated mammalian host cell of claim 11, comprising a DNA molecule encoding a Cas9 protein.

13. An isolated mammalian host cell comprising a donor construct for gene integration into a target locus within the mammalian host cell genome, the donor construct comprising (a) a coding sequence for at least one gene; (b) a polyA segment at the 3' end of the at least one gene coding sequence; (c) an internal ribosome entry site (ires) at the 5' end of the at least one gene coding sequence; (d) two copies of a sgRNA target sequence, one copy located at the 5' end of the ires and the other copy located at the 3' end of the poly A segment, wherein the sgRNA target sequence is about 20 to about 40 nucleotides in length and comprises the nucleotide sequence of SEQ ID NO:5 or its reverse complementary sequence; (e) tandem repeats of human insulator sequences located at the 5' end of the sgRNA target sequence site located at the 5' end of the ires; and (f) a nucleotide sequence containing multiple stop codons inserted at the 5' end of the ires element;

wherein the donor construct is a promoterless construct;

wherein the donor construct does not comprise substantial sequence identity to the target locus within the mammalian host cell genome;

and wherein the donor construct is integrated at a 3'UTR of the target locus within the mammalian host cell genome.

14. The isolated mammalian host cell of claim 13, which is a human cell.

15. The isolated mammalian host cell of claim 13, which is a human embryonic stem cell.

16. The isolated mammalian host cell of claim 13, further comprising a Cas9 protein or a DNA molecule encoding a Cas9 protein.

17. The isolated mammalian host cell of claim 16, comprising a DNA molecule encoding a Cas9 protein.

* * * * *